United States Patent
Kuzmich et al.

(10) Patent No.: US 8,338,610 B2
(45) Date of Patent: Dec. 25, 2012

(54) PYRIDINYL COMPOUNDS USEFUL AS INTERMEDIATES

(75) Inventors: Daniel Kuzmich, Danbury, CT (US); Pingrong Liu, Southbury, CT (US); Hossein Razavi, Danbury, CT (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 13/368,397

(22) Filed: Feb. 8, 2012

(65) Prior Publication Data

US 2012/0136158 A1 May 31, 2012

Related U.S. Application Data

(60) Division of application No. 13/273,509, filed on Oct. 14, 2011, now Pat. No. 8,163,918, which is a continuation of application No. 12/969,753, filed on Dec. 16, 2010, now Pat. No. 8,063,065, which is a division of application No. 12/564,129, filed on Sep. 22, 2009, now Pat. No. 7,879,873.

(60) Provisional application No. 61/100,401, filed on Sep. 26, 2008.

(51) Int. Cl.
C07D 213/02 (2006.01)

(52) U.S. Cl. ....................................... 546/294

(58) Field of Classification Search ................... 546/294
See application file for complete search history.

(56) References Cited

U.S. PATENT DOCUMENTS

| | | | |
|---|---|---|---|
| 4,999,363 A | 3/1991 | Oshima et al. |
| 5,118,701 A | 6/1992 | Oshima et al. |
| 5,242,931 A | 9/1993 | Oshima et al. |
| 5,302,596 A | 4/1994 | Oshima et al. |
| 5,534,481 A | 7/1996 | Suzuki et al. |
| 5,612,360 A | 3/1997 | Boyd et al. |
| 5,616,537 A | 4/1997 | Yokota et al. |
| 5,670,452 A | 9/1997 | Suzuki et al. |
| 5,760,028 A | 6/1998 | Jadhav et al. |
| 5,763,616 A | 6/1998 | Suzuki et al. |
| 5,770,544 A | 6/1998 | Yokota et al. |
| 5,973,156 A | 10/1999 | Chambers et al. |
| 6,025,374 A | 2/2000 | Castro Pineiro et al. |
| 6,107,321 A | 8/2000 | Madin |
| 6,211,219 B1 | 4/2001 | MacLeod et al. |
| 6,326,382 B1 | 12/2001 | Villalobos et al. |
| 6,331,640 B1 | 12/2001 | Fotouhi et al. |
| 6,498,255 B2 | 12/2002 | Villalobos et al. |
| 6,716,978 B2 | 4/2004 | Marfat |
| 6,784,182 B2 | 8/2004 | Liebeschuetz et al. |
| 6,803,384 B2 | 10/2004 | Fotouhi et al. |
| 6,855,715 B1 | 2/2005 | Liebeschuetz et al. |
| 6,878,725 B2 | 4/2005 | Liebeschuetz et al. |
| 6,900,196 B2 | 5/2005 | Liebeschuetz et al. |
| 6,936,611 B2 | 8/2005 | Liebeschuetz et al. |
| 7,049,297 B2 | 5/2006 | Zhang et al. |
| 7,053,078 B2 | 5/2006 | Liebeschuetz et al. |
| 7,129,264 B2 | 10/2006 | Smallheer et al. |
| 7,223,782 B2 | 5/2007 | Atkinson et al. |
| 7,429,609 B2 | 9/2008 | Ohi et al. |
| 7,879,873 B2 | 2/2011 | Cook et al. |
| 8,008,327 B2 | 8/2011 | DiSalvo et al. |
| 8,063,065 B2 | 11/2011 | Cook et al. |
| 8,263,597 B2 | 9/2012 | Kuzmich et al. |
| 2002/0037860 A1 | 3/2002 | D'Andrea et al. |
| 2002/0052373 A1 | 5/2002 | Zorn et al. |
| 2004/0127536 A1 | 7/2004 | Bhagwat et al. |
| 2005/0009876 A1 | 1/2005 | Bhagwat et al. |
| 2005/0020564 A1 | 1/2005 | Atkinson et al. |
| 2005/0108582 A1 | 5/2005 | Fung |
| 2005/0208582 A1 | 9/2005 | Ohi et al. |
| 2005/0261339 A1 | 11/2005 | Ohi et al. |
| 2006/0035938 A1* | 2/2006 | Bladh et al. .................. 514/346 |
| 2006/0252781 A1 | 11/2006 | Basarab et al. |
| 2006/0281739 A1 | 12/2006 | Gadek et al. |
| 2007/0004761 A1 | 1/2007 | Basarab et al. |

(Continued)

FOREIGN PATENT DOCUMENTS

EP 345747 A2 12/1989

(Continued)

OTHER PUBLICATIONS

Berge et al. J. Pharm. Sci., 1977, 66 (1), 1-19.*
Alzheimer's Disease. Retrieved online Dec. 15, 2010. http:/www.cnn.com/HEALTH/mentalhealt/alzheimers.
CAPLUS: 1990:478384, Bruneau, 1990.
CAPLUS: 2008:94643, Kitamura, 2008.
CAPLUS: 2009:583109, Doherty, 2009.
Carter, P.H. et al., "N-aryl pyrazoles,indazoles and azaindazoles as antagonists of CC chemokine receptor 1: patent cooperation treaty applications WO2010036632, WO2009134666 and WO2009137337". Expert Opinion Ther. Patents, 2010, 20(11), p. 1-10.

(Continued)

*Primary Examiner* — Rebecca Anderson
*Assistant Examiner* — Samantha Shterengarts
(74) *Attorney, Agent, or Firm* — Michael P. Morris; Anthony P. Bottino

(57) ABSTRACT

Disclosed are compounds of the formula (I), useful for treating a variety of diseases and disorders that are mediated or sustained through the activity of CCR1 including autoimmune diseases, such as rheumatoid arthritis and multiple sclerosis.

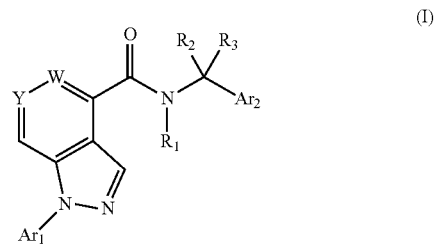

(I)

Also disclosed are intermediates thereof, and methods of making and methods of using same.

3 Claims, No Drawings

U.S. PATENT DOCUMENTS

| | | |
|---|---|---|
| 2008/0262040 A1 | 10/2008 | Callahan et al. |
| 2008/0280956 A1* | 11/2008 | Gilligan et al. .............. 514/347 |
| 2009/0054397 A1 | 2/2009 | Ohi et al. |
| 2010/0093724 A1 | 4/2010 | Cook et al. |
| 2011/0034512 A1 | 2/2011 | Disalvo et al. |
| 2011/0086846 A1 | 4/2011 | Cook et al. |
| 2011/0137042 A1 | 6/2011 | Razavi et al. |
| 2011/0230521 A1 | 9/2011 | Cook et al. |
| 2011/0294808 A1 | 12/2011 | Kuzmich et al. |
| 2012/0035370 A1 | 2/2012 | Cook et al. |
| 2012/0136158 A1 | 5/2012 | Cook et al. |

FOREIGN PATENT DOCUMENTS

| | | | |
|---|---|---|---|
| EP | 1201268 | A2 | 5/2002 |
| JP | 10001478 | A | 1/1998 |
| WO | 9217475 | A1 | 10/1992 |
| WO | 9401415 | A1 | 1/1994 |
| WO | 9500509 | | 5/1995 |
| WO | 9617842 | A1 | 6/1996 |
| WO | 9711945 | A1 | 4/1997 |
| WO | 9719073 | A1 | 5/1997 |
| WO | 9723480 | A1 | 7/1997 |
| WO | 9803504 | A1 | 1/1998 |
| WO | 9923076 | A1 | 5/1999 |
| WO | 0021920 | A1 | 4/2000 |
| WO | 0076970 | A2 | 12/2000 |
| WO | 0076971 | A2 | 12/2000 |
| WO | 0100656 | A2 | 1/2001 |
| WO | 0210137 | A2 | 2/2002 |
| WO | 03087085 | A1 | 10/2003 |
| WO | 03101968 | A1 | 12/2003 |
| WO | 03105853 | A1 | 12/2003 |
| WO | 2004043924 | A1 | 5/2004 |
| WO | 2004056831 | A1 | 7/2004 |
| WO | 2004094372 | A2 | 11/2004 |
| WO | 2005016929 | A1 | 2/2005 |
| WO | 2006091496 | A2 | 8/2006 |
| WO | 2006125119 | A1 | 11/2006 |
| WO | 2007002293 | A2 | 1/2007 |
| WO | 2007028083 | A2 | 3/2007 |
| WO | 2007102883 | A2 | 9/2007 |
| WO | 2008011131 | | 1/2008 |
| WO | 2009024585 | A2 | 2/2009 |
| WO | 2009037570 | A2 | 3/2009 |
| WO | 2009134666 | A1 | 11/2009 |
| WO | 2009137338 | A1 | 11/2009 |
| WO | 2010036632 | A1 | 4/2010 |
| WO | 2011049917 | A1 | 4/2011 |
| WO | 2011056440 | A1 | 5/2011 |
| WO | 2011071730 | A1 | 6/2011 |
| WO | 2011137109 | A1 | 11/2011 |
| WO | 2012087782 | A1 | 6/2012 |

OTHER PUBLICATIONS

Cheng, J-F, et al., "CCR1 Antagonists". Molecular Diversity, Kluwer Academic Publishers, vol. 12, No. 1, Jun. 17, 2008, p. 17-23.

Conlon, K. et al., "Comparison of lymphokine secretion and mRNA expression in the CD45RA+ and CD45RO+ subsets of human peripheral blood CD4+ and CD8+ lympocytes". European Journal of Immunology, 1995, vol. 25, p. 644-648.

Gerard, C. et al., "Chemokines and disease". 2001 Nature Publishing Group, Chemokine Reviews, Nature Immunology, vol. 2, No. 2, Feb. 2001, p. 108-115.

Haringman, J.J. et al., "Chemokine blockade and chronic inflammatory disease: proof of concept in patients with rheumatoid arthritis". Ann Rheum Dis, 2003, 62, p. 715-721.

International Search Report for PCT/US2009/057778 mailed Jan. 11, 2010.

Karpus, W. J. et al., "An Important Role for the Chemokine Macrophase Inflammatory Protein-1a in the Pathogenesis of the T Cell-Mediated Autoimmune Disease, Experimental Autoimmune Encephalomyelitis". The American Association of Immunologists, 1995, p. 5003-5010.

Koch, A. E., et al., "Macrophase Inflammatory Protein-1a. A Novel Chemotactic Cytokine for Macrophages in Rheumatoid Arthritis". The Journal of Clinical Investigation, Inc., vol. 93, Mar. 1994, p. 921-928.

Koch, A.E. et al., "Epithelial Neutrophil Activating Peptide-78: A Novel Chemotactic Cytokine for Neutrophils in Arthritis". The Journal of Clinical Investigations, Inc. vol. 94, Sep. 1994, p. 1012-1018.

Plater-Zyberk, C. et al., "Effectof a CC chemokine receptor antagonist on collagen induced arthritis in DBA/1 mice". Immunology Letters, 57, 1997, p. 117-120.

Revesz, L. et al., "Novel CCR1 antagonists with oral activity in the mouse collagen induced arthritis". Bioorganice and Medicinal Chemistry Letters, 2005, p. 1-5.

Trebst, C. et al., "CCR1+/CCR5+ Mononuclear Phagocytes Accumulate in the Central Nervous System on Patients with Multiple Sclerosis." American Journal of Pathology, vol. 159, No. 4, Nov. 2001, p. 1701-1710.

Volin, M.V. et al., "Rantes Expression and Contribution to Monocyte Chemotaxix in Arthritis". Clinical Immunology and Immunopathology, vol. 89, No. 1, Oct. 1998, Article II984590, p. 44-53.

Caplus: 2009:2329372, Loiseleur, 2009.

Engbersen, J.F.J. et al., "Synthesis of 2-Aminomethyl-1,10-phenanthroline. A new Chelating Agent and Versatile Synthon for other Chelating Compounds", Journal of Heterocyl Cehm., 1986, vol. 23, pp. 989-990.

Finar, I.L. et al. The Beckmann Rearrangement of Some Pyrazolyl Oximes. Journal Chemical Soc. Sec. C, 1969, p. 1495-1499.

* cited by examiner

PYRIDINYL COMPOUNDS USEFUL AS INTERMEDIATES

FIELD OF THE INVENTION

This invention relates to azaindazoles that are useful as antagonists of CCR1 activity and are thus useful for treating a variety of diseases and disorders that are mediated or sustained through the activity of CCR1 including autoimmune diseases, such as rheumatoid arthritis and multiple sclerosis. This invention also relates to pharmaceutical compositions comprising these compounds, methods of using these compounds in the treatment of various diseases and disorders, processes for preparing these compounds and intermediates useful in these processes.

BACKGROUND OF THE INVENTION

Chemotactic Cytokine Receptor 1 (CCR1) belongs to a large family (>20) of chemotactic cytokine (chemokine) receptors that interact with specific chemokines (>50) to mediate leukocyte trafficking, granule exocytosis, gene transcription, mitogenic effects and apoptosis. Chemokines are best known for their ability to mediate basal and inflammatory leukocyte trafficking. The binding of at least three chemokines (MIP-1 alpha/CCL3, MCP3/CCL7 and RANTES/CCL5) to CCR1 is responsible for the trafficking of monocytes, macrophages and TH1 cells to inflamed tissues of rheumatoid arthritis (RA) and multiple sclerosis (MS) patients (Trebst et al. (2001) *American J of Pathology* 159 p. 1701). Macrophage inflammatory protein 1 alpha (MIP-1 alpha), macrophage chemoattractant protein 3 (MCP-3) and regulated on activation, normal T-cell expressed and secreted (RANTES) are all found in the CNS of MS patients, while MIP-1 alpha and RANTES are found in the CNS in the experimental autoimmune encephalomyelitis (EAE) model of MS (Review: Gerard and Rollins (2001) *Nature Immunology*). Macrophages and Th1 cells in the inflamed synovia of RA patients are also major producers of MIP-1 alpha and RANTES, which continuously recruit leukocytes to the synovial tissues of RA patients to propagate chronic inflammation (Volin et al. (1998) *Clin. Immunol. Immunopathology*; Koch et al. (1994) *J. Clin. Investigation*; Conlon et al. (1995) *Eur. J. Immunology*). Antagonizing the interactions between CCR1 and its chemokine ligands is hypothesized to block chemotaxis of monocytes, macrophages and Th1 cells to inflamed tissues and thereby ameliorate the chronic inflammation associated with autoimmune diseases such as RA and MS.

Evidence for the role of CCR1 in the development and progression of chronic inflammation associated with experimental autoimmune encephalitis (EAE), a model of multiple sclerosis, is based on both genetic deletion and small molecule antagonists of CCR1. CCR1 deficient mice were shown to exhibit reduced susceptibility (55% vs. 100%) and reduced severity (1.2 vs. 2.5) of active EAE (Rottman et al. (2000) *Eur. J. Immunology*). Furthermore, administration of small molecule antagonist of CCR1, with moderate affinity ($K_i$=120 nM) for rat CCR1, was shown to delay the onset and reduce the severity of EAE when administered intravenously (Liang et al. (2000) *J. Biol. Chemistry*). Treatment of mice with antibodies specific for the CCR1 ligand MIP-1 alpha have also been shown to be effective in preventing development of acute and relapsing EAE by reducing the numbers of T cells and macrophages recruited to the CNS (Karpus et al. (1995) *J. Immunology*; Karpus and Kennedy (1997) *J. Leukocyte Biology*). Thus, at least one CCR1 ligand has been demonstrated to recruit leukocytes to the CNS and propagate chronic inflammation in EAE, providing further in vivo validation for the role of CCR1 in EAE and MS.

In vivo validation of CCR1 in the development and propagation of chronic inflammation associated with RA is also significant. For example, administration of a CCR1 antagonist in the collagen induced arthritis model (CIA) in DBA/1 mice has been shown to be effective in reducing synovial inflammation and joint destruction (Plater-Zyberk et al. (1997) *Immunology Letters*). Another publication described potent antagonists of murine CCR1 that reduced severity (58%) in LPS-accelerated collagen-induced arthritis (CIA), when administered orally (*Biorganic and Medicinal Chemistry Letters* 15, 2005, 5160-5164). Published results from a Phase Ib clinical trial with an oral CCR1 antagonist demonstrated a trend toward clinical improvement in the absence of adverse side effects (Haringman et al. (2003) *Ann. Rheum. Dis.*). One third of the patients achieved a 20% improvement in rheumatoid arthritis signs and symptoms (ACR20) on day 18 and CCR1 positive cells were reduced by 70% in the synovia of the treated patients, with significant reduction in specific cell types including 50% reduction in $CD4^+$ T cells, 50% reduction in $CD8^+$ T cells and 34% reduction in macrophages.

Studies such as those cited above support a role for CCR1 in MS and RA and provide a therapeutic rationale for the development of CCR1 antagonists.

BRIEF SUMMARY OF THE INVENTION

The present invention provides novel compounds which block the interaction of CCR1 and its ligands and are thus useful for treating a variety of diseases and disorders that are mediated or sustained through the activity of CCR1 including autoimmune diseases, such as rheumatoid arthritis and multiple sclerosis. This invention also relates to pharmaceutical compositions comprising these compounds, methods of using these compounds in the treatment of various diseases and disorders, processes for preparing these compounds and intermediates useful in these processes.

DETAILED DESCRIPTION OF THE INVENTION

In its broadest generic aspect the invention provides a compound of the formula (I)

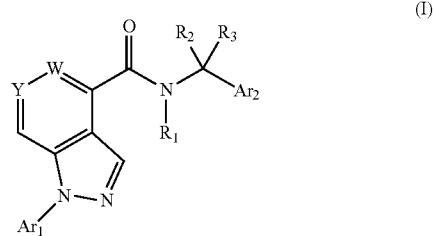

wherein
W is carbon and Y is nitrogen or, W is nitrogen and Y is carbon;
$Ar_1$ is carbocycle, heteroaryl or heterocyclyl each optionally substituted by one to three $R_a$;
$Ar_2$ is carbocycle, heteroaryl or heterocyclyl, each optionally substituted by one to three $R_b$;
$R_1$ is hydrogen, $C_{1-6}$ alkyl or $C_{1-6}$ alkoxy$C_{1-6}$ alkyl;

$R_2$, $R_3$ are each independently hydrogen, $C_{1-6}$ alkyl or $C_{1-6}$ alkenyl, wherein the $C_{1-6}$ alkyl or alkenyl is optionally partially or fully halogenated or substituted with one to three groups independently selected from cyano, $C_{1-6}$ alkoxy, hydroxyl, —$CO_2C_{1-6}$ alkyl, —$C(O)N(R_e)(R_f)$, —$N(R_e)(R_f)$ and heterocyclyl optionally substituted by oxo;

$R_a$ is $C_{1-6}$ alkyl, $C_{3-10}$ cycloalkyl, $C_{1-6}$ alkoxy, $C_{1-6}$ alkylthio, $C_{1-6}$ alkylsulfonyl, $C_{1-6}$ alkoxycarbonyl, amino, mono-or di-$C_{1-6}$ alkylamino, $C_{3-6}$ cycloalkylamino, $C_{1-6}$ alkylaminocarbonyl, $C_{1-6}$ acyl, $C_{1-6}$ acylamino, $C_{1-6}$ dialkylaminocarbonyl, hydroxyl, halogen, cyano, nitro, oxo, $R_4$—S$(O)_m$—NH—, $R_4$—NH—S$(O)_m$—, aryl or carboxyl;

$R_b$ is hydroxyl, carboxyl, halogen, —$(CH_2)_n$—CN, —$(CH_2)_n$—$CO_2C_{1-6}$alkyl, nitro, —$SO_3H$, $C_{1-6}$ alkyl, $C_{2-6}$ alkenyl, $C_{2-6}$ alkynyl, $C_{3-10}$ cycloalkyl, $C_{1-6}$ alkoxy, $C_{1-6}$alkylC(O)—, —$(CH_2)_n$—$NR_cR_d$, $R_4$—$S(O)_m(CH_2)_{0-1}$—, $R_4$—S$(O)_m$—$NR_e$—, $R_4$—$NR_e$—$S(O)_m(CH_2)_{0-1}$—, —$NR_f$—C(O)—$R_e$, —$(CH_2)_x$—C(O)—$(CH_2)_n$—$NR_cR_d$, heterocyclyl, aryl or heteroaryl, each $R_b$ where possible is optionally halogenated or substituted with 1 to 3 $C_{1-6}$ alkyl, hydroxyl, $C_{1-6}$ acyl, $C_{1-6}$ alkoxycarbonyl, $C_{1-6}$ alkyl-S$(O)_m$—, aryl or carboxyl; each $R_c$, $R_d$ are independently hydrogen, $C_{1-6}$ alkyl, $C_{1-6}$ acyl, $C_{3-10}$ cycloalkyl, $C_{1-6}$ alkoxy, hydroxy$C_{1-6}$ alkyl, $C_{1-6}$ alkoxy, hydroxy$C_{1-6}$alkyl, cyano-$C_{1-6}$alkyl, $C_{1-6}$alkyl$C_{1-6}$ alkoxy, $C_{1-6}$ alkylsulfonyl, $C_{1-6}$ alkoxycarbonyl$C_{0-3}$alkyl, —$(CH_2)_n$—C(O)—$NR_eR_f$ or —$(CH_2)_n$—$NR_eR_f$;

each $R_e$, $R_f$ are independently hydrogen, $C_{1-6}$ alkyl, $C_{3-10}$ cycloalkyl, $C_{1-6}$ alkoxy, $C_{1-6}$ alkoxy$C_{1-6}$alkyl, mono-or di$C_{1-6}$alkylamino$C_{1-6}$alkyl, hydroxy$C_{1-6}$ alkyl or $C_{1-6}$ acyl;

$R_4$ is hydrogen, $C_{1-6}$ alkyl, $C_{3-6}$cycloalkyl, heterocyclyl $(CH_2)_{0-1}$, mono-or di-$C_{1-6}$ alkylamino, mono-or di-$_{1-6}$ alkylamino$(CH_2)_{2-3}N(R_e)$—, aryl or heteroaryl each optionally substituted with 1 to 3 $C_{1-6}$ alkyl, $C_{3-6}$cycloalkyl, $C_{1-6}$alkoxy, halogen, hydroxyl, oxo, carboxyl, —$C(O)NR_eR_f$, amino, mono-or di-$C_{1-6}$ alkylamino, $C_{1-6}$ alkoxycarbonyl or $C_{1-6}$ acylamino;

each n, x are independently 0-3;
each m is independently 0-2;
or a pharmaceutically acceptable salt thereof.

In another embodiment of the invention there is provided a compound of the formula (I) as provided immediately above, and wherein $R_2$, $R_3$ are each independently hydrogen, $C_{1-6}$ alkyl or $C_{1-6}$ alkenyl, wherein the $C_{1-6}$ alkyl or alkenyl is optionally partially or fully halogenated or substituted with one to three groups independently selected from hydroxyl, —$CO_2C_{1-6}$ alkyl, —$C(O)N(R_e)(R_f)$, —$N(R_e)(R_f)$, and heterocyclyl;

each $R_c$, $R_d$ are independently hydrogen, $C_{1-6}$ alkyl, $C_{1-6}$ acyl, $C_{3-10}$ cycloalkyl, $C_{1-6}$ alkoxy, hydroxy$C_{1-6}$ alkyl, $C_{1-6}$ alkyl$C_{1-6}$ alkoxy, $C_{1-6}$ alkylsulfonyl, $C_{1-6}$ alkoxycarbonyl$C_{0-3}$alkyl or —$(CH_2)_n$—$NR_eR_f$.

In another embodiment of the invention there is provided a compound of the formula (I) as provided immediately above, and wherein W is carbon and Y is nitrogen;
$Ar_1$ is phenyl, cyclohexyl or tetrahydropyranyl each optionally substituted by one to three $R_a$;
$Ar_2$ is phenyl, pyridyl, pyrazolyl, imidazolyl, thiophenyl, thiazolyl, cyclohexyl, piperidinyl, morpholinyl or piperazinyl, each optionally substituted by one to three $R_b$;
$R_1$ is hydrogen;
$R_2$ is hydrogen, $C_{1-6}$ alkyl or $C_{1-6}$ alkenyl, wherein the $C_{1-6}$alkyl or alkenyl is optionally partially or fully halogenated or substituted with one to three groups independently selected from hydroxyl, —$CO_2C_{1-6}$alkyl, —$C(O)N(R_e)(R_f)$, —$N(R_e)(R_f)$, morpholinyl, thiomorpholinyl and piperidinyl;
$R_3$ is hydrogen;
$R_a$ is $C_{1-3}$alkyl, $C_{1-3}$ alkoxy, methylsulfonyl, mono-or di-$C_{1-3}$ alkylamino, $C_{1-3}$ acyl, $C_{1-3}$ acylamino, $C_{1-3}$ dialkylaminocarbonyl, halogen, cyano or nitro;
$R_b$ is hydroxyl, carboxyl, halogen, —$(CH_2)_n$—CN, —$(CH_2)_n$—$CO_2C_{1-6}$alkyl, nitro, —$SO_3H$, $C_{1-6}$ alkyl, $C_{2-6}$ alkenyl, $C_{2-6}$ alkynyl, $C_{3-10}$cycloalkyl, $C_{1-6}$alkoxy, $C_{1-6}$alkylC(O)—, —$(CH_2)_n$—$NR_cR_d$, $R_4$—$S(O)_m(CH_2)_{0-1}$—, $R_4$—S$(O)_m$—$NR_e$—, $R_4$—$NR_e$—$S(O)_m(CH_2)_{0-1}$—, —$NR_f$—C(O)—$R_e$, —$(CH_2)_x$—C(O)—$(CH_2)_n$—$NR_cR_d$, heterocyclyl, aryl or heteroaryl, each $R_b$ where possible is optionally halogenated or substituted with 1 to 3 $C_{1-6}$ alkyl, $C_{1-6}$ acyl, $C_{1-6}$ alkoxycarbonyl, $C_{1-6}$ alkyl-S$(O)_m$—, aryl or carboxyl;
each $R_c$, $R_d$ are independently hydrogen, $C_{1-6}$ alkyl, $C_{1-6}$ acyl, $C_{3-10}$ cycloalkyl, $C_{1-6}$ alkoxy, hydroxy$C_{1-6}$ alkyl, $C_{1-6}$ alkyl$C_{1-6}$ alkoxy, $C_{1-6}$ alkylsulfonyl, $C_{1-6}$ alkoxycarbonyl$C_{0-3}$alkyl or —$(CH_2)_n$—$NR_eR_f$;
each $R_e$, $R_f$ are independently hydrogen, $C_{1-6}$ alkyl, $C_{3-10}$ cycloalkyl, $C_{1-6}$ alkoxy, $C_{1-6}$ alkoxy$C_{1-6}$alkyl, mono-or di$C_{1-6}$alkylamino$C_{1-6}$alkyl, hydroxy$C_{1-6}$ alkyl or $C_{1-6}$ acyl;
$R_4$ is hydrogen, $C_{1-6}$ alkyl, $C_{3-6}$cycloalkyl, heterocyclyl $(CH_2)_{0-1}$, mono-or di-$C_{1-6}$ alkylamino, mono-or di-$_{1-6}$ alkylamino$(CH_2)_{2-3}N(C_{1-6}$alkyl)-, aryl or heteroaryl each optionally substituted with 1 to 2 $C_{1-6}$ alkyl, $C_{3-6}$cycloalkyl, $C_{1-6}$alkoxy, halogen, hydroxyl, oxo, carboxyl, —$C(O)NR_eR_f$, amino, mono-or di-$C_{1-6}$ alkylamino, $C_{1-6}$ alkoxycarbonyl or $C_{1-6}$ acylamino.

In a further embodiment of the invention there is provided a compound of the formula (I) as provided immediately above, and wherein $Ar_1$ is phenyl is substituted by one to two $R_a$;
$Ar_2$ is phenyl, pyridyl, pyrazolyl, thiophenyl, thiazolyl, cyclohexyl or piperidinyl, each optionally substituted by one or two $R_b$;
$R_2$ is hydrogen, $C_{1-3}$ alkyl, —$CH_2$—CH=$CH_2$, or —$CF_3$, wherein the $C_{1-3}$alkyl is optionally substituted with one to three groups independently selected from hydroxyl, —$CO_2C_{1-6}$alkyl, —$C(O)N(R_e)(R_f)$, —$N(R_e)(R_f)$ and morpholinyl;
$R_a$ is mono-or di-$C_{1-3}$ alkylamino, halogen or nitro;
$R_b$ is hydroxyl, carboxyl, —F, —Cl, —Br, —$CF_3$, —CN, —$SO_3H$, —$CH_3$, —$OCH_3$, $CH_3C(O)$—, —$(CH_2)_n$—$CO_2C_{1-6}$alkyl, —$NR_cR_d$, $R_4$—$S(O)_m(CH_2)_{0-1}$—, $R_4$—S$(O)_2$—$NR_e$—, $R_4$—$NR_e$—$S(O)_2(CH_2)_{0-1}$—, —$NR_f$—C(O)—$R_e$, —$C(O)_2NH_2$, morpholinyl or tetrazolyl;
each $R_c$, $R_d$ are independently hydrogen, $C_{1-3}$ alkyl, $C_{1-3}$ acyl or $C_{1-6}$ alkoxycarbonyl$C_{0-3}$alkyl;
each $R_e$, $R_f$ are independently hydrogen, $C_{1-3}$ alkyl, $C_{1-3}$ alkoxy$C_{1-3}$alkyl or mono-or di$C_{1-3}$alkylamino$C_{1-3}$alkyl;
$R_4$ is hydrogen, $C_{1-4}$alkyl, $C_{3-6}$cycloalkyl, —$N(CH_3)_2$, $(CH_3)_2NCH_2CH_2N(CH_3)$—, or heterocyclyl$(CH_2)_{0-1}$, wherein the heterocyclyl is selected from piperidinyl, morpholinyl, piperidinyl, tetrahydropyranyl, pyrrolidinyl and 1,1,-dioxo-perhydro-1,2-thiazin-2-yl, each $R_4$ optionally substituted with —$OCH_3$, hydroxyl, oxo, carboxyl, —$C(O)NH_2$, amino, —$N(CH_3)_2$ or $C_{1-2}$ alkoxycarbonyl.

In a another embodiment of the invention there is provided a compound of the formula (I) as provided immediately above, and wherein $R_2$ is hydrogen, $C_1$ alkyl, $C_2$ alkyl, $C_3$ alkyl, —$CH_2$—CH=$CH_2$, or —$CF_3$ wherein the $C_1$ alkyl, $C_2$ alkyl, or $C_3$ alkyl is optionally substituted with one to three groups independently selected from hydroxyl and —$CO_2C_{1-3}$ alkyl;

$R_a$ is —F or —Cl;

$R_b$ is hydroxyl, —F, —Cl, —Br, —$CF_3$, —CN, —$SO_3H$, —$OCH_3$, $CH_3C(O)$—, —$(CH_2)_n$—$CO_2C_{1-6}$alkyl, —$NR_cR_d$, $R_4$—$S(O)_m$—, $R_4$—$S(O)_2$—$NR_e$—, $R_4$—$NR_e$—$S(O)_2(CH_2)_{0-1}$—, —$C(O)_2NH_2$ morpholinyl or tetrazolyl;

each $R_c$, $R_d$ are independently hydrogen, $CH_3$ or $CH_3C(O)$—; each $R_e$, $R_f$ are independently hydrogen, —$CH_3$, or —$CH_2CH_2OCH_3$;

$R_4$ is hydrogen, $C_{1-4}$alkyl, $C_{3-6}$cycloalkyl, —$N(CH_3)_2$, $(CH_3)_2NCH_2CH_2N(CH_3)$—, or heterocyclyl, wherein the heterocyclyl is selected from piperidinyl, morpholinyl, piperidinyl, tetrahydropyranyl, pyrrolidinyl and 1,1,-dioxo-perhydro-1,2-thiazin-2-yl, each $R_4$ optionally substituted with —$OCH_3$, hydroxyl, oxo, amino, —$N(CH_3)_2$ or $C_{1-2}$ alkoxycarbonyl.

In a another embodiment of the invention there is provided a compound of the formula (I) as provided in the broadest generic embodiment in combination with any other embodiment above, and wherein $R_2$, $R_3$ are each independently hydrogen or $C_{1-6}$ alkyl optionally partially or fully halogenated or substituted with one to three groups selected from cyano, $C_{1-6}$ alkoxy and heterocyclyl optionally substituted by oxo.

In a another embodiment of the invention there is provided a compound of the formula (I) as provided immediately above, and wherein $R_2$, $R_3$ are each independently hydrogen or $C_{1-3}$ alkyl optionally partially or fully halogenated or substituted with one group selected from cyano, $C_{1-3}$ alkoxy and heterocyclyl chosen from dioxolanyl, tetrahydropyranyl, dioxanyl, tetrahydrofuranyl, benzofuranyl, benzopyranyl and benzodioxolyl each optionally substituted by oxo.

In a another embodiment of the invention there is provided a compound of the formula (I) as provided immediately above, and wherein $R_2$, $R_3$ are each independently hydrogen or $C_{1-3}$ alkyl optionally partially or fully halogenated or substituted with one group selected from cyano, $C_{1-3}$ alkoxy and dioxolanyl optionally substituted by oxo.

In a another embodiment of the invention there is provided a compound of the formula (I) as provided in the broadest generic embodiment in combination with any other embodiment above, and wherein $R_c$, is hydrogen or $C_{1-6}$ alkyl and $R_d$ is cyano-$C_{1-6}$ alkyl or —$(CH_2)_n$—$C(O)$—$NR_eR_f$; each $R_e$, $R_f$ are independently hydrogen, $C_{1-6}$ alkyl.

In another embodiment of the invention there is provided a compound of the formula (I) as provided in the broadest generic embodiment in combination with any other embodiment above, and wherein $Ar_2$ is pyridyl;

$R_b$ is $C_{1-6}$ alkyl optionally substituted with hydroxyl.

In a another embodiment of the invention there is provided a compound of the formula (I) as provided in the broadest generic embodiment in combination with any other embodiment above, and wherein $Ar_2$ is

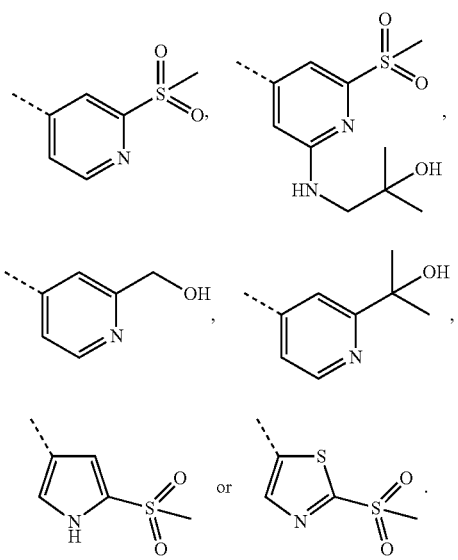

The following are representative compounds of the invention which can be made by the general synthetic schemes, the examples, and known methods in the art.

TABLE I

| STRUCTURE | Name | HPLC-MS[a,b] | |
|---|---|---|---|
| | | [M + H]+ | RT (min) |
| 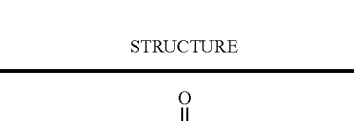 | 1-(4-Fluorophenyl)-1H-pyrazolo[3,4-c]pyridine-4-carboxylic acid 3-trifluoromethyl-benzylamide | 415.4 | 1.74 |

TABLE I-continued

| STRUCTURE | Name | HPLC-MS[a,b] | |
|---|---|---|---|
| | | [M + H]+ | RT (min) |
| 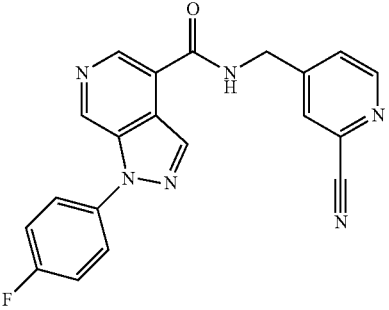 | 1-(4-Fluorophenyl)-1H-pyrazolo[3,4-c]pyridine-4-carboxylic acid (2-cyano-pyridin-4-ylmethyl)-amide | 373.6 | 1.42 |
| 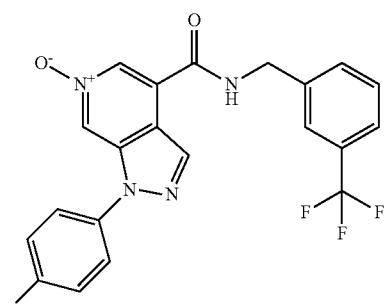 | 1-(4-Fluorophenyl)-6-oxy-1H-pyrazolo[3,4-c]pyridine-4-carboxylic acid 3-trifluoromethyl-benzylamide | 431.6 | 1.58 |
| 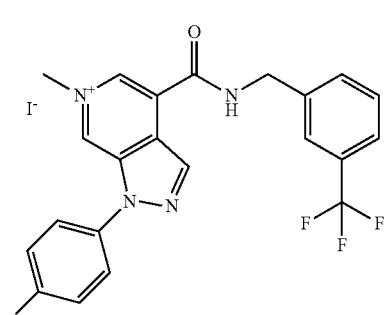 | 1-(4-Fluorophenyl)-6-methyl-4-(3-trifluoromethyl-benzylcarbamoyl)-1H-pyrazolo[3,4-c]pyridin-6-ium; iodide | 429.6 | 1.77 |
| 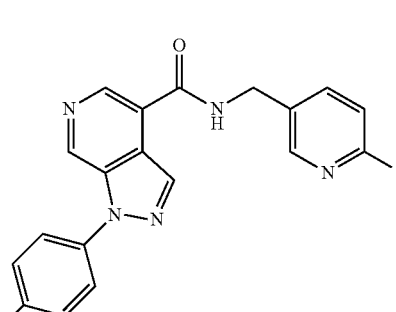 | 1-(4-Fluorophenyl)-1H-pyrazolo[3,4-c]pyridine-4-carboxylic acid (6-bromopyridin-3-ylmethyl)-amide | 428.4 | 1.52 |

TABLE I-continued

| STRUCTURE | Name | HPLC-MS[a,b] | |
|---|---|---|---|
| | | [M + H]+ | RT (min) |
| 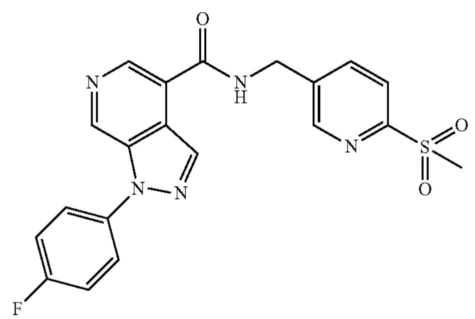 | 1-(4-Fluorophenyl)-1H-pyrazolo[3,4-c]pyridine-4-carboxylic acid (6-methane-sulfonyl-pyridin-3-ylmethyl)-amide | 426.6 | 1.34 |
| 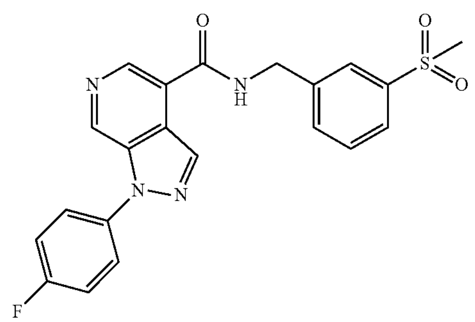 | 1-(4-Fluorophenyl)-1H-pyrazolo[3,4-c]pyridine-4-carboxylic acid 3-methane-sulfonyl-benzylamide | 425.4 | 1.39 |
| 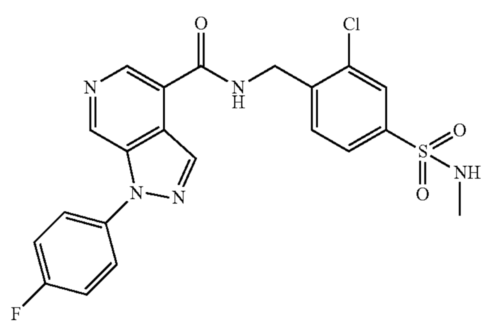 | 1-(4-Fluorophenyl)-1H-pyrazolo[3,4-c]pyridine-4-carboxylic acid 2-chloro-4-methylsulfamoyl-benzylamide | 474.5 | 1.54 |
| | 1-(4-Fluorophenyl)-1H-pyrazolo[3,4-c]pyridine-4-carboxylic acid 4-methylsulfamoyl-benzylamide | 440.6 | 1.43 |

TABLE I-continued

| STRUCTURE | Name | [M + H]⁺ | RT (min) |
|---|---|---|---|
| 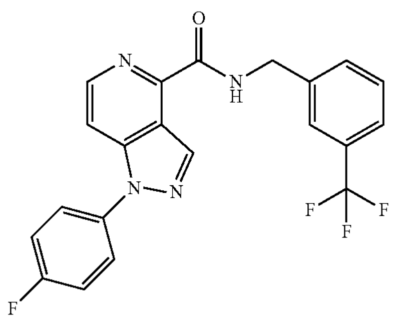 | 1-(4-Fluorophenyl)-1H-pyrazolo[4,3-c]pyridine-4-carboxylic acid 3-trifluoromethyl-benzylamide | 415.5 | 1.08 |
| 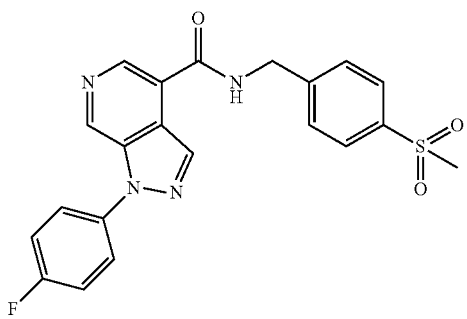 | 1-(4-Fluorophenyl)-1H-pyrazolo[3,4-c]pyridine-4-carboxylic acid 4-methanesulfonyl-benzylamide | 425.6 | 1.42 |
| 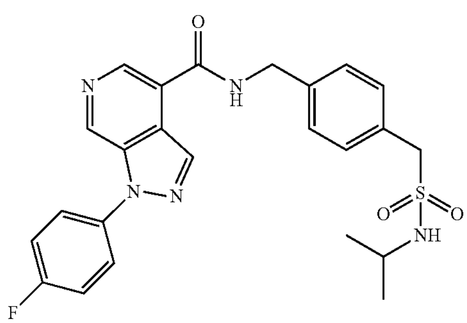 | 1-(4-Fluorophenyl)-1H-pyrazolo[3,4-c]pyridine-4-carboxylic acid 4-(isopropyl-sulfamoylmethyl)-benzylamide | 482.7 | 1.55 |
| 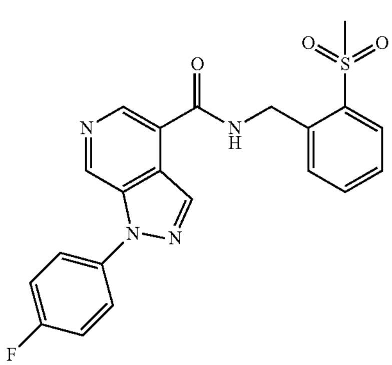 | 1-(4-Fluorophenyl)-1H-pyrazolo[3,4-c]pyridine-4-carboxylic acid 2-methane-sulfonyl-benzylamide | 425.7 | 1.49 |

TABLE I-continued

| STRUCTURE | Name | HPLC-MS[a,b] | |
|---|---|---|---|
| | | [M + H]+ | RT (min) |
| 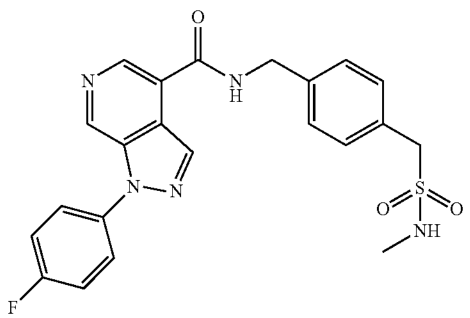 | 1-(4-Fluorophenyl)-1H-pyrazolo[3,4-c]pyridine-4-carboxylic acid 4-methyl-sulfamoylmethyl-benzylamide | 454.7 | 1.42 |
| 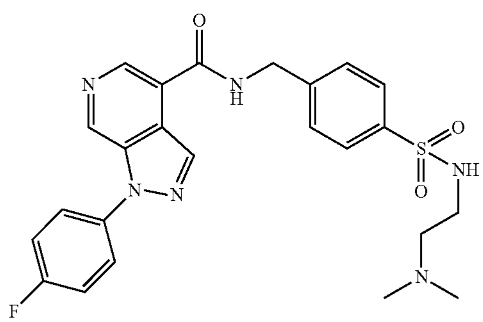 | 1-(4-Fluorophenyl)-1H-pyrazolo[3,4-c]pyridine-4-carboxylic acid 4-(2-dimethyl-aminoethylsulfa-moyl)-benzylamide | 497.7 | 2.29 |
| 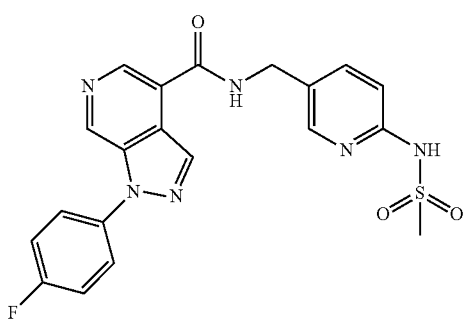 | 1-(4-Fluorophenyl)-1H-pyrazolo[3,4-c]pyridine-4-carboxylic acid (6-methane-sulfonylamino-pyridin-3-ylmethyl)-amide | 441.6 | 1.25 |
| 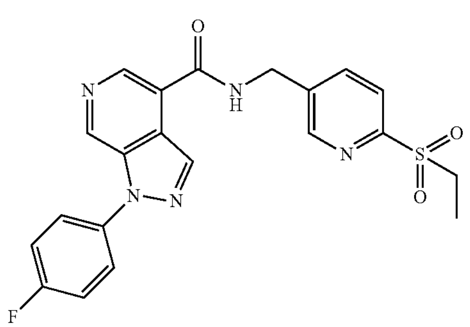 | 1-(4-Fluorophenyl)-1H-pyrazolo[3,4-c]pyridine-4-carboxylic acid (6-ethane-sulfonyl-pyridin-3-ylmethyl)-amide | 440.7 | 1.37 |

TABLE I-continued

| STRUCTURE | Name | [M + H]⁺ | RT (min) |
|---|---|---|---|
| 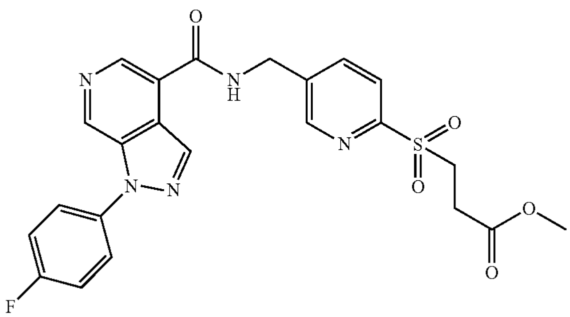 | 3-[5-({[1-(4-Fluorophenyl)-1H-pyrazolo[3,4-c]pyridine-4-carbonyl]-amino}-methyl)-pyridine-2-sulfonyl]-propionic acid methyl ester | 498.7 | 1.42 |
| 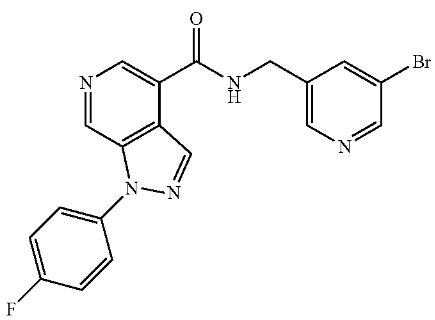 | 1-(4-Fluorophenyl)-1H-pyrazolo[3,4-c]pyridine-4-carboxylic acid (5-bromopyridin-3-ylmethyl)-amide | 426.6/428.6 | 1.49 |
| 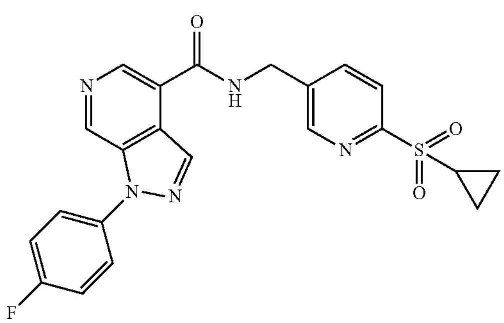 | 1-(4-Fluorophenyl)-1H-pyrazolo[3,4-c]pyridine-4-carboxylic acid (6-cyclopropane-sulfonyl-pyridin-3-ylmethyl)-amide | 452.6 | 1.40 |
| 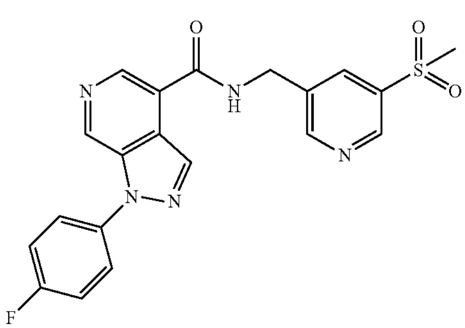 | 1-(4-Fluorophenyl)-1H-pyrazolo[3,4-c]pyridine-4-carboxylic acid (5-methane-sulfonyl-pyridin-3-ylmethyl)-amide | 426.7 | 1.28 |

TABLE I-continued

| STRUCTURE | Name | HPLC-MS[a,b] | |
|---|---|---|---|
| | | [M + H]+ | RT (min) |
| 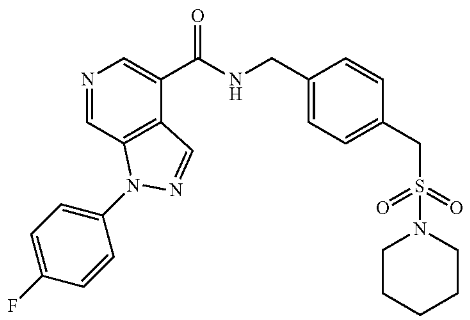 | 1-(4-Fluorophenyl)-1H-pyrazolo[3,4-c]pyridine-4-carboxylic acid 4-(piperidine-1-sulfonylmethyl)-benzylamide | 508.8 | 1.64 |
| 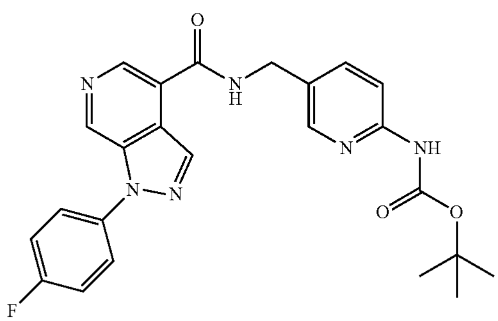 | [5-({[1-(4-Fluorophenyl)-1H-pyrazolo[3,4-c]pyridine-4-carbonyl]-amino}-methyl)-pyridin-2-yl]-carbamic acid tert-butyl ester | 463.7 | 1.52 |
| 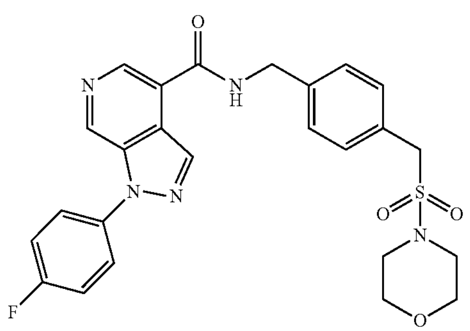 | 1-(4-Fluorophenyl)-1H-pyrazolo[3,4-c]pyridine-4-carboxylic acid 4-(morpholine-4-sulfonylmethyl)-benzylamide | 510.8 | 1.46 |
| 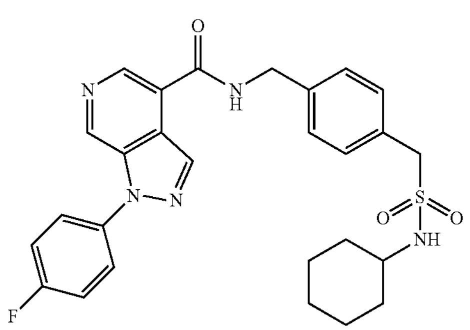 | 1-(4-Fluorophenyl)-1H-pyrazolo[3,4-c]pyridine-4-carboxylic acid 4-cyclohexyl-sulfamoylmethyl-benzylamide | 522.8 | 1.66 |

TABLE I-continued

| STRUCTURE | Name | HPLC-MS[a,b] | |
|---|---|---|---|
| | | [M + H]+ | RT (min) |
| 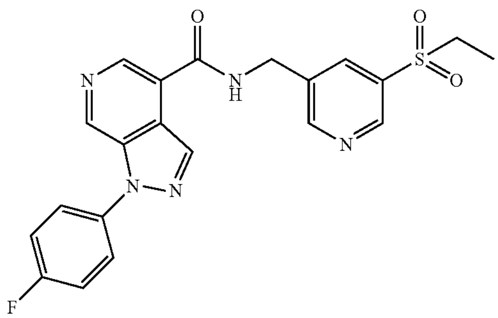 | 1-(4-Fluorophenyl)-1H-pyrazolo[3,4-c]pyridine-4-carboxylic acid (5-ethane-sulfonyl-pyridin-3-ylmethyl)-amide | 440.7 | 1.33 |
| 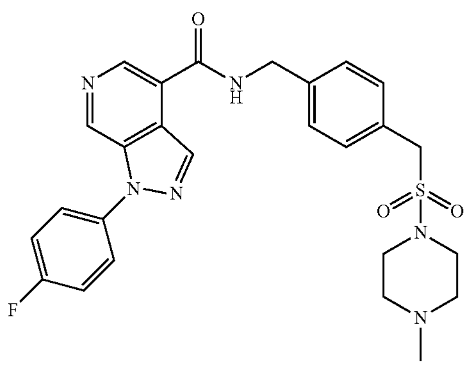 | 1-(4-Fluorophenyl)-1H-pyrazolo[3,4-c]pyridine-4-carboxylic acid 4-(4-methyl-piperazine-1-sulfon-ylmethyl)-benzyl-amide | 522.1 | 1.22 |
| 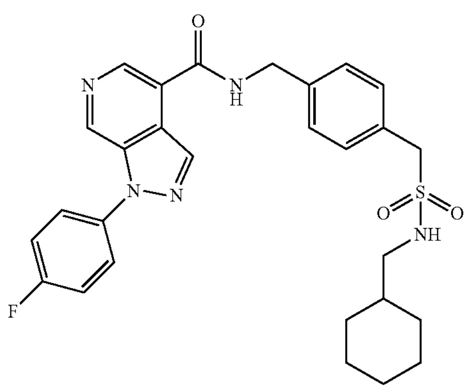 | 1-(4-Fluorophenyl)-1H-pyrazolo[3,4-c]pyridine-4-carboxylic acid 4-[(cyclohexyl-methyl-sulfamoyl)-methyl]-benzyl-amide | 536.9 | 1.75 |
| 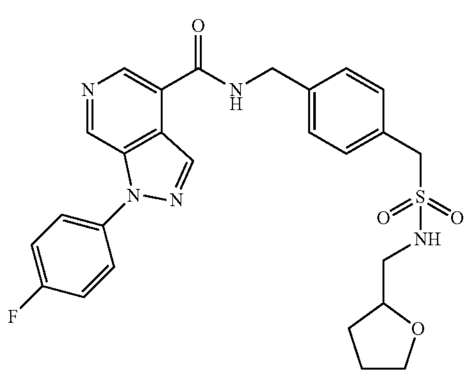 | 1-(4-Fluorophenyl)-1H-pyrazolo[3,4-c]pyridine-4-carboxylic acid 4-{[(tetrahydro-furan-2-ylmethyl)-sulfamoyl]-methyl}-benzylamide | 524.8 | 1.46 |

TABLE I-continued

| STRUCTURE | Name | HPLC-MS[a,b] | |
|---|---|---|---|
| | | [M + H]+ | RT (min) |
| 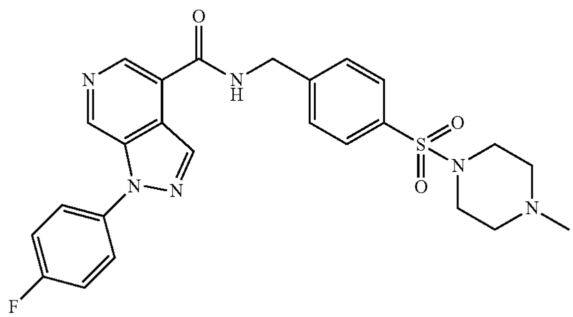 | 1-(4-Fluorophenyl)-1H-pyrazolo[3,4-c]pyridine-4-carboxylic acid 4-(4-methyl-piperazine-1-sulfonyl)-benzyl-amide | 509.7 | 1.35 |
| 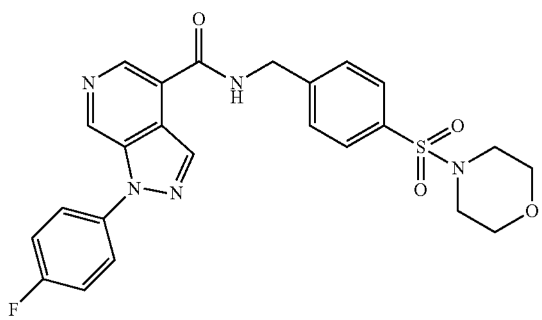 | 1-(4-Fluorophenyl)-1H-pyrazolo[3,4-c]pyridine-4-carboxylic acid 4-(morpholine-4-sulfonyl)-benzyl-amide | 496.3 | 1.51 |
| 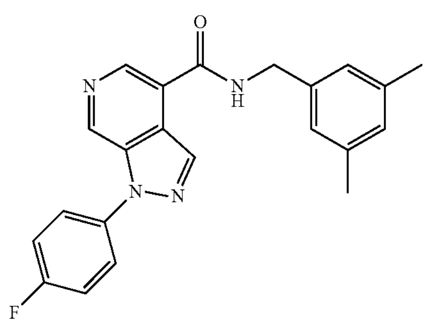 | 1-(4-Fluorophenyl)-1H-pyrazolo[3,4-c]pyridine-4-carboxylic acid 3,5-dimethyl-benzylamide | 375.8 | 1.74 |
| 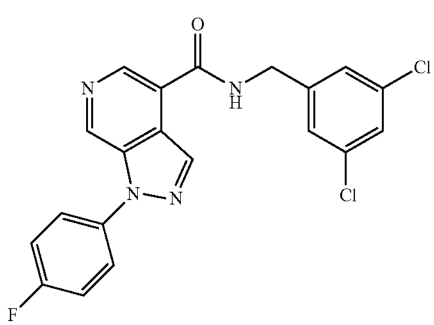 | 1-(4-Fluorophenyl)-1H-pyrazolo[3,4-c]pyridine-4-carboxylic acid 3,5-dichloro-benzylamide | 415.7 | 1.82 |

TABLE I-continued

| STRUCTURE | Name | HPLC-MS[a,b] | |
|---|---|---|---|
| | | [M + H]+ | RT (min) |
| 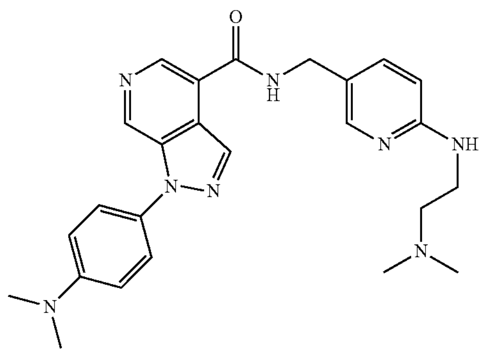 | 1-(4-Dimethylamino-phenyl)-1H-pyrazolo[3,4-c]pyridine-4-carboxylic acid [6-(2-dimethylamino-ethyl-amino)-pyridin-3-yl-methyl]-amide | 459.6 | 5.15 |
| 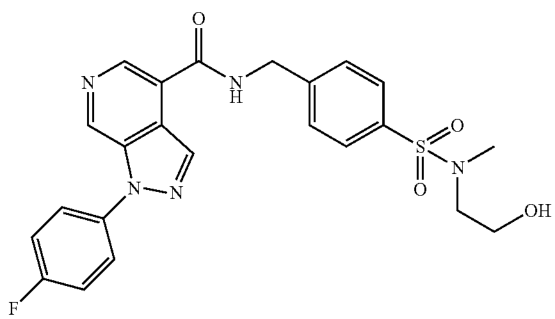 | 1-(4-Fluorophenyl)-1H-pyrazolo[3,4-c]pyridine-4-carboxylic acid 4-[(2-hydroxy-ethyl)-methyl-sulfamoyl]-benzylamide | 484.7 | 1.33 |
| 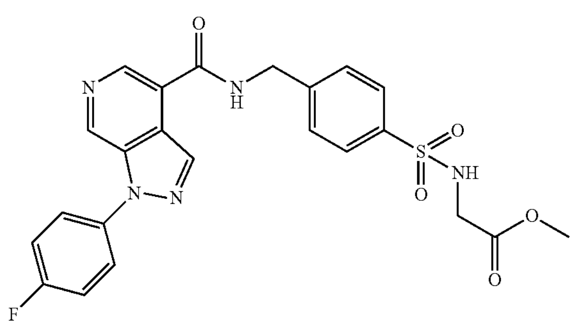 | [4-({[1-(4-Fluorophenyl)-1H-pyrazolo[3,4-c]pyridine-4-carbonyl]-amino}-methyl)-benzenesulfonyl-amino]-acetic acid methyl ester | 498.7 | 1.39 |
| 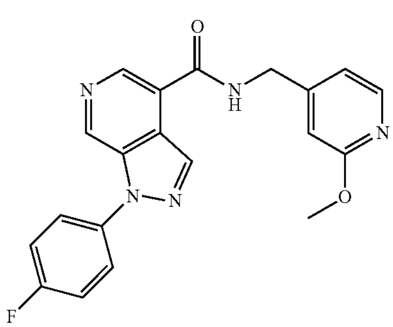 | 1-(4-Fluorophenyl)-1H-pyrazolo[3,4-c]pyridine-4-carboxylic acid (2-methoxy-pyridin-4-ylmethyl)-amide | 378.7 | 1.38 |

TABLE I-continued

| STRUCTURE | Name | HPLC-MS[a,b] | |
|---|---|---|---|
| | | [M + H]+ | RT (min) |
| 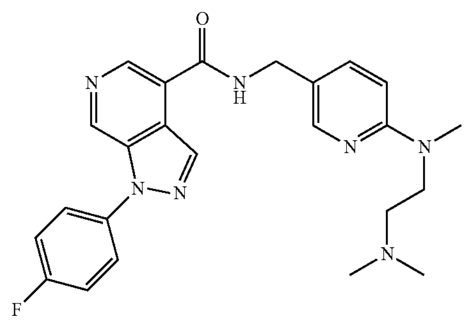 | 1-(4-Fluorophenyl)-1H-pyrazolo[3,4-c]pyridine-4-carboxylic acid {6-[(2-dimethyl-amino-ethyl)-methyl-amino]-pyridin-3-ylmethyl}-amide | 448.8 | 1.06 |
| 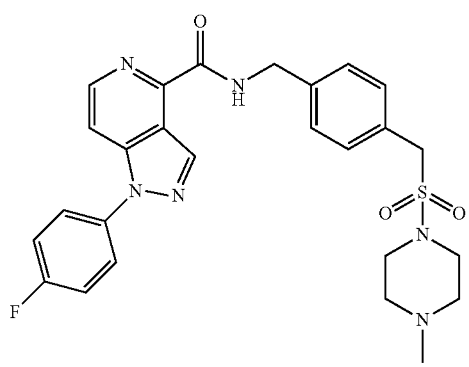 | 1-(4-Fluorophenyl)-1H-pyrazolo[4,3-c]pyridine-4-carboxylic acid 4-(4-methyl-piperazine-1-sulfonyl-methyl)-benzylamide | 523.8 | 1.40 |
| 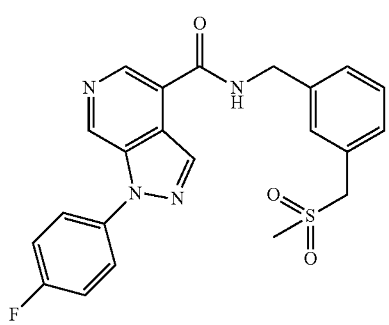 | 1-(4-Fluorophenyl)-1H-pyrazolo[3,4-c]pyridine-4-carboxylic acid 3-methane-sulfonylmethyl-benzylamide | 439.6 | 1.38 |
| 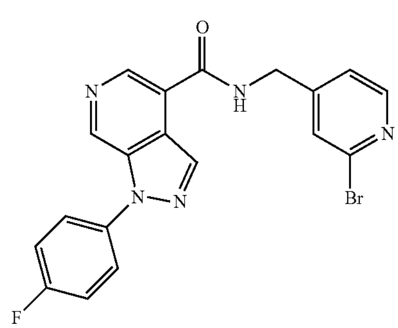 | 1-(4-Fluorophenyl)-1H-pyrazolo[3,4-c]pyridine-4-carboxylic acid (2-bromopyridin-4-ylmethyl)-amide | 426.7/428.6 | 1.46 |

TABLE I-continued

| STRUCTURE | Name | HPLC-MS[a,b] | |
|---|---|---|---|
| | | [M + H]+ | RT (min) |
| 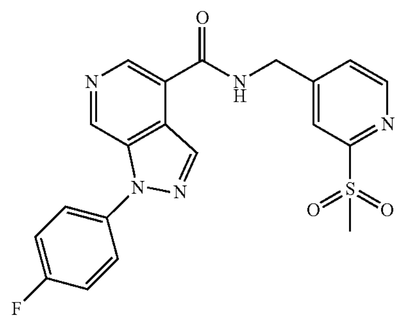 | 1-(4-Fluorophenyl)-1H-pyrazolo[3,4-c]pyridine-4-carboxylic acid (2-methane-sulfonyl-pyridin-4-ylmethyl)-amide | 426.7 | 1.30 |
| 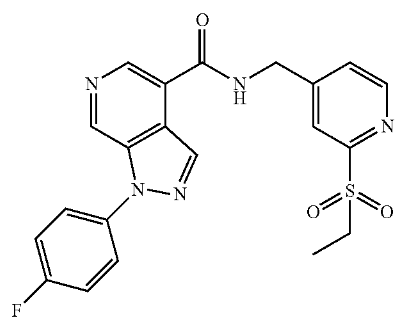 | 1-(4-Fluorophenyl)-1H-pyrazolo[3,4-c]pyridine-4-carboxylic acid (2-ethane-sulfonyl-pyridin-4-ylmethyl)-amide | 440.7 | 1.35 |
| 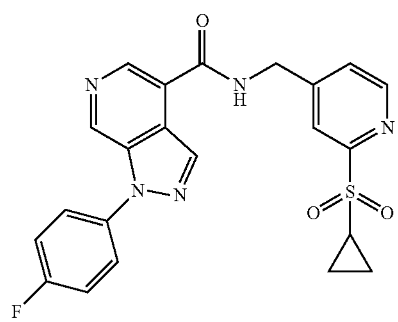 | 1-(4-Fluorophenyl)-1H-pyrazolo[3,4-c]pyridine-4-carboxylic acid (2-cyclopropane-sulfonyl-pyridin-4-ylmethyl)-amide | 452.7 | 1.37 |
| 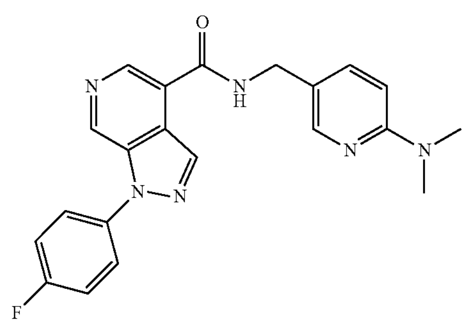 | 1-(4-Fluorophenyl)-1H-pyrazolo[3,4-c]pyridine-4-carboxylic acid (6-dimethyl-amino-pyridin-3-ylmethyl)-amide | 391.7 | 1.17 |

TABLE I-continued

| STRUCTURE | Name | HPLC-MS[a,b] | |
|---|---|---|---|
| | | [M + H]+ | RT (min) |
| 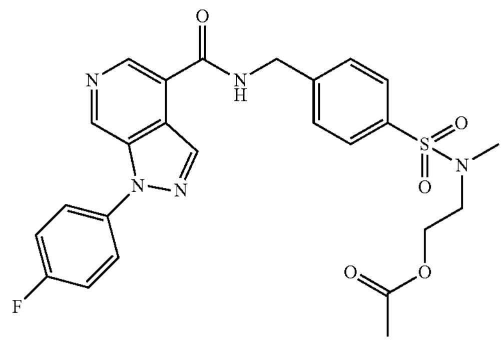 | Acetic acid 2-{[4-({[1-(4-fluorophenyl)-1H-pyrazolo[3,4-c]pyridine-4-carbonyl]-amino}-methyl)-benzenesulfonyl]-methyl-amino}-ethyl ester | 526.7 | 1.47 |
| 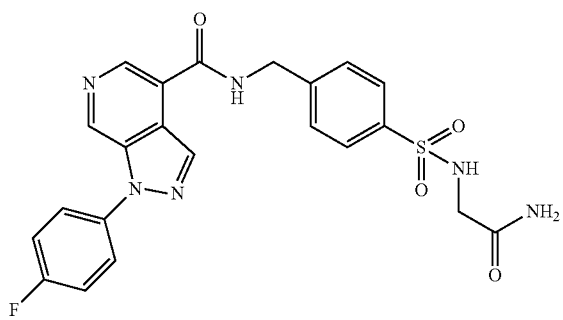 | 1-(4-Fluorophenyl)-1H-pyrazolo[3,4-c]pyridine-4-carboxylic acid 4-(carbamoyl-methyl-sulfamoyl)-benzylamide | 483.7 | 1.24 |
| 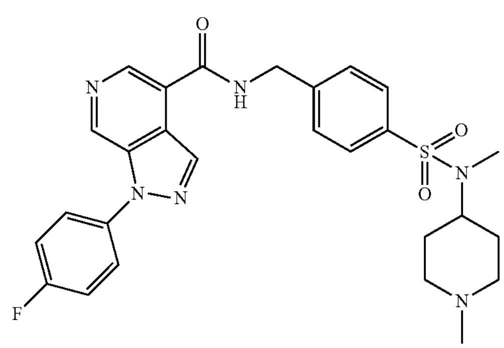 | 1-(4-Fluorophenyl)-1H-pyrazolo[3,4-c]pyridine-4-carboxylic acid 4-[methyl-(1-methyl-piperidin-4-yl)-sulfamoyl]-benzylamide | 537.7 | 1.25 |
| 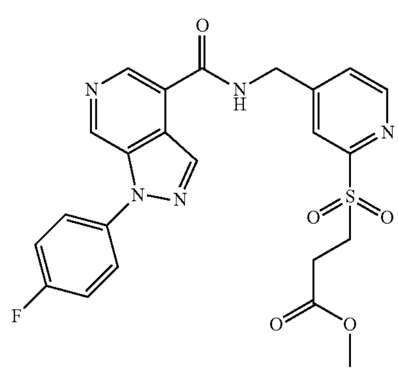 | 3-[4-({[1-(4-Fluorophenyl)-1H-pyrazolo[3,4-c]pyridine-4-carbonyl]-amino}-methyl)-pyridine-2-sulfonyl]-propionic acid methyl ester | 498.7 | 1.38 |

TABLE I-continued

| STRUCTURE | Name | HPLC-MS[a,b] | |
|---|---|---|---|
| | | [M + H]+ | RT (min) |
| 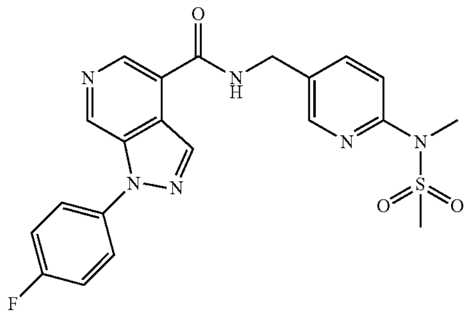 | 1-(4-Fluorophenyl)-1H-pyrazolo[3,4-c]pyridine-4-carboxylic acid [6-(methane-sulfonyl-methyl-amino)-pyridin-3-ylmethyl]-amide | 455.7 | 1.38 |
| 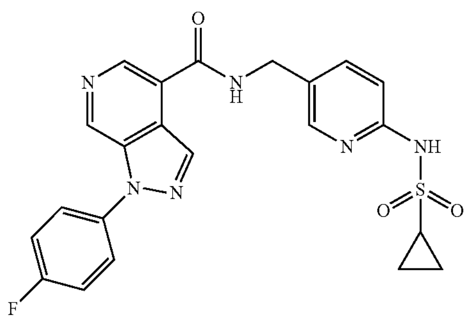 | 1-(4-Fluorophenyl)-1H-pyrazolo[3,4-c]pyridine-4-carboxylic acid (6-cyclopropane-sulfonylamino-pyridin-3-ylmethyl)-amide | 467.7 | 1.27 |
| 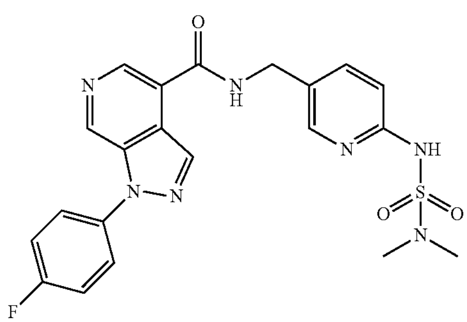 | 1-(4-Fluorophenyl)-1H-pyrazolo[3,4-c]pyridine-4-carboxylic acid [6-(dimethyl-amino-sulfonyl-amino)-pyridin-3-ylmethyl]-amide | 470.5 | 1.30 |
| 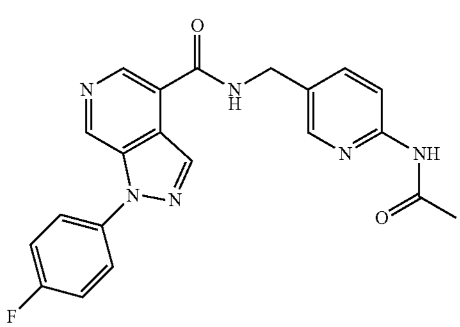 | 1-(4-Fluorophenyl)-1H-pyrazolo[3,4-c]pyridine-4-carboxylic acid (6-acetylamino-pyridin-3-ylmethyl)-amide | 405.7 | 1.21 |

TABLE I-continued

| STRUCTURE | Name | HPLC-MS[a,b] | |
|---|---|---|---|
| | | [M + H]+ | RT (min) |
| 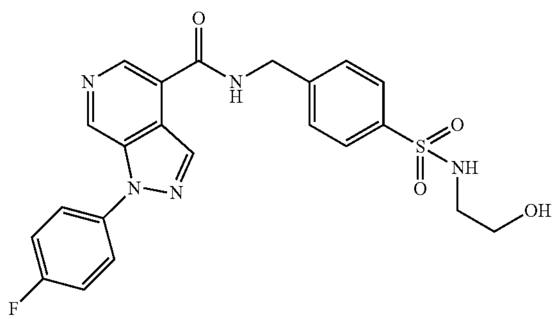 | 1-(4-Fluorophenyl)-1H-pyrazolo[3,4-c]pyridine-4-carboxylic acid 4-(2-hydroxy-ethylsulfamoyl)-benzylamide | 470.7 | 1.28 |
| 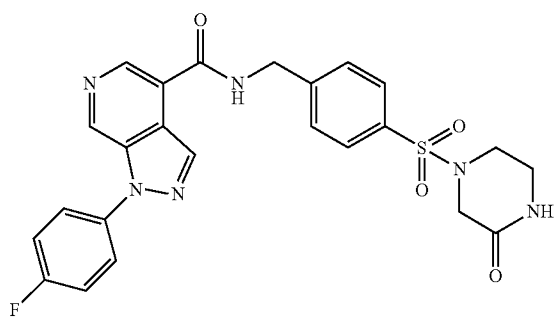 | 1-(4-Fluorophenyl)-1H-pyrazolo[3,4-c]pyridine-4-carboxylic acid 4-(3-oxo-piperazine-1-sulfonyl)-benzylamide | 509.7 | 1.31 |
| 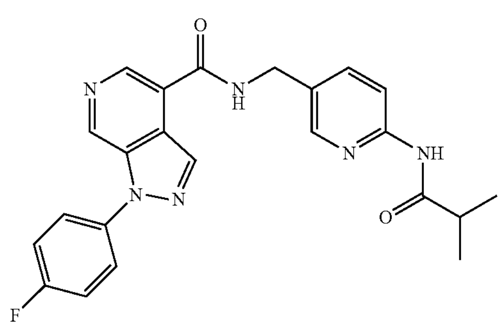 | 1-(4-Fluorophenyl)-1H-pyrazolo[3,4-c]pyridine-4-carboxylic acid (6-isobutyryl-amino-pyridin-3-ylmethyl)-amide | 433.7 | 1.34 |
| 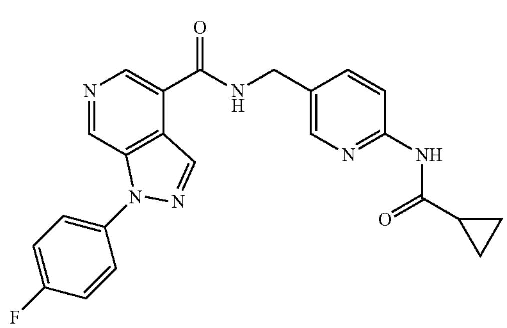 | 1-(4-Fluorophenyl)-1H-pyrazolo[3,4-c]pyridine-4-carboxylic acid [6-cyclopropane-carbonyl-amino)-pyridin-3-ylmethyl]-amide | 431.7 | 1.31 |

TABLE I-continued

| STRUCTURE | Name | HPLC-MS[a,b] | |
|---|---|---|---|
| | | [M + H]+ | RT (min) |
| 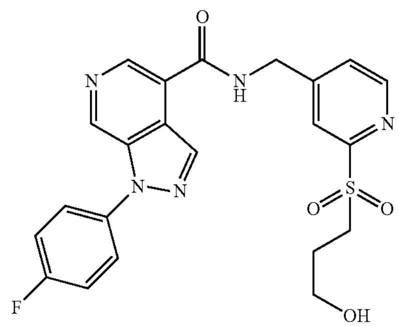 | 1-(4-Fluorophenyl)-1H-pyrazolo[3,4-c]pyridine-4-carboxylic acid [2-(3-hydroxy-propane-1-sulfonyl)-pyridin-4-ylmethyl]-amide | 470.6 | 1.22 |
| 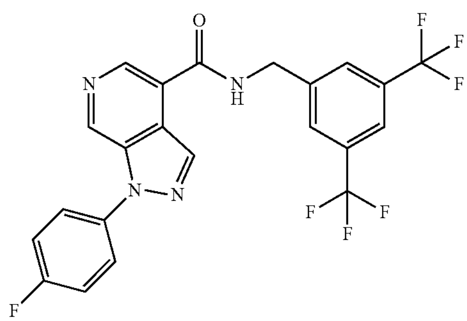 | 1-(4-Fluorophenyl)-1H-pyrazolo[3,4-c]pyridine-4-carboxylic acid 3,5-bistrifluoro-methyl-benzylamide | 483.7 | 1.86 |
| 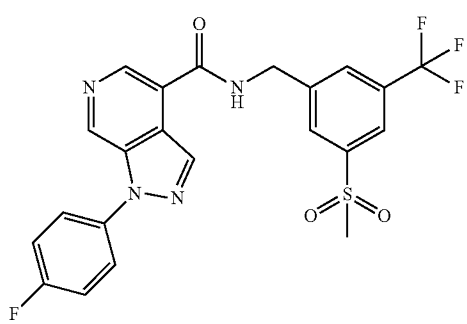 | 1-(4-Fluorophenyl)-1H-pyrazolo[3,4-c]pyridine-4-carboxylic acid 3-methane-sulfonyl-5-trifluoro-methyl-benzylamide | 493.5 | 1.77 |
| | 1-(4-Fluorophenyl)-1H-pyrazolo[3,4-c]pyridine-4-carboxylic acid {6-[(2-dimethyl-amino-ethyl)-methanesulfonyl-amino]-pyridin-3-ylmethyl}-amide | 512.7 | 1.19 |

TABLE I-continued

| STRUCTURE | Name | HPLC-MS[a,b] | |
|---|---|---|---|
| | | [M + H]+ | RT (min) |
| 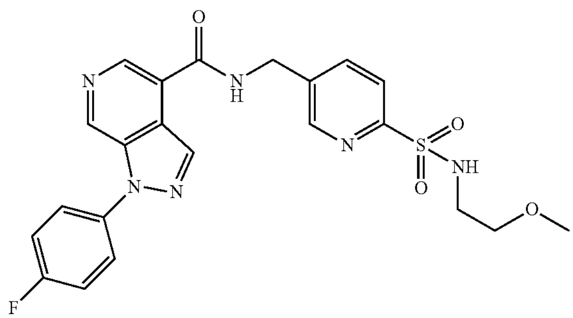 | 1-(4-Fluorophenyl)-1H-pyrazolo[3,4-c]pyridine-4-carboxylic acid [6-(2-methoxy-ethylsulfamoyl)-pyridin-3-ylmethyl]-amide | 485.5 | 1.34 |
| 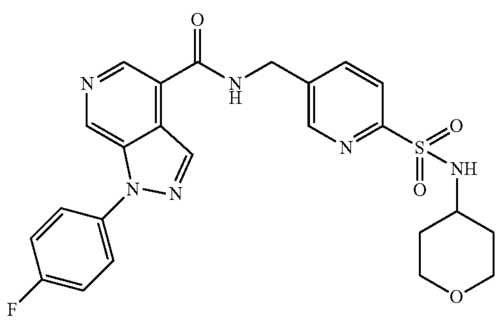 | 1-(4-Fluorophenyl)-1H-pyrazolo[3,4-c]pyridine-4-carboxylic acid [6-(tetrahydro-pyran-4-ylsulfamoyl)-pyridin-3-ylmethyl]-amide | 511.6 | 1.34 |
| 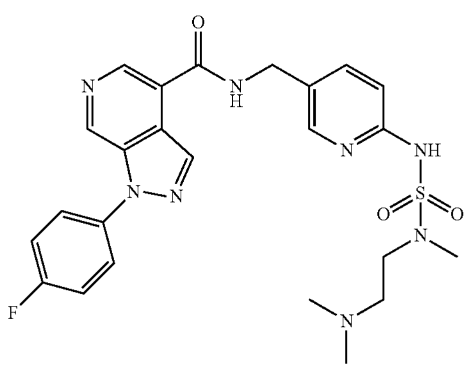 | 1-(4-Fluorophenyl)-1H-pyrazolo[3,4-c]pyridine-4-carboxylic acid [6-(2-dimethyl-aminoethyl-1-methyl-amino-sulfonylamino)-pyridin-3-ylmethyl]-amide | 527.7 | 1.08 |
| 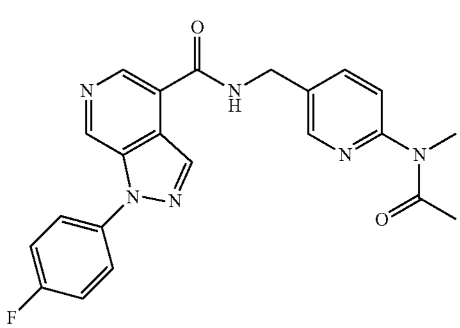 | 1-(4-Fluorophenyl)-1H-pyrazolo[3,4-c]pyridine-4-carboxylic acid [6-(acetyl-methyl-amino)-pyridin-3-ylmethyl]-amide | 419.7 | 1.23 |

TABLE I-continued

| STRUCTURE | Name | HPLC-MS[a,b] | |
|---|---|---|---|
| | | [M + H]+ | RT (min) |
| 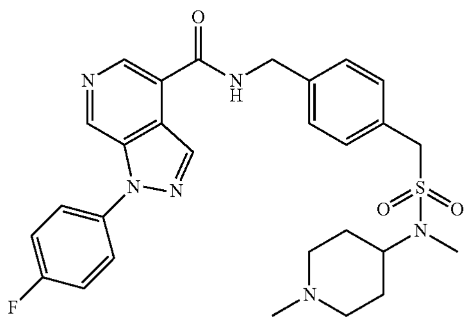 | 1-(4-Fluorophenyl)-1H-pyrazolo[3,4-c]pyridine-4-carboxylic acid 4-{[methyl-(1-methyl-piperidin-4-yl)-sulfamoyl]-methyl}-benzylamide | 551.8 | 1.20 |
| 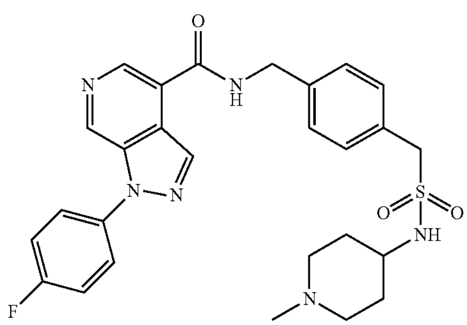 | 1-(4-Fluorophenyl)-1H-pyrazolo[3,4-c]pyridine-4-carboxylic acid 4-[(1-methyl-piperidin-4-ylsulfamoyl)-methyl]-benzylamide | 537.8 | 1.17 |
| | 1-(4-Fluorophenyl)-1H-pyrazolo[3,4-c]pyridine-4-carboxylic acid (6-dimethylsulfamoyl-pyridin-3-ylmethyl)-amide | 455.6 | 1.42 |
| | 1-(4-Fluorophenyl)-1H-pyrazolo[3,4-c]pyridine-4-carboxylic acid {6-[methanesulfonyl-(2-methoxy-ethyl)-amino]-pyridin-3-ylmethyl}-amide | 499.6 | 1.40 |

TABLE I-continued

| STRUCTURE | Name | [M + H]⁺ | RT (min) |
|---|---|---|---|
| 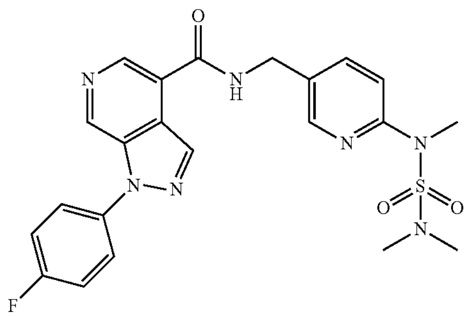 | 1-(4-Fluorophenyl)-1H-pyrazolo[3,4-c]pyridine-4-carboxylic acid [6-(dimethyl-amino-sulfonylmethyl-amino)pyridin-3-yl-methyl]-amide | 484.6 | 1.44 |
| 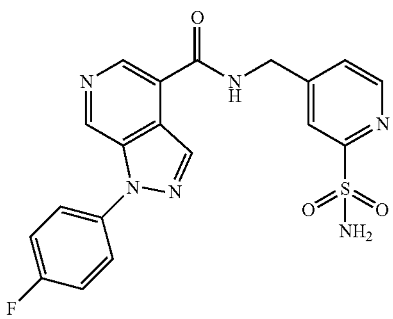 | 1-(4-Fluorophenyl)-1H-pyrazolo[3,4-c]pyridine-4-carboxylic acid (2-sulfamoyl-pyridin-4-ylmethyl)-amide | 427.7 | 1.38 |
| 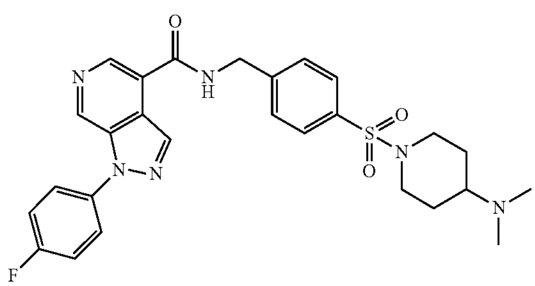 | 1-(4-Fluorophenyl)-1H-pyrazolo[3,4-c]pyridine-4-carboxylic acid 4-(4-dimethyl-amino-piperidine-1-sulfonyl)-benzylamide | 537.7 | 1.16 |
| 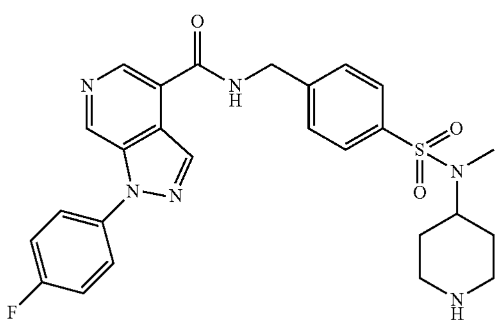 | 1-(4-Fluorophenyl)-1H-pyrazolo[3,4-c]pyridine-4-carboxylic acid 4-(methyl-piperidin-4-yl-sulfamoyl)-benzylamide | 523.7 | 1.29 |
| 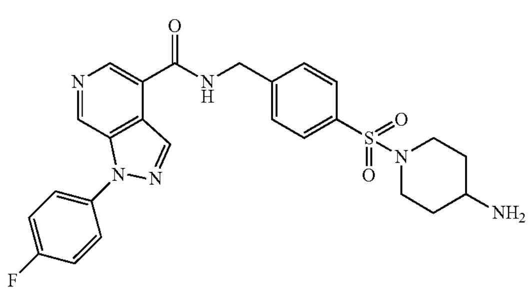 | 1-(4-Fluorophenyl)-1H-pyrazolo[3,4-c]pyridine-4-carboxylic acid 4-(4-amino-piperidine-1-sulfonyl)-benzylamide | 509.7 | 1.15 |

TABLE I-continued

| STRUCTURE | Name | [M + H]⁺ | RT (min) |
|---|---|---|---|
| 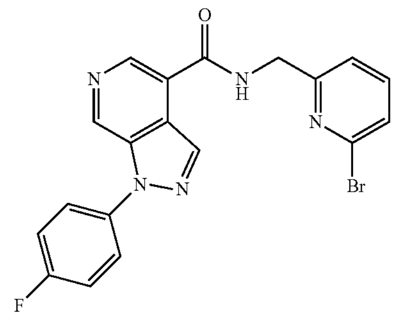 | 1-(4-Fluorophenyl)-1H-pyrazolo[3,4-c]pyridine-4-carboxylic acid (6-bromo-pyridin-2-ylmethyl)-amide | 426.5/428.4 | 1.73 |
| 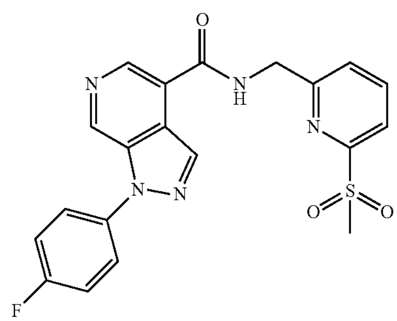 | 1-(4-Fluorophenyl)-1H-pyrazolo[3,4-c]pyridine-4-carboxylic acid (6-methane-sulfonyl-pyridin-2-ylmethyl)-amide | 426.7 | 1.50 |
| 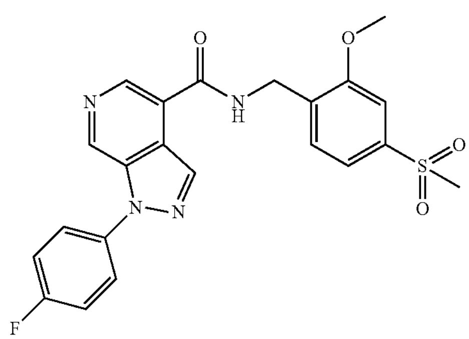 | 1-(4-Fluorophenyl)-1H-pyrazolo[3,4-c]pyridine-4-carboxylic acid 4-methane-sulfonyl-2-methoxy-benzylamide | 454.0 | 1.40 |
| 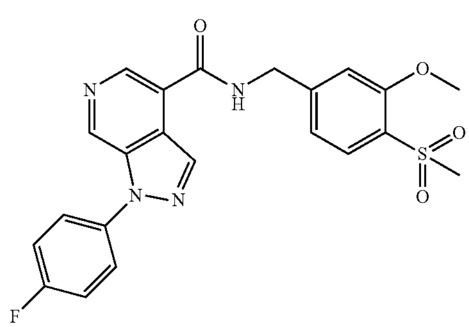 | 1-(4-Fluorophenyl)-1H-pyrazolo[3,4-c]pyridine-4-carboxylic acid 4-methane-sulfonyl-3-methoxy-benzylamide | 455.7 | 1.44 |

TABLE I-continued

| STRUCTURE | Name | HPLC-MS[a,b] | |
| --- | --- | --- | --- |
| | | [M + H]+ | RT (min) |
| 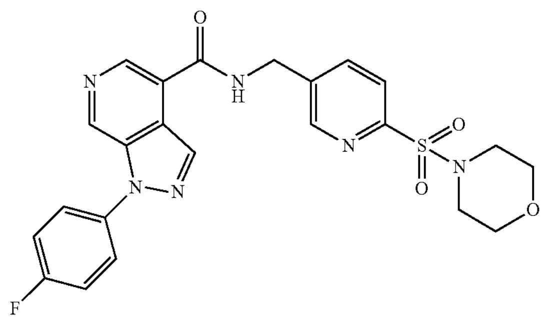 | 1-(4-Fluorophenyl)-1H-pyrazolo[3,4-c]pyridine-4-carboxylic acid [6-(morpholine-4-sulfonyl)-pyridin-3-ylmethyl]-amide | 497.6 | 1.40 |
| 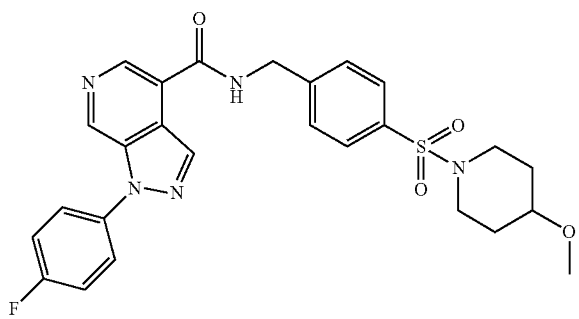 | 1-(4-Fluorophenyl)-1H-pyrazolo[3,4-c]pyridine-4-carboxylic acid 4-(4-methoxy-piperidine-1-sulfonyl)-benzylamide | 524.6 | 1.56 |
| 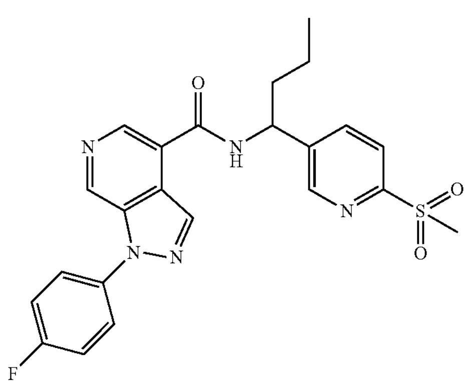 | 1-(4-Fluorophenyl)-1H-pyrazolo[3,4-c]pyridine-4-carboxylic acid [1-(6-methane-sulfonyl-pyridin-3-yl)-butyl]-amide | 468.6 | 1.53 |
| 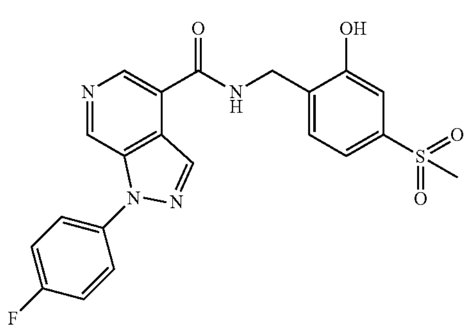 | 1-(4-Fluorophenyl)-1H-pyrazolo[3,4-c]pyridine-4-carboxylic acid 2-hydroxy-4-methanesulfonyl-benzylamide | 441.4 | 1.36 |

TABLE I-continued

| STRUCTURE | Name | HPLC-MS[a,b] | |
| --- | --- | --- | --- |
| | | [M + H]+ | RT (min) |
| 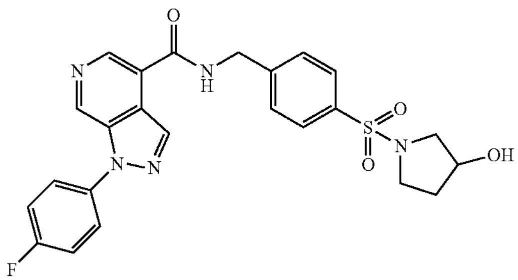 | 1-(4-Fluorophenyl)-1H-pyrazolo[3,4-c]pyridine-4-carboxylic acid 4-(3-hydroxy-pyrrolidine-1-sulfonyl)-benzylamide | 496.7 | 1.43 |
| 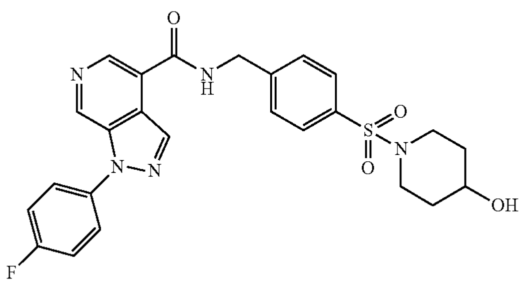 | 1-(4-Fluorophenyl)-1H-pyrazolo[3,4-c]pyridine-4-carboxylic acid 4-(4-hydroxy-piperidine-1-sulfonyl)-benzylamide | 510.8 | 1.45 |
| 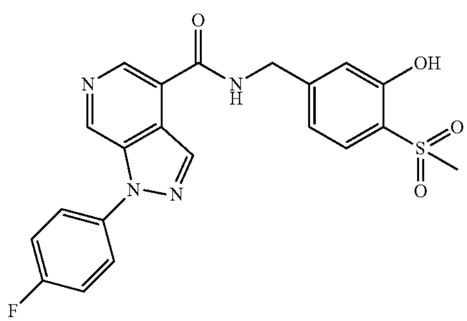 | 1-(4-Fluorophenyl)-1H-pyrazolo[3,4-c]pyridine-4-carboxylic acid 3-hydroxy-4-methanesulfonyl-benzylamide | 441.4 | 1.39 |
| 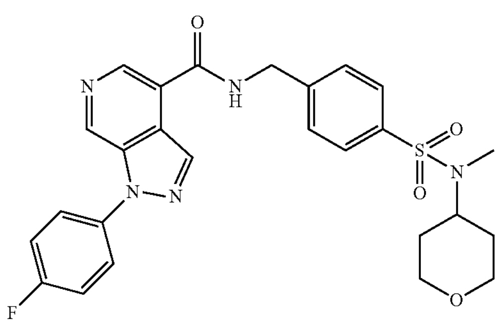 | 1-(4-Fluorophenyl)-1H-pyrazolo[3,4-c]pyridine-4-carboxylic acid 4-[methyl-(tetrahydropyran-4-yl)-sulfamoyl]-benzylamide | 524.9 | 1.60 |
| 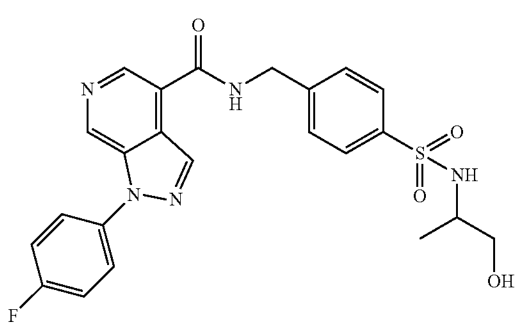 | 1-(4-Fluorophenyl)-1H-pyrazolo[3,4-c]pyridine-4-carboxylic acid 4-(2-hydroxy-1-methyl-ethylsulfamoyl)-benzylamide | 484.8 | 1.42 |

TABLE I-continued

| STRUCTURE | Name | HPLC-MS[a,b] | |
|---|---|---|---|
| | | [M + H]+ | RT (min) |
| | 1-(4-Fluorophenyl)-1H-pyrazolo[3,4-c]pyridine-4-carboxylic acid (5-methanesulfonyl-pyridin-2-ylmethyl)-amide | 426.7 | 1.29 |
| | 1-(4-Fluorophenyl)-1H-pyrazolo[3,4-c]pyridine-4-carboxylic acid 4-methanesulfonylamino-benzylamide | 440.7 | 1.44 |
| 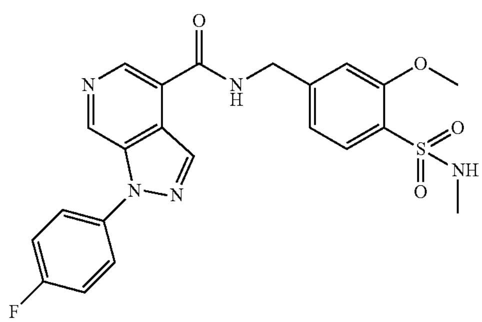 | 1-(4-Fluorophenyl)-1H-pyrazolo[3,4-c]pyridine-4-carboxylic acid 3-methoxy-4-methylsulfamoyl-benzylamide | 470.7 | 1.45 |
| 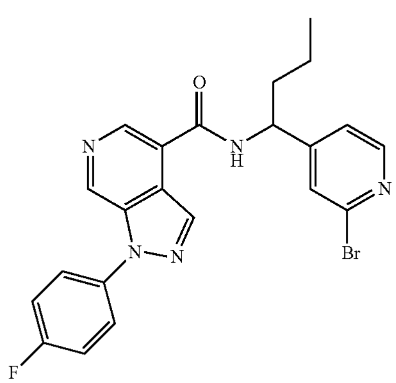 | 1-(4-Fluorophenyl)-1H-pyrazolo[3,4-c]pyridine-4-carboxylic acid [1-(2-bromo-pyridin-4-yl)-butyl]-amide | 468.6/470.6 | 1.77 |

TABLE I-continued

| STRUCTURE | Name | [M + H]⁺ | RT (min) |
|---|---|---|---|
| | 1-(4-Fluorophenyl)-1H-pyrazolo[3,4-c]pyridine-4-carboxylic acid [6-(1,1-dioxo-1λ⁶-perhydro-1,2-thiazin-2-yl)-pyridin-3-ylmethyl]-amide | 481.6 | 1.46 |
| 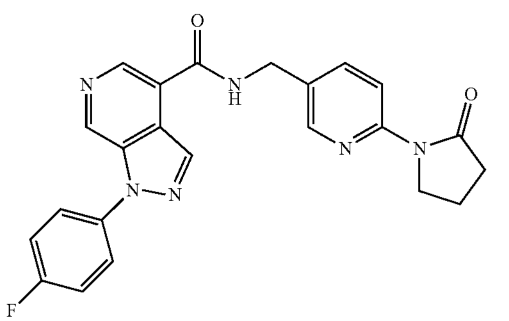 | 1-(4-Fluorophenyl)-1H-pyrazolo[3,4-c]pyridine-4-carboxylic acid [6-(2-oxo-pyrrolidin-1-yl)-pyridin-3-yl-methyl]-amide | 431.6 | 1.36 |
| | 1-(4-Fluorophenyl)-1H-pyrazolo[3,4-c]pyridine-4-carboxylic acid 4-methoxy-3-methylsulfamoyl-benzylamide | 470.6 | 1.42 |
| 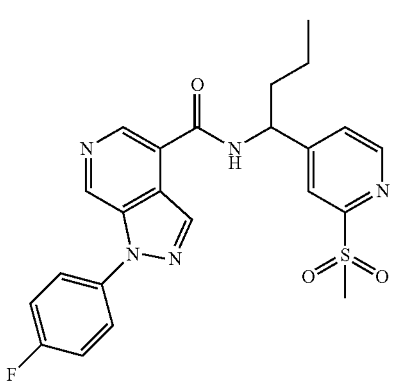 | 1-(4-Fluorophenyl)-1H-pyrazolo[3,4-c]pyridine-4-carboxylic acid [1-(2-methane-sulfonyl-pyridin-4-yl)-butyl]-amide | 468.6 | 1.59 |

TABLE I-continued

| STRUCTURE | Name | HPLC-MS[a,b] | |
|---|---|---|---|
| | | [M + H]+ | RT (min) |
| | 1-(4-Fluorophenyl)-1H-pyrazolo[3,4-c]pyridine-4-carboxylic acid [1-(2-ethanesulfonyl-pyridin-4-yl)-butyl]-amide | 482.6 | 1.58 |
| 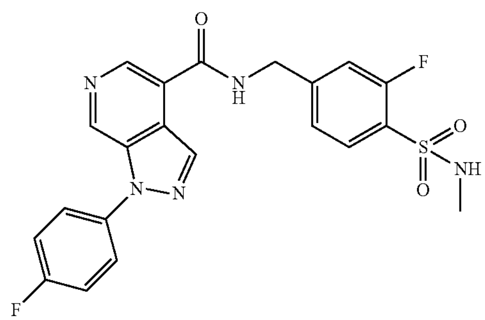 | 1-(4-Fluorophenyl)-1H-pyrazolo[3,4-c]pyridine-4-carboxylic acid 3-fluoro-4-methylsulfamoyl-benzylamide | 458.7 | 1.64 |
| 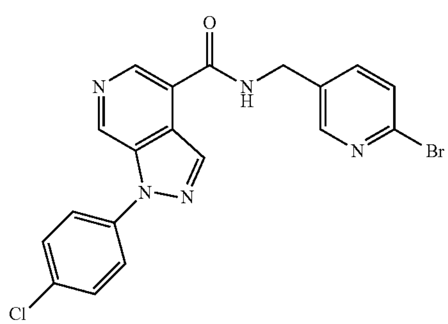 | 1-(4-Chlorophenyl)-1H-pyrazolo[3,4-c]pyridine-4-carboxylic acid (6-bromopyridin-3-ylmethyl)-amide | 444.5 | 1.66 |
| | 1-(4-Chlorophenyl)-1H-pyrazolo[3,4-c]pyridine-4-carboxylic acid (6-methanesulfonyl-pyridin-3-ylmethyl)-amide | 440.0 | 1.19 |

TABLE I-continued

| STRUCTURE | Name | HPLC-MS[a,b] | |
|---|---|---|---|
| | | [M + H]+ | RT (min) |
| 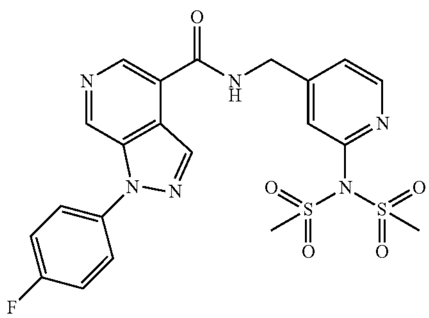 | 1-(4-Fluorophenyl)-1H-pyrazolo[3,4-c]pyridine-4-carboxylic acid [2-(dimethanesulfonyl)-amino-pyridin-4-ylmethyl]-amide | 519.5 | 1.47 |
| 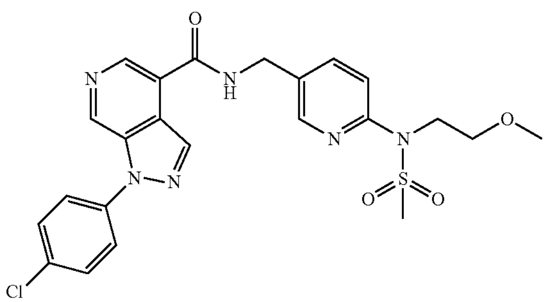 | 1-(4-Chlorophenyl)-1H-pyrazolo[3,4-c]pyridine-4-carboxylic acid {6-[methane-sulfonyl-(2-methoxy-ethyl)-amino]-pyridin-3-ylmethyl}-amide | 515.7 | 1.53 |
| 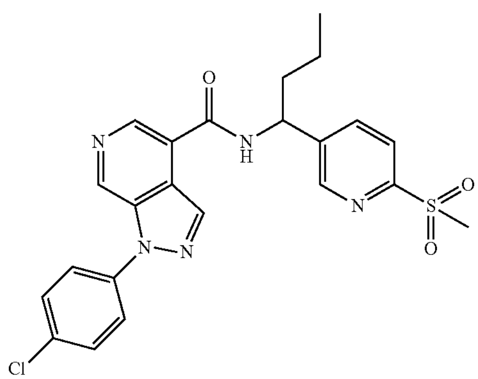 | 1-(4-Chlorophenyl)-1H-pyrazolo[3,4-c]pyridine-4-carboxylic acid [1-(6-methane-sulfonyl-pyridin-3-yl)-butyl]-amide | 484.6 | 1.64 |
| 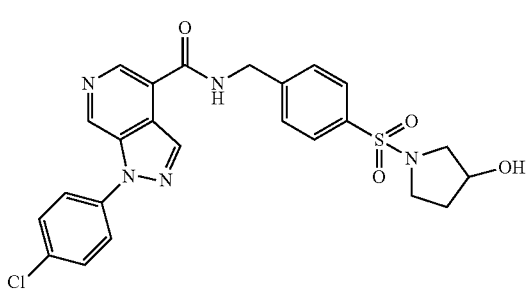 | 1-(4-Chlorophenyl)-1H-pyrazolo[3,4-c]pyridine-4-carboxylic acid 4-(3-hydroxy-pyrrolidine-1-sulfonyl)-benzyl-amide | 512.6 | 1.51 |

TABLE I-continued

| STRUCTURE | Name | HPLC-MS[a,b] | |
|---|---|---|---|
| | | [M + H]+ | RT (min) |
| 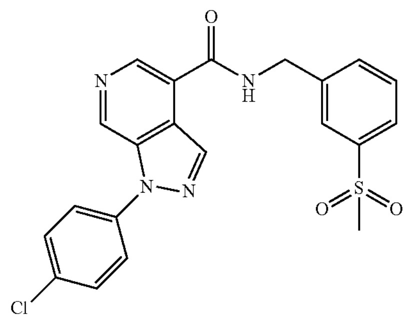 | 1-(4-Chlorophenyl)-1H-pyrazolo[3,4-c]pyridine-4-carboxylic acid 3-methanesulfonyl-benzylamide | 439.0 | 1.24 |
| 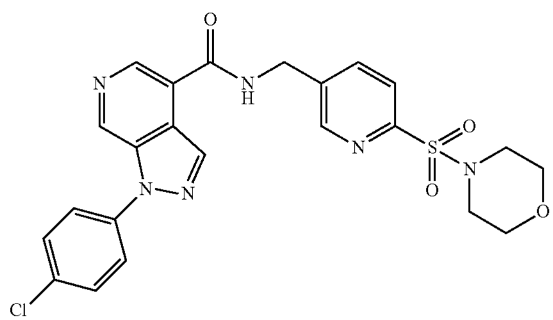 | 1-(4-Chlorophenyl)-1H-pyrazolo[3,4-c]pyridine-4-carboxylic acid [6-(morpholine-4-sulfonyl)-pyridin-3-ylmethyl]-amide | 512.5 | 1.70 |
| 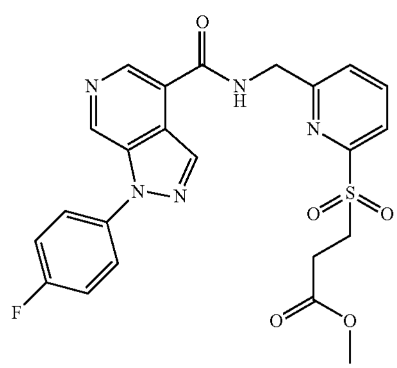 | 3-[6-({[1-(4-Fluorophenyl)-1H-pyrazolo[3,4-c]pyridine-4-carbonyl]-amino}-methyl)-pyridine-2-sulfonyl]-propionicacid methyl ester | 498.6 | 1.42 |
| 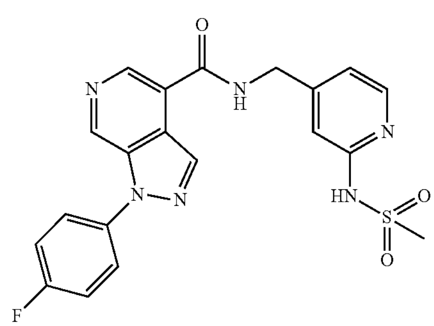 | 1-(4-Fluorophenyl)-1H-pyrazolo[3,4-c]pyridine-4-carboxylic acid (2-methane-sulfonylamino-pyridin-4-yl-methyl)-amide | 441.6 | 1.33 |

TABLE I-continued

| STRUCTURE | Name | HPLC-MS[a,b] | |
|---|---|---|---|
| | | [M + H]+ | RT (min) |
| 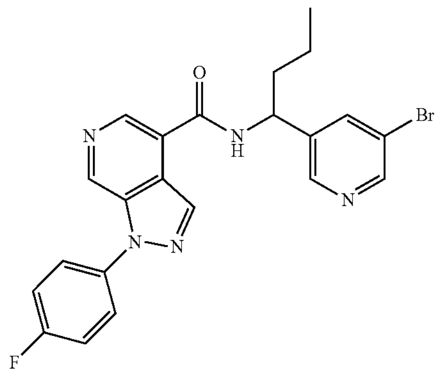 | 1-(4-Fluorophenyl)-1H-pyrazolo[3,4-c]pyridine-4-carboxylic acid [1-(5-bromo-pyridin-3-yl)-butyl]-amide | 470.3 | 1.72 |
| 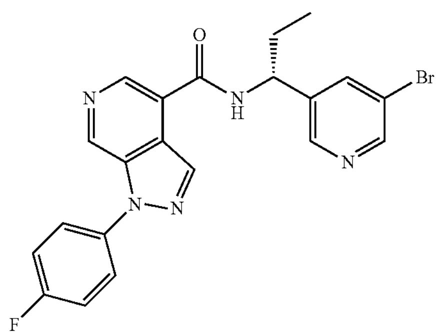 | 1-(4-Fluorophenyl)-1H-pyrazolo[3,4-c]pyridine-4-carboxylic acid [(R)-1-(5-bromo-pyridin-3-yl)-propyl]-amide | 454.6/456.6 | 1.69 |
| 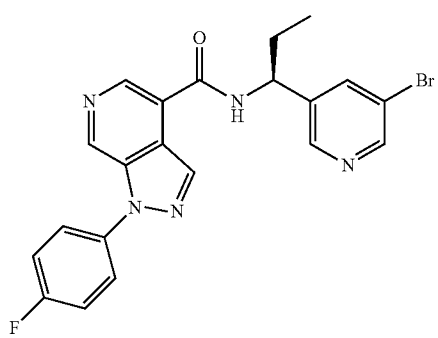 | 1-(4-Fluorophenyl)-1H-pyrazolo[3,4-c]pyridine-4-carboxylic acid [(S)-1-(5-bromo-pyridin-3-yl)-propyl]-amide | 454.6/456.6 | 1.61 |
| 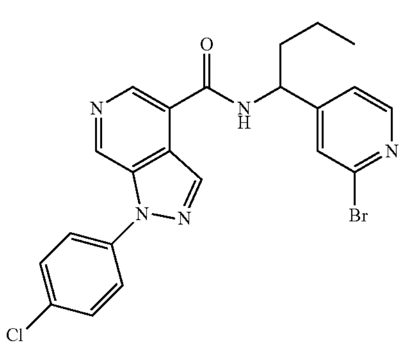 | 1-(4-Chlorophenyl)-1H-pyrazolo[3,4-c]pyridine-4-carboxylic acid [1-(2-bromo-pyridin-4-yl)-butyl]-amide | 484.7 | 1.97 |

TABLE I-continued

| STRUCTURE | Name | [M + H]⁺ | RT (min) |
|---|---|---|---|
| 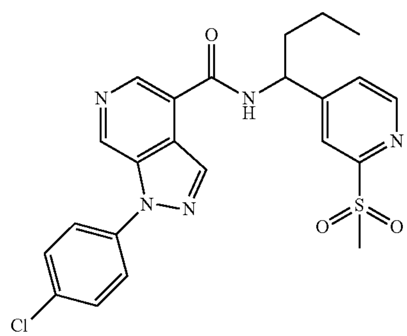 | 1-(4-Chlorophenyl)-1H-pyrazolo[3,4-c]pyridine-4-carboxylic acid [1-(2-methane-sulfonyl-pyridin-4-yl)-butyl]-amide | 484.4 | 1.64 |
| | 1-(4-Fluorophenyl)-1H-pyrazolo[3,4-c]pyridine-4-carboxylic acid (6-methylsulfamoyl-pyridin-2-ylmethyl)-amide | 441.5 | 1.34 |
| 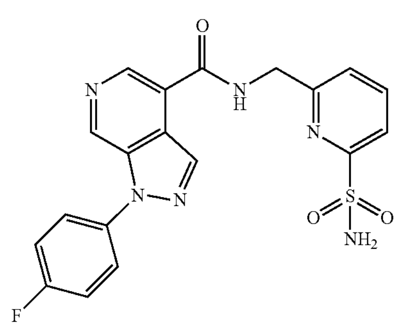 | 1-(4-Fluorophenyl)-1H-pyrazolo[3,4-c]pyridine-4-carboxylic acid (6-sulfamoyl-pyridin-2-ylmethyl)-amide | 427.5 | 1.26 |
| | 1-(4-Fluorophenyl)-1H-pyrazolo[3,4-c]pyridine-4-carboxylic acid 4-((R)-2-hydroxy-1-methyl-ethylsulfamoyl)-benzylamide | 484.6 | 1.49 |

TABLE I-continued

| STRUCTURE | Name | [M + H]⁺ | RT (min) |
|---|---|---|---|
| 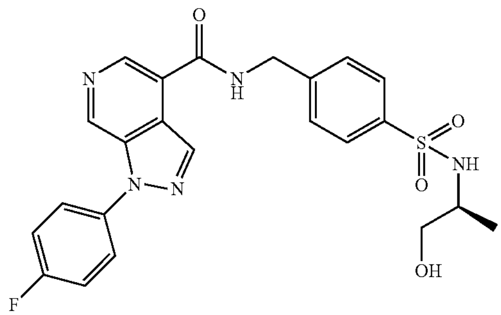 | 1-(4-Fluorophenyl)-1H-pyrazolo[3,4-c]pyridine-4-carboxylic acid 4-((S)-2-hydroxy-1-methyl-ethylsulfamoyl)-benzylamide | 484.6 | 1.49 |
| 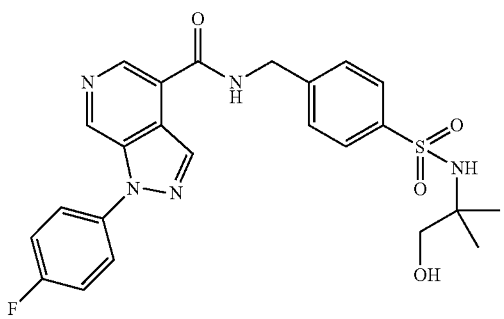 | 1-(4-Fluorophenyl)-1H-pyrazolo[3,4-c]pyridine-4-carboxylic acid 4-(2-hydroxy-1,1-dimethyl-ethylsulfamoyl)-benzylamide | 498.6 | 1.37 |
| | 1-(4-Fluorophenyl)-1H-pyrazolo[3,4-c]pyridine-4-carboxylic acid [1-(5-methane-sulfonyl-pyridin-3-yl)-butyl]-amide | 468.3 | 1.50 |
| | 1-(4-Fluorophenyl)-1H-pyrazolo[3,4-c]pyridine-4-carboxylic acid [1-(6-methane-sulfonyl-pyridin-3-yl)-propyl]-amide | 454.6 | 1.45 |

TABLE I-continued

| STRUCTURE | Name | [M + H]⁺ | RT (min) |
|---|---|---|---|
| 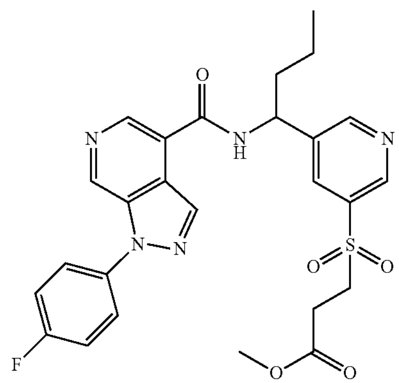 | 3-[5-(1-{[1-(4-Fluorophenyl)-1H-pyrazolo[3,4-c]pyridine-4-carbonyl]-amino}-butyl)-pyridine-3-sulfonyl]-propionic acid methyl ester | 540.3 | 1.57 |
| 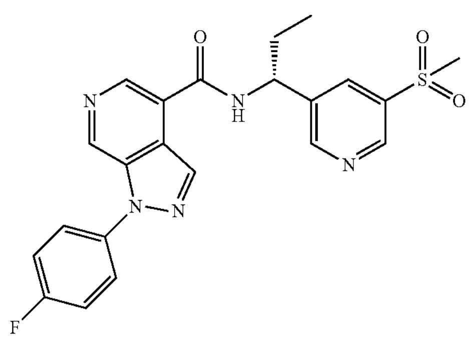 | 1-(4-Fluorophenyl)-1H-pyrazolo[3,4-c]pyridine-4-carboxylic acid [(R)-1-(5-methanesulfonyl-pyridin-3-yl)-propyl]-amide | 454.6 | 1.41 |
| 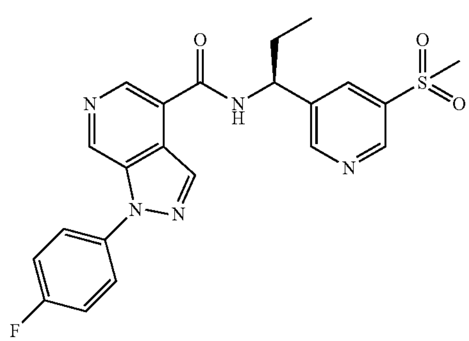 | 1-(4-Fluorophenyl)-1H-pyrazolo[3,4-c]pyridine-4-carboxylic acid [(S)-1-(5-methane-sulfonyl-pyridin-3-yl)-propyl]-amide | 454.6 | 1.41 |
| 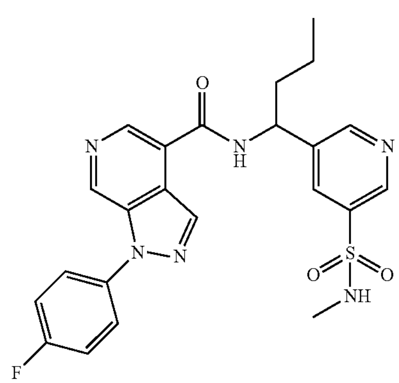 | 1-(4-Fluorophenyl)-1H-pyrazolo[3,4-c]pyridine-4-carboxylic acid [1-(5-methyl-sulfamoyl-pyridin-3-yl)-butyl]-amide | 483.3 | 1.50 |

TABLE I-continued

| STRUCTURE | Name | HPLC-MS[a,b] | |
|---|---|---|---|
| | | [M + H]+ | RT (min) |
| 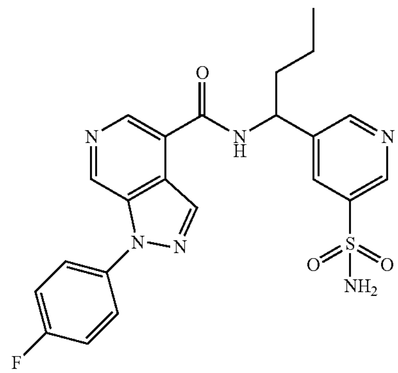 | 1-(4-Fluorophenyl)-1H-pyrazolo[3,4-c]pyridine-4-carboxylic acid [1-(5-sulfamoyl-pyridin-3-yl)-butyl]-amide | 469.3 | 1.42 |
| | 1-(4-Fluorophenyl)-1H-pyrazolo[3,4-c]pyridine-4-carboxylic acid [1-(2-bromo-pyridin-4-yl)-propyl]-amide | 454.5/456.5 | 1.62 |
| 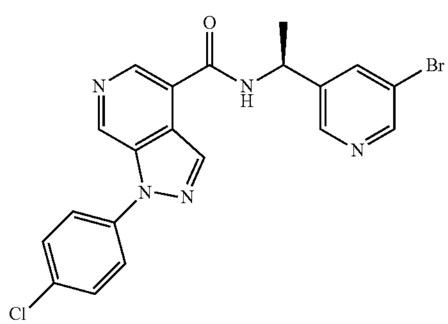 | 1-(4-Chlorophenyl)-1H-pyrazolo[3,4-c]pyridine-4-carboxylic acid [(S)-1-(5-bromo-pyridin-3-yl)-ethyl]-amide | 456.7/458.5 | 1.69 |
| 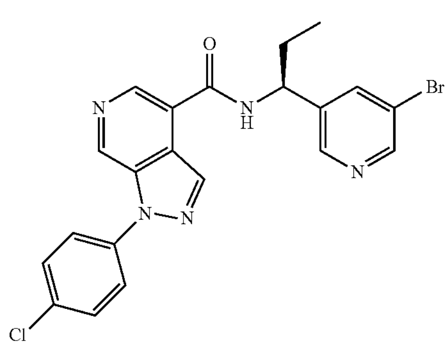 | 1-(4-Chlorophenyl)-1H-pyrazolo[3,4-c]pyridine-4-carboxylic acid [(S)-1-(5-bromo-pyridin-3-yl)-propyl]-amide | 471.2 | 1.70 |

TABLE I-continued

| STRUCTURE | Name | HPLC-MS[a,b] | |
|---|---|---|---|
| | | [M + H]+ | RT (min) |
| 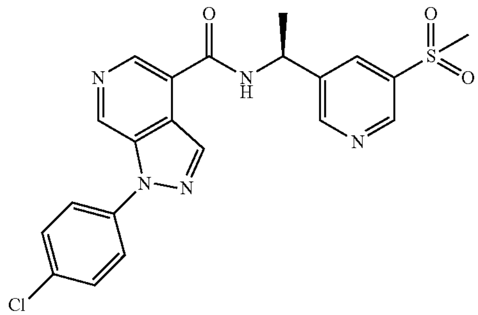 | 1-(4-Chlorophenyl)-1H-pyrazolo[3,4-c]pyridine-4-carboxylic acid [(S)-1-(5-methanesulfonyl-pyridin-3-yl)-ethyl]-amide | 456.1 | 1.54 |
| 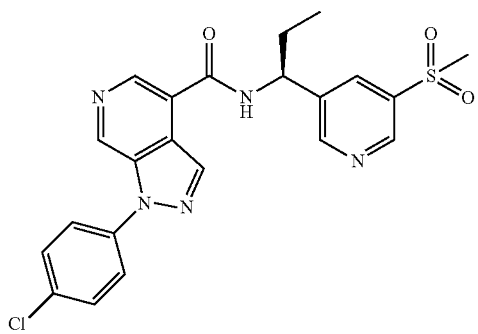 | 1-(4-Chlorophenyl)-1H-pyrazolo[3,4-c]pyridine-4-carboxylic acid [(S)-1-(5-methanesulfonyl-pyridin-3-yl)-propyl]-amide | 470.6 | 1.51 |
| 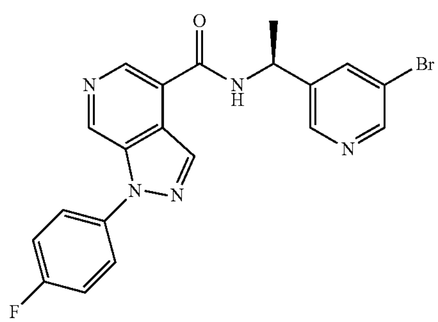 | 1-(4-Fluorophenyl)-1H-pyrazolo[3,4-c]pyridine-4-carboxylic acid [(S)-1-(5-bromo-pyridin-3-yl)-ethyl]-amide | 440.6/442.6 | 1.54 |
| 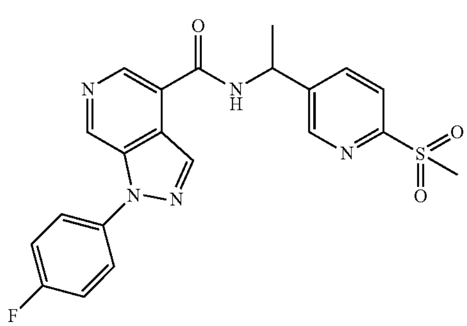 | 1-(4-Fluorophenyl)-1H-pyrazolo[3,4-c]pyridine-4-carboxylic acid [1-(6-methane-sulfonyl-pyridin-3-yl)-ethyl]-amide | 440.6 | 1.37 |

TABLE I-continued

| STRUCTURE | Name | HPLC-MS[a,b] | |
|---|---|---|---|
| | | [M + H]+ | RT (min) |
| 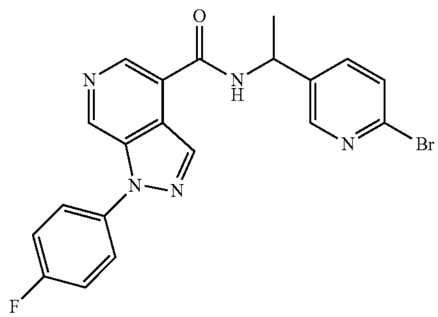 | 1-(4-Fluorophenyl)-1H-pyrazolo[3,4-c]pyridine-4-carboxylic acid [1-(6-bromo-pyridin-3-yl)-ethyl]-amide | 442.5/443.5 | 1.55 |
| 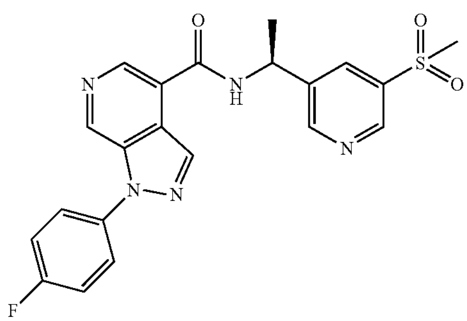 | 1-(4-Fluorophenyl)-1H-pyrazolo[3,4-c]pyridine-4-carboxylic acid [(S)-1-(5-methanesulfonyl-pyridin-3-yl)-ethyl]-amide | 440.3 | 1.33 |
| 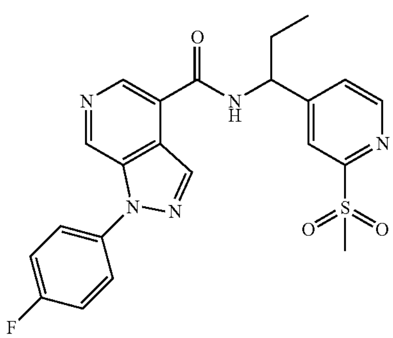 | 1-(4-Fluorophenyl)-1H-pyrazolo[3,4-c]pyridine-4-carboxylic acid [1-(2-methane-sulfonyl-pyridin-4-yl)-propyl]-amide | 454.6 | 1.44 |
| 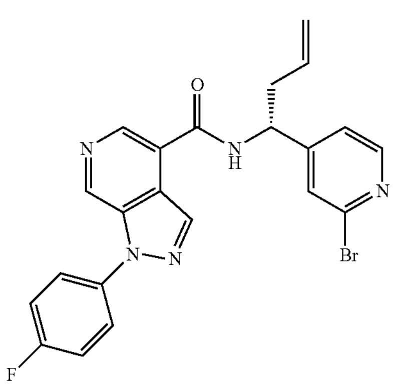 | 1-(4-Fluorophenyl)-1H-pyrazolo[3,4-c]pyridine-4-carboxylic acid [(R)-1-(2-bromo-pyridin-4-yl)-but-3-enyl]-amide | 468.5 | 1.66 |

TABLE I-continued

| STRUCTURE | Name | HPLC-MS[a,b] | |
|---|---|---|---|
| | | [M + H]+ | RT (min) |
| 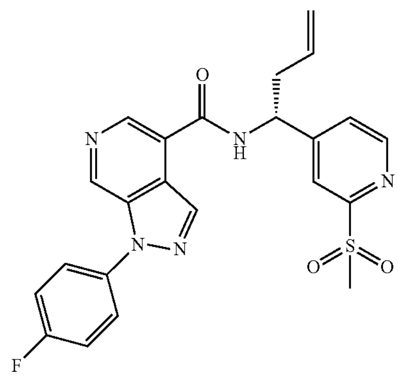 | 1-(4-Fluorophenyl)-1H-pyrazolo[3,4-c]pyridine-4-carboxylic acid [(R)-1-(2-methanesulfonyl-pyridin-4-yl)-but-3-enyl]-amide | 467.2 | 1.45 |
| 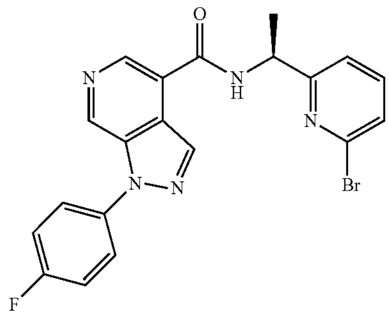 | 1-(4-Fluorophenyl)-1H-pyrazolo[3,4-c]pyridine-4-carboxylic acid [(S)-1-(6-bromo-pyridin-2-yl)-ethyl]-amide | 440.6/442.6 | 1.64 |
| 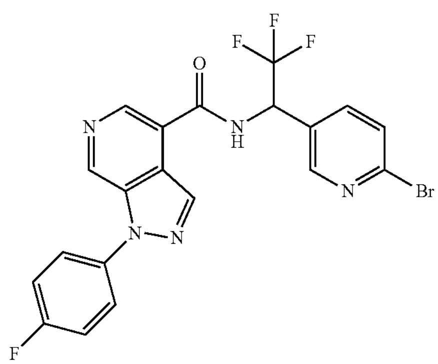 | 1-(4-Fluorophenyl)-1H-pyrazolo[3,4-c]pyridine-4-carboxylic acid [1-(6-bromo-pyridin-3-yl)-2,2,2-trifluoro-ethyl]-amide | 494.5/496.5 | 1.73 |
| | 1-(4-Fluorophenyl)-1H-pyrazolo[3,4-c]pyridine-4-carboxylic acid [2,2,2-trifluoro-1-(6-methanesulfonyl-pyridin-3-yl)-ethyl]-amide | 494.6 | 1.56 |

TABLE I-continued

| STRUCTURE | Name | HPLC-MS[a,b] | |
|---|---|---|---|
| | | [M + H]+ | RT (min) |
| 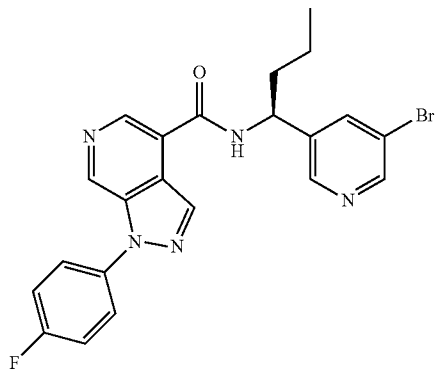 | 1-(4-Fluorophenyl)-1H-pyrazolo[3,4-c]pyridine-4-carboxylic acid [(S)-1-(5-bromo-pyridin-3-yl)-butyl]-amide | 470.5 | 1.74 |
| 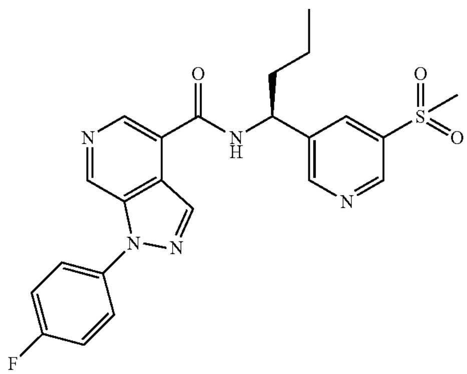 | 1-(4-Fluorophenyl)-1H-pyrazolo[3,4-c]pyridine-4-carboxylic acid [(S)-1-(5-methanesulfonyl-pyridin-3-yl)-butyl]-amide | 468.3 | 1.49 |
| 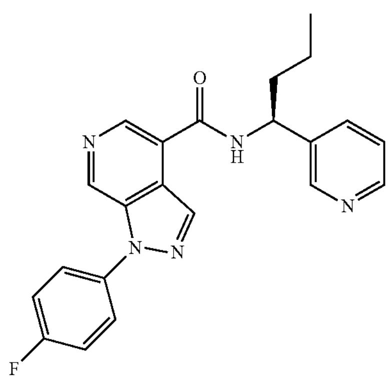 | 1-(4-Fluorophenyl)-1H-pyrazolo[3,4-c]pyridine-4-carboxylic acid ((S)-1-pyridin-3-yl-butyl)-amide | 390.3 | 1.32 |
| 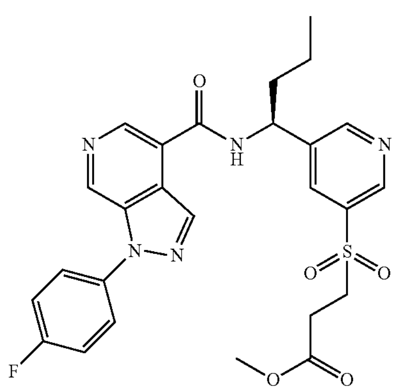 | 3-[5-((S)-1-{[1-(4-Fluorophenyl)-1H-pyrazolo[3,4-c]pyridine-4-carbonyl]-amino}-butyl)-pyridine-3-sulfonyl]-propionic acid methyl ester | 540.3 | 1.57 |

TABLE I-continued

| STRUCTURE | Name | HPLC-MS[a,b] | |
|---|---|---|---|
| | | [M + H]+ | RT (min) |
| 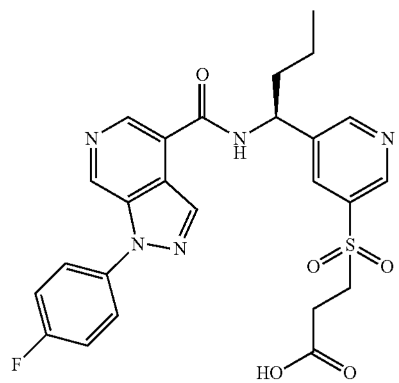 | 3-[5-((S)-1-{[1-(4-Fluorophenyl)-1H-pyrazolo[3,4-c]pyridine-4-carbonyl]-amino}-butyl)-pyridine-3-sulfonyl]-propionic acid | 526.3 | 1.44 |
| 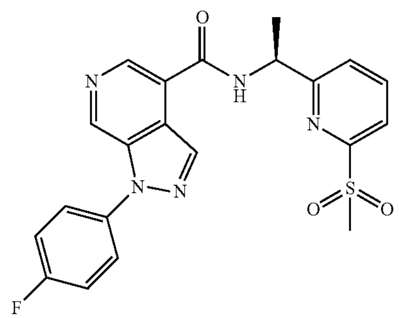 | 1-(4-Fluorophenyl)-1H-pyrazolo[3,4-c]pyridine-4-carboxylic acid [(S)-1-(6-methanesulfonyl-pyridin-2-yl)-ethyl]-amide | 440.6 | 1.40 |
| 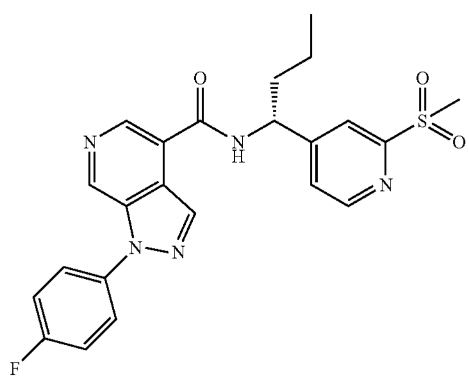 | 1-(4-Fluorophenyl)-1H-pyrazolo[3,4-c]pyridine-4-carboxylic acid [(R)-1-(2-methanesulfonyl-pyridin-4-yl)-butyl]-amide | 468.6 | 1.53 |
| 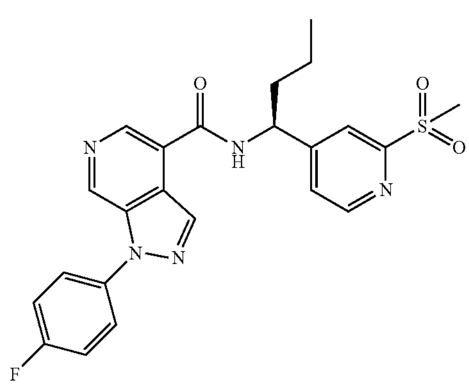 | 1-(4-Fluorophenyl)-1H-pyrazolo[3,4-c]pyridine-4-carboxylic acid [(S)-1-(2-methanesulfonyl-pyridin-4-yl)-butyl]-amide | 468.6 | 1.53 |

TABLE I-continued

| STRUCTURE | Name | [M + H]+ | RT (min) |
|---|---|---|---|
| 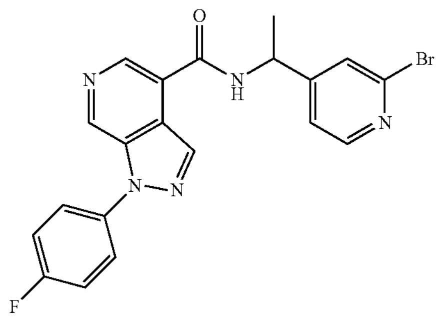 | 1-(4-Fluorophenyl)-1H-pyrazolo[3,4-c]pyridine-4-carboxylic acid [1-(2-bromo-pyridin-4-yl)-ethyl]-amide | 440.5/442.5 | 1.53 |
| 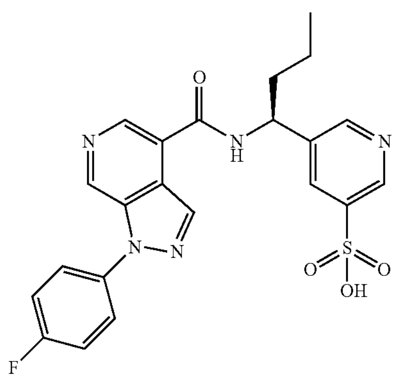 | 5-((S)-1-{[1-(4-Fluorophenyl)-1H-pyrazolo[3,4-c]pyridine-4-carbonyl]-amino}-butyl)-pyridine-3-sulfonic acid | 470.3 | 1.17 |
| | 1-(4-Fluorophenyl)-1H-pyrazolo[3,4-c]pyridine-4-carboxylic acid [(S)-1-(5-methylsulfamoyl-pyridin-3-yl)-butyl]-amide | 483.3 | 1.50 |
| | 1-(4-Fluorophenyl)-1H-pyrazolo[3,4-c]pyridine-4-carboxylic acid [(S)-1-(5-sulfamoyl-pyridin-3-yl)-butyl]-amide | 469.3 | 1.42 |

TABLE I-continued

| STRUCTURE | Name | [M + H]⁺ | RT (min) |
|---|---|---|---|
| 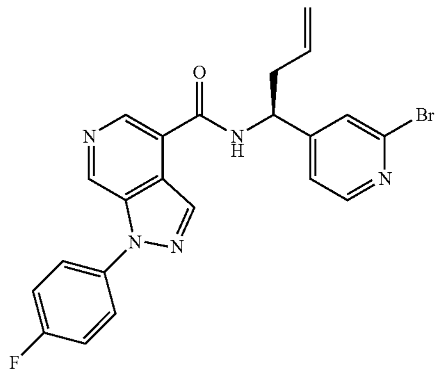 | 1-(4-Fluorophenyl)-1H-pyrazolo[3,4-c]pyridine-4-carboxylic acid [(S)-1-(2-bromo-pyridin-4-yl)-but-3-enyl]-amide | 466.5/468.6 | 1.66 |
| 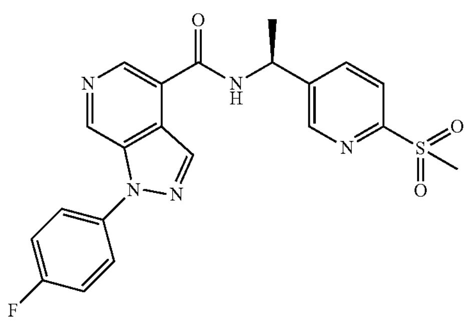 | 1-(4-Fluorophenyl)-1H-pyrazolo[3,4-c]pyridine-4-carboxylic acid [(S)-1-(6-methane-sulfonyl-pyridin-3-yl)-ethyl]-amide | 440.6 | 1.37 |
| 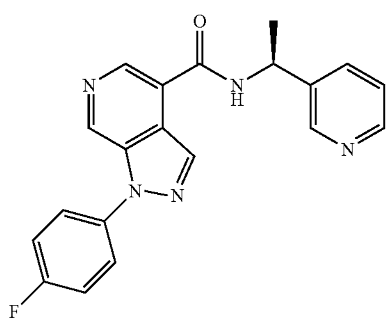 | 1-(4-Fluorophenyl)-1H-pyrazolo[3,4-c]pyridine-4-carboxylic acid ((S)-1-pyridin-3-yl-ethyl)-amide | 362.7 | 1.12 |
| 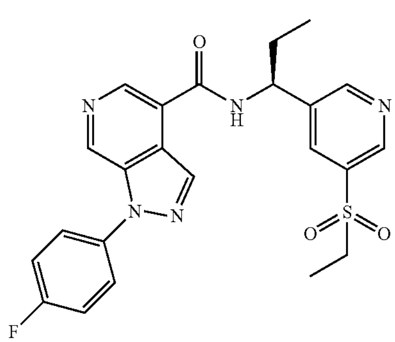 | 1-(4-Fluorophenyl)-1H-pyrazolo[3,4-c]pyridine-4-carboxylic acid [(S)-1-(5-ethane-sulfonyl-pyridin-3-yl)-propyl]-amide | 466.8 | 1.46 |

TABLE I-continued

| STRUCTURE | Name | HPLC-MS[a,b] | |
|---|---|---|---|
| | | [M + H]+ | RT (min) |
| 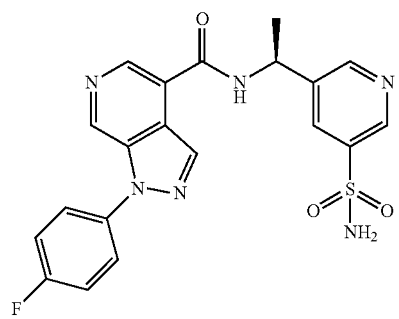 | 1-(4-Fluorophenyl)-1H-pyrazolo[3,4-c]pyridine-4-carboxylic acid [(S)-1-(5-sulfamoyl-pyridin-3-yl)-ethyl]-amide | 441.6 | 1.28 |
| 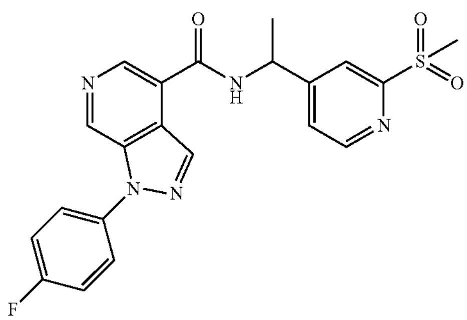 | 1-(4-Fluorophenyl)-1H-pyrazolo[3,4-c]pyridine-4-carboxylic acid [1-(2-methanesulfonyl-pyridin-4-yl)-ethyl]-amide | 440.6 | 1.38 |
| | 1-(4-Fluorophenyl)-1H-pyrazolo[3,4-c]pyridine-4-carboxylic acid 4-((R)-2-hydroxypropylsulfamoyl)-benzylamide | 484.6 | 1.34 |
| | 1-(4-Fluorophenyl)-1H-pyrazolo[3,4-c]pyridine-4-carboxylic acid 4-((S)-2-hydroxypropylsulfamoyl)-benzylamide | 484.6 | 1.35 |

TABLE I-continued

| STRUCTURE | Name | HPLC-MS[a,b] | |
|---|---|---|---|
| | | [M + H]+ | RT (min) |
| 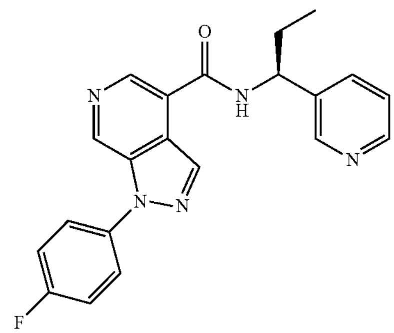 | 1-(4-Fluorophenyl)-1H-pyrazolo[3,4-c]pyridine-4-carboxylic acid ((S)-1-pyridin-3-yl-propyl)-amide | 376.6 | 1.18 |
| 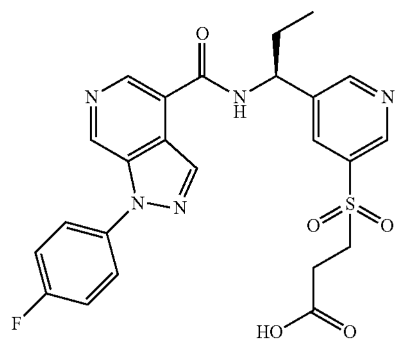 | 3-[5-((S)-1-{[1-(4-Fluorophenyl)-1H-pyrazolo[3,4-c]pyridine-4-carbonyl]-amino}-propyl)-pyridine-3-sulfonyl]-propionic acid | 512.6 | 1.37 |
| 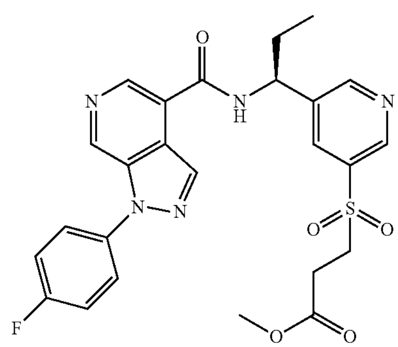 | 3-[5-((S)-1-{[1-(4-Fluorophenyl)-1H-pyrazolo[3,4-c]pyridine-4-carbonyl]-amino}-propyl)-pyridine-3-sulfonyl]-propionic acid methyl ester | 526.6 | 1.48 |
| 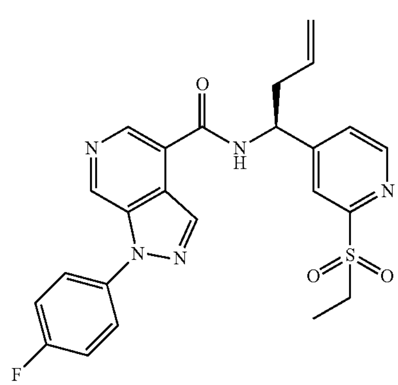 | 1-(4-Fluorophenyl)-1H-pyrazolo[3,4-c]pyridine-4-carboxylic acid [(S)-1-(2-ethane-sulfonyl-pyridin-4-yl)-but-3-enyl]-amide | 480.6 | 1.53 |

TABLE I-continued

| STRUCTURE | Name | HPLC-MS[a,b] | |
|---|---|---|---|
| | | [M + H]+ | RT (min) |
| 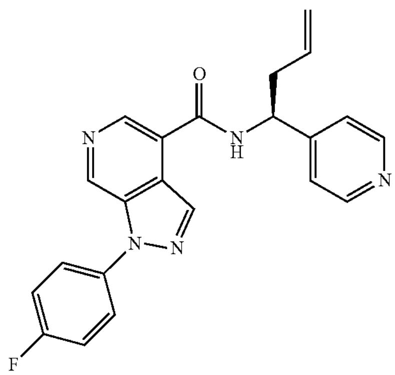 | 1-(4-Fluorophenyl)-1H-pyrazolo[3,4-c]pyridine-4-carboxylic acid ((S)-1-pyridin-4-yl-but-3-enyl)-amide | 388.7 | 1.24 |
| 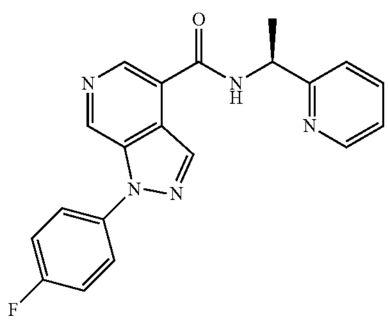 | 1-(4-Fluorophenyl)-1H-pyrazolo[3,4-c]pyridine-4-carboxylic acid ((S)-1-pyridin-2-yl-ethyl)-amide | 362.7 | 1.22 |
| | 1-(4-Fluorophenyl)-1H-pyrazolo[3,4-c]pyridine-4-carboxylic acid [(S)-1-(2-ethane-sulfonyl-pyridin-4-yl)-butyl]-amide | 482.6 | 1.58 |
| | 1-(4-Fluorophenyl)-1H-pyrazolo[3,4-c]pyridine-4-carboxylic acid [(S)-1-(5-sulfa-moyl-pyridin-3-yl)-propyl]-amide | 455.6 | 1.35 |

TABLE I-continued

| STRUCTURE | Name | HPLC-MS[a,b] | |
|---|---|---|---|
| | | [M + H]+ | RT (min) |
| 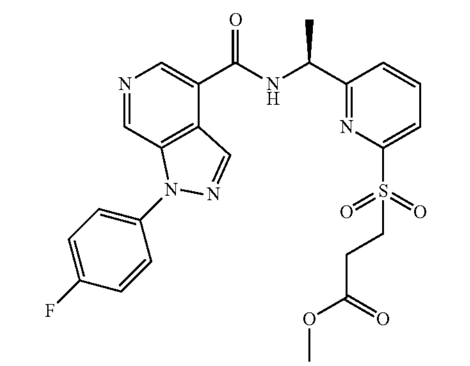 | 3-[6-((S)-1-{[1-(4-Fluorophenyl)-1H-pyrazolo[3,4-c]pyridine-4-carbonyl]-amino}-ethyl)-pyridine-2-sulfonyl]-propionic acid methyl ester | 512.6 | 1.48 |
| 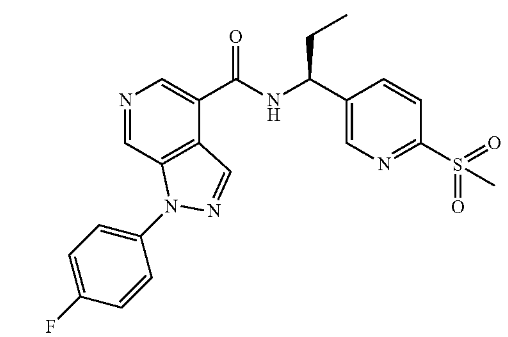 | 1-(4-Fluorophenyl)-1H-pyrazolo[3,4-c]pyridine-4-carboxylic acid [(S)-1-(6-methanesulfonyl-pyridin-3-yl)-propyl]-amide | 454.6 | 1.44 |
| | 1-(4-Fluorophenyl)-1H-pyrazolo[3,4-c]pyridine-4-carboxylic acid [(S)-1-(5-ethane-sulfonyl-pyridin-3-yl)-ethyl]-amide | 454.6 | 1.39 |
| 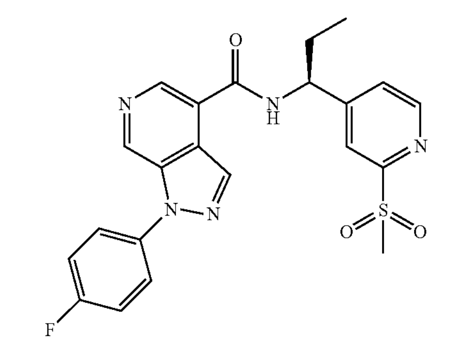 | 1-(4-Fluorophenyl)-1H-pyrazolo[3,4-c]pyridine-4-carboxylic acid [(S)-1-(2-methanesulfonyl-pyridin-4-yl)-propyl]-amide | 454.7 | 1.44 |

TABLE I-continued

| STRUCTURE | Name | HPLC-MS[a,b] | |
|---|---|---|---|
| | | [M + H]+ | RT (min) |
| | 1-(4-Fluorophenyl)-1H-pyrazolo[3,4-c]pyridine-4-carboxylic acid [(S)-1-(2-ethanesulfonyl-pyridin-4-yl)-propyl]-amide | 468.6 | 1.49 |
| | 1-(4-Fluorophenyl)-1H-pyrazolo[3,4-c]pyridine-4-carboxylic acid [(S)-1-(6-sulfamoyl-pyridin-2-yl)-ethyl]-amide | 441.3 | 1.33 |
| 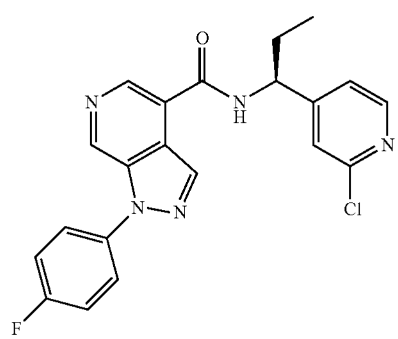 | 1-(4-Fluorophenyl)-1H-pyrazolo[3,4-c]pyridine-4-carboxylic acid [(S)-1-(2-chloro-pyridin-4-yl)-propyl]-amide | 410.6 | 1.59 |
| 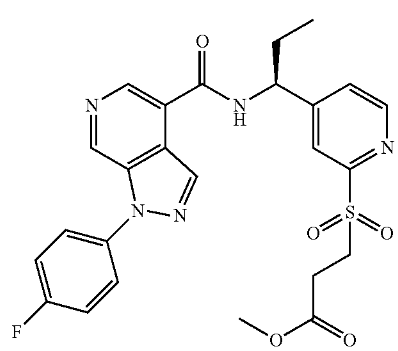 | 3-[4-((S)-1-{[1-(4-Fluorophenyl)-1H-pyrazolo[3,4-c]pyridine-4-carbonyl]-amino}-propyl)-pyridine-2-sulfonyl]-propionic acid methyl ester | 526.6 | 1.51 |

TABLE I-continued

| STRUCTURE | Name | HPLC-MS[a,b] | |
|---|---|---|---|
| | | [M + H]+ | RT (min) |
| 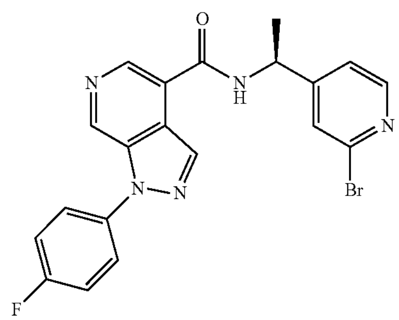 | 1-(4-Fluorophenyl)-1H-pyrazolo[3,4-c]pyridine-4-carboxylic acid [(S)-1-(2-bromo-pyridin-4-yl)-ethyl]-amide | 440.0 | 1.28 |
| 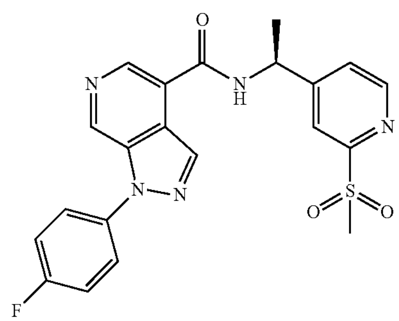 | 1-(4-Fluorophenyl)-1H-pyrazolo[3,4-c]pyridine-4-carboxylic acid [(S)-1-(2-methanesulfonyl-pyridin-4-yl)-ethyl]-amide | 420.0 | 1.15 |
| 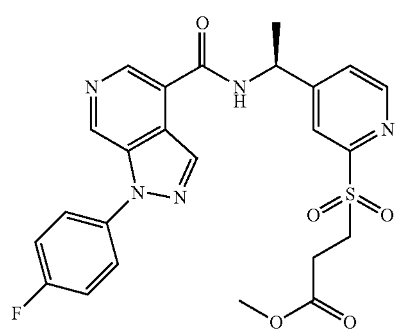 | 3-[4-((S)-1-{[1-(4-Fluorophenyl)-1H-pyrazolo[3,4-c]pyridine-4-carbonyl]-amino}-ethyl)-pyridine-2-sulfonyl]-propionic acid methyl ester | 512.3 | 1.43 |
| 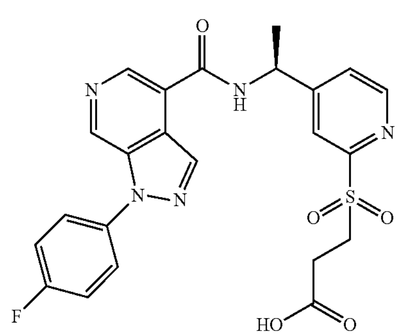 | 3-[4-((S)-1-{[1-(4-Fluorophenyl)-1H-pyrazolo[3,4-c]pyridine-4-carbonyl]-amino}-ethyl)-pyridine-2-sulfonyl]-propionic acid | 498.3 | 1.30 |

TABLE I-continued

| STRUCTURE | Name | [M + H]+ | RT (min) |
|---|---|---|---|
| 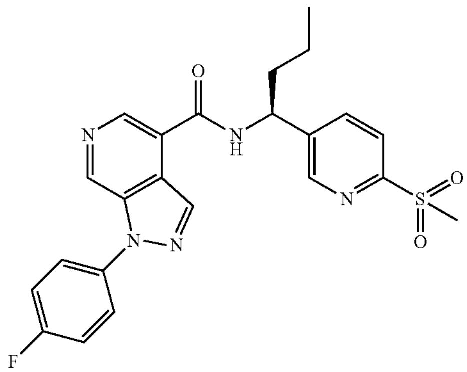 | 1-(4-Fluorophenyl)-1H-pyrazolo[3,4-c]pyridine-4-carboxylic acid [(S)-1-(6-methanesulfonyl-pyridin-3-yl)-butyl]-amide | 468.6 | 1.53 |
| 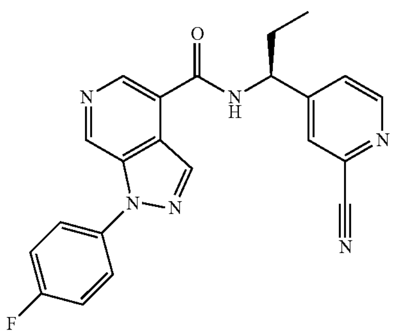 | 1-(4-Fluorophenyl)-1H-pyrazolo[3,4-c]pyridine-4-carboxylic acid [(S)-1-(2-cyano-pyridin-4-yl)-propyl]-amide | 401.6 | 1.51 |
| 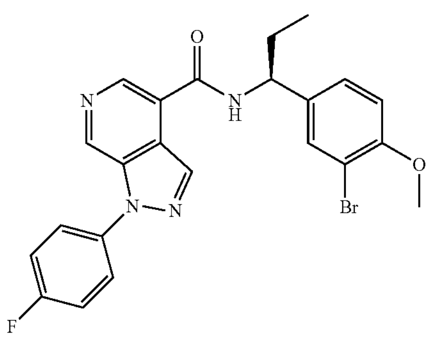 | 1-(4-Fluorophenyl)-1H-pyrazolo[3,4-c]pyridine-4-carboxylic acid [(S)-1-(3-bromo-4-methoxy-phenyl)-propyl]-amide | 484.7 | 1.80 |
| 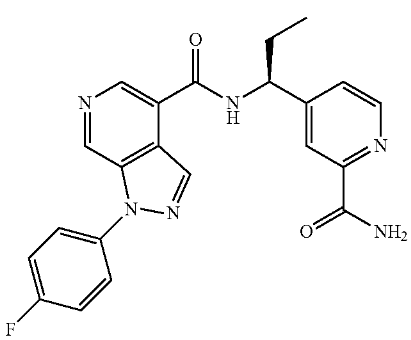 | 1-(4-Fluorophenyl)-1H-pyrazolo[3,4-c]pyridine-4-carboxylic acid [(S)-1-(2-carbamoyl-pyridin-4-yl)-propyl]-amide | 419.7 | 1.36 |

TABLE I-continued

| STRUCTURE | Name | HPLC-MS[a,b] | |
|---|---|---|---|
| | | [M + H]+ | RT (min) |
| 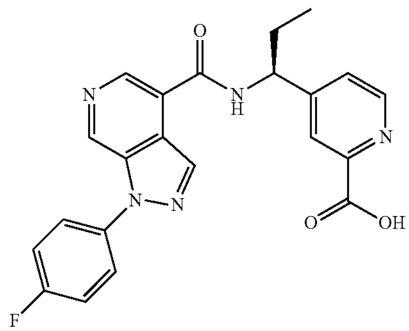 | 4-((S)-1-{[1-(4-Fluorophenyl)-1H-pyrazolo[3,4-c]pyridine-4-carbonyl]-amino}-propyl)-pyridine-2-carboxylic acid | 420.6 | 1.18 |
| 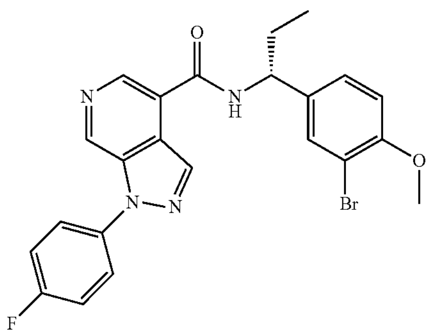 | 1-(4-Fluorophenyl)-1H-pyrazolo[3,4-c]pyridine-4-carboxylic acid [(R)-1-(3-bromo-4-methoxy-phenyl)-propyl]-amide | 485.6/485.6 | 1.81 |
| 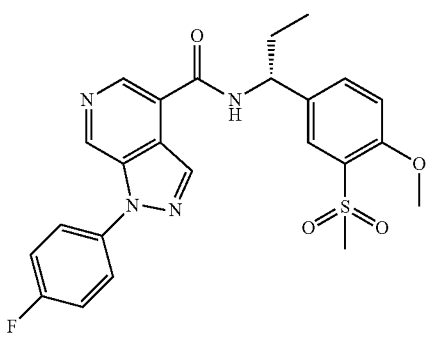 | 1-(4-Fluorophenyl)-1H-pyrazolo[3,4-c]pyridine-4-carboxylic acid [(R)-1-(3-methane-sulfonyl-4-methoxy-phenyl)-propyl]-amide | 483.3 | 1.51 |
| 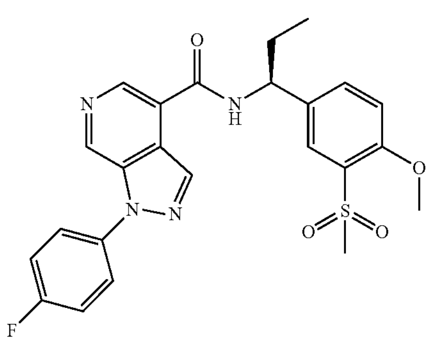 | 1-(4-Fluorophenyl)-1H-pyrazolo[3,4-c]pyridine-4-carboxylic acid [(S)-1-(3-methane-sulfonyl-4-methoxy-phenyl)-propyl]-amide | 481.8 | 1.49 |

TABLE I-continued

| STRUCTURE | Name | HPLC-MS[a,b] [M + H]+ | RT (min) |
|---|---|---|---|
|  | 1-(4-Fluorophenyl)-1H-pyrazolo[3,4-c]pyridine-4-carboxylic acid [(S)-1-(6-ethanesulfonyl-pyridin-3-yl)-propyl]-amide | 468.6 | 1.49 |
| 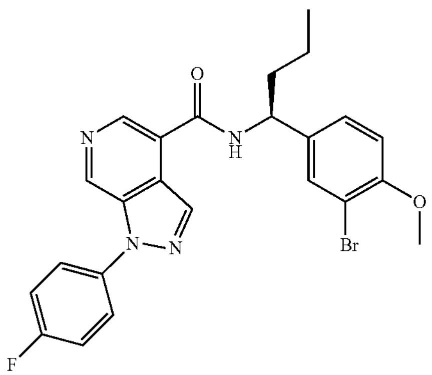 | 1-(4-Fluorophenyl)-1H-pyrazolo[3,4-c]pyridine-4-carboxylic acid [(S)-1-(3-bromo-4-methoxy-phenyl)-butyl]-amide | 497.7 | 1.98 |
| 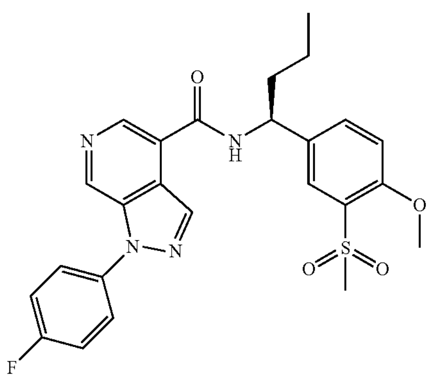 | 1-(4-Fluorophenyl)-1H-pyrazolo[3,4-c]pyridine-4-carboxylic acid [(S)-1-(3-methanesulfonyl-4-methoxy-phenyl)-butyl]-amide | 497.3 | 1.62 |
| 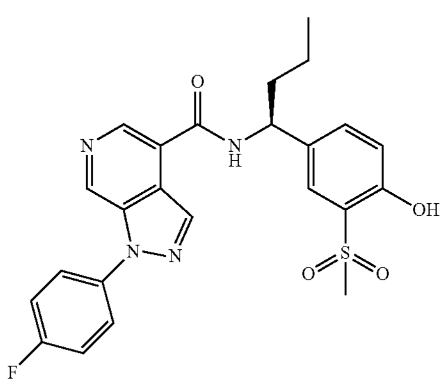 | 1-(4-Fluorophenyl)-1H-pyrazolo[3,4-c]pyridine-4-carboxylic acid [(S)-1-(4-hydroxy-3-methanesulfonyl-phenyl)-butyl]-amide | 493.6 | 1.53 |

TABLE I-continued

| STRUCTURE | Name | HPLC-MS[a,b] | |
|---|---|---|---|
| | | [M + H]+ | RT (min) |
| 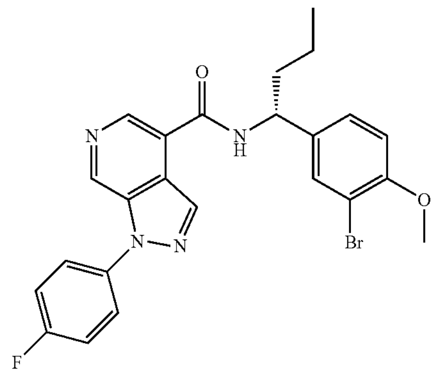 | 1-(4-Fluorophenyl)-1H-pyrazolo[3,4-c]pyridine-4-carboxylic acid [(R)-1-(3-bromo-4-methoxy-phenyl)-butyl]-amide | 497.8/499.6 | 1.97 |
| 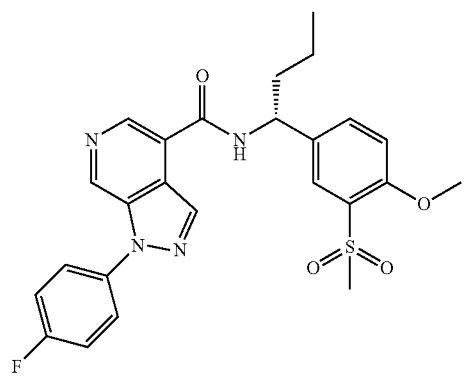 | 1-(4-Fluorophenyl)-1H-pyrazolo[3,4-c]pyridine-4-carboxylic acid [(R)-1-(3-methanesulfonyl-4-methoxy-phenyl)-butyl]-amide | 496.8 | 1.61 |
| | 1-(4-Fluorophenyl)-1H-pyrazolo[3,4-c]pyridine-4-carboxylic acid [(S)-1-(6-ethanesulfonyl-pyridin-2-yl)-ethyl]-amide | 454.6 | 1.46 |
| | 1-(4-Fluorophenyl)-1H-pyrazolo[3,4-c]pyridine-4-carboxylic acid [(R)-1-(4-hydroxy-3-methanesulfonyl-phenyl)-butyl]-amide | 483.7 | 1.52 |

TABLE I-continued

| STRUCTURE | Name | HPLC-MS[a,b] | |
|---|---|---|---|
| | | [M + H]+ | RT (min) |
| 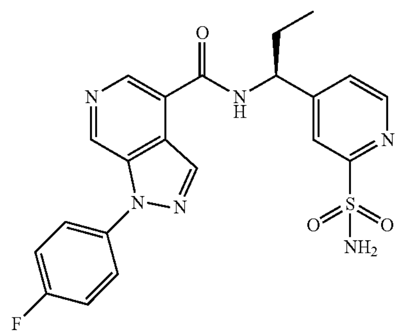 | 1-(4-Fluorophenyl)-1H-pyrazolo[3,4-c]pyridine-4-carboxylic acid [(S)-1-(2-sulfamoyl-pyridin-4-yl)-propyl]-amide | 455.3 | 1.34 |
| 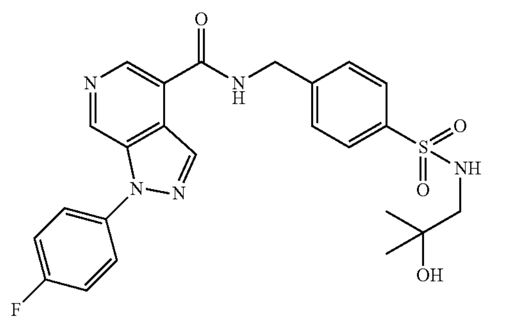 | 1-(4-Fluorophenyl)-1H-pyrazolo[3,4-c]pyridine-4-carboxylic acid 4-(2-hydroxy-2-methyl-propylsulfamoyl)-benzylamide | 498.7 | 1.37 |
| 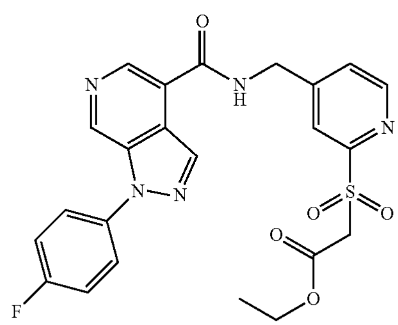 | [4-({[1-(4-Fluorophenyl)-1H-pyrazolo[3,4-c]pyridine-4-carbonyl]-amino}-methyl)-pyridine-2-sulfonyl]-acetic acid ethyl ester | 498.6 | 1.48 |
| 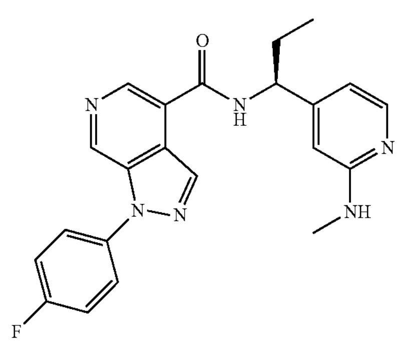 | 1-(4-Fluorophenyl)-1H-pyrazolo[3,4-c]pyridine-4-carboxylic acid [(S)-1-(2-methylamino-pyridin-4-yl)-propyl]-amide | 405.4 | 1.18 |

TABLE I-continued

| STRUCTURE | Name | HPLC-MS[a,b] | |
|---|---|---|---|
| | | [M + H]+ | RT (min) |
| 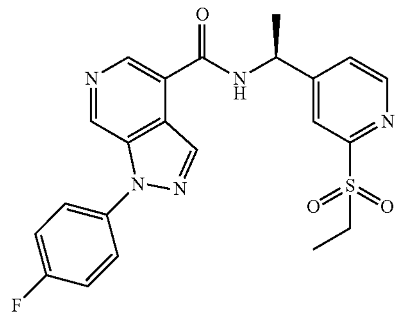 | 1-(4-Fluorophenyl)-1H-pyrazolo[3,4-c]pyridine-4-carboxylic acid [(S)-1-(2-ethane-sulfonyl-pyridin-4-yl)-ethyl]-amide | 454.3 | 1.40 |
| 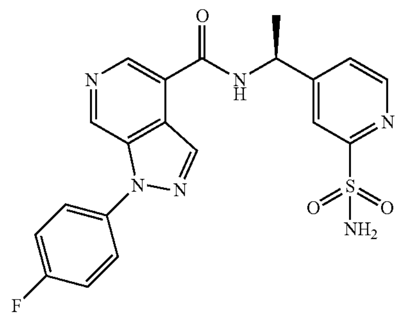 | 1-(4-Fluorophenyl)-1H-pyrazolo[3,4-c]pyridine-4-carboxylic acid [(S)-1-(2-sulfamoyl-pyridin-4-yl)-ethyl]-amide | 441.3 | 1.27 |
| 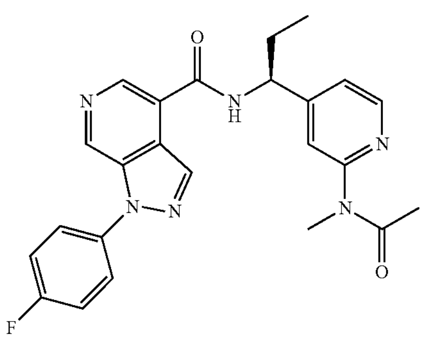 | 1-(4-Fluorophenyl)-1H-pyrazolo[3,4-c]pyridine-4-carboxylic acid {(S)-1-[2-(acetyl-methyl-amino)-pyridin-4-yl]-propyl}-amide | 447.8 | 1.36 |
| 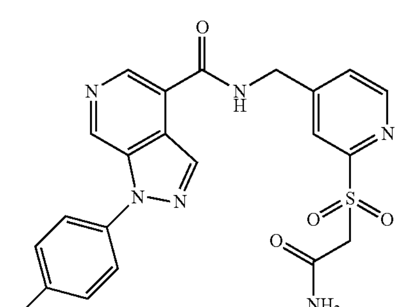 | 1-(4-Fluorophenyl)-1H-pyrazolo[3,4-c]pyridine-4-carboxylic acid (2-carbamoyl-methanesulfonyl-pyridin-4-ylmethyl)-amide | 469.6 | 1.23 |

TABLE I-continued

| STRUCTURE | Name | HPLC-MS[a,b] | |
|---|---|---|---|
| | | [M + H]+ | RT (min) |
| 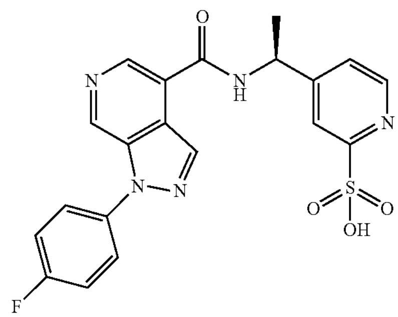 | 4-((S)-1-{[1-(4-Fluorophenyl)-1H-pyrazolo[3,4-c]pyridine-4-carbonyl]-amino}-ethyl)-pyridine-2-sulfonic acid | 442.3 | 1.06 |
| 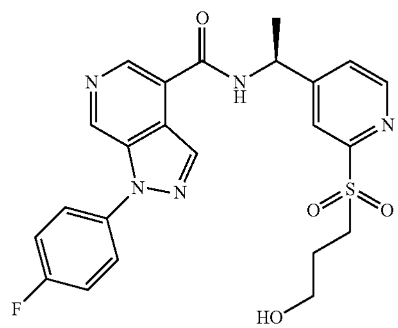 | 1-(4-Fluorophenyl)-1H-pyrazolo[3,4-c]pyridine-4-carboxylic acid {(S)-1-[2-(3-hydroxy-propane-1-sulfonyl)-pyridin-4-yl]-ethyl}-amide | 484.4 | 1.28 |
| 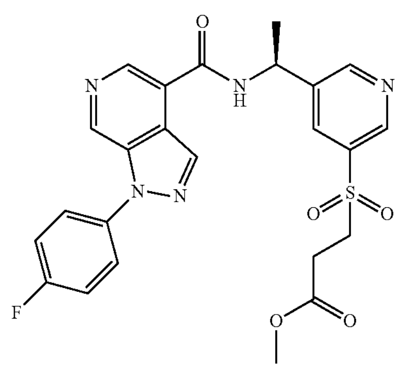 | 3-[5-((S)-1-{[1-(4-Fluorophenyl)-1H-pyrazolo[3,4-c]pyridine-4-carbonyl]-amino}-ethyl)-pyridine-3-sulfonyl]-propionic acid methyl ester | 512.6 | 1.40 |
| 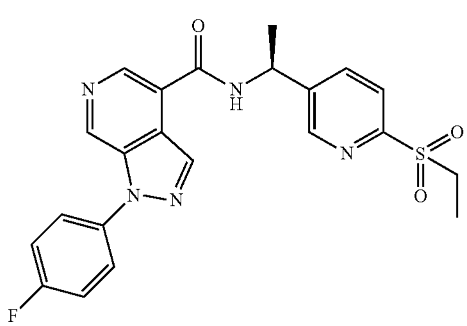 | 1-(4-Fluorophenyl)-1H-pyrazolo[3,4-c]pyridine-4-carboxylic acid [(S)-1-(6-ethanesulfonyl-pyridin-3-yl)-ethyl]-amide | 454.6 | 1.40 |

TABLE I-continued

| STRUCTURE | Name | HPLC-MS[a,b] | |
|---|---|---|---|
| | | [M + H]+ | RT (min) |
| 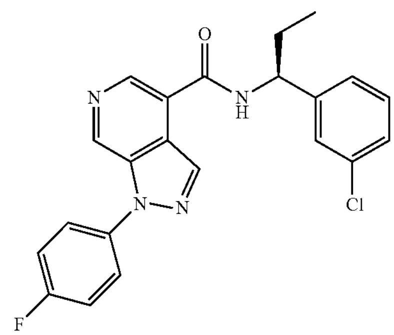 | 1-(4-Fluorophenyl)-1H-pyrazolo[3,4-c]pyridine-4-carboxylic acid [(S)-1-(3-chlorophenyl)-propyl]-amide | 409.7 | 1.82 |
| 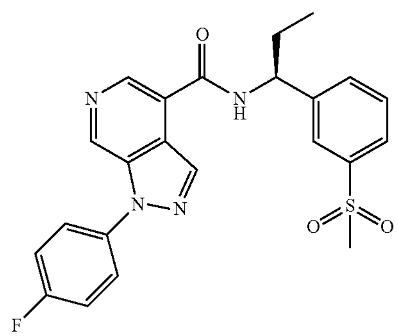 | 1-(4-Fluorophenyl)-1H-pyrazolo[3,4-c]pyridine-4-carboxylic acid [(S)-1-(3-methanesulfonyl-phenyl)-propyl]-amide | 453.7 | 1.52 |
| | 1-(4-Fluorophenyl)-1H-pyrazolo[3,4-c]pyridine-4-carboxylic acid [(S)-1-(3-chlorophenyl)-ethyl]-amide | 395.7 | 1.75 |
| 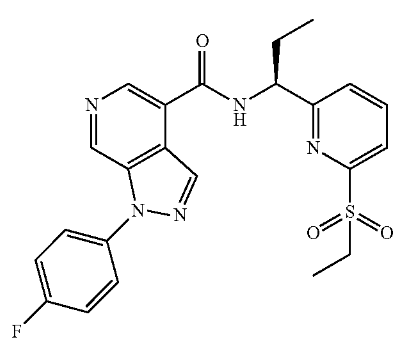 | 1-(4-Fluorophenyl)-1H-pyrazolo[3,4-c]pyridine-4-carboxylic acid [(S)-1-(6-ethanesulfonyl-pyridin-2-yl)-propyl]-amide | 468.7 | 1.53 |

TABLE I-continued

| STRUCTURE | Name | HPLC-MS[a,b] | |
|---|---|---|---|
| | | [M + H]+ | RT (min) |
| 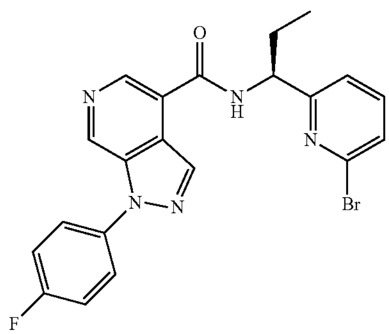 | 1-(4-Fluorophenyl)-1H-pyrazolo[3,4-c]pyridine-4-carboxylic acid [(S)-1-(6-bromopyridin-2-yl)-propyl]-amide | 454.6/456.6 | 1.72 |
| 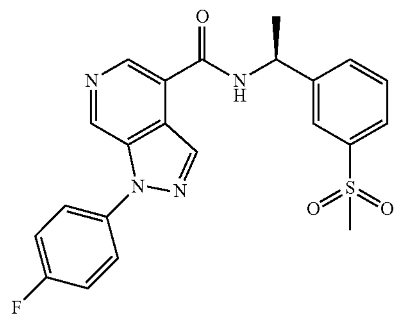 | 1-(4-Fluorophenyl)-1H-pyrazolo[3,4-c]pyridine-4-carboxylic acid [(S)-1-(3-methane-sulfonyl-phenyl)-ethyl]-amide | 439.7 | 1.46 |
| 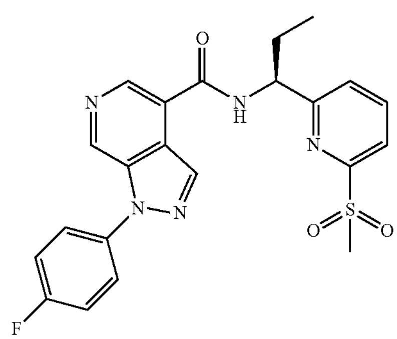 | 1-(4-Fluorophenyl)-1H-pyrazolo[3,4-c]pyridine-4-carboxylic acid [(S)-1-(6-methane-sulfonyl-pyridin-2-yl)-propyl]-amide | 454.7 | 1.48 |
| 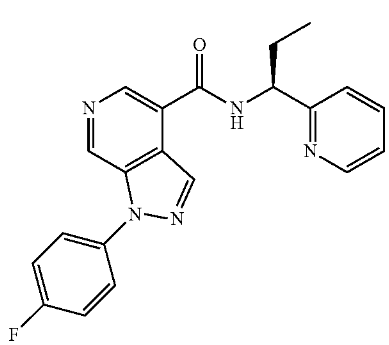 | 1-(4-Fluorophenyl)-1H-pyrazolo[3,4-c]pyridine-4-carboxylic acid ((S)-1-pyridin-2-yl-propyl)-amide | 376.7 | 1.34 |

TABLE I-continued

| STRUCTURE | Name | HPLC-MS[a,b] | |
|---|---|---|---|
| | | [M + H]+ | RT (min) |
| 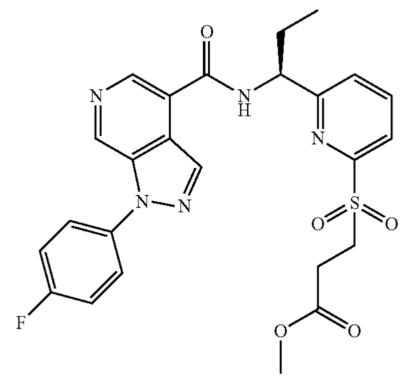 | 3-[6-((S)-1-{[1-(4-Fluorophenyl)-1H-pyrazolo[3,4-c]pyridine-4-carbonyl]-amino}-propyl)-pyridine-2-sulfonyl]-propionic acid methyl ester | 526.7 | 1.55 |
| 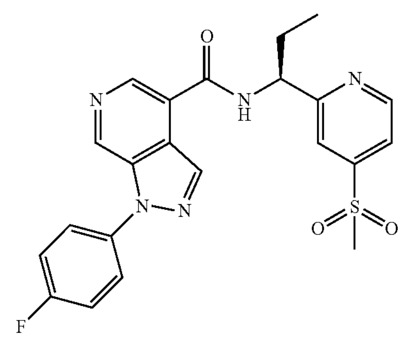 | 1-(4-Fluorophenyl)-1H-pyrazolo[3,4-c]pyridine-4-carboxylic acid [(S)-1-(4-methane-sulfonyl-pyridin-2-yl)-propyl]-amide | 454.6 | 1.45 |
| 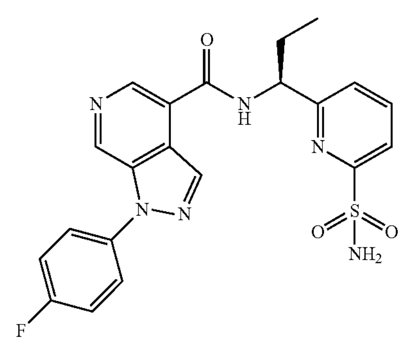 | 1-(4-Fluorophenyl)-1H-pyrazolo[3,4-c]pyridine-4-carboxylic acid [(S)-1-(6-sulfamoyl-pyridin-2-yl)-propyl]-amide | 455.7 | 1.40 |
| 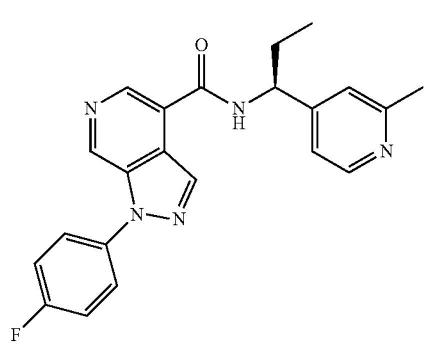 | 1-(4-Fluorophenyl)-1H-pyrazolo[3,4-c]pyridine-4-carboxylic acid [(S)-1-(2-methyl-pyridin-4-yl)-propyl]-amide | 390.7 | 1.27 |

TABLE I-continued

| STRUCTURE | Name | HPLC-MS[a,b] | |
|---|---|---|---|
| | | [M + H]+ | RT (min) |
| 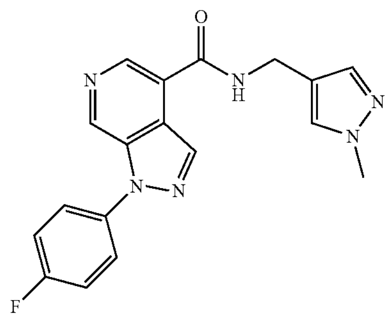 | 1-(4-Fluorophenyl)-1H-pyrazolo[3,4-c]pyridine-4-carboxylic acid (1-methyl-1H-pyrazol-4-ylmethyl)-amide | 351.7 | 1.25 |
| 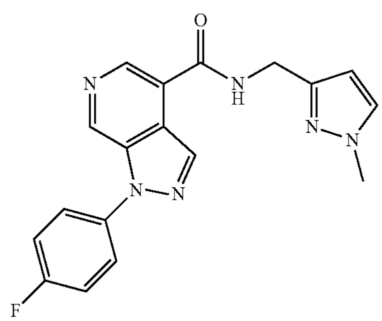 | 1-(4-Fluorophenyl)-1H-pyrazolo[3,4-c]pyridine-4-carboxylic acid (1-methyl-1H-pyrazol-3-ylmethyl)-amide | 351.7 | 1.28 |
| 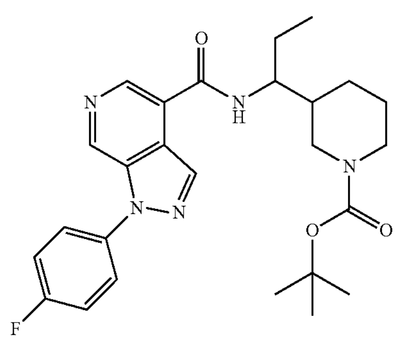 | 3-(1-{[1-(4-Fluorophenyl)-1H-pyrazolo[3,4-c]pyridine-4-carbonyl]-amino}-propyl)-piperidine-1-carboxylic acid tert-butyl ester | 482.5 | 1.78 |
| 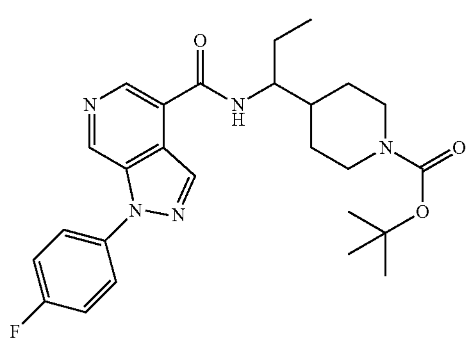 | 4-(1-{[1-(4-Fluorophenyl)-1H-pyrazolo[3,4-c]pyridine-4-carbonyl]-amino}-propyl)-piperidine-1-carboxylic acid tert-butyl ester | 482.5 | 1.76 |

TABLE I-continued

| STRUCTURE | Name | HPLC-MS[a,b] | |
|---|---|---|---|
| | | [M + H]+ | RT (min) |
| 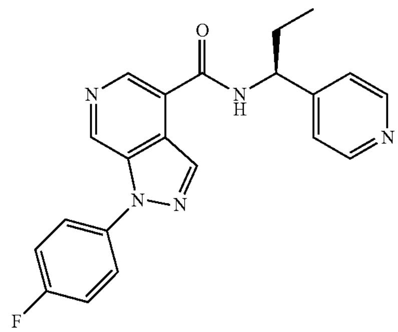 | 1-(4-Fluorophenyl)-1H-pyrazolo[3,4-c]pyridine-4-carboxylic acid ((S)-1-pyridin-4-yl-propyl)-amide | 376.7 | 1.15 |
| 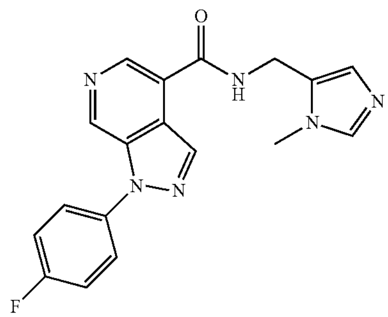 | 1-(4-Fluorophenyl)-1H-pyrazolo[3,4-c]pyridine-4-carboxylic acid (3-methyl-3H-imidazol-4-ylmethyl)-amide | 351.7 | 1.12 |
| 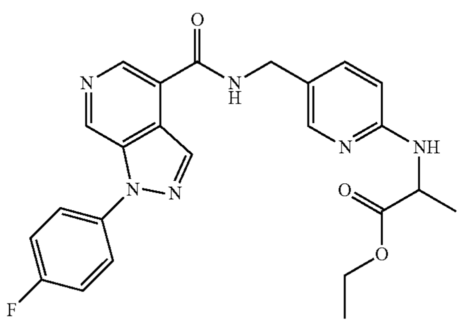 | 2-[5-({[1-(4-Fluorophenyl)-1H-pyrazolo[3,4-c]pyridine-4-carbonyl]-amino}-methyl)-pyridin-2-ylamino]-propionic acid ethyl ester | 463.6 | 1.34 |
| 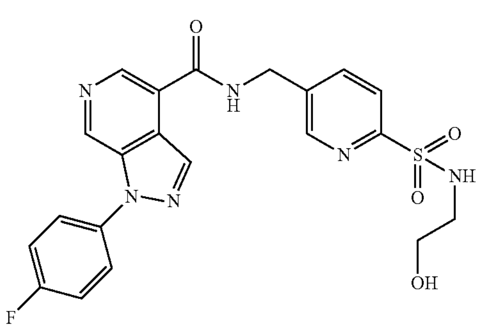 | 1-(4-Fluorophenyl)-1H-pyrazolo[3,4-c]pyridine-4-carboxylic acid [6-(2-hydroxy-ethylsulfamoyl)-pyridin-3-ylmethyl]-amide | 471.5 | 1.23 |

TABLE I-continued

| STRUCTURE | Name | HPLC-MS[a,b] | |
|---|---|---|---|
| | | [M + H]+ | RT (min) |
| | 1-(4-Fluorophenyl)-1H-pyrazolo[3,4-c]pyridine-4-carboxylic acid (1-piperidin-3-yl-propyl)-amide | 382.4 | 1.11 |
| | 1-(4-Fluorophenyl)-1H-pyrazolo[3,4-c]pyridine-4-carboxylic acid (1-piperidin-3-yl-propyl)-amide | 382.7 | 1.11 |
| | 1-(4-Fluorophenyl)-1H-pyrazolo[3,4-c]pyridine-4-carboxylic acid [(S)-1-(2-methylsulfanyl-pyridin-4-yl)-propyl]-amide | 422.4 | 1.56 |
| | 1-(4-Fluorophenyl)-1H-pyrazolo[3,4-c]pyridine-4-carboxylic acid [(S)-1-(5-bromothiophen-2-yl)-propyl]-amide | 459.6/461.6 | 1.86 |

TABLE I-continued

| STRUCTURE | Name | [M + H]⁺ | RT (min) |
|---|---|---|---|
| | 1-(4-Fluorophenyl)-1H-pyrazolo[3,4-c]pyridine-4-carboxylic acid [1-(6-methanesulfonyl-1-oxy-pyridin-3-yl)-propyl]-amide | 470.7 | 1.34 |
| | 1-(4-Fluorophenyl)-1H-pyrazolo[3,4-c]pyridine-4-carboxylic acid [(S)-1-(4-hydroxy-3-methanesulfonyl-phenyl)-propyl]-amide | 469.7 | 1.44 |
| | 1-(4-Fluorophenyl)-1H-pyrazolo[3,4-c]pyridine-4-carboxylic acid [(S)-1-(6-cyclopropylsulfamoyl-pyridin-3-yl)-propyl]-amide | 495.7 | 1.50 |
| | 1-(4-Fluorophenyl)-1H-pyrazolo[3,4-c]pyridine-4-carboxylic acid [1-(1-methanesulfonyl-piperidin-3-yl)-propyl]-amide | 460.4 | 1.48 |

TABLE I-continued

| STRUCTURE | Name | HPLC-MS[a,b] | |
|---|---|---|---|
| | | [M + H]+ | RT (min) |
| 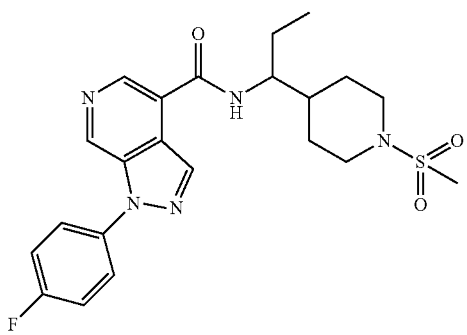 | 1-(4-Fluorophenyl)-1H-pyrazolo[3,4-c]pyridine-4-carboxylic acid [1-(1-methane-sulfonyl-piperidin-4-yl)-propyl]-amide | 460.4 | 1.44 |
| 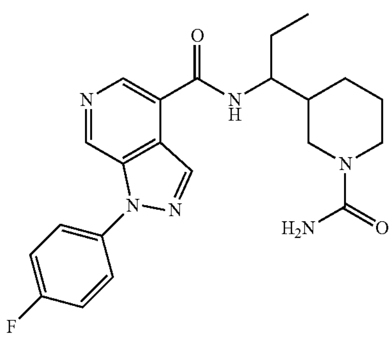 | 1-(4-Fluorophenyl)-1H-pyrazolo[3,4-c]pyridine-4-carboxylic acid [1-(1-carbamoyl-piperidin-3-yl)-propyl]-amide | 425.4 | 1.29 |
| 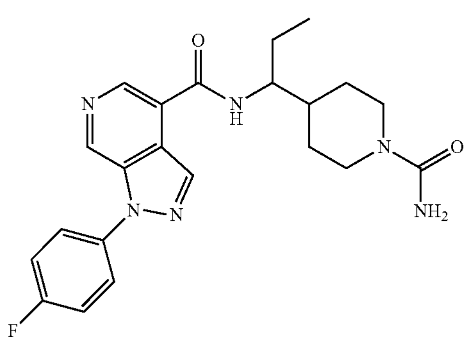 | 1-(4-Fluorophenyl)-1H-pyrazolo[3,4-c]pyridine-4-carboxylic acid [1-(1-carbamoyl-piperidin-4-yl)-propyl]-amide | 425.8 | 1.45 |
| 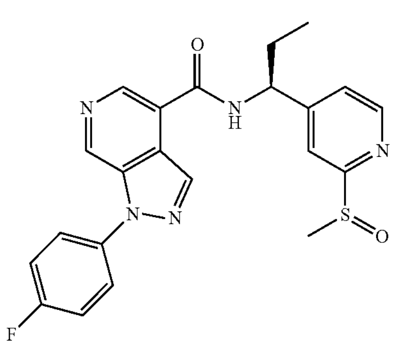 | 1-(4-Fluorophenyl)-1H-pyrazolo[3,4-c]pyridine-4-carboxylic acid [(S)-1-(2-methane-sulfinyl-pyridin-4-yl)-propyl]-amide | 438.9 | 1.52 |

TABLE I-continued

| STRUCTURE | Name | HPLC-MS[a,b] | |
|---|---|---|---|
| | | [M + H]+ | RT (min) |
| | 1-(4-Fluorophenyl)-1H-pyrazolo[3,4-c]pyridine-4-carboxylic acid [(S)-1-(5-methanesulfonyl-thiophen-2-yl)-propyl]-amide | 459.7 | 1.54 |
| 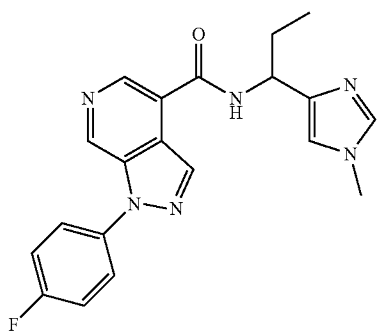 | 1-(4-Fluorophenyl)-1H-pyrazolo[3,4-c]pyridine-4-carboxylic acid [1-(1-methyl-1H-imidazol-4-yl)-propyl]-amide | 379.7 | 1.18 |
| 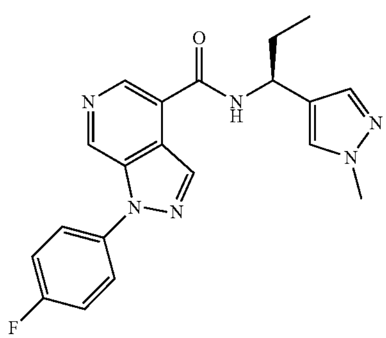 | 1-(4-Fluorophenyl)-1H-pyrazolo[3,4-c]pyridine-4-carboxylic acid [(S)-1-(1-methyl-1H-pyrazol-4-yl)-propyl]-amide | 379.7 | 1.38 |
| 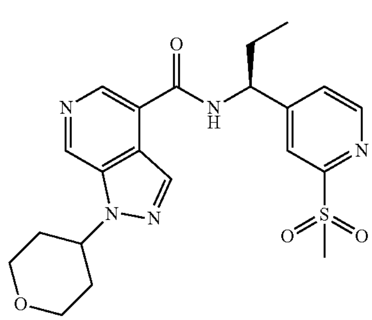 | 1-(Tetrahydropyran-4-yl)-1H-pyrazolo[3,4-c]pyridine-4-carboxylic acid [(S)-1-(2-methanesulfonyl-pyridin-4-yl)-propyl]-amide | 444.8 | 1.16 |

TABLE I-continued

| STRUCTURE | Name | HPLC-MS[a,b] | |
|---|---|---|---|
| | | [M + H]+ | RT (min) |
| 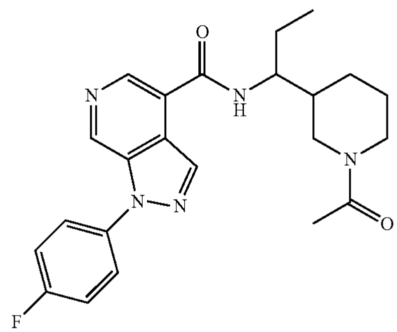 | 1-(4-Fluorophenyl)-1H-pyrazolo[3,4-c]pyridine-4-carboxylic acid [1-(1-acetyl-piperidin-3-yl)-propyl]-amide | 425.7 | 1.35 |
| 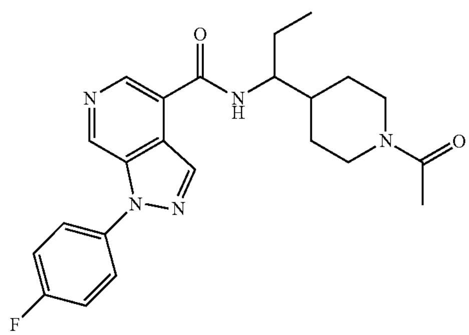 | 1-(4-Fluorophenyl)-1H-pyrazolo[3,4-c]pyridine-4-carboxylic acid [1-(1-acetyl-piperidin-4-yl)-propyl]-amide | 425.7 | 1.33 |
| 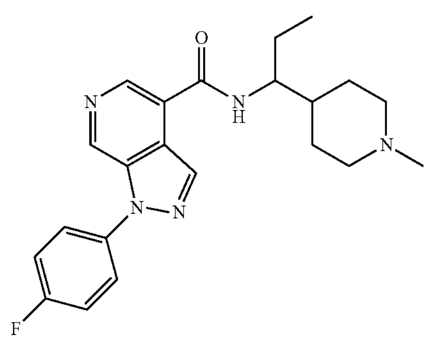 | 1-(4-Fluorophenyl)-1H-pyrazolo[3,4-c]pyridine-4-carboxylic acid [1-(1-methyl-piperidin-4-yl)-propyl]-amide | 396.4 | 1.00 |
| 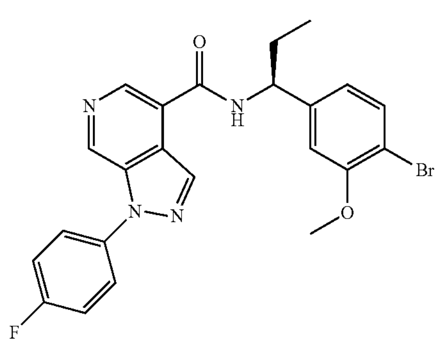 | 1-(4-Fluorophenyl)-1H-pyrazolo[3,4-c]pyridine-4-carboxylic acid [(S)-1-(4-bromo-3-methoxy-phenyl)-propyl]-amide | 483.5/485.7 | 1.83 |

TABLE I-continued

| STRUCTURE | Name | HPLC-MS[a,b] | |
|---|---|---|---|
| | | [M + H]+ | RT (min) |
| 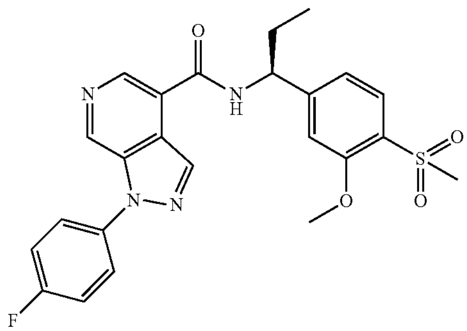 | 1-(4-Fluorophenyl)-1H-pyrazolo[3,4-c]pyridine-4-carboxylic acid [(S)-1-(4-methane-sulfonyl-3-methoxy-phenyl)-propyl]-amide | 483.7 | 1.57 |
| 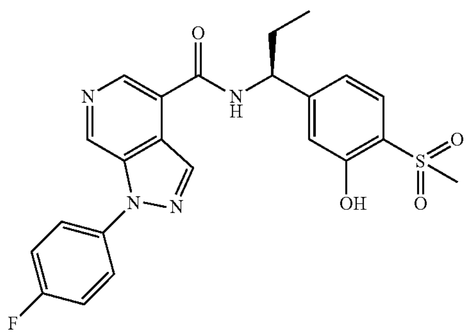 | 1-(4-Fluorophenyl)-1H-pyrazolo[3,4-c]pyridine-4-carboxylic acid [(S)-1-(3-hydroxy-4-methane-sulfonyl-phenyl)-propyl]-amide | 469.7 | 1.44 |
| 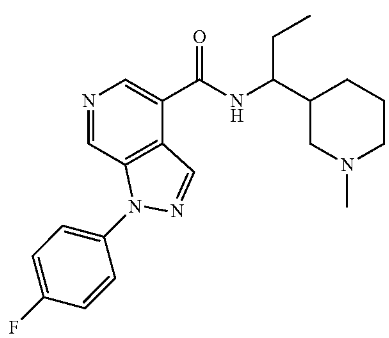 | 1-(4-Fluorophenyl)-1H-pyrazolo[3,4-c]pyridine-4-carboxylic acid [1-(1-methyl-piperidin-3-yl)-propyl]-amide | 396.4 | 1.10 |
| 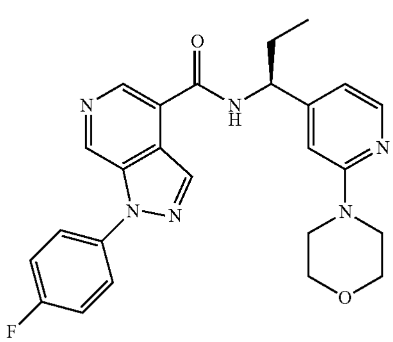 | 1-(4-Fluorophenyl)-1H-pyrazolo[3,4-c]pyridine-4-carboxylic acid [(S)-1-(2-morpholin-4-yl-pyridin-4-yl)-propyl]-amide | 461.8 | 1.28 |

TABLE I-continued

| STRUCTURE | Name | HPLC-MS[a,b] | |
|---|---|---|---|
| | | [M + H]+ | RT (min) |
| 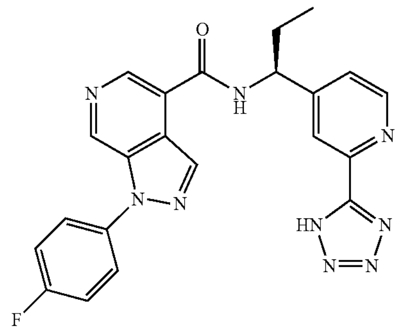 | 1-(4-Fluorophenyl)-1H-pyrazolo[3,4-c]pyridine-4-carboxylic acid {(S)-1-[2-(1H-tetrazol-5-yl)-pyridin-4-yl]-propyl}-amide | 444.8 | 1.38 |
| 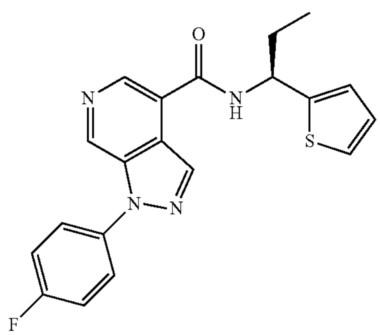 | 1-(4-Fluorophenyl)-1H-pyrazolo[3,4-c]pyridine-4-carboxylic acid ((S)-1-thiophen-2-yl-propyl)-amide | 381.6 | 1.68 |
| 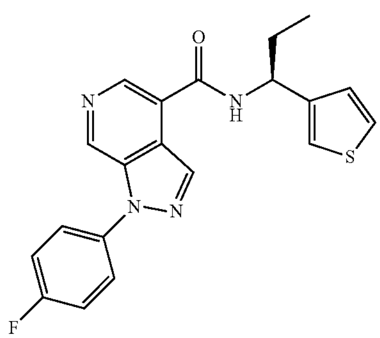 | 1-(4-Fluorophenyl)-1H-pyrazolo[3,4-c]pyridine-4-carboxylic acid ((S)-1-thiophen-3-yl-propyl)-amide | 381.7 | 1.69 |
| 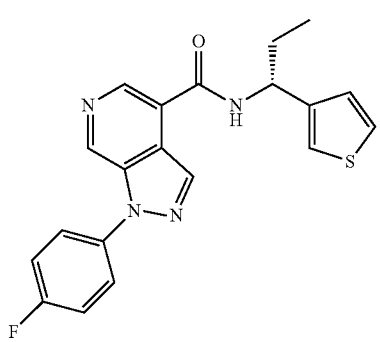 | 1-(4-Fluorophenyl)-1H-pyrazolo[3,4-c]pyridine-4-carboxylic acid ((R)-1-thiophen-3-yl-propyl)-amide | 381.6 | 1.67 |

TABLE I-continued

| STRUCTURE | Name | HPLC-MS[a,b] | |
|---|---|---|---|
| | | [M + H]+ | RT (min) |
| | 1-(4-Fluorophenyl)-1H-pyrazolo[3,4-c]pyridine-4-carboxylic acid (2-methanesulfonyl-1-oxy-pyridin-4-ylmethyl)-amide | 442.6 | 1.34 |
| | 1-(4-Fluorophenyl)-1H-pyrazolo[3,4-c]pyridine-4-carboxylic acid [(S)-1-(2-methanesulfonyl-pyridin-4-yl)-but-3-enyl]-amide | 466.8 | 1.49 |
| | 1-(4-Fluorophenyl)-1H-pyrazolo[3,4-c]pyridine-4-carboxylic acid (2-methanesulfonyl-6-methoxy-pyridin-4-ylmethyl)-amide | 456.6 | 1.46 |
| | 1-(4-Fluorophenyl)-1H-pyrazolo[3,4-c]pyridine-4-carboxylic acid [(1S,3S)-3,4-dihydroxy-1-(2-methanesulfonyl-pyridin-4-yl)-butyl]-amide | 500.8 | 1.20 |

TABLE I-continued

| STRUCTURE | Name | HPLC-MS[a,b] [M + H]+ | RT (min) |
|---|---|---|---|
| | 1-(4-Fluorophenyl)-1H-pyrazolo[3,4-c]pyridine-4-carboxylic acid [(1S,3R)-3,4-di-hydroxy-1-(2-methane-sulfonyl-pyridin-4-yl)-butyl]-amide | 500.8 | 1.19 |
| 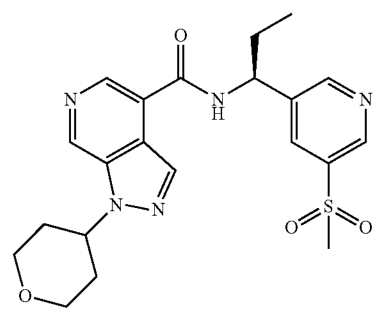 | 1-(Tetrahydropyran-4-yl)-1H-pyrazolo[3,4-c]pyridine-4-carboxylic acid [(S)-1-(5-methanesulfonyl-pyridin-3-yl)-propyl]-amide | 444.8 | 1.14 |
| 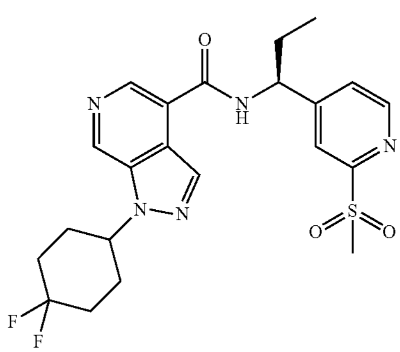 | 1-(4,4-Difluorocyclo-hexyl)-1H-pyrazolo[3,4-c]pyridine-4-carboxylic acid [(S)-1-(2-methanesulfonyl-pyridin-4-yl)-propyl]-amide | 478.8 | 1.43 |
| 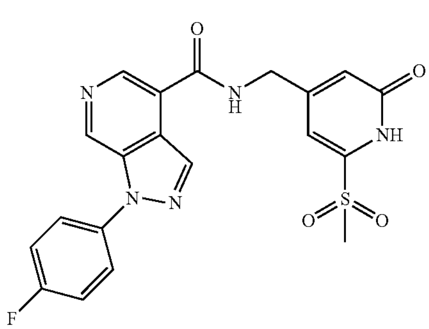 | 1-(4-Fluorophenyl)-1H-pyrazolo[3,4-c]pyridine-4-carboxylic acid (6-methane-sulfonyl-2-oxo-1,2-dihydropyridin-4-ylmethyl)-amide | 442.7 | 1.28 |

TABLE I-continued

| STRUCTURE | Name | [M + H]+ | RT (min) |
|---|---|---|---|
| | (S)-3-{[1-(4-Fluorophenyl)-1H-pyrazolo[3,4-c]pyridine-4-carbonyl]-amino}-3-(2-methanesulfonyl-pyridin-4-yl)-propionic acid methyl ester | 498.7 | 1.39 |
| 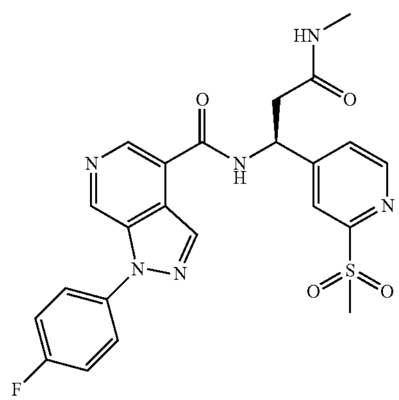 | 1-(4-Fluorophenyl)-1H-pyrazolo[3,4-c]pyridine-4-carboxylic acid [(S)-1-(2-methanesulfonyl-pyridin-4-yl)-2-methylcarbamoyl-ethyl]-amide | 497.7 | 1.24 |
| 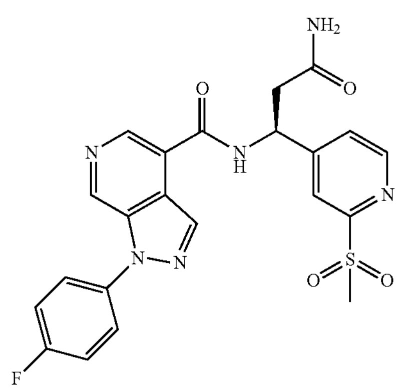 | 1-(4-Fluorophenyl)-1H-pyrazolo[3,4-c]pyridine-4-carboxylic acid [(S)-2-carbamoyl-1-(2-methanesulfonyl-pyridin-4-yl)-ethyl]-amide | 483.7 | 1.21 |
| 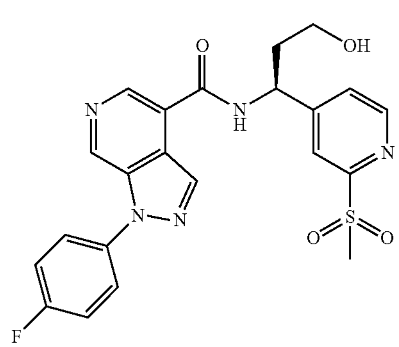 | 1-(4-Fluorophenyl)-1H-pyrazolo[3,4-c]pyridine-4-carboxylic acid [(S)-3-hydroxy-1-(2-methanesulfonyl-pyridin-4-yl)-propyl]-amide | 470.7 | 1.25 |

TABLE I-continued

| STRUCTURE | Name | HPLC-MS[a,b] [M + H]+ | RT (min) |
|---|---|---|---|
| | 1-(4-Fluorophenyl)-1H-pyrazolo[3,4-c]pyridine-4-carboxylic acid [(S)-1-(2-methanesulfonyl-pyridin-4-yl)-3-morpholin-4-yl-propyl]-amide | 539.8 | 1.20 |
| | 1-(4-Fluorophenyl)-1H-pyrazolo[3,4-c]pyridine-4-carboxylic acid [(S)-1-(2-methanesulfonyl-pyridin-4-yl)-3-methylaminopropyl]-amino | 483.8 | 1.18 |
| | 1-(4-Fluorophenyl)-1H-pyrazolo[3,4-c]pyridine-4-carboxylic acid [(S)-1-(2-methanesulfonyl-thiazol-5-yl)-propyl]-amide | 460.6 | 1.50 |
| | 1-(4-Fluorophenyl)-1H-pyrazolo[3,4-c]pyridine-4-carboxylic acid [(S)-1-(4-methanesulfonyl-thiophen-2-yl)-propyl]-amide | 459.6 | 1.49 |

TABLE I-continued

| STRUCTURE | Name | [M + H]+ | RT (min) |
|---|---|---|---|
| 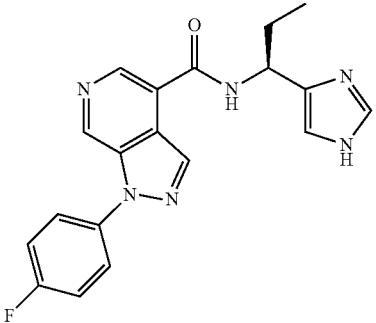 | 1-(4-Fluorophenyl)-1H-pyrazolo[3,4-c]pyridine-4-carboxylic acid [(S)-1-(1H-imidazol-4-yl)-propyl]-amide | 365.7 | 1.11 |
| 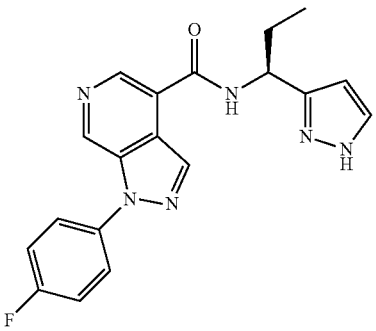 | 1-(4-Fluorophenyl)-1H-pyrazolo[3,4-c]pyridine-4-carboxylic acid [(S)-1-(1H-pyrazol-3-yl)-propyl]-amide | 365.7 | 1.35 |
| 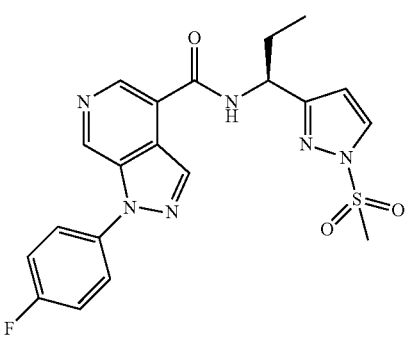 | 1-(4-Fluorophenyl)-1H-pyrazolo[3,4-c]pyridine-4-carboxylic acid [(S)-1-(1-methanesulfonyl-1H-pyrazol-3-yl)-propyl]-amide | 443.7 | 1.54 |
| 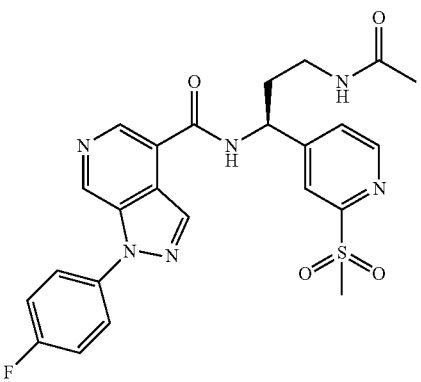 | 1-(4-Fluorophenyl)-1H-pyrazolo[3,4-c]pyridine-4-carboxylic acid [(S)-3-acetyl-amino-1-(2-methanesulfonyl-pyridin-4-yl)-propyl]-amide | 511.7 | 1.22 |

TABLE I-continued

| STRUCTURE | Name | HPLC-MS[a,b] | |
|---|---|---|---|
| | | [M + H]+ | RT (min) |
| 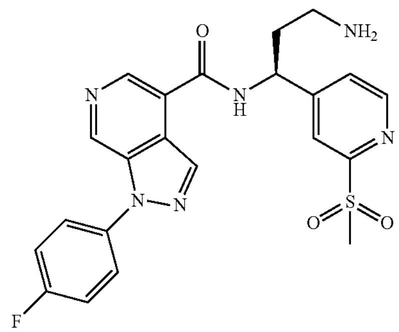 | 1-(4-Fluorophenyl)-1H-pyrazolo[3,4-c]pyridine-4-carboxylic acid [(S)-3-amino-1-(2-methanesulfonyl-pyridin-4-yl)-propyl]-amide | 469.8 | 1.14 |
| 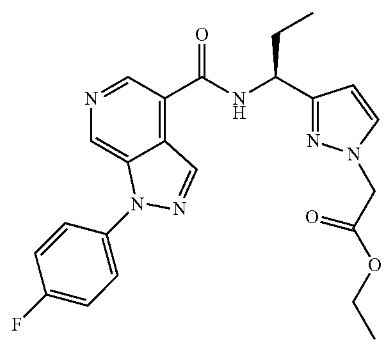 | [3-((S)-1-{[1-(4-Fluorophenyl)-1H-pyrazolo[3,4-c]pyridine-4-carbonyl]-amino}-propyl)-pyrazol-1-yl]-acetic acid ethyl ester | 452.1 | 1.84 |
| 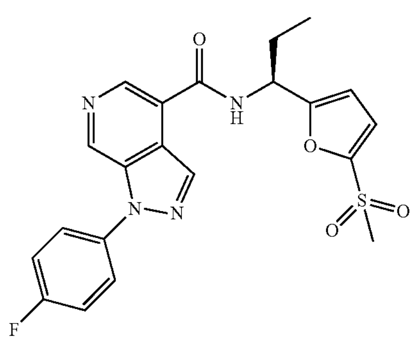 | 1-(4-Fluorophenyl)-1H-pyrazolo[3,4-c]pyridine-4-carboxylic acid [(S)-1-(5-methanesulfonyl-furan-2-yl)-propyl]-amide | 443.7 | 1.50 |
| 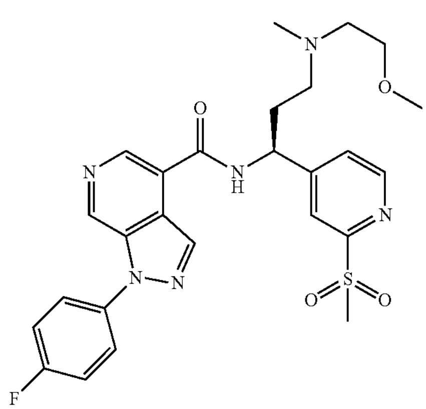 | 1-(4-Fluorophenyl)-1H-pyrazolo[3,4-c]pyridine-4-carboxylic acid {(S)-1-(2-methanesulfonyl-pyridin-4-yl)-3-[(2-methoxy-ethyl)-methyl-amino]-propyl}-amide | 541.8 | 1.19 |

TABLE I-continued

| STRUCTURE | Name | [M + H]⁺ | RT (min) |
|---|---|---|---|
| 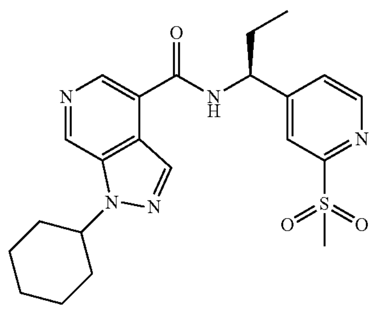 | 1-Cyclohexyl-1H-pyrazolo[3,4-c]pyridine-4-carboxylic acid [(S)-1-(2-methanesulfonyl-pyridin-4-yl)-propyl]-amide | 442.8 | 1.46 |
| 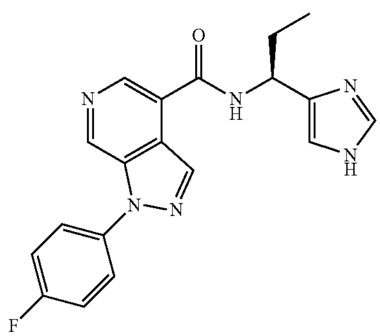 | 1-(4-Fluorophenyl)-1H-pyrazolo[3,4-c]pyridine-4-carboxylic acid [(S)-1-(1H-imidazol-4-yl)-propyl]-amide | 365.7 | 1.11 |
| 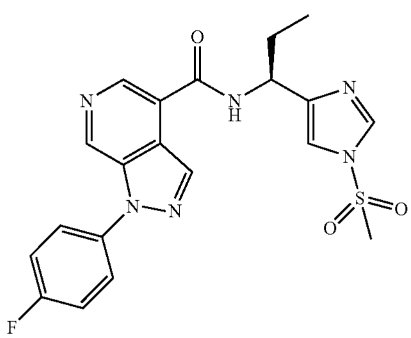 | 1-(4-Fluorophenyl)-1H-pyrazolo[3,4-c]pyridine-4-carboxylic acid [(S)-1-(1-methanesulfonyl-1H-imidazol-4-yl)-propyl]-amide | 443.7 | 1.42 |
| 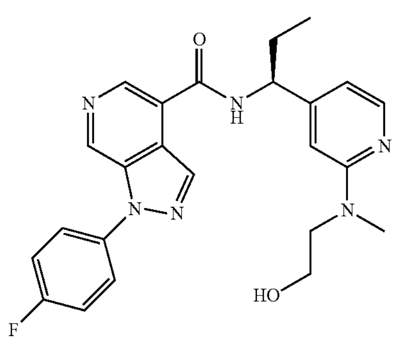 | 1-(4-Fluorophenyl)-1H-pyrazolo[3,4-c]pyridine-4-carboxylic acid ((S)-1-{2-[(2-hydroxy-ethyl)-methyl-amino]-pyridin-4-yl}-propyl)-amide | 449.8 | 1.20 |

TABLE I-continued

| STRUCTURE | Name | HPLC-MS[a,b] | |
|---|---|---|---|
| | | [M + H]+ | RT (min) |
| 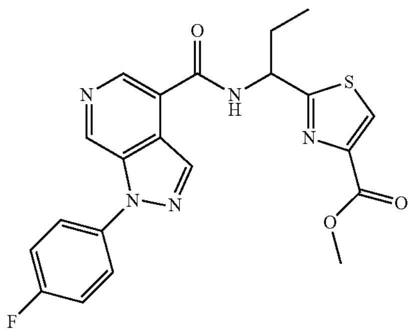 | 2-(1-{[1-(4-Fluorophenyl)-1H-pyrazolo[3,4-c]pyridine-4-carbonyl]-amino}-propyl)-thiazole-4-carboxylic acid methyl ester | 440.7 | 1.54 |
| 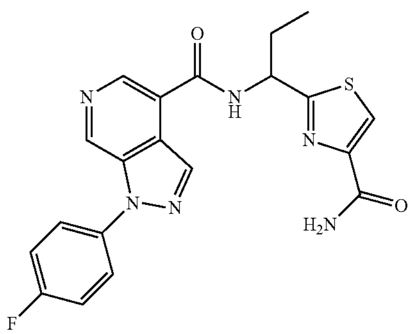 | 1-(4-Fluorophenyl)-1H-pyrazolo[3,4-c]pyridine-4-carboxylic acid [(S)-1-(4-carbamoyl-thiazol-2-yl)-propyl]-amide | 425.7 | 1.37 |
| 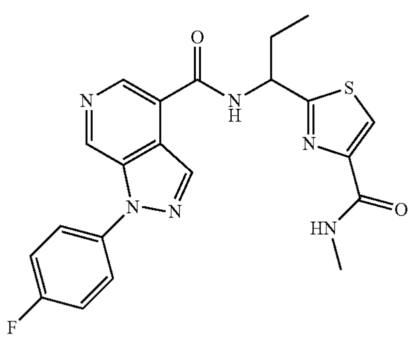 | 1-(4-Fluorophenyl)-1H-pyrazolo[3,4-c]pyridine-4-carboxylic acid [(S)-1-(4-methyl-carbamoyl-thiazol-2-yl)-propyl]-amide | 439.7 | 1.43 |
| 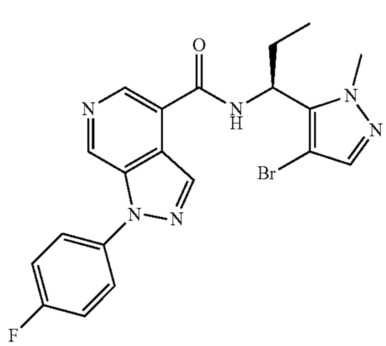 | 1-(4-Fluorophenyl)-1H-pyrazolo[3,4-c]pyridine-4-carboxylic acid [(S)-1-(4-bromo-2-methyl-2H-pyrazol-3-yl)-propyl]-amide | 457.3/459.6 | 1.59 |

TABLE I-continued

| STRUCTURE | Name | HPLC-MS[a,b] | |
|---|---|---|---|
| | | [M + H]+ | RT (min) |
| 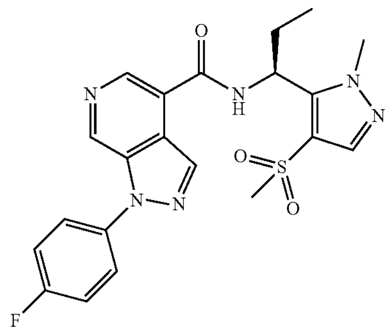 | 1-(4-Fluorophenyl)-1H-pyrazolo[3,4-c]pyridine-4-carboxylic acid [(S)-1-(4-methanesulfonyl-2-methyl-2H-pyrazol-3-yl)-propyl]-amide | 455.9 | 1.47 |
| 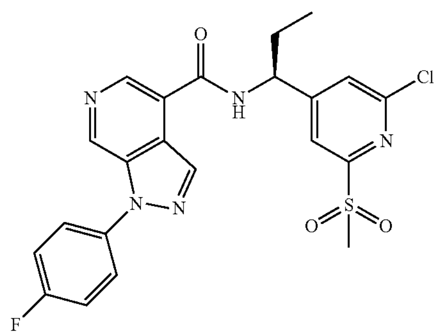 | 1-(4-Fluorophenyl)-1H-pyrazolo[3,4-c]pyridine-4-carboxylic acid [(S)-1-(2-chloro-6-methanesulfonyl-pyridin-4-yl)-propyl]-amide | 488.7 | 1.63 |
| 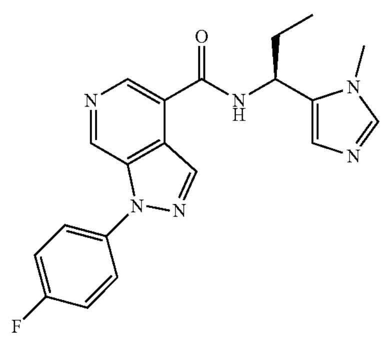 | 1-(4-Fluorophenyl)-1H-pyrazolo[3,4-c]pyridine-4-carboxylic acid [(S)-1-(3-methyl-3H-imidazol-4-yl)-propyl]-amide | 379.8 | 1.15 |
| 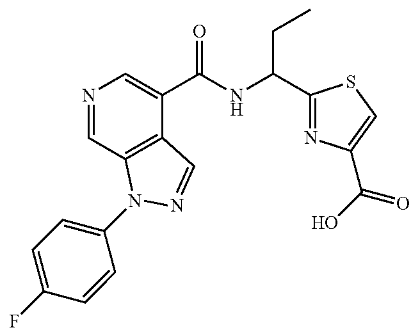 | 2-(1-{[1-(4-Fluoro-phenyl)-1H-pyrazolo[3,4-c]pyridine-4-carbonyl]-amino}-propyl)-thiazole-4-carboxylic acid | 426.6 | 1.36 |

TABLE I-continued

| STRUCTURE | Name | HPLC-MS[a,b] | |
|---|---|---|---|
| | | [M + H]+ | RT (min) |
| 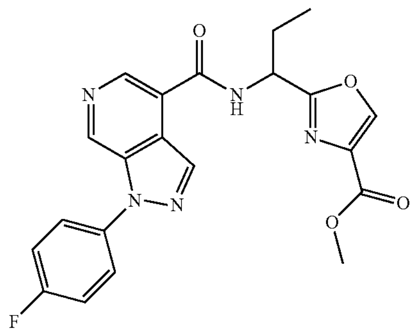 | 2-((S)-1-{[1-(4-Fluorophenyl)-1H-pyrazolo[3,4-c]pyridine-4-carbonyl]-amino}-propyl)-oxazole-4-carboxylic acid methyl ester | 424.7 | 1.50 |
| 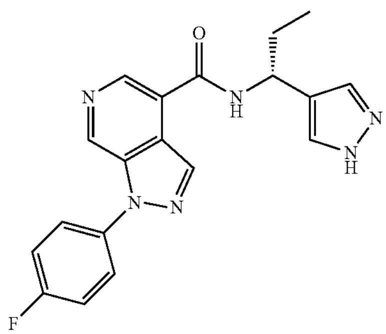 | 1-(4-Fluorophenyl)-1H-pyrazolo[3,4-c]pyridine-4-carboxylic acid [(R)-1-(1H-pyrazol-4-yl)-propyl]-amide | 365.8 | 1.32 |
| 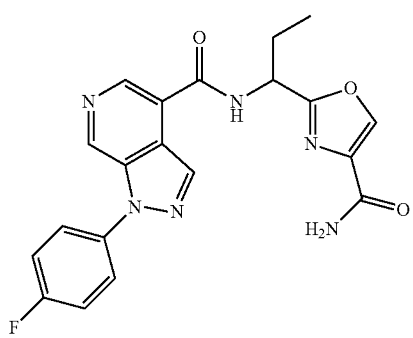 | 1-(4-Fluorophenyl)-1H-pyrazolo[3,4-c]pyridine-4-carboxylic acid [1-(4-carbamoyl-oxazol-2-yl)-propyl]-amide | 409.7 | 1.32 |
| | 1-(4-Fluorophenyl)-1H-pyrazolo[3,4-c]pyridine-4-carboxylic acid [1-(4-methyl-carbamoyl-oxazol-2-yl)-propyl]-amide | 423.7 | 1.37 |

TABLE I-continued

| STRUCTURE | Name | HPLC-MS[a,b] | |
|---|---|---|---|
| | | [M + H]+ | RT (min) |
| 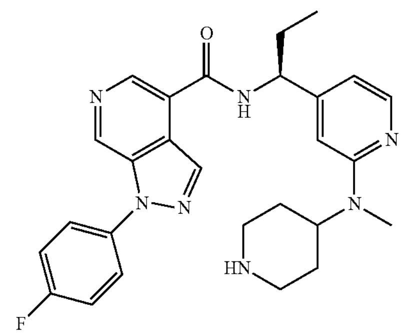 | 1-(4-Fluorophenyl)-1H-pyrazolo[3,4-c]pyridine-4-carboxylic acid {(S)-1-[2-(methyl-piperidin-4-yl-amino)-pyridin-4-yl]-propyl}-amide | 488.7 | 1.05 |
| 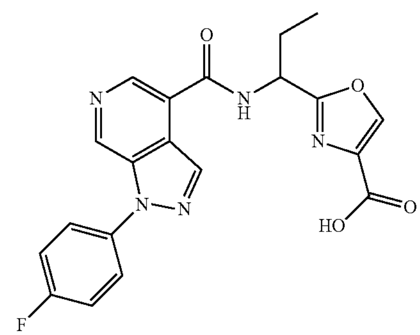 | 2-(1-{[1-(4-Fluorophenyl)-1H-pyrazolo[3,4-c]pyridine-4-carbonyl]-amino}-propyl)-oxazole-4-carboxylic acid | 410.7 | 1.35 |
| 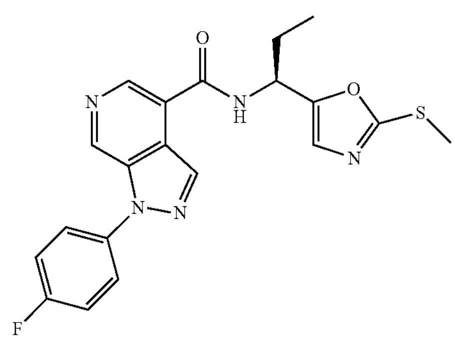 | 1-(4-Fluorophenyl)-1H-pyrazolo[3,4-c]pyridine-4-carboxylic acid [(S)-1-(2-methyl-sulfanyl-oxazol-5-yl)-propyl]-amide | 412.7 | 1.59 |
| 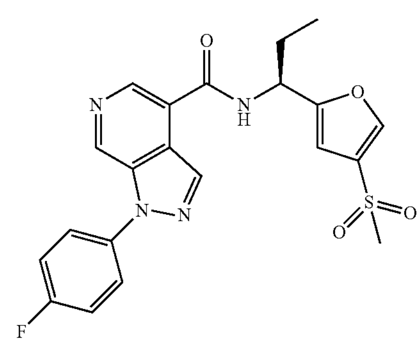 | 1-(4-Fluorophenyl)-1H-pyrazolo[3,4-c]pyridine-4-carboxylic acid [(S)-1-(4-methanesulfonyl-furan-2-yl)-propyl]-amide | 443.7 | 1.51 |

TABLE I-continued

| STRUCTURE | Name | [M + H]+ | RT (min) |
|---|---|---|---|
| 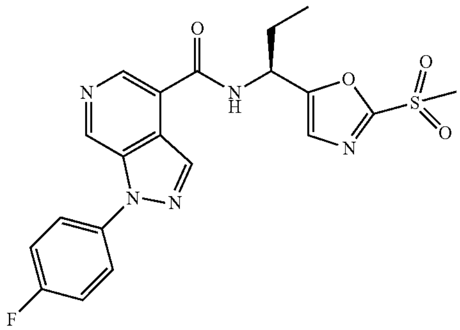 | 1-(4-Fluorophenyl)-1H-pyrazolo[3,4-c]pyridine-4-carboxylic acid [(S)-1-(2-methanesulfonyl-oxazol-5-yl)-propyl]-amide | 444.6 | 1.51 |
| | 1-(4-Fluorophenyl)-1H-pyrazolo[3,4-c]pyridine-4-carboxylic acid (5-bromothiophen-2-ylmethyl)-amide | 431.5/433.5 | 1.74 |
| | 1-(4-Fluorophenyl)-1H-pyrazolo[3,4-c]pyridine-4-carboxylic acid (4-bromothiophen-2-ylmethyl)-amide | 431.5/433.5 | 1.71 |
| 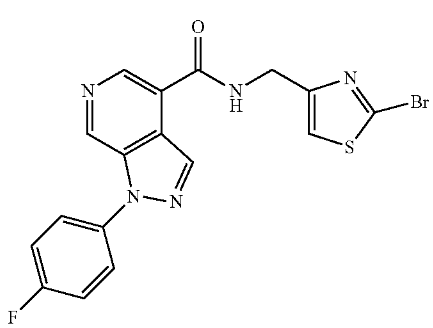 | 1-(4-Fluorophenyl)-1H-pyrazolo[3,4-c]pyridine-4-carboxylic acid (2-bromothiazol-4-ylmethyl)-amide | 432.5/434.5 | 1.55 |

TABLE I-continued

| STRUCTURE | Name | HPLC-MS[a,b] [M + H]+ | RT (min) |
|---|---|---|---|
| 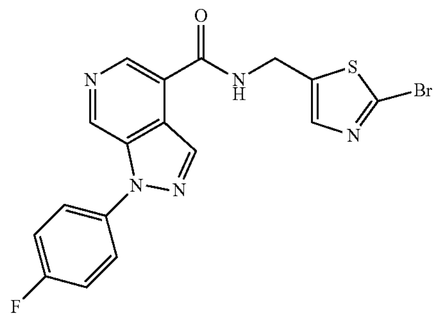 | 1-(4-Fluorophenyl)-1H-pyrazolo[3,4-c]pyridine-4-carboxylic acid (2-bromothiazol-5-ylmethyl)-amide | 432.5/434.5 | 1.56 |
| 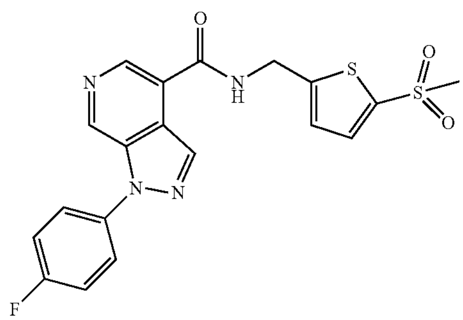 | 1-(4-Fluorophenyl)-1H-pyrazolo[3,4-c]pyridine-4-carboxylic acid (5-methane-sulfonyl-thiophen-2-ylmethyl)-amide | 431.6 | 1.44 |
| 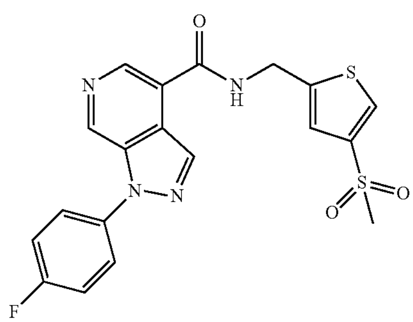 | 1-(4-Fluorophenyl)-1H-pyrazolo[3,4-c]pyridine-4-carboxylic acid (4-methane-sulfonyl-thiophen-2-ylmethyl)-amide | 431.6 | 1.41 |
| 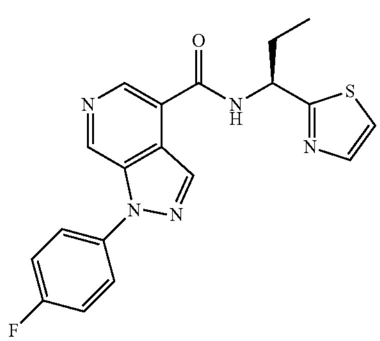 | 1-(4-Fluorophenyl)-1H-pyrazolo[3,4-c]pyridine-4-carboxylic acid ((S)-1-thiazol-2-yl-propyl)-amide | 382.6 | 1.50 |

TABLE I-continued

| STRUCTURE | Name | HPLC-MS[a,b] | |
|---|---|---|---|
| | | [M + H]+ | RT (min) |
| 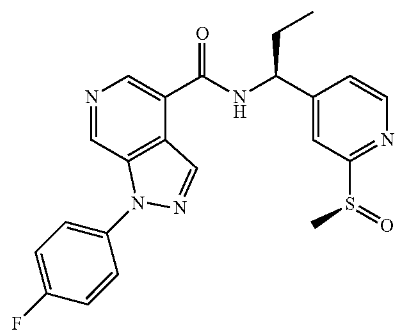 | 1-(4-Fluorophenyl)-1H-pyrazolo[3,4-c]pyridine-4-carboxylic acid {(S)-1-[2-((S)-methanesulfinyl)-pyridin-4-yl]-propyl}-amide | 438.3 | 1.40 |
| 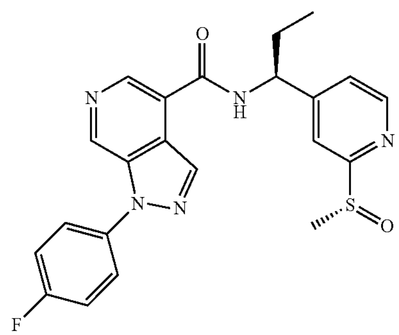 | 1-(4-Fluorophenyl)-1H-pyrazolo[3,4-c]pyridine-4-carboxylic acid {(S)-1-[2-((R)-methanesulfinyl)-pyridin-4-yl]-propyl}-amide | 438.4 | 1.41 |
| 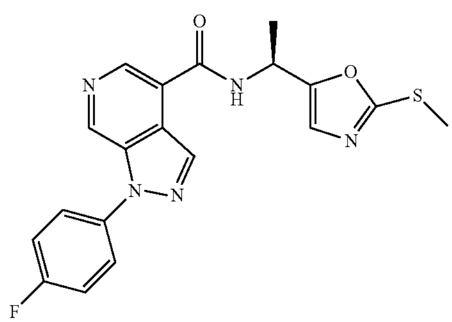 | 1-(4-Fluorophenyl)-1H-pyrazolo[3,4-c]pyridine-4-carboxylic acid [(S)-1-(2-methylsulfanyl-oxazol-5-yl)-ethyl]-amide | 398.6 | 1.50 |
| 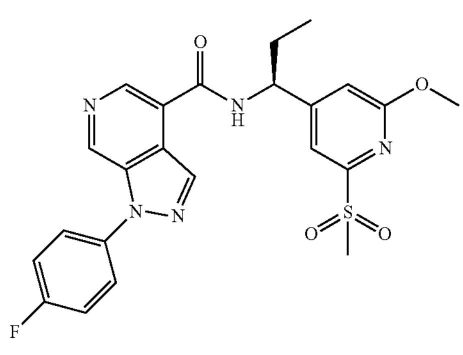 | 1-(4-Fluorophenyl)-1H-pyrazolo[3,4-c]pyridine-4-carboxylic acid [(S)-1-(2-methanesulfonyl-6-methoxy-pyridin-4-yl)-propyl]-amide | 484.6 | 1.60 |

TABLE I-continued

| STRUCTURE | Name | HPLC-MS[a,b] [M + H]+ | RT (min) |
|---|---|---|---|
| 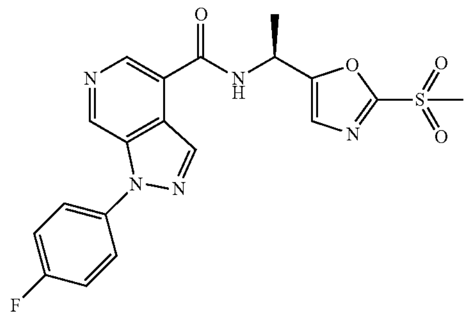 | 1-(4-Fluorophenyl)-1H-pyrazolo[3,4-c]pyridine-4-carboxylic acid [(S)-1-(2-methanesulfonyl-oxazol-5-yl)-ethyl]-amide | 430.6 | 1.43 |
| 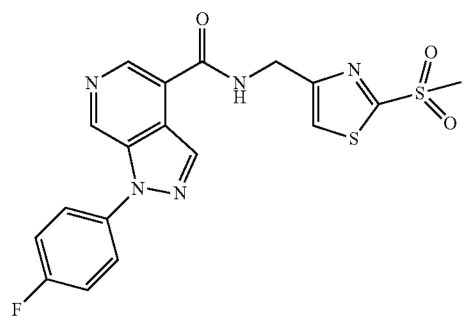 | 1-(4-Fluorophenyl)-1H-pyrazolo[3,4-c]pyridine-4-carboxylic acid (2-methane-sulfonyl-thiazol-4-ylmethyl)-amide | 432.6 | 1.39 |
| 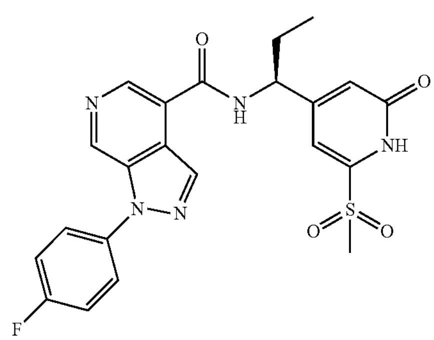 | 1-(4-Fluorophenyl)-1H-pyrazolo[3,4-c]pyridine-4-carboxylic acid [(S)-1-(6-methanesulfonyl-2-oxo-1,2-dihydro-pyridin-4-yl)-propyl]-amide | 470.7 | 1.41 |
| 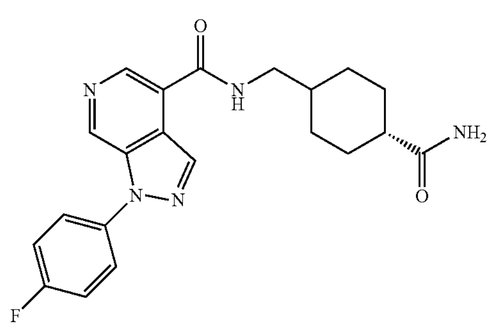 | 1-(4-Fluorophenyl)-1H-pyrazolo[3,4-c]pyridine-4-carboxylic acid (4-carbamoyl-cyclohexylmethyl)-amide | 396.3 | 1.32 |

TABLE I-continued

| STRUCTURE | Name | HPLC-MS[a,b] | |
|---|---|---|---|
| | | [M + H]+ | RT (min) |
| 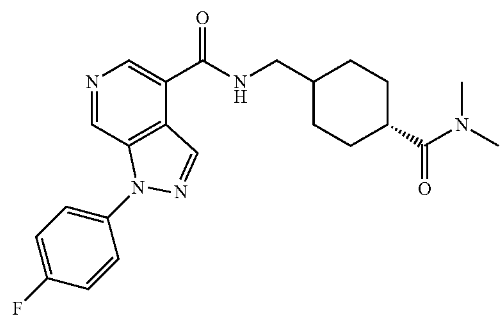 | 1-(4-Fluorophenyl)-1H-pyrazolo[3,4-c]pyridine-4-carboxylic acid (4-dimethyl-carbamoylcyclo-hexylmethyl)-amide | 424.4 | 1.42 |
| 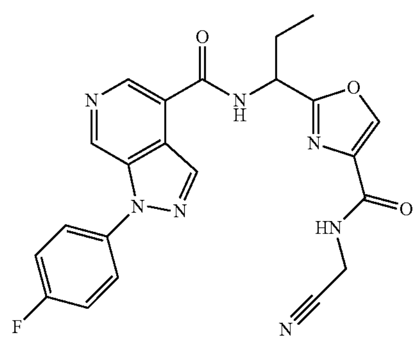 | 1-(4-Fluorophenyl)-1H-pyrazolo[3,4-c]pyridine-4-carboxylic acid {1-[4-(cyano-methyl-carbamoyl)-oxazol-2-yl]-propyl}-amide | 448.7 | 1.43 |
| 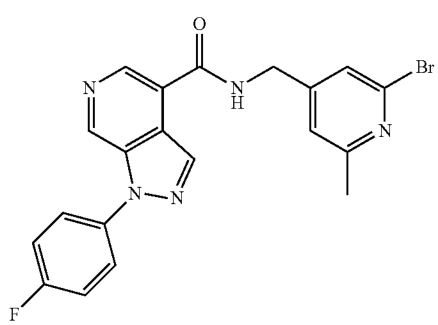 | 1-(4-Fluorophenyl)-1H-pyrazolo[3,4-c]pyridine-4-carboxylic acid (2-bromo-6-methyl-pyridin-4-ylmethyl)-amide | 440.6/442.6 | 1.55 |
| 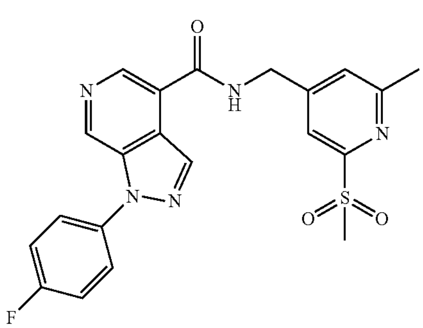 | 1-(4-Fluorophenyl)-1H-pyrazolo[3,4-c]pyridine-4-carboxylic acid (2-methane-sulfonyl-6-methyl-pyridin-4-ylmethyl)-amide | 440.7 | 1.40 |

TABLE I-continued

| STRUCTURE | Name | HPLC-MS[a,b] | |
|---|---|---|---|
| | | [M + H]+ | RT (min) |
| | 1-(4-Fluorophenyl)-1H-pyrazolo[3,4-c]pyridine-4-carboxylic acid (2-methanesulfonyl-thiazol-4-ylmethyl)-amide | 432.5 | 1.40 |
| | 2-(1-{[1-(4-Fluorophenyl)-1H-pyrazolo[3,4-c]pyridine-4-carbonyl]-amino}-propyl)-5-methyl-oxazole-4-carboxylic acid methyl ester | 438.7 | 1.56 |
| 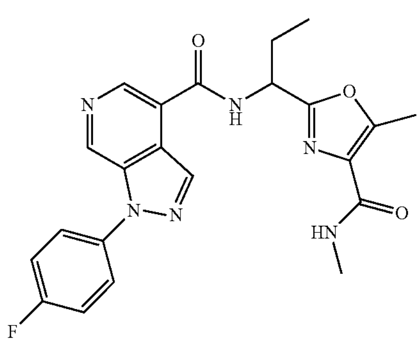 | 1-(4-Fluorophenyl)-1H-pyrazolo[3,4-c]pyridine-4-carboxylic acid [1-(5-methyl-4-methylcarbamoyl-oxazol-2-yl)-propyl]-amide | 437.6 | 1.58 |
| 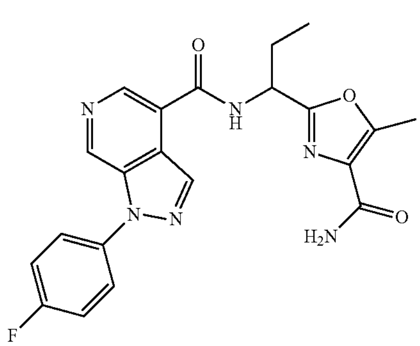 | 1-(4-Fluorophenyl)-1H-pyrazolo[3,4-c]pyridine-4-carboxylic acid [1-(4-carbamoyl-5-methyl-oxazol-2-yl)-propyl]-amide | 423.8 | 1.51 |

TABLE I-continued

| STRUCTURE | Name | HPLC-MS[a,b] | |
|---|---|---|---|
| | | [M + H]+ | RT (min) |
| 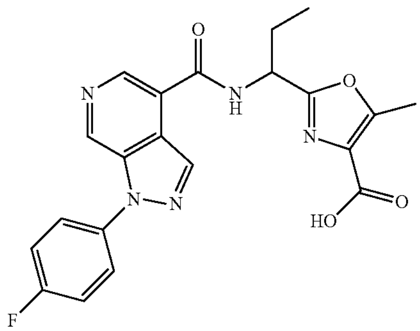 | 2-(1-{[1-(4-Fluorophenyl)-1H-pyrazolo[3,4-c]pyridine-4-carbonyl]-amino}-propyl)-5-methyl-oxazole-4-carboxylic acid | 424.7 | 1.41 |
| 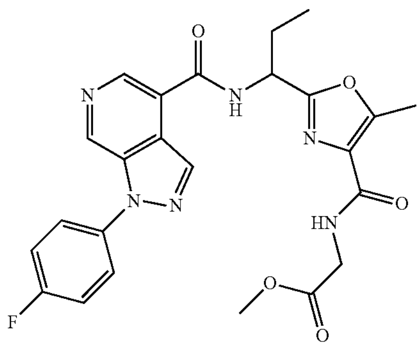 | {[2-(1-{[1-(4-Fluorophenyl)-1H-pyrazolo[3,4-c]pyridine-4-carbonyl]-amino}-propyl)-5-methyl-oxazole-4-carbonyl]-amino}-acetic acid methyl ester | 495.7 | 1.53 |
| 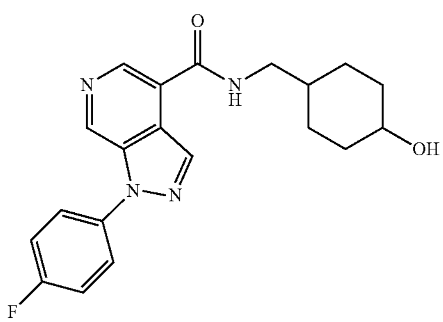 | 1-(4-Fluorophenyl)-1H-pyrazolo[3,4-c]pyridine-4-carboxylic acid (4-hydroxy-cyclohexylmethyl)-amide | 369.6 | 1.27 |
| 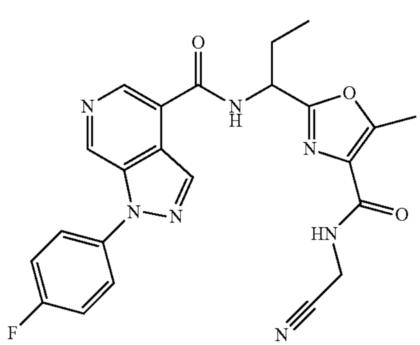 | 1-(4-Fluorophenyl)-1H-pyrazolo[3,4-c]pyridine-4-carboxylic acid {1-[4-(cyano-methyl-carbamoyl)-5-methyl-oxazol-2-yl]-propyl}-amide | 462.7 | 1.49 |

TABLE I-continued

| STRUCTURE | Name | HPLC-MS[a,b] | |
|---|---|---|---|
| | | [M + H]+ | RT (min) |
| 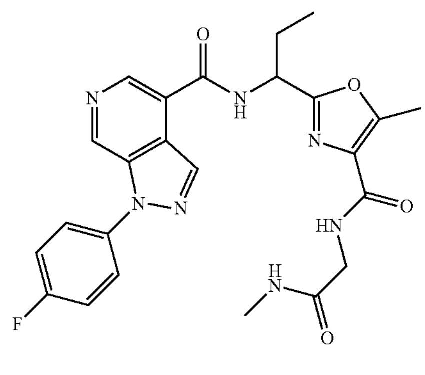 | 1-(4-Fluorophenyl)-1H-pyrazolo[3,4-c]pyridine-4-carboxylic acid {1-[5-methyl-4-(methylcarbamoyl-methylcarbamoyl)-oxazol-2-yl]-propyl}-amide | 494.7 | 1.33 |
| 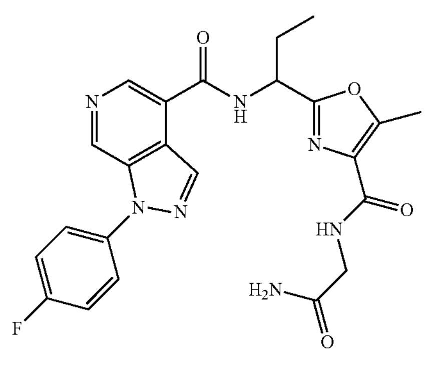 | 1-(4-Fluorophenyl)-1H-pyrazolo[3,4-c]pyridine-4-carboxylic acid{1-[4-(carbamoyl-methylcarbamoyl)-5-methyloxazol-2-yl]-propyl}-amide | 480.7 | 1.61 |
| 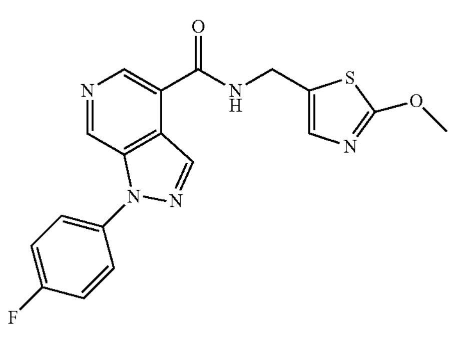 | 1-(4-Fluorophenyl)-1H-pyrazolo[3,4-c]pyridine-4-carboxylic acid (2-methoxy-thiazol-5-ylmethyl)-amide | 384.7 | 1.73 |
| 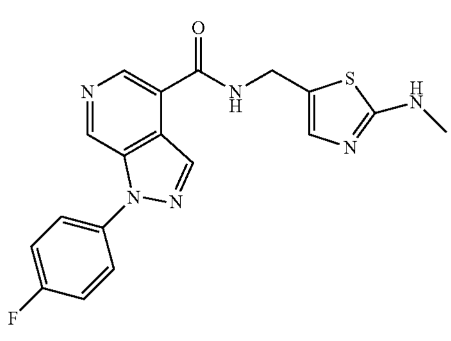 | 1-(4-Fluorophenyl)-1H-pyrazolo[3,4-c]pyridine-4-carboxylic acid (2-methylamino-thiazol-5-ylmethyl)-amide | 383.6 | 1.22 |

TABLE I-continued

| STRUCTURE | Name | [M + H]⁺ | RT (min) |
|---|---|---|---|
| 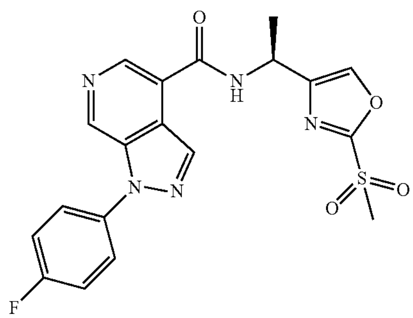 | 1-(4-Fluorophenyl)-1H-pyrazolo[3,4-c]pyridine-4-carboxylic acid [(S)-1-(2-methanesulfonyl-oxazol-4-yl)-ethyl]-amide | 430.6 | 1.44 |
| 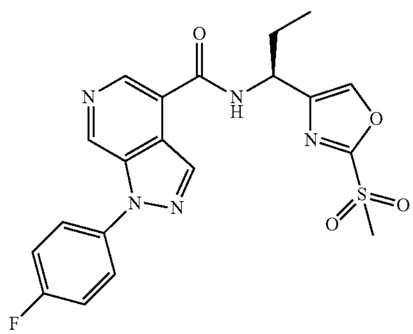 | 1-(4-Fluorophenyl)-1H-pyrazolo[3,4-c]pyridine-4-carboxylic acid [(S)-1-(2-methanesulfonyl-oxazol-4-yl)-propyl]-amide | 444.6 | 1.79 |
| 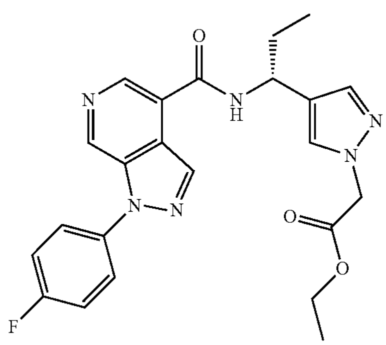 | [4-((R)-1-{[1-(4-Fluorophenyl)-1H-pyrazolo[3,4-c]pyridine-4-carbonyl]-amino}-propyl)-pyrazol-1-yl]-acetic acid ethyl ester | 451.8 | 1.56 |
| 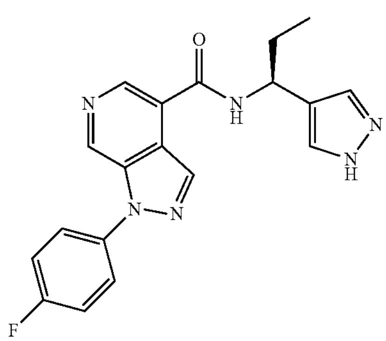 | 1-(4-Fluorophenyl)-1H-pyrazolo[3,4-c]pyridine-4-carboxylic acid [(S)-1-(1H-pyrazol-4-yl)-propyl]-amide | 365.4 | 1.34 |

TABLE I-continued

| STRUCTURE | Name | HPLC-MS[a,b] | |
|---|---|---|---|
| | | [M + H]+ | RT (min) |
| 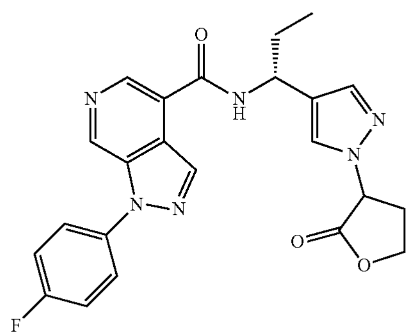 | 1-(4-Fluorophenyl)-1H-pyrazolo[3,4-c]pyridine-4-carboxylic acid {(R)-1-[1-(2-oxo-tetrahydro-furan-3-yl)-1H-pyrazol-4-yl]-propyl}-amide | 449.7 | 1.34 |
| 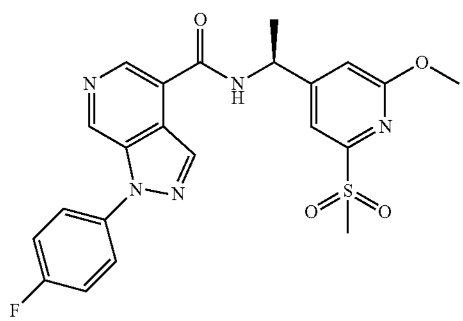 | 1-(4-Fluorophenyl)-1H-pyrazolo[3,4-c]pyridine-4-carboxylic acid [(S)-1-(2-methanesulfonyl-6-methoxy-pyridin-4-yl)-ethyl]-amide | 470.6 | 1.53 |
| 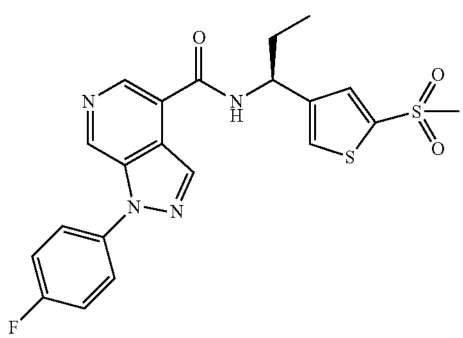 | 1-(4-Fluorophenyl)-1H-pyrazolo[3,4-c]pyridine-4-carboxylic acid [(S)-1-(5-methanesulfonyl-thiophen-3-yl)-propyl]-amide | 459.6 | 1.55 |
| 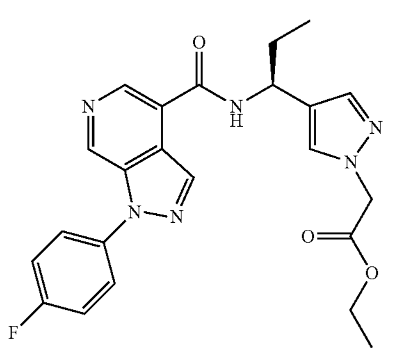 | [4-((S)-1-{[1-(4-Fluorophenyl)-1H-pyrazolo[3,4-c]pyridine-4-carbonyl]-amino}-propyl)-pyrazol-1-yl]-acetic acid ethyl ester | 451.8 | 1.56 |

TABLE I-continued

| STRUCTURE | Name | HPLC-MS[a,b] | |
|---|---|---|---|
| | | [M + H]+ | RT (min) |
| | 1-(4-Fluorophenyl)-1H-pyrazolo[3,4-c]pyridine-4-carboxylic acid [2-(methanesulfonyl-methyl-amino)-pyrimidin-5-ylmethyl]-amide | 456.3 | 1.39 |
| 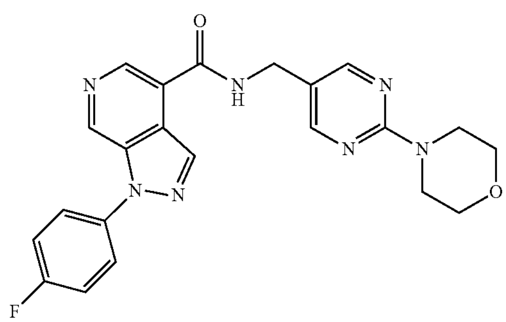 | 1-(4-Fluorophenyl)-1H-pyrazolo[3,4-c]pyridine-4-carboxylic-acid (2-morpholin-4-yl-pyrimidin-5-ylmethyl)-amide | 434.7 | 1.41 |
| 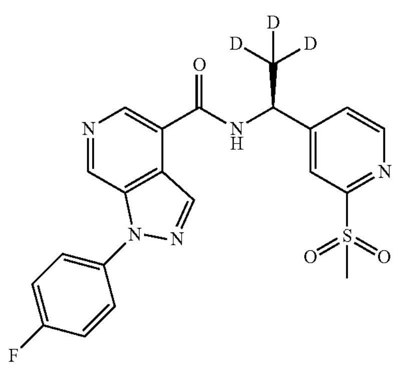 | 1-(4-Fluorophenyl)-1H-pyrazolo[3,4-c]pyridine-4-carboxylic acid [(S)-1-(2-methanesulfonyl-pyridin-4-yl)-ethyl-2,2,2-D3]-amide | 443.7 | 1.39 |
| 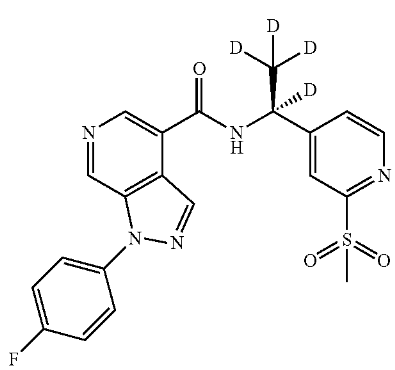 | 1-(4-Fluorophenyl)-1H-pyrazolo[3,4-c]pyridine-4-carboxylic acid [(S)-1-(2-methanesulfonyl-pyridin-4-yl)-ethyl-1,2,2,2-D4]-amide | 444.7 | 1.38 |

TABLE I-continued

| STRUCTURE | Name | HPLC-MS[a,b] | |
|---|---|---|---|
| | | [M + H]+ | RT (min) |
| 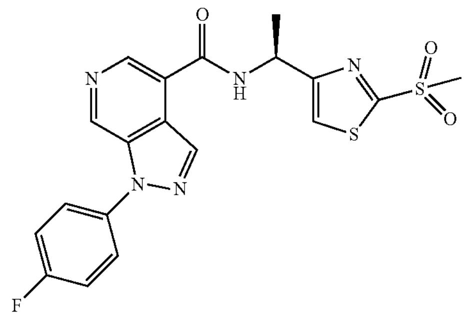 | 1-(4-Fluorophenyl)-1H-pyrazolo[3,4-c]pyridine-4-carboxylic acid [(S)-1-(2-methanesulfonyl-thiazol-4-yl)-ethyl]-amide | 446.5 | 2.20 |
| 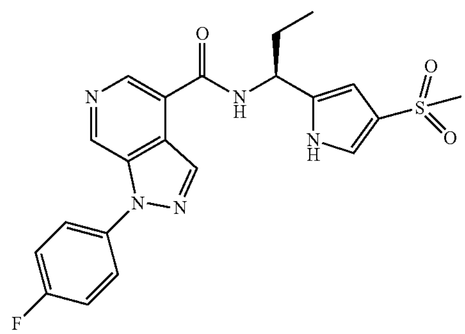 | 1-(4-Fluorophenyl)-1H-pyrazolo[3,4-c]pyridine-4-carboxylic acid [(S)-1-(4-methanesulfonyl-1H-pyrrol-2-yl)-propyl]-amide | 442.4 | 1.37 |
| 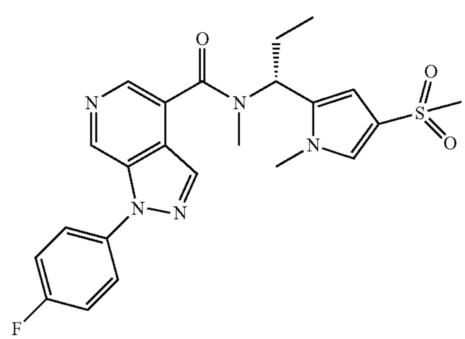 | 1-(4-Fluorophenyl)-1H-pyrazolo[3,4-c]pyridine-4-carboxylic acid [(R)-1-(4-methanesulfonyl-1-methyl-1H-pyrrol-2-yl)-propyl]-methyl-amide | 470.2 | 1.47 |
| 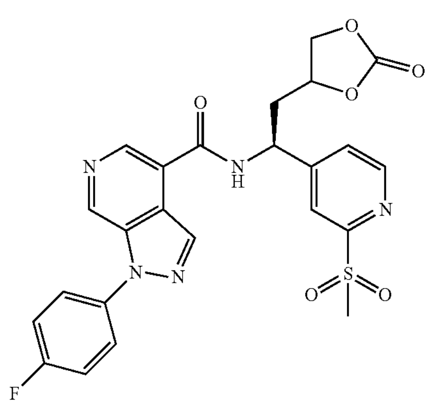 | 1-(4-Fluorophenyl)-1H-pyrazolo[3,4-c]pyridine-4-carboxylic acid [(S)-1-(2-methanesulfonyl-pyridin-4-yl)-2-(2-oxo-1,3-dioxolan-4-yl)-ethyl]-amide | 526.6 | 1.39 |

TABLE I-continued

| STRUCTURE | Name | HPLC-MS[a,b] | |
|---|---|---|---|
| | | [M + H]+ | RT (min) |
| 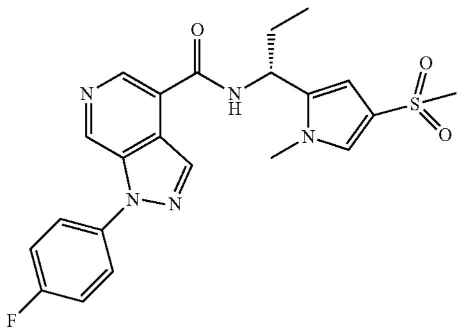 | 1-(4-Fluorophenyl)-1H-pyrazolo[3,4-c]pyridine-4-carboxylic acid [(R)-1-(4-methanesulfonyl-1-methyl-1H-pyrrol-2-yl)-propyl]-amide | 456.7 | 1.46 |
| 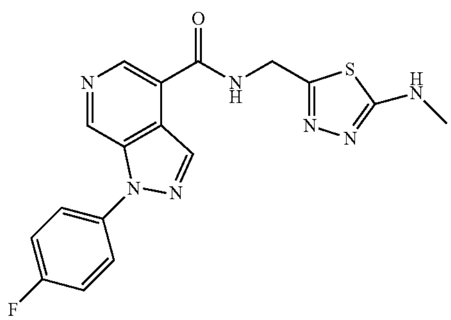 | 1-(4-Fluorophenyl)-1H-pyrazolo[3,4-c]pyridine-4-carboxylic acid (5-methylamino-1,3,4-thiadiazol-2-ylmethyl)-amide | 384.7 | 1.25 |
| 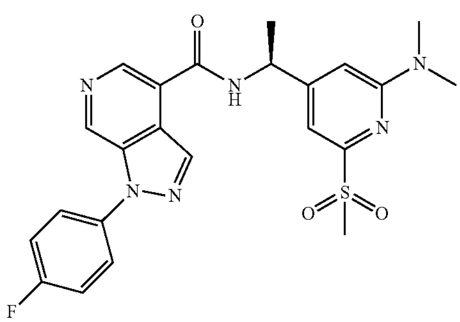 | 1-(4-Fluorophenyl)-1H-pyrazolo[3,4-c]pyridine-4-carboxylic acid [(S)-1-(2-dimethylamino-6-methanesulfonyl-pyridin-4-yl)-ethyl]-amide | 483.7 | 1.56 |
| 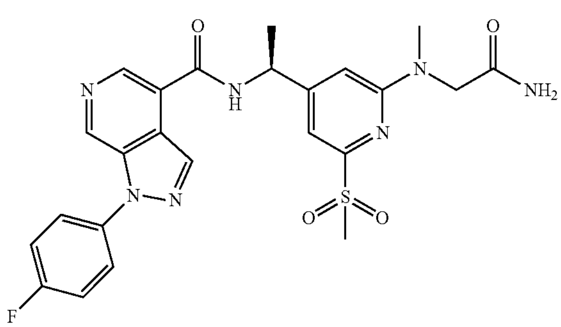 | 1-(4-Fluorophenyl)-1H-pyrazolo[3,4-c]pyridine-4-carboxylic acid {(S)-1-[2-(carbamoylmethyl-methylamino)-6-methanesulfonyl-pyridin-4-yl]-ethyl}-amide | 526.7 | 1.32 |

TABLE I-continued

| STRUCTURE | Name | HPLC-MS[a,b] | |
|---|---|---|---|
| | | [M + H]+ | RT (min) |
| 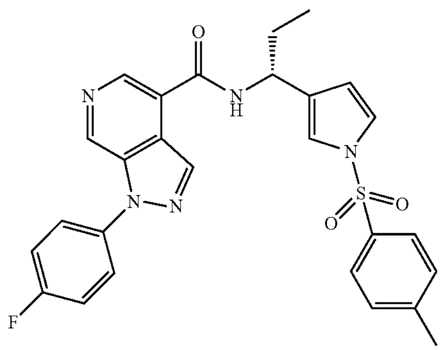 | 1-(4-Fluorophenyl)-1H-pyrazolo[3,4-c]pyridine-4-carboxylic acid {(R)-1-[1-(toluene-4-sulfonyl)-1H-pyrrol-3-yl]-propyl}-amide | 518.7 | 1.95 |
| 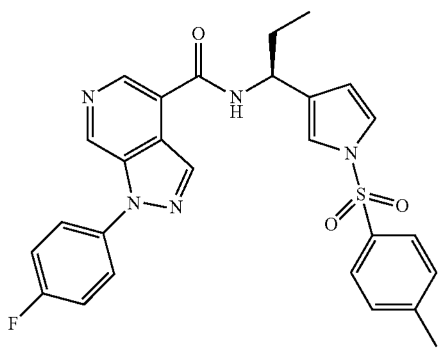 | 1-(4-Fluorophenyl)-1H-pyrazolo[3,4-c]pyridine-4-carboxylic acid {(S)-1-[1-(toluene-4-sulfonyl)-1H-pyrrol-3-yl]-propyl}-amide | 518.7 | 1.74 |
| 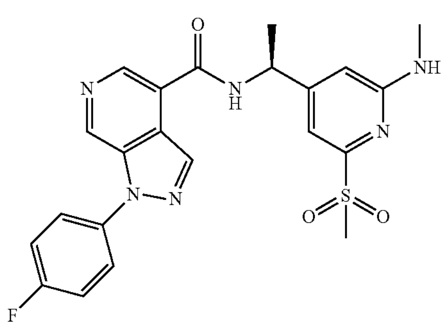 | 1-(4-Fluorophenyl)-1H-pyrazolo[3,4-c]pyridine-4-carboxylic acid [(S)-1-(2-methanesulfonyl-6-methylamino-pyridin-4-yl)-ethyl]-amide | 469.6 | 1.46 |
| 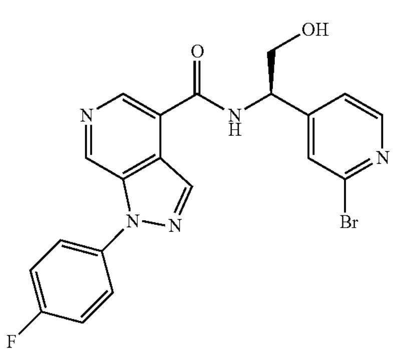 | 1-(4-Fluorophenyl)-1H-pyrazolo[3,4-c]pyridine-4-carboxylic acid [(R)-1-(2-bromo-pyridin-4-yl)-2-hydroxy-ethyl]-amide | 456.5/458.5 | 1.35 |

TABLE I-continued

| STRUCTURE | Name | HPLC-MS[a,b] | |
|---|---|---|---|
| | | [M + H]+ | RT (min) |
| 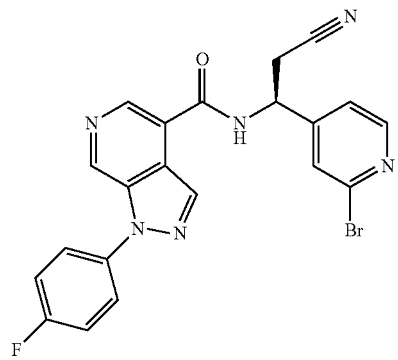 | 1-(4-Fluorophenyl)-1H-pyrazolo[3,4-c]pyridine-4-carboxylic acid [(S)-1-(2-bromo-pyridin-4-yl)-2-cyano-ethyl]-amide | 465.6/467.6 | 1.52 |
| 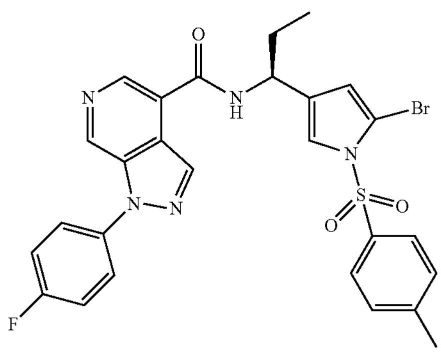 | 1-(4-Fluorophenyl)-1H-pyrazolo[3,4-c]pyridine-4-carboxylic acid {(S)-1-[5-bromo-1-(toluene-4-sulfonyl)-1H-pyrrol-3-yl]-propyl}-amide | 596.6/598.4 | 1.98 |
| 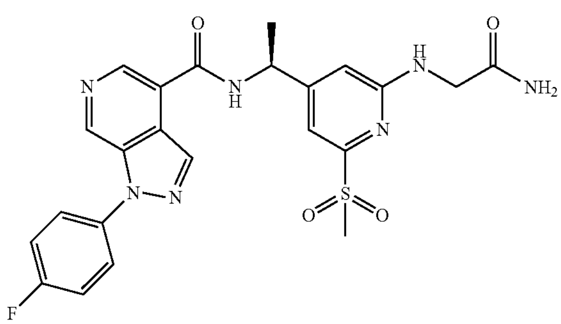 | 1-(4-Fluorophenyl)-1H-pyrazolo[3,4-c]pyridine-4-carboxylic acid {(S)-1-[2-(carbamoylmethyl-amino)-6-methane-sulfonyl-pyridin-4-yl]-ethyl}-amide | 510.9 | 1.26 |
| 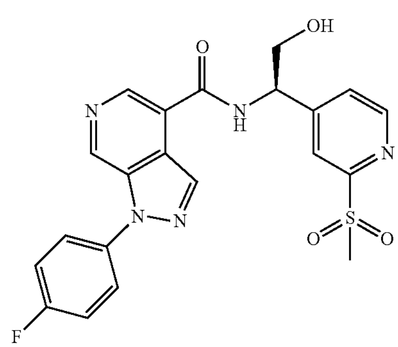 | 1-(4-Fluorophenyl)-1H-pyrazolo[3,4-c]pyridine-4-carboxylic acid [(R)-2-hydroxy-1-(2-methane-sulfonyl-pyridin-4-yl)-ethyl]-amide | 456.6 | 1.26 |

TABLE I-continued

| STRUCTURE | Name | HPLC-MS[a,b] [M + H]+ | RT (min) |
|---|---|---|---|
| | 1-(4-Fluorophenyl)-1H-pyrazolo[3,4-c]pyridine-4-carboxylic acid [(S)-2-cyano-1-(2-methanesulfonyl-pyridin-4-yl)-ethyl]-amide | 465.6 | 1.39 |
| 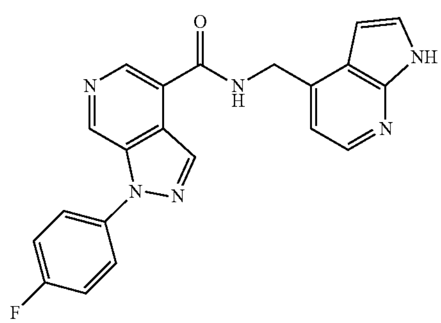 | 1-(4-Fluorophenyl)-1H-pyrazolo[3,4-c]pyridine-4-carboxylic acid (1H-pyrrolo[2,3-b]pyridin-4-ylmethyl)-amide | 387.7 | 1.24 |
| 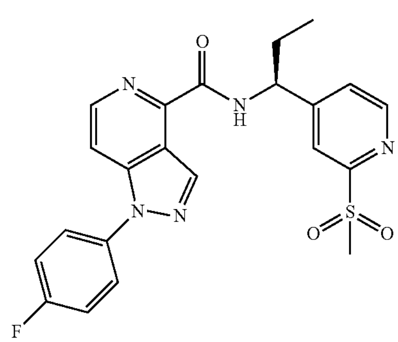 | 1-(4-Fluorophenyl)-1H-pyrazolo[4,3-c]pyridine-4-carboxylic acid [(S)-1-(2-methanesulfonyl-pyridin-4-yl)-propyl]-amide | 454.7 | 1.64 |
| 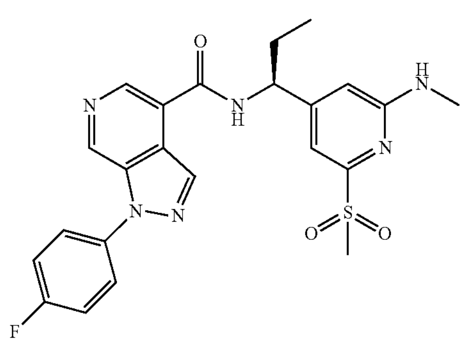 | 1-(4-Fluorophenyl)-1H-pyrazolo[3,4-c]pyridine-4-carboxylic acid [(S)-1-(2-methanesulfonyl-6-methyl-amino-pyridin-4-yl)-propyl]-amide | 483.7 | 1.51 |

TABLE I-continued

| STRUCTURE | Name | HPLC-MS[a,b] | |
|---|---|---|---|
| | | [M + H]+ | RT (min) |
| 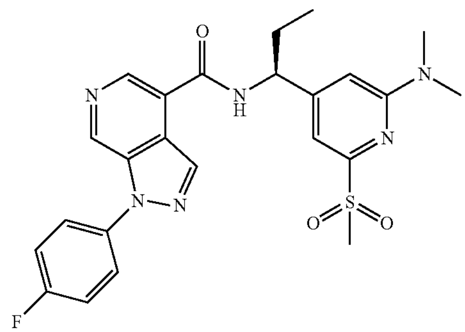 | 1-(4-Fluorophenyl)-1H-pyrazolo[3,4-c]pyridine-4-carboxylic acid [(S)-1-(2-dimethylamino-6-methanesulfonyl-pyridin-4-yl)-propyl]-amide | 497.7 | 1.56 |
| 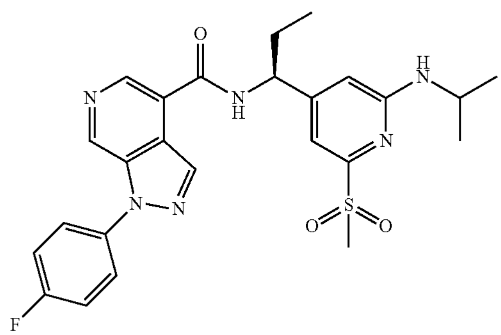 | 1-(4-Fluorophenyl)-1H-pyrazolo[3,4-c]pyridine-4-carboxylic acid [(S)-1-(2-isopropylamino-6-methanesulfonyl-pyridin-4-yl) propyl]-amide | 511.7 | 1.59 |
| 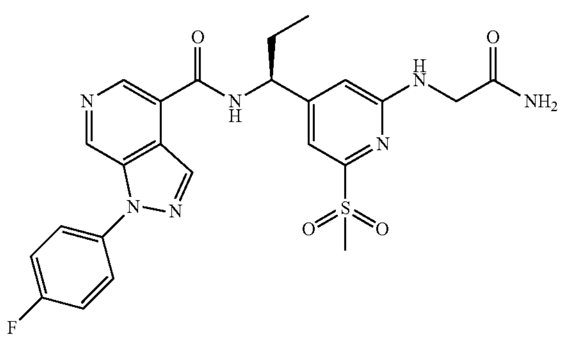 | 1-(4-Fluorophenyl)-1H-pyrazolo[3,4-c]pyridine-4-carboxylic acid {(S)-1-[2-(carbamoylmethyl-amino)-6-methane-sulfonyl-pyridin-4-yl]-propyl}-amide | 526.7 | 1.32 |
| 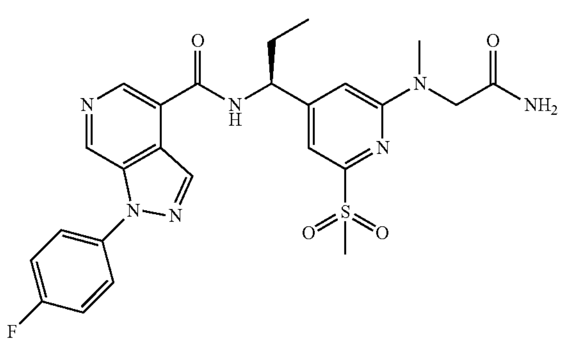 | 1-(4-Fluorophenyl)-1H-pyrazolo[3,4-c]pyridine-4-carboxylic acid {(S)-1-[2-(carba-moylmethyl-methyl-amino)-6-methane-sulfonyl-pyridin-4-yl]-propyl}-amide | 540.6 | 1.35 |

TABLE I-continued

| STRUCTURE | Name | HPLC-MS[a,b] [M + H]+ | RT (min) |
|---|---|---|---|
| 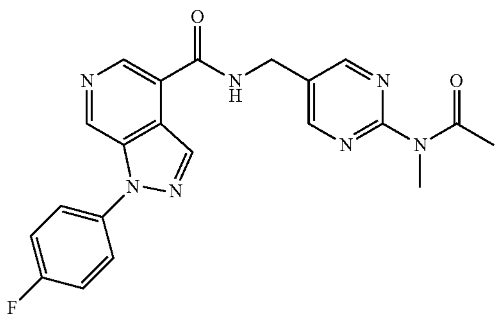 | 1-(4-Fluorophenyl)-1H-pyrazolo[3,4-c]pyridine-4-carboxylic acid [2-(acetyl-methyl-amino)-pyrimidin-5-yl-methyl]-amide | 420.7 | 1.33 |
| 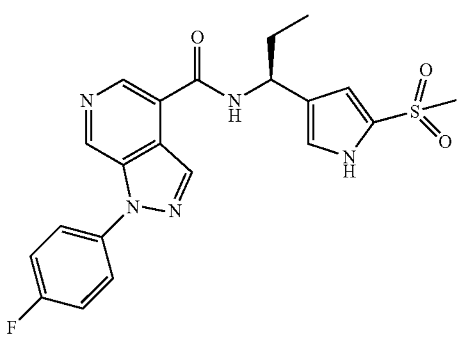 | 1-(4-Fluorophenyl)-1H-pyrazolo[3,4-c]pyridine-4-carboxylic acid [(S)-1-(5-methanesulfonyl-1H-pyrrol-3-yl)-propyl]-amide | 440.9 | 1.43 |
| 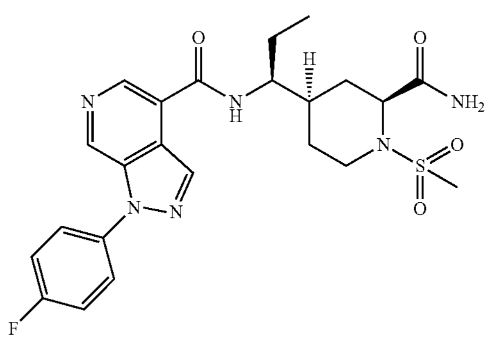 | 1-(4-Fluorophenyl)-1H-pyrazolo[3,4-c]pyridine-4-carboxylic acid [(S)-1-((2S,4R)-2-carbamoyl-1-methanesulfonyl-piperidin-4-yl)-propyl]-amide | 503.6 | 1.33 |
| 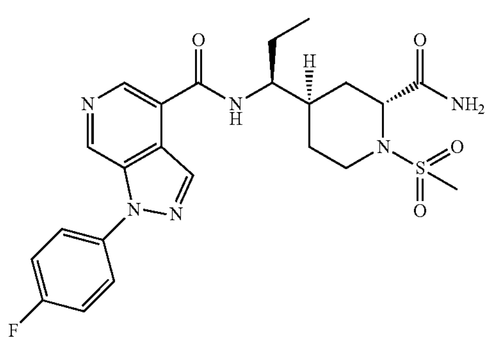 | 1-(4-Fluorophenyl)-1H-pyrazolo[3,4-c]pyridine-4-carboxylic acid [(S)-1-((2R,4R)-2-carbamoyl-1-methanesulfonyl-piperidin-4-yl)-propyl]-amide | 503.6 | 1.30 |

TABLE I-continued

| STRUCTURE | Name | HPLC-MS[a,b] | |
|---|---|---|---|
| | | [M + H]+ | RT (min) |
| 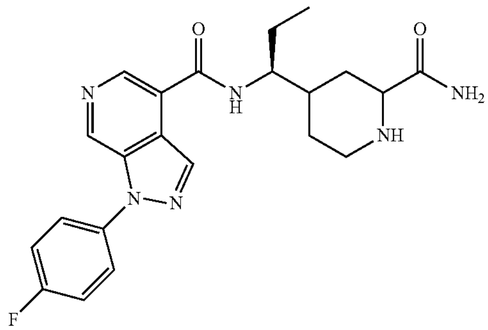 | 1-(4-Fluorophenyl)-1H-pyrazolo[3,4-c]pyridine-4-carboxylic acid [(S)-1-(2-carbamoyl-piperidin-4-yl)-propyl]-amide | 425.5 | 1.13 |
| 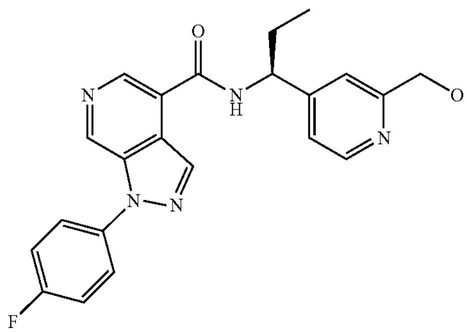 | 1-(4-Fluorophenyl)-1H-pyrazolo[3,4-c]pyridine-4-carboxylic acid [(S)-1-(2-hydroxymethyl-pyridin-4-yl)-propyl]-amide | 406.6 | 1.15 |
| 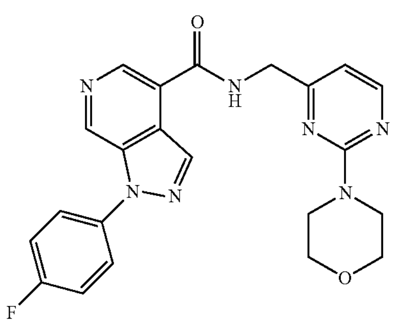 | 1-(4-Fluorophenyl)-1H-pyrazolo[3,4-c]pyridine-4-carboxylic acid (2-morpholin-4-yl-pyrimidin-4-ylmethyl)-amide | 434.8 | 1.42 |
| 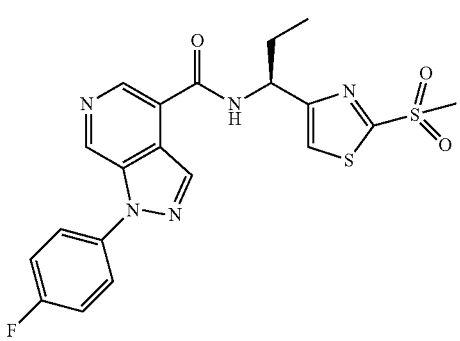 | 1-(4-Fluorophenyl)-1H-pyrazolo[3,4-c]pyridine-4-carboxylic acid [(S)-1-(2-methane-sulfonyl-thiazol-4-yl)-propyl]-amide | 460.7 | 1.52 |

TABLE I-continued

| STRUCTURE | Name | HPLC-MS[a,b] | |
|---|---|---|---|
| | | [M + H]+ | RT (min) |
| | 1-(4-Fluorophenyl)-1H-pyrazolo[3,4-c]pyridine-4-carboxylic acid (1-methanesulfonyl-1H-pyrrolo[2,3-b]pyridin-4-ylmethyl)-amide | 465.6 | 1.49 |
| | 1-(4-Fluorophenyl)-1H-pyrazolo[3,4-c]pyridine-4-carboxylic acid [2-(methanesulfonyl-methyl-amino)-pyrimidin-4-ylmethyl]-amide | 456.7 | 1.42 |
| | 1-(4-Fluorophenyl)-1H-pyrazolo[3,4-c]pyridine-4-carboxylic acid {1-[2-(methanesulfonyl-methyl-amino)-pyrimidin-5-yl]-propyl}-amide | 484.6 | 1.52 |
| | 1-(4-Fluorophenyl)-1H-pyrazolo[3,4-c]pyridine-4-carboxylic acid [2-(carbamoyl-methyl-methyl-amino)-6-methanesulfonyl-pyridin-4-ylmethyl]-amide | 512.7 | 1.28 |

TABLE I-continued

| STRUCTURE | Name | HPLC-MS[a,b] | |
|---|---|---|---|
| | | [M + H]+ | RT (min) |
| 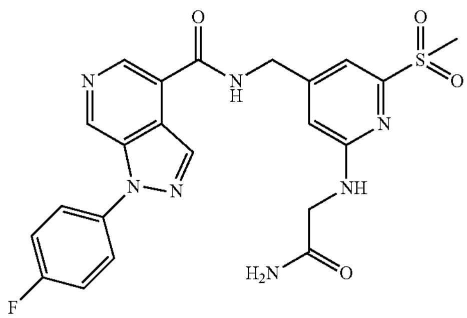 | 1-(4-Fluorophenyl)-1H-pyrazolo[3,4-c]pyridine-4-carboxylic acid [2-(carbamoyl-methyl-amino)-6-methanesulfonyl-pyridin-4-yl-methyl]-amide | 498.7 | 1.24 |
| 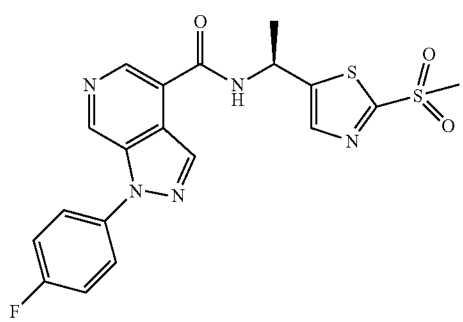 | 1-(4-Fluorophenyl)-1H-pyrazolo[3,4-c]pyridine-4-carboxylic acid [(S)-1-(2-methanesulfonyl-thiazol-5-yl)-ethyl]-amide | 446.5 | 1.45 |
| 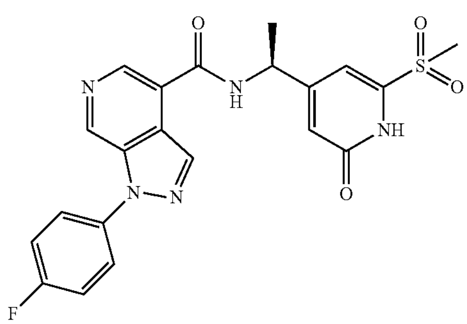 | 1-(4-Fluorophenyl)-1H-pyrazolo[3,4-c]pyridine-4-carboxylic acid [(S)-1-(6-methanesulfonyl-2-oxo-1,2-dihydro-pyridin-4-yl)-ethyl]-amide | 456.6 | 1.35 |
| 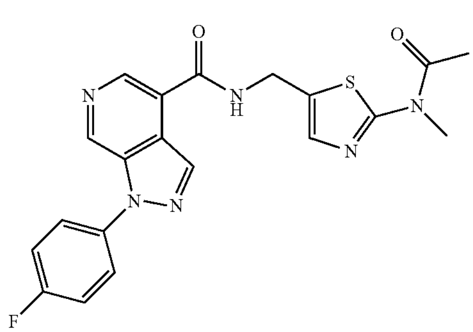 | 1-(4-Fluorophenyl)-1H-pyrazolo[3,4-c]pyridine-4-carboxylic acid [2-(acetyl-methyl-amino)-thiazol-5-ylmethyl]-amide | 425.7 | 1.39 |

TABLE I-continued

| STRUCTURE | Name | [M + H]⁺ | RT (min) |
|---|---|---|---|
| 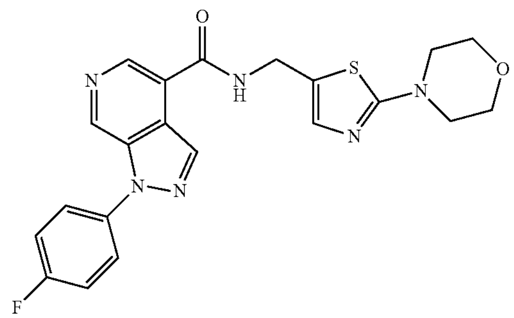 | 1-(4-Fluorophenyl)-1H-pyrazolo[3,4-c]pyridine-4-carboxylic acid (2-morpholin-4-yl-thiazol-5-ylmethyl)-amide | 439.7 | 1.32 |
| 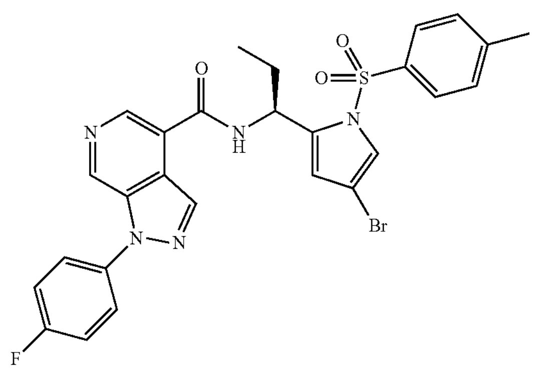 | 1-(4-Fluorophenyl)-1H-pyrazolo[3,4-c]pyridine-4-carboxylic acid {(S)-1-[4-bromo-1-(toluene-4-sulfonyl)-1H-pyrrol-2-yl]-propyl}-amide | 596.6/598.6 | 2.03 |
| 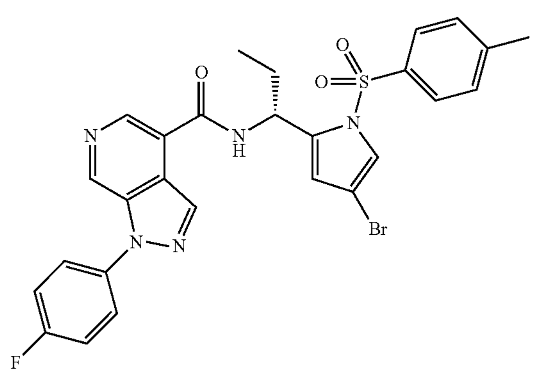 | 1-(4-Fluorophenyl)-1H-pyrazolo[3,4-c]pyridine-4-carboxylic acid {(R)-1-[4-bromo-1-(toluene-4-sulfonyl)-1H-pyrrol-2-yl]-propyl}-amide | 596.6/598.6 | 2.04 |
| 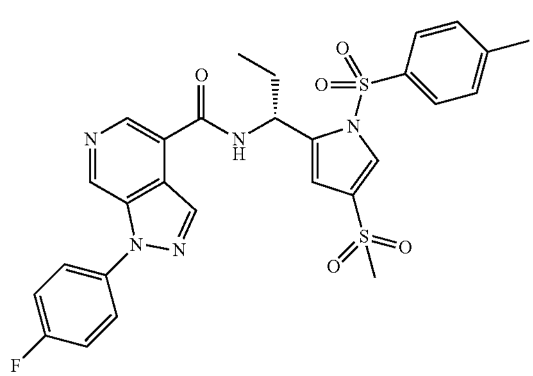 | 1-(4-Fluorophenyl)-1H-pyrazolo[3,4-c]pyridine-4-carboxylic acid {(R)-1-[4-methanesulfonyl-1-(toluene-4-sulfonyl)-1H-pyrrol-2-yl]-propyl}-amide | 596.5 | 1.65 |

TABLE I-continued

| STRUCTURE | Name | HPLC-MS[a,b] | |
|---|---|---|---|
| | | [M + H]+ | RT (min) |
| 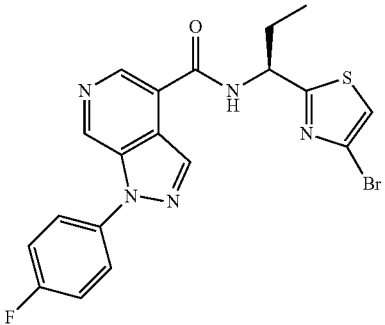 | 1-(4-Fluorophenyl)-1H-pyrazolo[3,4-c]pyridine-4-carboxylic acid [(S)-1-(4-bromo-thiazol-2-yl)-propyl]-amide | 460.0/462.1 | 1.64 |
| 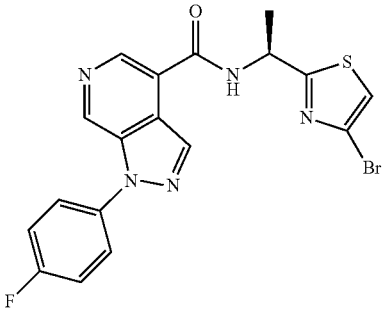 | 1-(4-Fluorophenyl)-1H-pyrazolo[3,4-c]pyridine-4-carboxylic acid [(S)-1-(4-bromo-thiazol-2-yl)-ethyl]-amide | 446.1/448.1 | 1.58 |
| 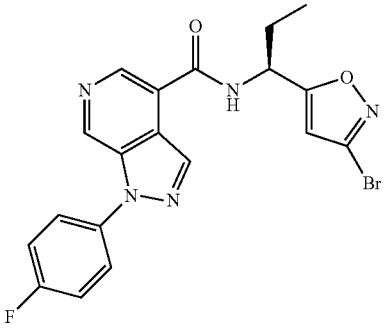 | 1-(4-Fluorophenyl)-1H-pyrazolo[3,4-c]pyridine-4-carboxylic acid [(S)-1-(3-bromo-isoxazol-5-yl)-propyl]-amide | 444.0/446.0 | 1.63 |
| 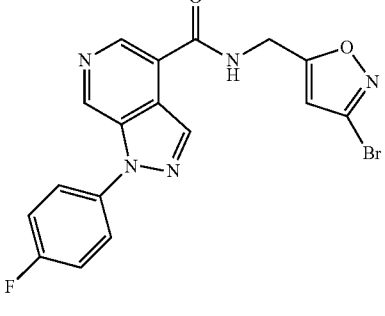 | 1-(4-Fluorophenyl)-1H-pyrazolo[3,4-c]pyridine-4-carboxylic acid (3-bromo-isoxazol-5-ylmethyl)-amide | 416.0/417.9 | 1.51 |

TABLE I-continued

| STRUCTURE | Name | [M + H]+ | RT (min) |
|---|---|---|---|
| 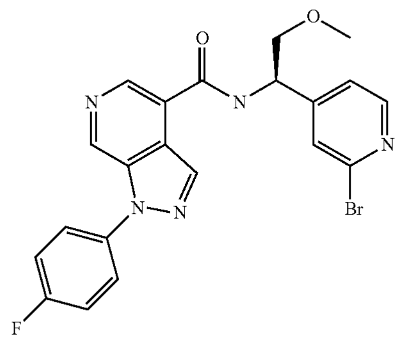 | 1-(4-Fluorophenyl)-1H-pyrazolo[3,4-c]pyridine-4-carboxylic acid [(R)-1-(2-bromo-pyridin-4-yl)-2-methoxy-ethyl]-amide | 470.0/472.0 | 1.52 |
| 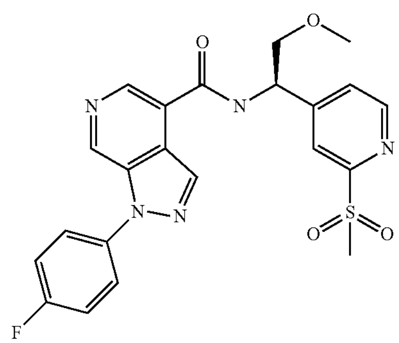 | 1-(4-Fluorophenyl)-1H-pyrazolo[3,4-c]pyridine-4-carboxylic acid [(R)-1-(2-methanesulfonyl-pyridin-4-yl)-2-methoxy-ethyl]-amide | 470.1 | 1.41 |
| 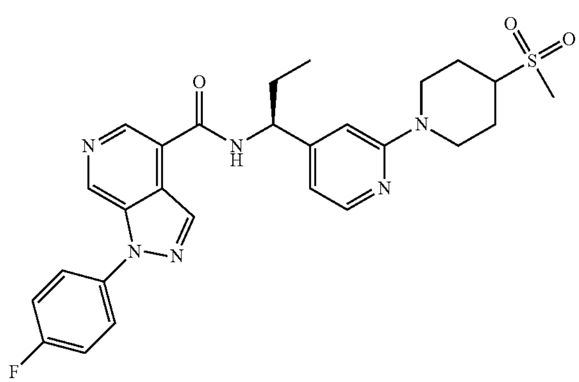 | 1-(4-Fluorophenyl)-1H-pyrazolo[3,4-c]pyridine-4-carboxylic acid [(S)-1-(4-methanesulfonyl-3,4,5,6-tetrahydro-2H-[1,2']bipyridinyl-4'-yl)-propyl]-amide | 537.1 | 0.63 |
| 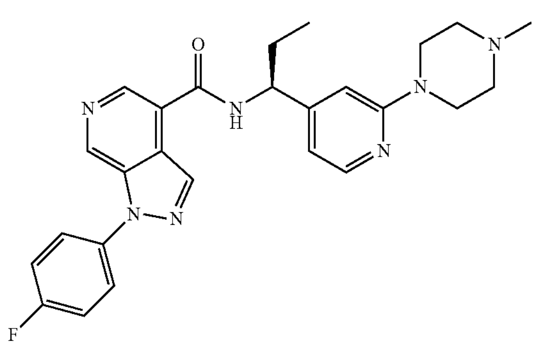 | 1-(4-Fluorophenyl)-1H-pyrazolo[3,4-c]pyridine-4-carboxylic acid {(S)-1-[2-(4-methyl-piperazin-1-yl)-pyridin-4-yl]-propyl}-amide | 474.1 | 0.58 |

TABLE I-continued

| STRUCTURE | Name | HPLC-MS[a,b] | |
|---|---|---|---|
| | | [M + H]+ | RT (min) |
| 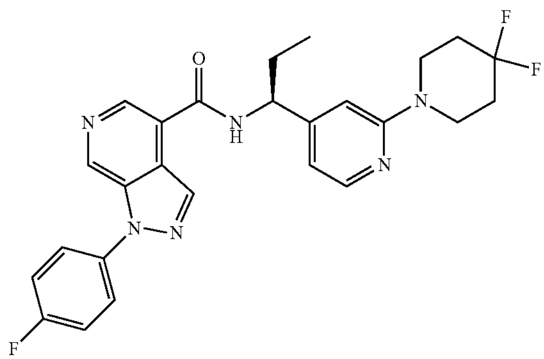 | 1-(4-Fluorophenyl)-1H-pyrazolo[3,4-c]pyridine-4-carboxylic acid [(S)-1-(4,4-difluoro-3,4,5,6-tetrahydro-2H-[1,2']bipyridinyl-4'-yl)-propyl]-amide | 495.9 | 0.80 |
| 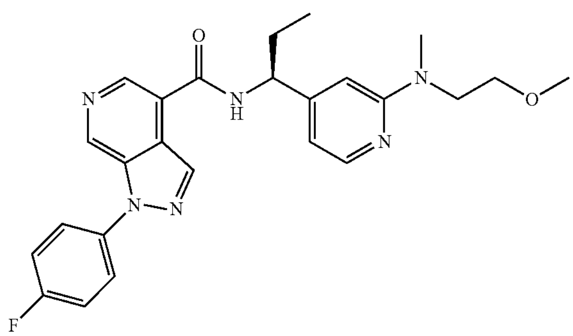 | 1-(4-Fluorophenyl)-1H-pyrazolo[3,4-c]pyridine-4-carboxylic acid ((S)-1-{2-[(2-methoxy-ethyl)-methyl-amino]-pyridin-4-yl}-propyl)-amide | 463.0 | 0.64 |
| 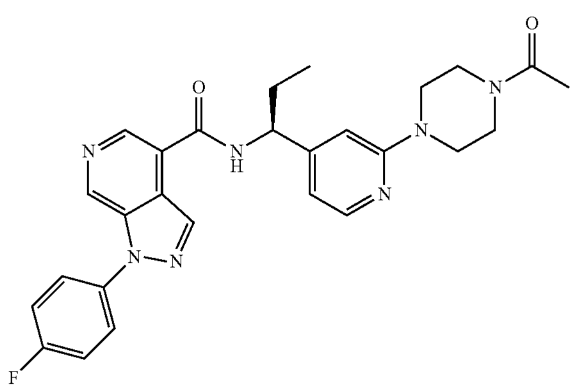 | 1-(4-Fluorophenyl)-1H-pyrazolo[3,4-c]pyridine-4-carboxylic acid {(S)-1-[2-(4-acetyl-piperazin-1-yl)-pyridin-4-yl]-propyl}-amide | 502.2 | 0.61 |
| | 1-(4-Fluorophenyl)-1H-pyrazolo[3,4-c]pyridine-4-carboxylic acid {(S)-1-[2-(1,1-dioxo-1$\lambda^6$-thio-morpholin-4-yl)-pyridin-4-yl]-propyl}-amide | 509.1 | 0.77 |

TABLE I-continued

| STRUCTURE | Name | [M + H]+ | RT (min) |
|---|---|---|---|
| 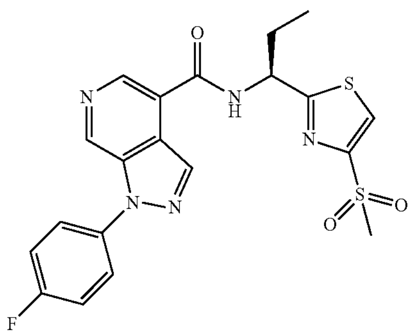 | 1-(4-Fluorophenyl)-1H-pyrazolo[3,4-c]pyridine-4-carboxylic acid [(S)-1-(4-methanesulfonyl-thiazol-2-yl)-propyl]-amide | 460.1 | 1.46 |
| 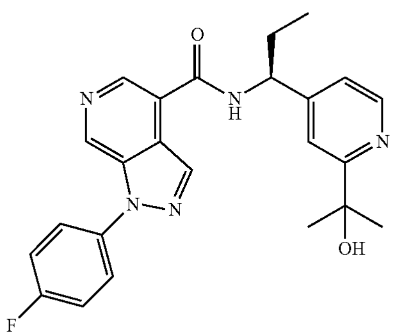 | 1-(4-Fluorophenyl)-1H-pyrazolo[3,4-c]pyridine-4-carboxylic acid {(S)-1-[2-(1-hydroxy-1-methyl-ethyl)-pyridin-4-yl]-propyl}-amide | 434.0 | 1.18 |
| 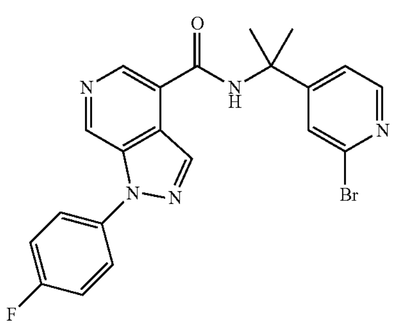 | 1-(4-Fluorophenyl)-1H-pyrazolo[3,4-c]pyridine-4-carboxylic acid [1-(2-bromo-pyridin-4-yl)-1-methyl-ethyl]-amide | 454.1/456.0 | 1.54 |
| 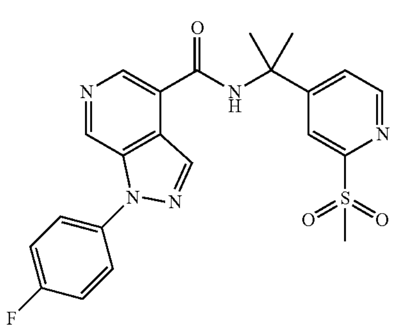 | 1-(4-Fluorophenyl)-1H-pyrazolo[3,4-c]pyridine-4-carboxylic acid [1-(2-methane-sulfonyl-pyridin-4-yl)-1-methyl-ethyl]-amide | 454.6 | 1.41 |

TABLE I-continued

| STRUCTURE | Name | HPLC-MS[a,b] | |
|---|---|---|---|
| | | [M + H]+ | RT (min) |
| 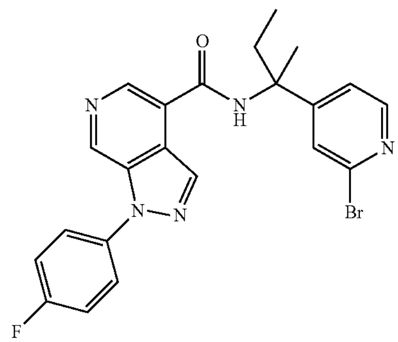 | 1-(4-Fluorophenyl)-1H-pyrazolo[3,4-c]pyridine-4-carboxylic acid [1-(2-bromo-pyridin-4-yl)-1-methyl-propyl]-amide | 468.1/470.0 | 1.64 |
| 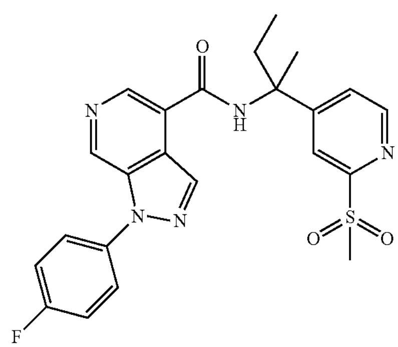 | 1-(4-Fluorophenyl)-1H-pyrazolo[3,4-c]pyridine-4-carboxylic acid [1-(2-methane-sulfonyl-pyridin-4-yl)-1-methyl-propyl]-amide | 468.2 | 1.46 |
| 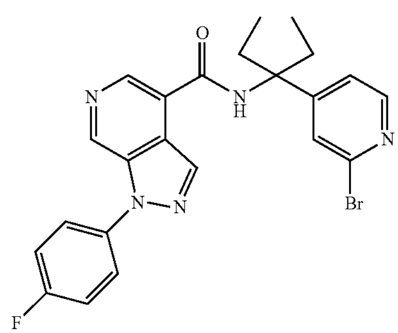 | 1-(4-Fluorophenyl)-1H-pyrazolo[3,4-c]pyridine-4-carboxylic acid [1-(2-bromo-pyridin-4-yl)-1-ethyl-propyl]-amide | 482.1/484.0 | 1.67 |
| 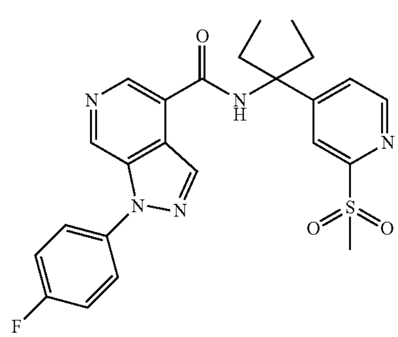 | 1-(4-Fluorophenyl)-1H-pyrazolo[3,4-c]pyridine-4-carboxylic acid [1-ethyl-1-(2-methanesulfonyl-pyridin-4-yl)-propyl]-amide | 482.2 | 1.50 |

TABLE I-continued

| STRUCTURE | Name | HPLC-MS[a,b] [M + H]+ | RT (min) |
|---|---|---|---|
| 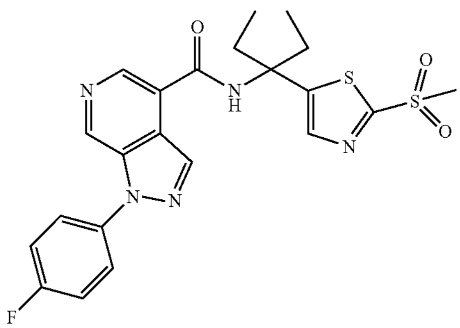 | 1-(4-Fluorophenyl)-1H-pyrazolo[3,4-c]pyridine-4-carboxylic acid [1-ethyl-1-(2-methanesulfonyl-thiazol-5-yl)-propyl]-amide | 488.6 | 1.61 |
| 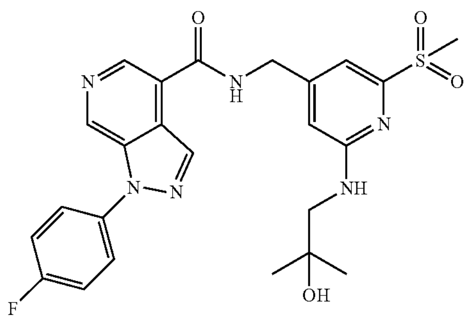 | 1-(4-Fluorophenyl)-1H-pyrazolo[3,4-c]pyridine-4-carboxylic acid [2-(2-hydroxy-2-methyl-propyl-amino)-6-methane-sulfonyl-pyridin-4-ylmethyl]-amide | 513.2 | 1.37 |

[a] See Synthetic Example Section of HPLC-MS methods
[b] The observed mass for bromo containing compounds are reported in Table I as M+ and M + 2. or the pharmaceutically acceptable salts thereof.

For all compounds disclosed hereinabove in this application, in the event the nomenclature is in conflict with the structure, it shall be understood that the compound is defined by the structure.

Another aspect of the invention provides for a process of making a compound of the formula (I):

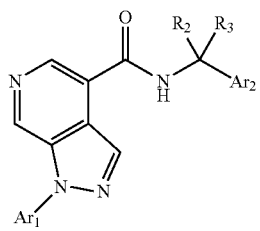

(I)

wherein $Ar_1$, $Ar_2$, $R_3$ and $R_2$ are defined in separate embodiments as they are defined in each of the separate embodiments for formula (I) above;

comprising:

i) reacting a compound of the formula (II) (wherein $X_1$ and $X_2$ are each independently a halogen chosen from Br and I) with compound of the formula (III) (free base or a suitable salt form such as a hydrochloride salt) to provide a compound of the formula (IV):

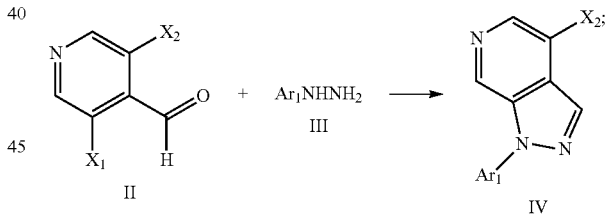

wherein the reaction is performed in a suitable polar aprotic solvent such as NMP, DMF, DMAC, or DMPU, preferably NMP; with a suitable base such as an aqueous hydroxide base such as KOH, NaOH, LiOH or CsOH, or an alkoxide base such as NaOMe, NaOEt, KOt-Bu or KOt-amyl, preferably, KOH; at a temperature range of 20-100° C., preferably, most preferably about 80° C.;

ii) carboxylating IV with a suitable reagent such as Grignard reagent R—MgCl with $CO_2$ in a polar aprotic solvent such as THF, MTBE, $Et_2O$, DME or dioxane, wherein R is chosen from isopropyl, n-butyl, sec-butyl and cyclohexyl, preferably isopropyl;

wherein the reaction is performed at a temperature range of −70 to 30° C., most preferably about −20° C.;

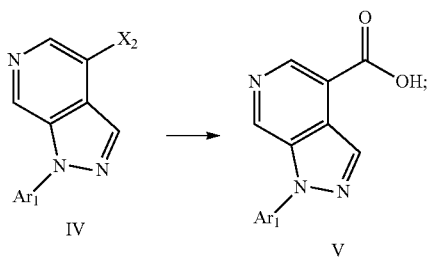

iii) reacting (V) with an activating agent such as propylphosphonic anhydride or CDI (N,N-carbonyldiimidazole), (preferably propylphosphonic anhydride), and an amine of the formula (VI) in the presence of an amine base such as N-methylmorpholine, triethylamine, or diisopropylethylamine, in a suitable polar aprotic solvent such as DMF, or NMP, DMAC, DMPU to provide (I), and subsequently isolating (I),

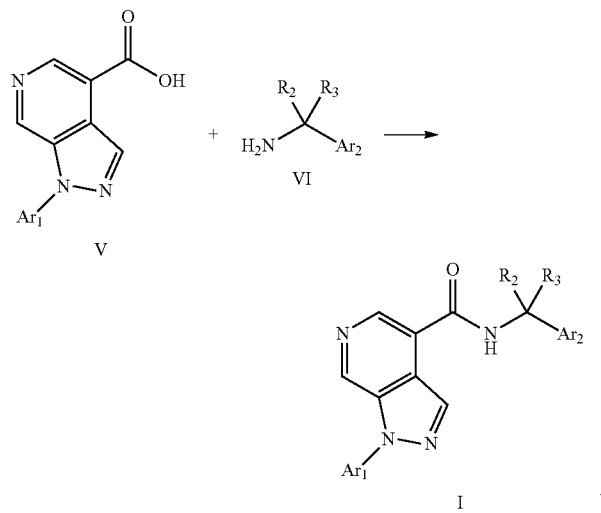

In another aspect of the invention there is provided a process of making a compound of the formula (IV):

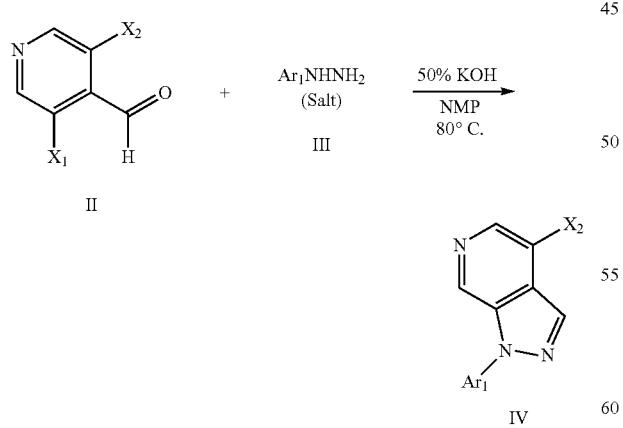

wherein
$X_1$ and $X_2$ are each independently a halogen chosen from Br and I;
$Ar_1$ is defined as above;
wherein the reaction is performed in a suitable polar aprotic solvent such as NMP, DMF, DMAC, or DMPU, preferably NMP; with a suitable base such as an aqueous hydroxide base such as KOH, NaOH, LiOH or CsOH, or an alkoxide base such as NaOMe, NaOEt, KOt-Bu or KOt-amyl, preferably, most preferably KOH; at a temperature range of 20-100° C., most preferably about 80° C.;
to provide a compound of the formula (IV), and optionally subsequently isolating (IV).

In another aspect of the invention there is provided a process of making a compound of the formula (VIa):

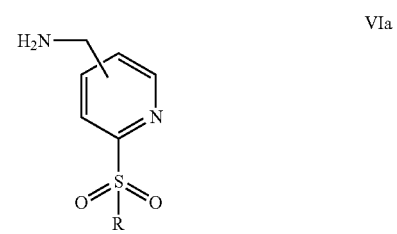

in the form of a salt, preferably an HCl salt, comprising
i) reacting the compound (VII) with NaS-R wherein R is chosen from C1-10 alkyl and aryl, in the presence of a polar solvent such as THF, diethyl ether, 1,4-dioxane, methyl tert-butyl ether, NMP, DMF, DMAC, preferably THF, at 0 to 100° C., preferably 55° C., and subsequently oxidizing with $NaBO_3$ in AcOH to provide the sulfone of formula (VIII);

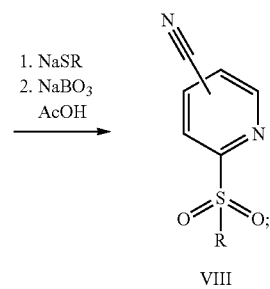

ii) reacting compound VIII with $NaBH_4$ in the presence of an acid such as TFA (trifluoroacetic acid), chlorotrimethylsilane, zinc bromide, and sulfuric acid, preferably TFA and zinc bromide, in a polar solvent, preferably an ether based solvent, more preferably chosen from THF, diethyl ether, 1,4-dioxane, methyl tert-butyl ether and 1,2-dimethoxyethane, most preferably THF, at 0-40° C., preferably 20-25° C., and subsequently adding a protecting group, such as $Boc_2O$ (tert-butoxycarbonyl anhydride) or acetic anhydride or trifluoroacetic anhydride, preferably $Boc_2O$, to provide the protected amine IX:

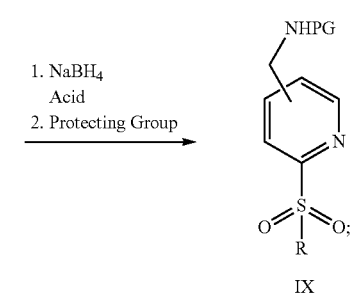

iii) removing the protecting group (PG) with an acid such as HCl or TFA, preferably HCl, in a polar solvent, such as isopropanol, methanol, ethanol, n-propanol, and n-butanol, preferably isopropanol, at 20 to 80° C., preferably 65° C., to provide the desired compound of formula VIa:

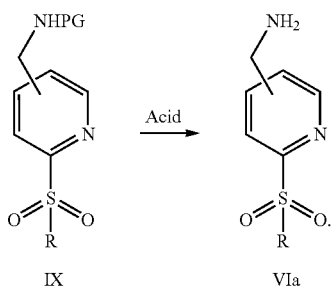

DMF=dimethylformamide
NMP=N-methylpyrrolidinone
DMAC=N,N-dimethylacetamide
DMPU=N,N'-dimethylpropylene urea
MTBE=methyl tert-butyl ether
DME=1,2-dimethoxyethane The invention also relates to pharmaceutical preparations, containing as active substance one or more compounds of the invention, or the pharmaceutically acceptable derivatives thereof, optionally combined with conventional excipients and/or carriers.

Compounds of the invention also include their isotopically-labelled forms. An isotopically-labelled form of an active agent of a combination of the present invention is identical to said active agent but for the fact that one or more atoms of said active agent have been replaced by an atom or atoms having an atomic mass or mass number different from the atomic mass or mass number of said atom which is usually found in nature. Examples of isotopes which are readily available commercially and which can be incorporated into an active agent of a combination of the present invention in accordance with well established procedures, include isotopes of hydrogen, carbon, nitrogen, oxygen, phosphorous, fluorine and chlorine, e.g., $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. An active agent of a combination of the present invention, a prodrug thereof, or a pharmaceutically acceptable salt of either which contains one or more of the above-mentioned isotopes and/or other isotopes of other atoms is contemplated to be within the scope of the present invention.

The invention includes the use of any compounds of described above containing one or more asymmetric carbon atoms may occur as racemates and racemic mixtures, single enantiomers, diastereomeric mixtures and individual diastereomers. Isomers shall be defined as being enantiomers and diastereomers. All such isomeric forms of these compounds are expressly included in the present invention. Each stereogenic carbon may be in the R or S configuration, or a combination of configurations.

Some of the compounds of the invention can exist in more than one tautomeric form. The invention includes methods using all such tautomers.

All terms as used herein in this specification, unless otherwise stated, shall be understood in their ordinary meaning as known in the art. For example, "$C_{1-4}$ alkoxy" is a $C_{1-4}$ alkyl with a terminal oxygen, such as methoxy, ethoxy, propoxy, butoxy. All alkyl, alkenyl and alkynyl groups shall be understood as being branched or unbranched where structurally possible and unless otherwise specified. Other more specific definitions are as follows:

Carbocycles include hydrocarbon rings containing from three to twelve carbon atoms. These carbocycles may be either aromatic or non-aromatic ring systems. The non-aromatic ring systems may be mono- or polyunsaturated. Preferred carbocycles include but are not limited to cyclopropyl, cyclobutyl, cyclopentyl, cyclopentenyl, cyclohexyl, cyclohexenyl, cycloheptanyl, cycloheptenyl, phenyl, indanyl, indenyl, benzocyclobutanyl, dihydronaphthyl, tetrahydronaphthyl, naphthyl, decahydronaphthyl, benzocycloheptanyl and benzocycloheptenyl. Certain terms for cycloalkyl such as cyclobutanyl and cyclobutyl shall be used interchangeably.

The term "heterocycle" refers to a stable nonaromatic 4-8 membered (but preferably, 5 or 6 membered) monocyclic or nonaromatic 8-11 membered bicyclic or spirocyclic heterocycle radical which may be either saturated or unsaturated. Each heterocycle consists of carbon atoms and one or more, preferably from 1 to 4 heteroatoms chosen from nitrogen, oxygen and sulfur. The heterocycle may be attached by any atom of the cycle, which results in the creation of a stable structure.

The term "heteroaryl" shall be understood to mean an aromatic 5-8 membered monocyclic or 8-11 membered bicyclic ring containing 1-4 heteroatoms such as N, O and S.

Unless otherwise stated, heterocycles and heteroaryl include but are not limited to, for example furanyl, pyranyl, benzoxazolyl, benzothiazolyl, benzimidazolyl, tetrahydropyranyl, dioxanyl, dioxolanyl, tetrahydrofuranyl, oxazolyl, isoxazolyl, thiazolyl, pyrazolyl, pyrrolyl, imidazolyl, thienyl, thiadiazolyl, thiomorpholinyl, 1,1-dioxo-1$\lambda^6$-thiomorpholinyl, morpholinyl, pyridinyl, pyrimidinyl, pyridazinyl, pyrazinyl, triazinyl, pyrrolidinyl, piperidinyl, piperazinyl, purinyl, quinolinyl, dihydro-2H-quinolinyl, isoquinolinyl, quinazolinyl, indazolyl, thieno[2,3-d]pyrimidinyl, indolyl, isoindolyl, benzofuranyl, benzopyranyl and benzodioxolyl.

The term "heteroatom" as used herein shall be understood to mean atoms other than carbon such as O, N, S and P.

In all alkyl groups or carbon chains one or more carbon atoms can be optionally replaced by heteroatoms: O, S or N, it shall be understood that if N is not substituted then it is NH, it shall also be understood that the heteroatoms may replace either terminal carbon atoms or internal carbon atoms within a branched or unbranched carbon chain. Such groups can be substituted as herein above described by groups such as oxo to result in definitions such as but not limited to: alkoxycarbonyl, acyl, amido and thioxo.

The term "aryl" as used herein shall be understood to mean aromatic carbocycle or heteroaryl as defined herein. Each aryl or heteroaryl unless otherwise specified includes it's partially or fully hydrogenated derivative. For example, quinolinyl may include decahydroquinolinyl and tetrahydroquinolinyl, naphthyl may include its hydrogenated derivatives such as tetrahydranaphthyl. Other partially or fully hydrogenated derivatives of the aryl and heteroaryl compounds described herein will be apparent to one of ordinary skill in the art.

As used herein, "nitrogen" and "sulfur" include any oxidized form of nitrogen and sulfur and the quaternized form of any basic nitrogen. For example, for an —S—$C_{1-6}$ alkyl radical, unless otherwise specified, this shall be understood to include —S(O)—$C_{1-6}$ alkyl and —S(O)$_2$—$C_{1-6}$ alkyl.

The term "alkyl" refers to a saturated aliphatic radical containing from one to ten carbon atoms or a mono- or polyunsaturated aliphatic hydrocarbon radical containing from two to twelve carbon atoms. A mono- or polyunsaturated aliphatic hydrocarbon radical must contain at least one double or triple bond, respectively. "Alkyl" refers to both branched and unbranched alkyl groups. It should be understood that any combination term using an "alk" or "alkyl" prefix refers to analogs according to the above definition of "alkyl".

For example, terms such as "alkoxy", "alkylhio" refer to alkyl groups linked to a second group via an oxygen or sulfur atom. "Alkanoyl" refers to an alkyl group linked to a carbonyl group (C=O).

The term "halogen" as used in the present specification shall be understood to mean bromine, chlorine, fluorine or iodine, preferably fluorine. The definitions "halogenated", "partially or fully halogenated"; partially or fully fluorinated; "substituted by one or more halogen atoms", includes for example, mono, di or tri halo derivatives on one or more carbon atoms. For alkyl, a nonlimiting example would be —$CH_2CHF_2$, —$CF_3$ etc.

Each alkyl, carbocycle, heterocycle or heteroaryl, or the analogs thereof, described herein shall be understood to be optionally partially or fully halogenated.

The compounds of the invention are only those which are contemplated to be 'chemically stable' as will be appreciated by those skilled in the art. For example, a compound which would have a 'dangling valency', or a 'carbanion' are not compounds contemplated by the inventive methods disclosed herein.

The invention includes pharmaceutically acceptable derivatives of compounds of formula (I). A "pharmaceutically acceptable derivative" refers to any pharmaceutically acceptable salt or ester, or any other compound which, upon administration to a patient, is capable of providing (directly or indirectly) a compound useful for the invention, or a pharmacologically active metabolite or pharmacologically active residue thereof. A pharmacologically active metabolite shall be understood to mean any compound of the invention capable of being metabolized enzymatically or chemically. This includes, for example, hydroxylated or oxidized derivative compounds of the invention.

Pharmaceutically acceptable salts include those derived from pharmaceutically acceptable inorganic and organic acids and bases. Examples of suitable acids include hydrochloric, hydrobromic, sulfuric, nitric, perchloric, fumaric, maleic, phosphoric, glycolic, lactic, salicylic, succinic, toluene-p-sulfuric, tartaric, acetic, citric, methanesulfonic, formic, benzoic, malonic, naphthalene-2-sulfuric and benzenesulfonic acids. Other acids, such as oxalic acid, while not themselves pharmaceutically acceptable, may be employed in the preparation of salts useful as intermediates in obtaining the compounds and their pharmaceutically acceptable acid addition salts. Salts derived from appropriate bases include alkali metal (e.g., sodium), alkaline earth metal (e.g., magnesium), ammonium and N—$(C_1-C_4$ alkyl$)_4^+$ salts.

In addition, within the scope of the invention is use of prodrugs of compounds of the invention. Prodrugs include those compounds that, upon simple chemical transformation, are modified to produce compounds of the invention. Simple chemical transformations include hydrolysis, oxidation and reduction. Specifically, when a prodrug is administered to a patient, the prodrug may be transformed into a compound disclosed hereinabove, thereby imparting the desired pharmacological effect.

The compounds of formula I may be made using the general synthetic methods described below, which also constitute part of the invention.

General Synthetic Methods

The invention additionally provides for methods for making compounds of formula I. The compounds of the invention may be prepared by the general methods and examples presented below, and methods known to those of ordinary skill in the art and reported in the chemical literature. Unless otherwise specified, solvents, temperatures, pressures, and other reaction conditions may be readily selected by one of ordinary skill in the art. Specific procedures are provided in the Synthetic Examples section. Intermediate benzyl amines are commercially available, or may be synthesized via catalytic reduction of the corresponding aryl nitriles with Pd/C (Van Rompaey, K. et al. *Tetrahedron*, 2003, 59 (24), 4421) or Raney Ni (Gould, F. et al. *J. Org. Chem.*, 1960, 25, 1658) or through displacement of a benzyl bromide with sodium azide and reduction. Intermediate aminomethylpyridines may also be commercially available or prepared by methods known to those skilled in the art. For example, methods of preparing 1-substituted-1-(pyridyl)methylamines from aldehydes or ketones are known (see, Kuduk, S. D. et al. *Tetrahedron Lett.* 2004, 45, 6641 and Chelucci, G. *Tetrahedron: Asymmetry* 2006, 17, 3163) and methods of preparing homoallylic primary amines are known (see, Kobayashi, S. et al. *J. Am. Chem. Soc.* 2006, 128, 11038). Methods of preparing 2,2,2-trifluoro-1-pyridyl-ethylamine are known (see, Olah, G. A., et al. *Angew. Chem. Int. Ed.* 2001, 40, 589). Intermediate carbocyclyl or heterocyclyl hydrazines may also be commercially available or prepared by methods known to those skilled in the art (see, for example, Nishino, S. et al. (2006) EP1661894 and Inoue, H. et al. (2004) EP1454897). Amide bond formations may be carried out by standard coupling conditions well-known in the art (see, for example, M. Bodanszky, *The Practice of Peptide Synthesis* (Springer-Verlag: 1984), which is hereby incorporated by reference in its entirety), for example, by reacting a carboxylic acid and an amine in the presence of 1-(3-dimethylaminopropyl)-3-ethylcarbodiimide (EDC) and 1-hydroxybenzotriazole. Reaction progress may be monitored by conventional methods such as thin layer chromatography (TLC). Intermediates and products may be purified by methods known in the art, including column chromatography, HPLC or recrystallization.

The methods described below and in the Synthetic Examples section may be used to prepare the compounds of formula Ia where W is carbon and Y is nitrogen (Scheme I and II) and of formula Ib where W is nitrogen and Y is carbon (Scheme III and IV). In the schemes below, $Ar_1$, $Ar_2$, and $R_1$-$R_3$, shall have the meanings defined in the detailed description of formula I.

Compounds of formula Ia where W is carbon and Y is nitrogen may be prepared as shown in Scheme I.

Scheme I

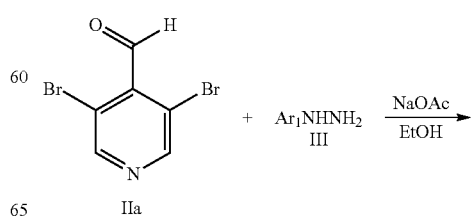

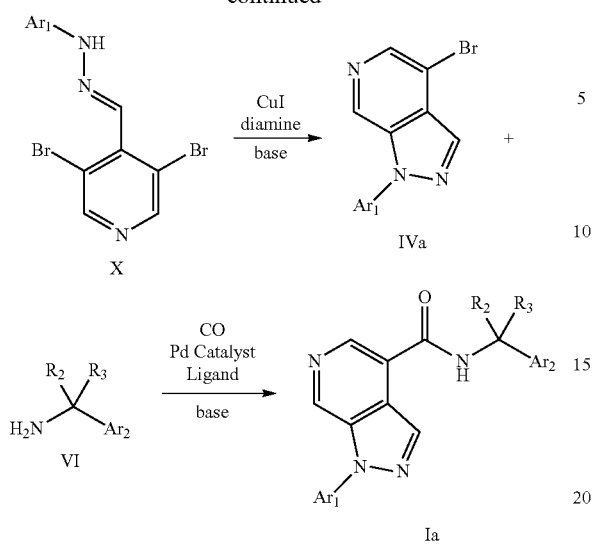

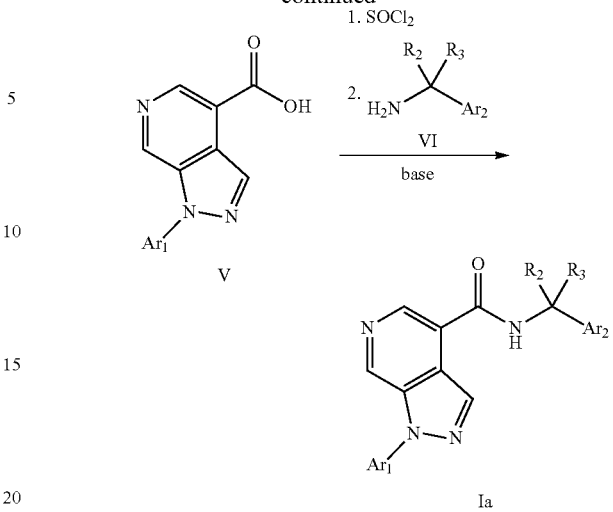

As illustrated above, a hydrazine of the formula (III) (free base or a suitable salt form such as a hydrochloride salt) bearing $Ar_1$ is reacted with 3,5-dibromo-4-pyridinecarboxaldehyde (IIa) in the presence of sodium acetate in a suitable solvent such as EtOH to provide the hydrazone X. Reaction of X with a suitable diamine catalyst such as trans-N,N'-dimethylcyclohexane-1,2-diamine in the presence of a copper salt such as CuI and a suitable base such as $K_2CO_3$ and in a suitable solvent such as N-methyl-2-pyrrolidinone (NMP) provides the 1-substituted-4-bromo-azaindazole IVa. Heating IVa in sealed pressure vessel with the optionally substituted intermediate VI in the presence of a suitable Pd catalyst such as $Pd[PhCN]_2Cl_2$, a suitable ligand such as 1,1-bis(diphenylphosphino)ferrocene (dppf) and a base such as $Et_3N$, in a solvent such as toluene in a CO atmosphere pressurized at about 15 bars provides the desired compound of formula Ia.

An alternate approach that may be used to obtain compounds of formula I where W is carbon and Y is nitrogen is illustrated in Scheme II.

Scheme II

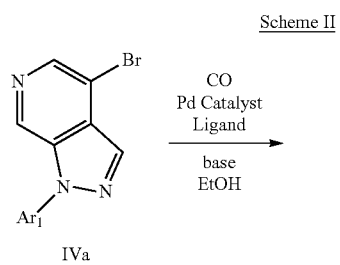

As illustrated in Scheme II, intermediate IVa may be heated with pressurized CO, in the presence of a suitable base and catalyst as described above in absolute ethanol to provide the ethyl ester XI. The ester is then hydrolyzed for example by treatment with a suitable base such as KOH under aqueous conditions to provide carboxylic acid V. This may then be reacted with an amine of formula VI under coupling conditions well known in the art such as by treatment with $SOCl_2$ to form the intermediate acyl chloride followed by reaction with intermediate VI in the presence of a base such as $Et_3N$ or $K_2CO_3$ to provide the desired compound of formula Ia. The intermediate acyl chloride may be reacted in situ or isolated first if desired.

Compounds of formula Ib where W is nitrogen and Y is carbon may be prepared as shown in Scheme III. In the schemes below, $Ar_1$, $Ar_2$, and $R_1$-$R_3$, shall have the meanings defined in the detailed description of formula I.

Scheme III

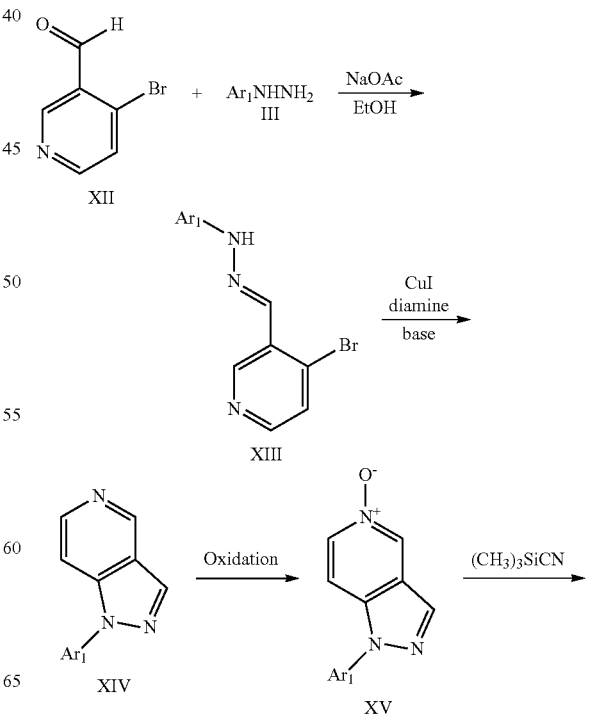

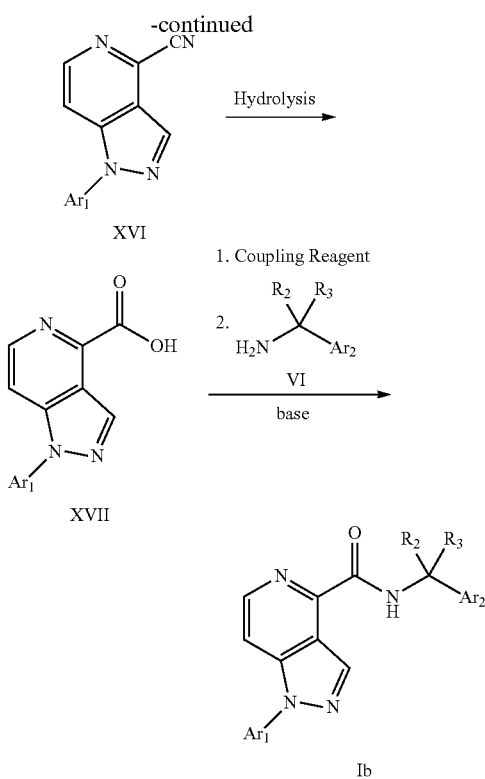

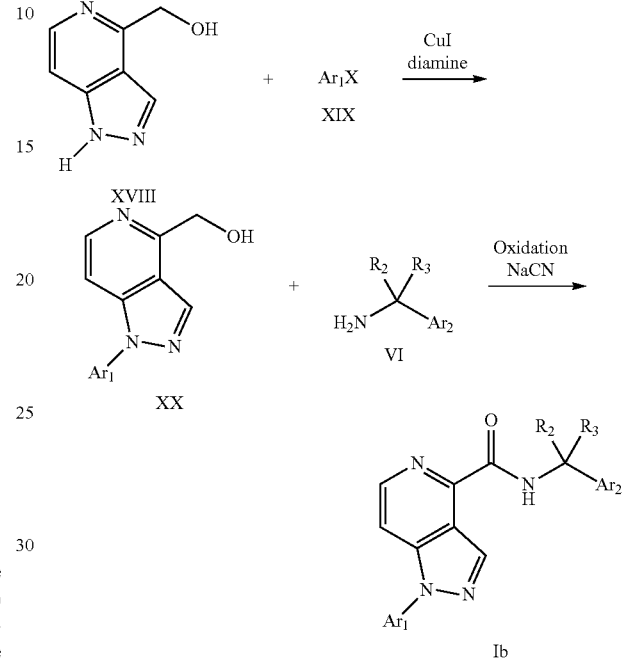

As illustrated above, a hydrazine of the formula (III) (free base or a suitable salt form such as a hydrochloride salt) bearing $Ar_1$ is reacted with 4-bromo-3-pyridinecarboxaldehyde XII in the presence of sodium acetate in a suitable solvent such as EtOH to provide the hydrazone XIII. Reaction of XIII with a suitable diamine catalyst such as trans-N,N'-dimethylcyclohexane-1,2-diamine in the presence of a copper salt such as CuI and a suitable base such as $K_2CO_3$ and in a suitable solvent such as N-methyl-2-pyrrolidinone (NMP) provides the 1-substituted-5-azaindazole XIV. Oxidation of azaindazole XIV with a suitable oxidizing agent such as m-chloroperbenzoic acid or hydrogen peroxide in a suitable solvent such as dichloromethane (DCM) or EtOAc provides the N-oxide XV. Treatment of XV with trimethylsilyl cyanide in a suitable solvent such as acetonitrile in the presence of a suitable base such as $Et_3N$ provides 1-substituted-4-cyano-5-azaindazole XVI. The cyanoazaindazole XVI is hydrolyzed by treatment with a suitable base such as KOH under aqueous conditions to provide carboxylic acid XVII. This may then be reacted with an amine of formula XVII under coupling conditions well known in the art such as by treatment with $SOCl_2$ or, benzotriazol-1-yloxy)tripyrrolidinophosphonium-hexafluorophosphate (PyBOP) or, O-(7-azabenzotriazol-1-yl)-N,N,N',N'-tetramethyluronium hexafluorophosphate (HATU) or, O-(benzotriazol-1-yl-N,N,N',N'-tetramethyluronium hexafluorophosphate (HBTU) in the presence of a base such as $Et_3N$ or N,N-diisopropylethylamine (DIPEA) in a suitable solvent such as DMF to provide the desired compound of formula Ib.

An alternate approach that may be used to obtain compounds of formula Ib where W is nitrogen and Y is carbon is illustrated in Scheme IV.

As illustrated above, 5-azaindazole XVIII is reacted with $Ar_1X$ (XIX) where X is a halogen (Br or I) in the presence of a suitable diamine catalyst such as trans-N,N'-dimethylcyclohexane-1,2-diamine in the presence of a copper salt such as CuI and a suitable base such as $K_2CO_3$ in a suitable solvent such as DMF to provide a 1-substituted-5-azaindazole XX. Alcohol XX may then be treated with manganese (IV) oxide in the presence of sodium cyanide and an amine of formula VI in a suitable solvent such as THF to provide the desired compound of formula Ib.

Compounds of formula I (which includes Ia and Ib) prepared by the above methods may be further converted to additional compounds of formula I by methods known in the art and exemplified in the Synthetic Examples section below.

SYNTHETIC EXAMPLES

General Methods: All reactions were run at room temperature unless note otherwise. All compounds were characterized by one or all of the following methods: $^1H$ NMR, HPLC, HPLC-MS, and melting point.

Retention times (RT) are reported in Table I using one of the following methods:

| HPLC Method | Time (min) | Mobile Phase | | Flow (mL/min) | Column |
| --- | --- | --- | --- | --- | --- |
| | | $H_2O$ (0.1% FA) | $CH_3CN$ (0.1% FA) | | |
| A1 | 0 | 95 | 5 | 2.5 | Agilent Zorbax C18 SB 3.5 um |
| | 1.7 | 5 | 95 | 2.5 | 4.6 × 30 mm cartridge |
| | 2 | 5 | 95 | 2.5 | |
| | 2.1 | 95 | 5 | 2.5 | |
| | 2.3 | 95 | 5 | 2.5 | |

| HPLC Method | Time (min) | 95% H₂O + 5% CH₃CN (0.05% Formic Acid) | CH₃CN (0.05% Formic Acid) | Flow (mL/min) | Column |
|---|---|---|---|---|---|
| B1 | 0 | 70 | 30 | 2.5 | Agilent Zorbax C18 SB 3.5 um |
|    | 1.7 | 5 | 95 | 2.5 | 4.6 × 30 mm cartridge |
|    | 2 | 5 | 95 | 2.5 | |
|    | 2.1 | 70 | 30 | 2.5 | |
|    | 2.3 | 70 | 30 | 2.5 | |
| C1 | 0 | 99 | 1 | 2.5 | Agilent Zorbax C18 SB 3.5 um |
|    | 1.7 | 50 | 50 | 2.5 | 4.6 × 30 mm cartridge |
|    | 2 | 5 | 95 | 2.5 | |
|    | 2.1 | 5 | 95 | 2.5 | |
|    | 2.3 | 99 | 1 | 2.5 | |
| D1 | 0 | 95 | 5 | 1.5 | Agilent Zorbax Eclipse XDB- |
|    | 7 | 5 | 95 | 1.5 | C8 5 um 4.6 × 150 mm |
|    | 9 | 5 | 95 | 1.5 | |
|    | 9.3 | 95 | 5 | 1.5 | |
|    | 10 | 95 | 5 | 1.5 | |
| C2 | 0 | 99 | 1 | 2.5 | Agilent Zorbax C18 SB 3.5 um |
|    | 1.6 | 80 | 20 | 2.5 | 4.6 × 30 mm cartridge |
|    | 1.7 | 5 | 95 | 2.5 | |
|    | 2 | 5 | 95 | 2.5 | |
|    | 2.1 | 99 | 1 | 2.5 | |
|    | 2.3 | 99 | 1 | 2.5 | |
| D2 | 0 | 99 | 1 | 1.5 | Agilent Zorbax Eclipse XDB- |
|    | 2 | 80 | 20 | 1.5 | C8 5 um 4.6 × 150 mm column |
|    | 7 | 5 | 95 | 1.5 | |
|    | 9 | 5 | 95 | 1.5 | |
|    | 9.3 | 99 | 1 | 1.5 | |
|    | 10 | 99 | 1 | 1.5 | |
| A3 | 0 | 88 | 12 | 1.5 | Agilent SB-C18 1.8 um 3 × 50 mm |
|    | 0.25 | 70 | 30 | 1.5 | column |
|    | 0.3 | 60 | 40 | 1.5 | |
|    | 1.19 | 5 | 95 | 1.5 | |
|    | 1.75 | 0 | 100 | 1.5 | |
| B3 | 0 | 60 | 40 | 1.5 | Agilent Eclipse C8 1.8 um |
|    | 1.19 | 15 | 85 | 1.5 | 3 × 50 mm column |
|    | 1.75 | 0 | 100 | 1.5 | |
| C3 | 0 | 95 | 5 | 1.5 | Agilent SB-AQ 1.8 um 3 × 50 mm |
|    | 0.25 | 50 | 50 | 1.5 | column |
|    | 0.3 | 70 | 30 | 1.5 | |
|    | 1.3 | 10 | 90 | 1.5 | |
|    | 1.7 | 0 | 100 | 1.5 | |
| D3 | 0 | 95 | 5 | 1.5 | Agilent SB-C18 1.8 um 3 × 50 mm |
|    | 3.8 | 10 | 90 | 1.5 | column |
|    | 4.5 | 0 | 100 | 1.5 | |

| HPLC Method | Time (min) | 95% H₂O + 5% CH₃CN (0.05% Formic Acid) | CH₃CN (0.05% Formic Acid) | Flow (mL/min) | Column |
|---|---|---|---|---|---|
| E | 0 | 90 | 10 | 0.8 | BEH 2.1 × 50 mm C18, 1.7 um particle diameter |
|   | 1.19 | 5 | 95 | 0.8 | |
|   | 1.7 | 5 | 95 | 0.8 | |

Example 1

Synthesis of 1-(4-Fluorophenyl)-1H-pyrazolo[3,4-c]pyridine-4-carboxylic acid 3-trifluoromethyl-benzylamide (1)

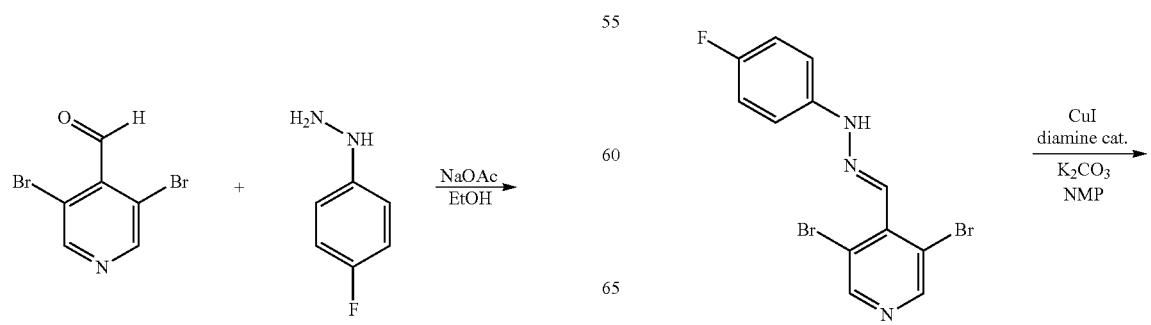

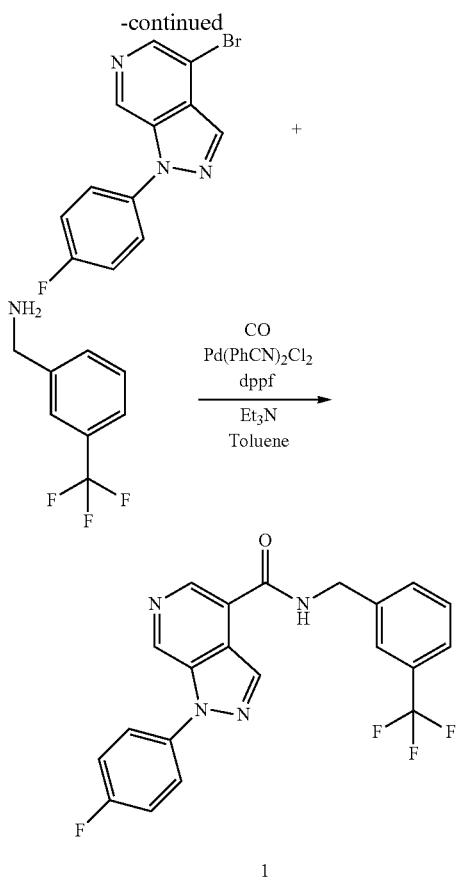

To a solution of 3,5-dibromo-4-pyridinecarboxaldehyde (30.0 g, 113 mmol) in ethanol (1200 mL) at reflux was added 4-fluorophenylhydrazine hydrochloride (20.0 g, 123 mmol) in several portions followed by a solution of sodium acetate (31.0 g, 228 mmol) in water (200 mL). The mixture turned from a deep red to a bright yellow and over time a yellow solid precipitated. After 20 minutes, the mixture was cooled, diluted with water (1000 mL) and the yellow solid was collected by filtration. The solid was washed with water and dried to afford N-[1-(3,5-dibromopyridin-4-yl)-meth-(E)-ylidene]-N-(4-fluorophenyl)-hydrazine.

A mixture of N-[1-(3,5-dibromopyridin-4-yl)-meth-(E)-ylidene]-N'-(4-fluorophenyl)-hydrazine (2.0 g, 5.4 mmol), CuI (50.0 mg, 0.260 mmol), trans-N,N'-dimethylcyclohexane-1,2-diamine (0.200 mL, 1.27 mmol), and $K_2CO_3$ (1.4 g, 0.010 mol) in NMP (10 mL) was warmed at 120° C. for 30 minutes. The reaction was monitored by HPLC-MS indicating the desired mass. The mixture was diluted with aqueous ammonium chloride (100 mL) and the resulting solid collected by filtration. The solid was dissolved in hot ethyl acetate (EtOAc), dried over magnesium sulfate, treated with activated carbon, filtered through diatomaceous earth and concentrated. The residue was passed through a pad of silica gel eluting with dichloromethane to afford 4-bromo-1-(4-fluorophenyl)-1H-pyrazolo[3,4-c]pyridine.

The following intermediate 4-bromo-1-substituted 6-azaindazoles were also prepared by the methods described in Example 1:
4-Bromo-1-(4-chlorophenyl)-1H-pyrazolo[3,4-c]pyridine,
4-Bromo-1-tetrahydropyran-4-yl)-1H-pyrazolo[3,4-c]pyridine, and
4-Bromo-1-(4,4-difluorocyclohexyl)-1H-pyrazolo[3,4-c]pyridine.

A mixture of 4-bromo-1-(4-fluorophenyl)-1H-pyrazolo[3,4-c]pyridine (340 mg, 1.2 mmol), $Et_3N$ (320 µL, 2.3 mmol), 3-trifluoromethylbenzylamine (250 µL, 1.7 mmol), $Pd[PhCN]_2Cl_2$ (10 mg, 0.03 mmol), and 1,1-bis(diphenylphosphino)ferrocene (dppf) (0.04 g, 0.07 mmol) in toluene (15 mL) was sealed in a bomb with stifling, placed under 15 bars of carbon monoxide and warmed at 140° C. After 3 hours, the mixture was cooled to room temperature, returned to atmospheric pressure and opened. The reaction was monitored by HPLC-MS indicating the desired mass M+=415.43. The reaction was diluted with saturated aqueous ammonium chloride (50 mL) and extracted with EtOAc (3×20 mL). The combined organic layers were washed with saturated aqueous ammonium chloride (3×20 mL), brine (20 mL), dried over magnesium sulfate, filtered and concentrated. The crude material was dissolved in dichloromethane and purified by silica gel chromatography using a gradient of 0-30% EtOAc in dichloromethane to afford partially purified material. The material from the column was triturated with ether-hexanes to afford an off-white solid. This material was dissolved in dichloromethane and passed through a pad of silica gel (15 mL funnel) eluting with a gradient of 0-40% dichloromethane in EtOAc. The material from the pad was triturated with ether to afford the title compound, mp 172-173° C.

The following compound was also prepared by the methods described in Example 1:
1-(4-Fluorophenyl)-1H-pyrazolo[3,4-c]pyridine-4-carboxylic acid 3-methanesulfonyl-benzylamide.

Example 2

Synthesis of 1-(4-Fluorophenyl)-1H-pyrazolo[3,4-c]pyridine-4-carboxylic acid 2-methanesulfonyl-benzylamide (2)

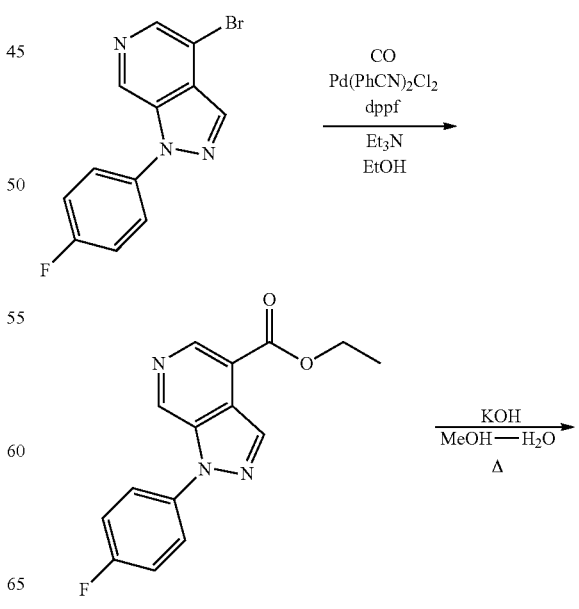

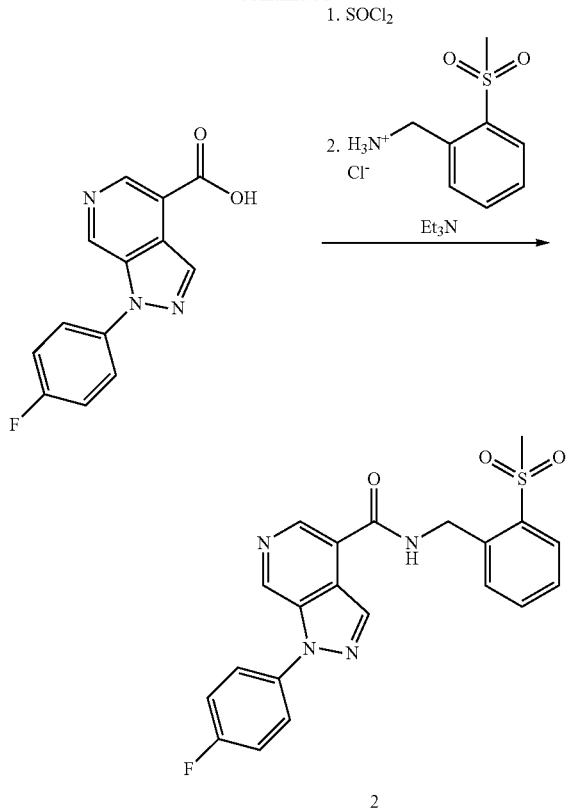

A mixture of 4-bromo-1-(4-fluorophenyl)-1H-pyrazolo[3,4-c]pyridine (3.5 g, 12 mmol), Et₃N (3.5 mL, 25 mmol), Pd[PhCN]₂Cl₂ (105 mg, 0.273 mmol), and dppf (418 mg, 0.754 mmol) in absolute ethanol (90 mL) was placed in a sealed bomb with stifling and placed under 15 bars of carbon monoxide and warmed to 140° C. for 4 hours. The mixture was then cooled to room temperature, returned to atmospheric pressure and opened. The reaction was monitored by TLC (EtOAc-hexanes 4:6 and EtOAc) indicating the starting material was consumed. The reaction was diluted with water (300 mL) and the solid was collected by filtration washing with water. The filtrate was diluted with water (200 mL) and extracted with EtOAc (2×100 mL). The combined organic layers were washed with brine (2×100 mL). The still moist filter cake was dissolved in EtOAc and combined with the extracted organic layers, dried over magnesium sulfate, treated with activated carbon) and filtered through a pad of diatomaceous earth and a layer of silica gel. The material from the pad was dissolved in dichloromethane and passed through a pad of silica gel eluting with dichloromethane to afford 1-(4-fluorophenyl)-1H-pyrazolo[3,4-c]pyridine-4-carboxylic acid ethyl ester.

A mixture of 1-(4-fluorophenyl)-1H-pyrazolo[3,4-c]pyridine-4-carboxylic acid ethyl ester (2.75 g, 9.64 mmol) and 85% potassium hydroxide pellets (6.4 g, 84 mmol) in methanol-water was warmed at reflux for 15 minutes and then stirred overnight. The mixture was then diluted with water (300 mL) and then a dilute solution of aqueous HCl (1 equivalent based on mass of KOH) was added in several portions (final pH=5). The resulting solid was collected by filtration and dried by pulling vacuum through the filter cake to afford 1-(4-fluorophenyl)-1H-pyrazolo[3,4-c]pyridine-4-carboxylic acid.

The following intermediate carboxylic acids were also prepared by the methods described in Example 2:
1-(4-Chlorophenyl)-1H-pyrazolo[3,4-c]pyridine-4-carboxylic acid,
1-(Tetrahydropyran-4-yl)-1H-pyrazolo[3,4-c]pyridine-4-carboxylic acid, and
1-(4,4-Difluorocyclohexyl)-1H-pyrazolo[3,4-c]pyridine-4-carboxylic acid.

A suspension of 1-(4-fluorophenyl)-1H-pyrazolo[3,4-c]pyridine-4-carboxylic acid (75 mg, 0.29 mmol) in 3 mL of thionyl chloride was warmed at reflux for 1 hour. The yellow suspension dissolved after approximately 30 minutes. The mixture was then concentrated to dryness under a stream of nitrogen. To the yellow solid was added dichloromethane (15 mL) followed by 2-(methylsulfonyl)benzylamine hydrochloride (70 mg, 0.3 mmol) and Et₃N (0.600 mL, 4.31 mmol). After 30 minutes, the mixture was concentrated, diluted with saturated aqueous ammonium chloride and extracted with EtOAc (3×10 mL). The combined organic layers were washed with saturated aqueous ammonium chloride (3×10 mL), dried over magnesium sulfate, filtered and concentrated. The crude solid was dissolved in dichloromethane and passed through a pad of silica gel eluting with EtOAc-dichloromethane (0:100, then 1:1). The material from the column was triturated with ether to afford the title compound as a white solid.

The following compounds were also prepared by the methods described in Example 2:
1-(4-Fluorophenyl)-1H-pyrazolo[3,4-c]pyridine-4-carboxylic acid (2-cyano-pyridin-4-ylmethyl)-amide,
1-(4-Fluorophenyl)-1H-pyrazolo[3,4-c]pyridine-4-carboxylic acid (6-bromopyridin-3-ylmethyl)-amide,
1-(4-Fluorophenyl)-1H-pyrazolo[3,4-c]pyridine-4-carboxylic acid 2-chloro-4-methylsulfamoyl-benzylamide,
1-(4-Fluorophenyl)-1H-pyrazolo[3,4-c]pyridine-4-carboxylic acid 4-methylsulfamoyl-benzylamide,
1-(4-Fluorophenyl)-1H-pyrazolo[3,4-c]pyridine-4-carboxylic acid 4-methanesulfonyl-benzylamide,
1-(4-Fluorophenyl)-1H-pyrazolo[3,4-c]pyridine-4-carboxylic acid 4-(isopropylsulfamoyl-methyl)-benzylamide,
1-(4-Fluorophenyl)-1H-pyrazolo[3,4-c]pyridine-4-carboxylic acid 4-methylsulfamoylmethyl-benzylamide,
1-(4-Fluorophenyl)-1H-pyrazolo[3,4-c]pyridine-4-carboxylic acid 4-(2-dimethylamino-ethylsulfamoyl)-benzylamide,
1-(4-Fluorophenyl)-1H-pyrazolo[3,4-c]pyridine-4-carboxylic acid (5-bromopyridin-3-ylmethyl)-amide,
1-(4-Fluorophenyl)-1H-pyrazolo[3,4-c]pyridine-4-carboxylic acid (2-bromopyridin-4-ylmethyl)-amide,
1-(4-Fluorophenyl)-1H-pyrazolo[3,4-c]pyridine-4-carboxylic acid 4-(piperidine-1-sulfonylmethyl)-benzylamide,
[5-({[1-(4-Fluorophenyl)-1H-pyrazolo[3,4-c]pyridine-4-carbonyl]-amino}-methyl)-pyridin-2-yl]-carbamic acid tert-butyl ester,
1-(4-Fluorophenyl)-1H-pyrazolo[3,4-c]pyridine-4-carboxylic acid 4-(morpholine-4-sulfonylmethyl)-benzylamide,
1-(4-Fluorophenyl)-1H-pyrazolo[3,4-c]pyridine-4-carboxylic acid 4-cyclohexylsulfamoylmethyl-benzylamide,
1-(4-Fluorophenyl)-1H-pyrazolo[3,4-c]pyridine-4-carboxylic acid 4-(4-methyl-piperazine-1-sulfonylmethyl)-benzylamide,
1-(4-Fluorophenyl)-1H-pyrazolo[3,4-c]pyridine-4-carboxylic acid 4-[(cyclohexylmethyl-sulfamoyl)-methyl]-benzylamide,
1-(4-Fluorophenyl)-1H-pyrazolo[3,4-c]pyridine-4-carboxylic acid 4-{[(tetrahydro-furan-2-ylmethyl)-sulfamoyl]-methyl}-benzylamide, 1-(4-Fluorophenyl)-1H-pyrazolo[3,4-c]pyridine-4-carboxylic acid 3-methanesulfonylmethyl-benzylamide,
1-(4-Fluorophenyl)-1H-pyrazolo[3,4-c]pyridine-4-carboxylic acid (6-dimethylamino-pyridin-3-ylmethyl)-amide,
1-(4-Fluorophenyl)-1H-pyrazolo[3,4-c]pyridine-4-carboxylic acid 4-[methyl-(1-methyl-piperidin-4-yl)-sulfamoyl]-benzylamide,
1-(4-Fluorophenyl)-1H-pyrazolo[3,4-c]pyridine-4-carboxylic acid [6-(methanesulfonyl-methyl-amino)-pyridin-3-ylmethyl]-amide,
1-(4-Fluorophenyl)-1H-pyrazolo[3,4-c]pyridine-4-carboxylic acid (6-cyclopropanesulfonylamino-pyridin-3-ylmethyl)-amide,
1-(4-Fluorophenyl)-1H-pyrazolo[3,4-c]pyridine-4-carboxylic acid [6-(dimethylamino-sulfonylamino)-pyridin-3-ylmethyl]-amide,
1-(4-Fluorophenyl)-1H-pyrazolo[3,4-c]pyridine-4-carboxylic acid 4-(2-hydroxy-ethylsulfamoyl)-benzylamide,
1-(4-Fluorophenyl)-1H-pyrazolo[3,4-c]pyridine-4-carboxylic acid 4-(3-oxo-piperazine-1-sulfonyl)-benzylamide,
1-(4-Fluorophenyl)-1H-pyrazolo[3,4-c]pyridine-4-carboxylic acid 3-methanesulfonyl-5-trifluoromethyl-benzylamide,
1-(4-Fluorophenyl)-1H-pyrazolo[3,4-c]pyridine-4-carboxylic acid {6-[(2-dimethylamino-ethyl)-methanesulfonyl-amino]-pyridin-3-ylmethyl}-amide,
1-(4-Fluorophenyl)-1H-pyrazolo[3,4-c]pyridine-4-carboxylic acid [6-(2-dimethylaminoethyl-1-methylamino-sulfonylamino)-pyridin-3-ylmethyl]-amide,
1-(4-Fluorophenyl)-1H-pyrazolo[3,4-c]pyridine-4-carboxylic acid (6-dimethylsulfamoyl-pyridin-3-ylmethyl)-amide,
1-(4-Fluorophenyl)-1H-pyrazolo[3,4-c]pyridine-4-carboxylic acid {6-[methanesulfonyl-(2-methoxy-ethyl)-amino]-pyridin-3-ylmethyl}-amide,
1-(4-Fluorophenyl)-1H-pyrazolo[3,4-c]pyridine-4-carboxylic acid [1-(2-bromopyridin-4-yl)-propyl]-amide,
1-(4-Fluorophenyl)-1H-pyrazolo[3,4-c]pyridine-4-carboxylic acid [(S)-1-(5-bromopyridin-3-yl)-ethyl]-amide,
1-(4-Fluorophenyl)-1H-pyrazolo[3,4-c]pyridine-4-carboxylic acid [1-(6-bromopyridin-3-yl)-ethyl]-amide,
1-(4-Fluorophenyl)-1H-pyrazolo[3,4-c]pyridine-4-carboxylic acid [(R)-1-(2-methanesulfonyl-pyridin-4-yl)-but-3-enyl]-amide,
1-(4-Fluorophenyl)-1H-pyrazolo[3,4-c]pyridine-4-carboxylic acid [(S)-1-(6-bromopyridin-2-yl)-ethyl]-amide,
1-(4-Fluorophenyl)-1H-pyrazolo[3,4-c]pyridine-4-carboxylic acid [(S)-1-(5-bromopyridin-3-yl)-butyl]-amide,
1-(4-Fluorophenyl)-1H-pyrazolo[3,4-c]pyridine-4-carboxylic acid [1-(2-bromopyridin-4-yl)-ethyl]-amide,
1-(4-Fluorophenyl)-1H-pyrazolo[3,4-c]pyridine-4-carboxylic acid [(S)-1-(2-bromopyridin-4-yl)-but-3-enyl]-amide,
1-(4-Fluorophenyl)-1H-pyrazolo[3,4-c]pyridine-4-carboxylic acid [(S)-1-(2-bromopyridin-4-yl)-ethyl]-amide,
1-(4-Fluorophenyl)-1H-pyrazolo[3,4-c]pyridine-4-carboxylic acid [(S)-1-(3-bromophenyl)-propyl]-amide,
1-(4-Fluorophenyl)-1H-pyrazolo[3,4-c]pyridine-4-carboxylic acid [(S)-1-(6-bromopyridin-2-yl)-propyl]-amide,
1-(4-Fluorophenyl)-1H-pyrazolo[3,4-c]pyridine-4-carboxylic acid [(S)-1-(2-methyl-pyridin-4-yl)-propyl]-amide,
1-(4-Fluorophenyl)-1H-pyrazolo[3,4-c]pyridine-4-carboxylic acid (1-methyl-1H-pyrazol-4-ylmethyl)-amide,
1-(4-Fluorophenyl)-1H-pyrazolo[3,4-c]pyridine-4-carboxylic acid (1-methyl-1H-pyrazol-3-ylmethyl)-amide,
3-(1-{[1-(4-Fluorophenyl)-1H-pyrazolo[3,4-c]pyridine-4-carbonyl]-amino}-propyl)-piperidine-1-carboxylic acid tert-butyl ester,
4-(1-{[1-(4-Fluorophenyl)-1H-pyrazolo[3,4-c]pyridine-4-carbonyl]-amino}-propyl)-piperidine-1-carboxylic acid tert-butyl ester,
1-(4-Fluorophenyl)-1H-pyrazolo[3,4-c]pyridine-4-carboxylic acid (3-methyl-3H-imidazol-4-ylmethyl)-amide,
1-(4-Fluorophenyl)-1H-pyrazolo[3,4-c]pyridine-4-carboxylic acid [(S)-1-(5-bromo-thiophen-2-yl)-propyl]-amide, and
1-(4-Fluorophenyl)-1H-pyrazolo[3,4-c]pyridine-4-carboxylic acid 4-(2-hydroxy-1-methyl-ethylsulfamoyl)-benzylamide.

Example 3

Synthesis of 1-(4-Fluorophenyl)-6-oxy-1H-pyrazolo[3,4-c]pyridine-4-carboxylic acid 3-trifluoromethyl-benzylamide (3)

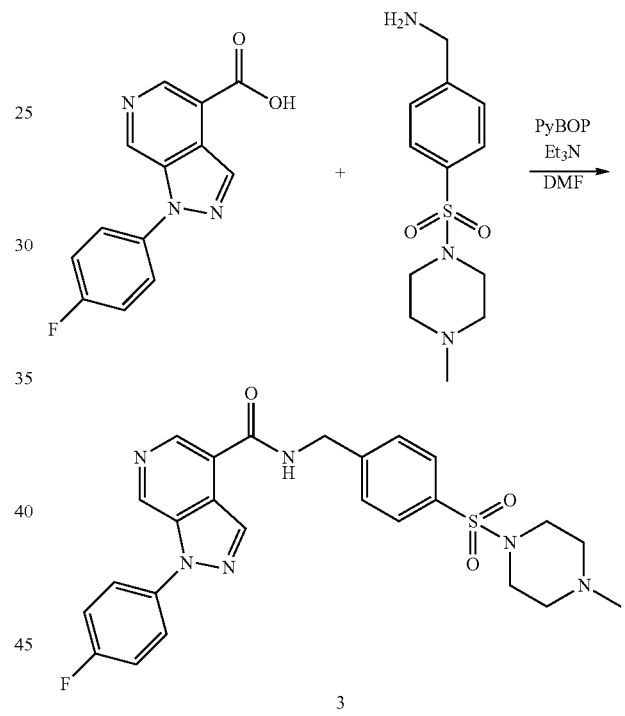

To a mixture of 1-(4-fluorophenyl)-1H-pyrazolo[3,4-c]pyridine-4-carboxylic acid (0.070 g, 0.27 mmol) in DMF (3 mL) was added Et₃N (110 μL, 0.79 mmol) followed by benzotriazol-1-yloxy)tripyrrolidinophosphonium-hexafluorophosphate (PyBOP) (170 mg, 0.33 mmol). The mixture was stirred for 5 minutes at room temperature and then 4-(4-methyl-piperazine-1-sulfonyl)-benzylamine (80 mg, 0.3 mmol) was added. After 3 hours, the mixture was diluted with saturated aqueous ammonium chloride and extracted with EtOAc. The EtOAc layer was washed with aqueous NaHCO₃, brine, dried over sodium sulfate and concentrated. The residue was purified by silica gel chromatography eluting with a gradient of 0-25% methanol in dichloromethane to afford the title compound as a colorless powder.

The following compounds were also prepared by methods described in Example 3:
1-(4-Fluorophenyl)-1H-pyrazolo[3,4-c]pyridine-4-carboxylic acid 4-(tetrahydropyran-4-ylsulfamoyl)-benzylamide, 1-(4-Fluorophenyl)-1H-pyrazolo[3,4-c]pyridine-4-carboxylic acid 4-(4-methyl-piperazine-1-sulfonyl)-benzylamide,
1-(4-Fluorophenyl)-1H-pyrazolo[3,4-c]pyridine-4-carboxylic acid 4-(morpholine-4-sulfonyl)-benzylamide,
1-(4-Fluorophenyl)-1H-pyrazolo[3,4-c]pyridine-4-carboxylic acid 3,5-dimethyl-benzylamide,
1-(4-Fluorophenyl)-1H-pyrazolo[3,4-c]pyridine-4-carboxylic acid 3,5-dichloro-benzylamide,
1-(4-Fluorophenyl)-1H-pyrazolo[3,4-c]pyridine-4-carboxylic acid 4-[(2-hydroxy-ethyl)-methyl-sulfamoyl]-benzylamide,
[4-({[1-(4-Fluorophenyl)-1H-pyrazolo[3,4-c]pyridine-4-carbonyl]-amino}-methyl)-benzenesulfonylamino]-acetic acid methyl ester,
1-(4-Fluorophenyl)-1H-pyrazolo[3,4-c]pyridine-4-carboxylic acid 3,5-bis-trifluoromethyl-benzylamide,
1-(4-Fluorophenyl)-1H-pyrazolo[3,4-c]pyridine-4-carboxylic acid 4-{[methyl-(1-methyl-piperidin-4-yl)-sulfamoyl]-methyl}-benzylamide,
1-(4-Fluorophenyl)-1H-pyrazolo[3,4-c]pyridine-4-carboxylic acid 4-[(1-methyl-piperidin-4-ylsulfamoyl)-methyl]-benzylamide,
1-(4-Fluorophenyl)-1H-pyrazolo[3,4-c]pyridine-4-carboxylic acid 3-methoxy-4-methylsulfamoyl-benzylamide,
1-(4-Chlorophenyl)-1H-pyrazolo[3,4-c]pyridine-4-carboxylic acid [(S)-1-(5-bromopyridin-3-yl)-ethyl]-amide,
1-(4-Chlorophenyl)-1H-pyrazolo[3,4-c]pyridine-4-carboxylic acid [(S)-1-(5-bromopyridin-3-yl)-propyl]-amide,
1-(4-Fluorophenyl)-1H-pyrazolo[3,4-c]pyridine-4-carboxylic acid [(R)-1-(2-bromopyridin-4-yl)-but-3-enyl]-amide,
1-(4-Fluorophenyl)-1H-pyrazolo[3,4-c]pyridine-4-carboxylic acid 4-((R)-2-hydroxy-propylsulfamoyl)-benzylamide,
1-(4-Fluorophenyl)-1H-pyrazolo[3,4-c]pyridine-4-carboxylic acid 4-((S)-2-hydroxy-propylsulfamoyl)-benzylamide,
1-(4-Fluorophenyl)-1H-pyrazolo[3,4-c]pyridine-4-carboxylic acid [(S)-1-(3-bromo-4-methoxy-phenyl)-propyl]-amide,
1-(4-Fluorophenyl)-1H-pyrazolo[3,4-c]pyridine-4-carboxylic acid [(R)-1-(3-bromo-4-methoxy-phenyl)-propyl]-amide,
1-(4-Fluorophenyl)-1H-pyrazolo[3,4-c]pyridine-4-carboxylic acid [(S)-1-(3-bromo-4-methoxy-phenyl)-butyl]-amide,
1-(4-Fluorophenyl)-1H-pyrazolo[3,4-c]pyridine-4-carboxylic acid [(R)-1-(3-bromo-4-methoxy-phenyl)-butyl]-amide,
1-(4-Fluorophenyl)-1H-pyrazolo[3,4-c]pyridine-4-carboxylic acid 4-(2-hydroxy-2-methyl-propylsulfamoyl)-benzylamide,
2-[5-({[1-(4-Fluorophenyl)-1H-pyrazolo[3,4-c]pyridine-4-carbonyl]-amino}-methyl)-pyridin-2-ylamino]-propionic acid ethyl ester,
1-(4-Fluorophenyl)-1H-pyrazolo[3,4-c]pyridine-4-carboxylic acid [(S)-1-(4-bromo-3-methoxy-phenyl)-propyl]-amide,
1-(4-Fluorophenyl)-1H-pyrazolo[3,4-c]pyridine-4-carboxylic acid [(S)-1-(2-methylsulfanyl-oxazol-5-yl)-ethyl]-amide,
1-(4-Fluorophenyl)-1H-pyrazolo[3,4-c]pyridine-4-carboxylic acid [(S)-1-(1H-imidazol-4-yl)-propyl]-amide,
1-(4-Fluorophenyl)-1H-pyrazolo[3,4-c]pyridine-4-carboxylic acid [(S)-1-(4-bromo-2-methyl-2H-pyrazol-3-yl)-propyl]-amide,
1-(4-Fluorophenyl)-1H-pyrazolo[3,4-c]pyridine-4-carboxylic acid [(R)-1-(1H-pyrazol-4-yl)-propyl]-amide,
1-(4-Fluorophenyl)-1H-pyrazolo[3,4-c]pyridine-4-carboxylic acid [(S)-1-(1H-pyrazol-4-yl)-propyl]-amide,
1-(4-Fluorophenyl)-1H-pyrazolo[3,4-c]pyridine-4-carboxylic acid [2-(methanesulfonyl-methyl-amino)-pyrimidin-5-ylmethyl]-amide,
1-(4-Fluorophenyl)-1H-pyrazolo[3,4-c]pyridine-4-carboxylic acid (2-morpholin-4-yl-pyrimidin-5-ylmethyl)-amide,
1-(4-Fluorophenyl)-1H-pyrazolo[3,4-c]pyridine-4-carboxylic acid [(S)-1-(4-methanesulfonyl-1H-pyrrol-2-yl)-propyl]-amide,
1-(4-Fluorophenyl)-1H-pyrazolo[3,4-c]pyridine-4-carboxylic acid {(R)-1-[1-(toluene-4-sulfonyl)-1H-pyrrol-3-yl]-propyl}-amide,
1-(4-Fluorophenyl)-1H-pyrazolo[3,4-c]pyridine-4-carboxylic acid {(S)-1-[1-(toluene-4-sulfonyl)-1H-pyrrol-3-yl]-propyl}-amide,
1-(4-Fluorophenyl)-1H-pyrazolo[3,4-c]pyridine-4-carboxylic acid {(S)-1-[5-bromo-1-(toluene-4-sulfonyl)-1H-pyrrol-3-yl]-propyl}-amide,
1-(4-Fluorophenyl)-1H-pyrazolo[3,4-c]pyridine-4-carboxylic acid [2-(acetyl-methyl-amino)-pyrimidin-5-ylmethyl]-amide,
1-(4-Fluorophenyl)-1H-pyrazolo[3,4-c]pyridine-4-carboxylic acid (2-morpholin-4-yl-pyrimidin-4-ylmethyl)-amide,
1-(4-Fluorophenyl)-1H-pyrazolo[3,4-c]pyridine-4-carboxylic acid [2-(methanesulfonyl-methyl-amino)-pyrimidin-4-ylmethyl]-amide,
1-(4-Fluorophenyl)-1H-pyrazolo[3,4-c]pyridine-4-carboxylic acid {1-[2-(methanesulfonyl-methyl-amino)-pyrimidin-5-yl]-propyl}-amide,
1-(4-Fluorophenyl)-1H-pyrazolo[3,4-c]pyridine-4-carboxylic acid {(S)-1-[4-bromo-1-(toluene-4-sulfonyl)-1H-pyrrol-2-yl]-propyl}-amide, and
1-(4-Fluorophenyl)-1H-pyrazolo[3,4-c]pyridine-4-carboxylic acid {(R)-1-[4-bromo-1-(toluene-4-sulfonyl)-1H-pyrrol-2-yl]-propyl}-amide.

The following compounds were also prepared by methods described in Example 3 with the following modification. The coupling reagent benzotriazol-1-yloxy)tripyrrolidinophosphoniumhexafluorophosphate (PyBOP) was replaced with O-(7-azabenzotriazol-1-yl)-N,N,N',N'-tetramethyluronium hexafluorophosphate (HATU):
1-(4-Fluorophenyl)-1H-pyrazolo[3,4-c]pyridine-4-carboxylic acid [(S)-1-(2-methylsulfanyl-pyridin-4-yl)-propyl]-amide,
1-(4-Fluorophenyl)-1H-pyrazolo[3,4-c]pyridine-4-carboxylic acid [1-(6-methanesulfonyl-1-oxy-pyridin-3-yl)-propyl]-amide,
1-(4-Fluorophenyl)-1H-pyrazolo[3,4-c]pyridine-4-carboxylic acid [1-(1-methyl-1H-imidazol-4-yl)-propyl]-amide,
1-(4-Fluorophenyl)-1H-pyrazolo[3,4-c]pyridine-4-carboxylic acid [(S)-1-(1-methyl-1H-pyrazol-4-yl)-propyl]-amide,
1-(Tetrahydropyran-4-yl)-1H-pyrazolo[3,4-c]pyridine-4-carboxylic acid [(S)-1-(2-methanesulfonyl-pyridin-4-yl)-propyl]-amide,
1-(4-Fluorophenyl)-1H-pyrazolo[3,4-c]pyridine-4-carboxylic acid ((S)-1-thiophen-3-yl-propyl)-amide,
1-(4-Fluorophenyl)-1H-pyrazolo[3,4-c]pyridine-4-carboxylic acid ((R)-1-thiophen-3-yl-propyl)-amide,
1-(4-Fluorophenyl)-1H-pyrazolo[3,4-c]pyridine-4-carboxylic acid (2-methanesulfonyl-1-oxy-pyridin-4-ylmethyl)-amide,
1-(4-Fluorophenyl)-1H-pyrazolo[3,4-c]pyridine-4-carboxylic acid [(S)-1-(2-methanesulfonyl-thiazol-5-yl)-propyl]-amide,
1-(4-Fluorophenyl)-1H-pyrazolo[3,4-c]pyridine-4-carboxylic acid [(S)-1-(4-methanesulfonyl-thiophen-2-yl)-propyl]-amide, 1-(4-Fluorophenyl)-1H-pyrazolo[3,4-c]pyridine-4-carboxylic acid [(S)-1-(2-bromopyridin-4-yl)-but-3-enyl]-amide,
1-(Tetrahydropyran-4-yl)-1H-pyrazolo[3,4-c]pyridine-4-carboxylic acid [(S)-1-(5-methanesulfonyl-pyridin-3-yl)-propyl]-amide,
1-(4,4-Difluorocyclohexyl)-1H-pyrazolo[3,4-c]pyridine-4-carboxylic acid [(S)-1-(2-methanesulfonyl-pyridin-4-yl)-propyl]-amide,
1-(4-Fluorophenyl)-1H-pyrazolo[3,4-c]pyridine-4-carboxylic acid [(S)-1-(2-methanesulfonyl-thiazol-4-yl)-propyl]-amide,
1-(4-Fluorophenyl)-1H-pyrazolo[3,4-c]pyridine-4-carboxylic acid [(S)-1-(4-bromo-thiazol-2-yl)-propyl]-amide,
1-(4-Fluorophenyl)-1H-pyrazolo[3,4-c]pyridine-4-carboxylic acid [(S)-1-(4-bromo-thiazol-2-yl)-ethyl]-amide,
1-(4-Fluorophenyl)-1H-pyrazolo[3,4-c]pyridine-4-carboxylic acid [(S)-1-(2-bromo-pyridin-4-yl)-2-cyano-ethyl]-amide,
1-(4-Fluorophenyl)-1H-pyrazolo[3,4-c]pyridine-4-carboxylic acid [(R)-1-(2-bromo-pyridin-4-yl)-2-hydroxy-ethyl]-amide,
1-(4-Fluorophenyl)-1H-pyrazolo[3,4-c]pyridine-4-carboxylic acid (2-bromo-6-methyl-pyridin-4-ylmethyl)-amide,
1-(4-Fluorophenyl)-1H-pyrazolo[3,4-c]pyridine-4-carboxylic acid (1H-pyrrolo[2,3-b]pyridin-4-ylmethyl)-amide,
1-(4-Fluorophenyl)-1H-pyrazolo[3,4-c]pyridine-4-carboxylic acid (1-methanesulfonyl-1H-pyrrolo[2,3-b]pyridin-4-ylmethyl)-amide,
1-(4-Fluorophenyl)-1H-pyrazolo[3,4-c]pyridine-4-carboxylic acid [(S)-1-(2-methanesulfonyl-pyridin-4-yl)-ethyl-2,2,2-D3]-amide,
1-(4-Fluorophenyl)-1H-pyrazolo[3,4-c]pyridine-4-carboxylic acid [(S)-1-(2-methanesulfonyl-pyridin-4-yl)-ethyl-1,2,2,2-D4]-amide,
1-(4-Fluorophenyl)-1H-pyrazolo[3,4-c]pyridine-4-carboxylic acid [(S)-1-(3-bromo-isoxazol-5-yl)-propyl]-amide, and
1-(4-Fluorophenyl)-1H-pyrazolo[3,4-c]pyridine-4-carboxylic acid (3-bromo-isoxazol-5-ylmethyl)-amide.

The following compounds were also prepared by methods described in Example 3 with the following modification. The coupling reagent benzotriazol-1-yloxy)tripyrrolidinophosphoniumhexafluorophosphate (PyBOP) was replaced with O-(benzotriazol-1-yl-N,N,N',N'-tetramethyluronium hexafluorophosphate (HBTU):
1-(4-Fluorophenyl)-1H-pyrazolo[3,4-c]pyridine-4-carboxylic acid (2-methanesulfonyl-6-methoxy-pyridin-4-ylmethyl)-amide,
1-(4-Fluorophenyl)-1H-pyrazolo[3,4-c]pyridine-4-carboxylic acid [(S)-1-(5-methanesulfonyl-furan-2-yl)-propyl]-amide,
1-(4-Fluorophenyl)-1H-pyrazolo[3,4-c]pyridine-4-carboxylic acid [(S)-1-(2-chloro-6-methanesulfonyl-pyridin-4-yl)-propyl]-amide,
1-(4-Fluorophenyl)-1H-pyrazolo[3,4-c]pyridine-4-carboxylic acid [(S)-1-(3-methyl-3H-imidazol-4-yl)-propyl]-amide,
1-(4-Fluorophenyl)-1H-pyrazolo[3,4-c]pyridine-4-carboxylic acid (5-bromo-thiophen-2-ylmethyl)-amide,
1-(4-Fluorophenyl)-1H-pyrazolo[3,4-c]pyridine-4-carboxylic acid (4-bromo-thiophen-2-ylmethyl)-amide,
1-(4-Fluorophenyl)-1H-pyrazolo[3,4-c]pyridine-4-carboxylic acid (2-bromo-thiazol-4-ylmethyl)-amide,
1-(4-Fluorophenyl)-1H-pyrazolo[3,4-c]pyridine-4-carboxylic acid (2-bromo-thiazol-5-ylmethyl)-amide,
1-(4-Fluorophenyl)-1H-pyrazolo[3,4-c]pyridine-4-carboxylic acid [1-ethyl-1-(2-methanesulfonyl-thiazol-5-yl)-propyl]-amide,
1-(4-Fluorophenyl)-1H-pyrazolo[3,4-c]pyridine-4-carboxylic acid ((S)-1-thiazol-2-yl-propyl)-amide, and
1-(4-Fluorophenyl)-1H-pyrazolo[3,4-c]pyridine-4-carboxylic acid [(S)-1-(5-methanesulfonyl-thiophen-3-yl)-propyl]-amide.

Example 4

Synthesis of 1-(4-Fluorophenyl)-6-oxy-1H-pyrazolo[3,4-c]pyridine-4-carboxylic acid 3-trifluoromethyl-benzylamide (4)

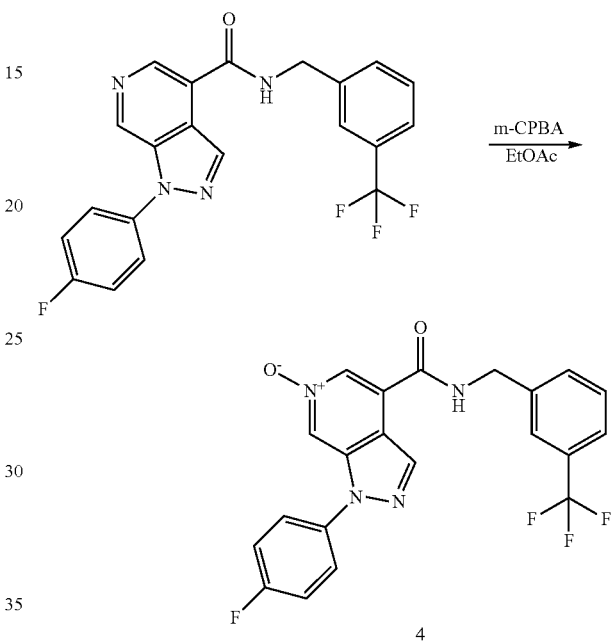

To a solution of 1-(4-fluorophenyl)-1H-pyrazolo[3,4-c]pyridine-4-carboxylic acid 3-trifluoromethyl-benzylamide (0.060 g, 0.14 mmol) in EtOAc (2 mL) was added 77% m-chloroperbenzoic acid (m-CPBA) (50 mg, 0.2 mmol). After 18 hours, a precipitate formed and the mixture was diluted with ether (5 mL) and the precipitate collected by filtration washing with ether to afford the title compound.

Example 5

Synthesis of 1-(4-Fluorophenyl)-6-methyl-4-(3-trifluoromethyl-benzylcarbamoyl)-1H-pyrazolo[3,4-c]pyridin-6-ium iodide (5)

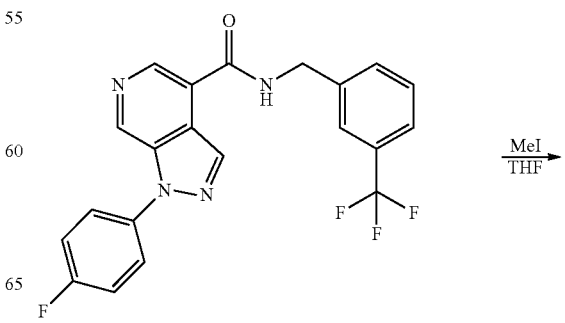

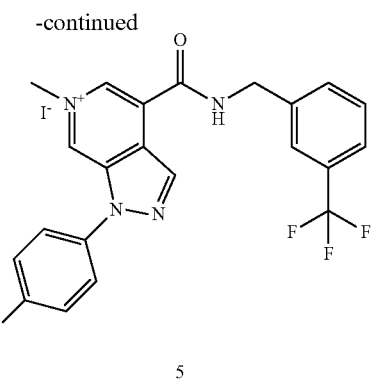

To a solution of 1-(4-fluorophenyl)-1H-pyrazolo[3,4-c]pyridine-4-carboxylic acid 3-trifluoromethyl-benzylamide (0.060 g, 0.14 mmol) in THF (2 mL) was added iodomethane (0.50 mL, 4.0 mmol). The reaction was monitored by TLC (EtOAc-hexanes 4:6). After 11 days, the reaction afforded a white precipitate. The mixture was concentrated under a stream of nitrogen and the residue triturated with ether with a few drops of methanol and then hexanes was added. The solid was collected by filtration to afford the title compound as a yellow solid.

Example 6

Synthesis of 1-(4-Fluorophenyl)-1H-pyrazolo[3,4-c] pyridine-4-carboxylic acid (6-methanesulfonyl-pyridin-3-ylmethyl)-amide (6)

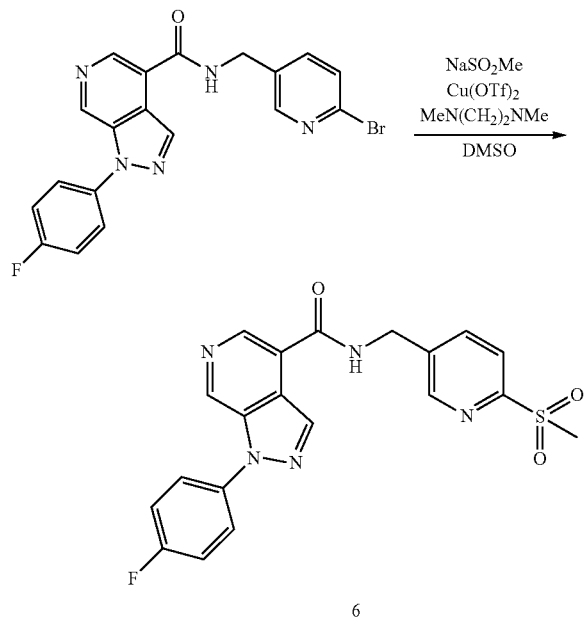

To a microwave tube charged with 1-(4-fluorophenyl)-1H-pyrazolo[3,4-c]pyridine-4-carboxylic acid (6-bromopyridin-3-ylmethyl)-amide (62 mg, 0.15 mmol) in DMSO (1 mL) was added copper (II) trifluoromethanesulfonate (53 mg, 0.15 mmol), sodium methanesulfinate (24 mg, 0.24 mmol) and N,N' dimethylethylene diamine (47 µL, 0.44 mmol). The mixture was warmed at 110° C. for 45 minutes in the microwave. The reaction was monitored by TLC (EtOAc). The reaction was the diluted with saturated aqueous ammonium chloride (10 mL) and extracted with EtOAc (4×7 mL). The combined organic layers were washed with saturated aqueous ammonium chloride (3×7 mL), brine (7 mL), aqueous $K_2CO_3$ (7 mL), brine (7 mL), dried over magnesium sulfate, filtered and concentrated. The solid was triturated with ether to afford the title compound.

The following compounds were also prepared by methods described in Example 6:

1-(4-Fluorophenyl)-1H-pyrazolo[3,4-c]pyridine-4-carboxylic acid (5-methanesulfonyl-pyridin-3-ylmethyl)-amide, 1-(4-Chlorophenyl)-1H-pyrazolo[3,4-c]pyridine-4-carboxylic acid [(S)-1-(5-methaneSulfonyl-pyridin-3-yl)-ethyl]-amide, 1-(4-Chlorophenyl)-1H-pyrazolo[3,4-c]pyridine-4-carboxylic acid [(S)-1-(5-methanesulfonyl-pyridin-3-yl)-propyl]-amide, 1-(4-Fluorophenyl)-1H-pyrazolo[3,4-c]pyridine-4-carboxylic acid [1-(2-methanesulfonyl-pyridin-4-yl)-propyl]-amide, 1-(4-Fluorophenyl)-1H-pyrazolo[3,4-c]pyridine-4-carboxylic acid [(R)-1-(2-methanesulfonyl-pyridin-4-yl)-but-3-enyl]-amide, 1-(4-Fluorophenyl)-1H-pyrazolo[3,4-c]pyridine-4-carboxylic acid [2,2,2-trifluoro-1-(6-methanesulfonyl-pyridin-3-yl)-ethyl]-amide, 1-(4-Fluorophenyl)-1H-pyrazolo[3,4-c]pyridine-4-carboxylic acid [(S)-1-(6-methanesulfonyl-pyridin-3-yl)-ethyl]-amide, 1-(4-Fluorophenyl)-1H-pyrazolo[3,4-c]pyridine-4-carboxylic acid [1-(2-methanesulfonyl-pyridin-4-yl)-ethyl]-amide, 1-(4-Fluorophenyl)-1H-pyrazolo[3,4-c]pyridine-4-carboxylic acid [(S)-1-(6-methanesulfonyl-pyridin-3-yl)-propyl]-amide, 1-(4-Fluorophenyl)-1H-pyrazolo[3,4-c]pyridine-4-carboxylic acid [(S)-1-(6-methanesulfonyl-pyridin-3-yl)-butyl]-amide, 1-(4-Fluorophenyl)-1H-pyrazolo[3,4-c]pyridine-4-carboxylic acid [(R)-1-(3-methanesulfonyl-4-methoxy-phenyl)-propyl]-amide, 1-(4-Fluorophenyl)-1H-pyrazolo[3,4-c]pyridine-4-carboxylic acid [(S)-1-(3-methanesulfonyl-4-methoxy-phenyl)-propyl]-amide, 1-(4-Fluorophenyl)-1H-pyrazolo[3,4-c]pyridine-4-carboxylic acid [(S)-1-(3-methanesulfonyl-4-methoxy-phenyl)-butyl]-amide, 1-(4-Fluorophenyl)-1H-pyrazolo[3,4-c]pyridine-4-carboxylic acid [(R)-1-(3-methanesulfonyl-4-methoxy-phenyl)-butyl]-amide, 1-(4-Fluorophenyl)-1H-pyrazolo[3,4-c]pyridine-4-carboxylic acid [(S)-1-(3-methanesulfonyl-phenyl)-propyl]-amide, 1-(4-Fluorophenyl)-1H-pyrazolo[3,4-c]pyridine-4-carboxylic acid [(S)-1-(3-methanesulfonyl-phenyl)-ethyl]-amide, 1-(4-Fluorophenyl)-1H-pyrazolo[3,4-c]pyridine-4-carboxylic acid [(S)-1-(4-methanesulfonyl-pyridin-2-yl)-propyl]-amide, 1-(4-Fluorophenyl)-1H-pyrazolo[3,4-c]pyridine-4-carboxylic acid [(S)-1-(5-methanesulfonyl-thiophen-2-yl)-propyl]-amide, and 1-(4-Fluorophenyl)-1H-pyrazolo[3,4-c]pyridine-4-carboxylic acid [(S)-1-(2-methanesulfonyl-pyridin-4-yl)-propyl]-amide.

Example 7

Synthesis of 1-(4-Fluorophenyl)-1H-pyrazolo[3,4-c]pyridine-4-carboxylic acid (6-ethanesulfonyl-pyridin-3-ylmethyl)-amide (7)

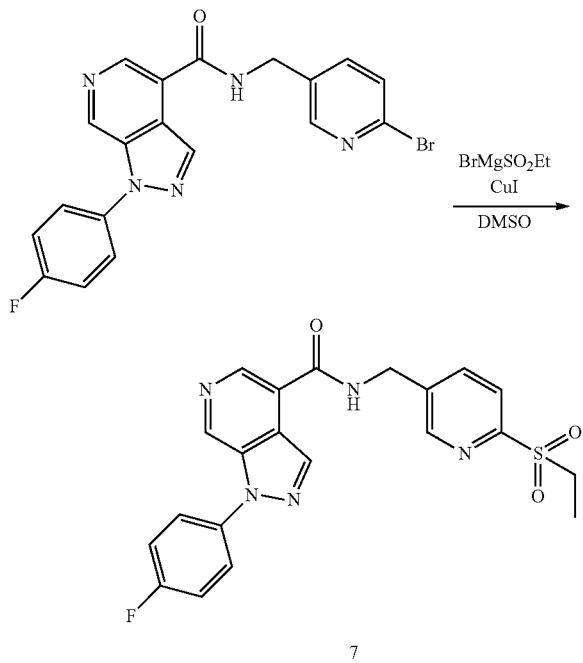

To a microwave tube charged with 1-(4-fluorophenyl)-1H-pyrazolo[3,4-c]pyridine-4-carboxylic acid (6-bromopyridin-3-ylmethyl)-amide (80 mg, 0.2 mmol) in DMSO (3 mL) was added magnesium bromide ethanesulfinate salt (122 mg, 0.618 mmol) (prepared by treating the Grignard reagent, ethylmagnesium bromide with $SO_2$) followed by copper iodide (210 mg, 1.1 mmol). The mixture was warmed in a microwave at 130° C. for 1 hour. The reaction was monitored by TLC (EtOAc) indicating a major new more polar product than starting bromide. The reaction was diluted with first saturated aqueous potassium carbonate (5 mL) and then saturated aqueous ammonium chloride (10 mL) and extracted with EtOAc (5×10 mL). The combined organic layers were washed with saturated aqueous ammonium chloride (3×10 mL), brine (3×10 mL), dried over magnesium sulfate, treated with activated carbon, filtered through diatomaceous earth and concentrated. The solid was dissolved in dichloromethane and purified by silica gel chromatography eluting with EtOAc-dichloromethane (25:75, then 1:1, then 66:34, then 75:25). The material from the column was triturated with ether to afford the title compound as a white solid.

The following compounds were also prepared by methods described in Example 7:

1-(4-Fluorophenyl)-1H-pyrazolo[3,4-c]pyridine-4-carboxylic acid (6-cyclopropanesulfonyl-pyridin-3-ylmethyl)-amide,
1-(4-Fluorophenyl)-1H-pyrazolo[3,4-c]pyridine-4-carboxylic acid (5-ethanesulfonyl-pyridin-3-ylmethyl)-amide,
1-(4-Fluorophenyl)-1H-pyrazolo[3,4-c]pyridine-4-carboxylic acid (2-ethanesulfonyl-pyridin-4-ylmethyl)-amide,
1-(4-Fluorophenyl)-1H-pyrazolo[3,4-c]pyridine-4-carboxylic acid (2-cyclopropanesulfonyl-pyridin-4-ylmethyl)-amide,
1-(4-Fluorophenyl)-1H-pyrazolo[3,4-c]pyridine-4-carboxylic acid [(S)-1-(5-ethaneSulfonyl-pyridin-3-yl)-propyl]-amide,
1-(4-Fluorophenyl)-1H-pyrazolo[3,4-c]pyridine-4-carboxylic acid [(S)-1-(2-ethanesulfonyl-pyridin-4-yl)-but-3-enyl]-amide, The following compound was also isolated during the preparation of 1-(4-Fluorophenyl)-1H-pyrazolo[3,4-c]pyridine-4-carboxylic acid [(S)-1-(2-ethanesulfonyl-pyridin-4-yl)-but-3-enyl]-amide from methods described in Example 7:

1-(4-Fluorophenyl)-1H-pyrazolo[3,4-c]pyridine-4-carboxylic acid ((S)-1-pyridin-4-yl-but-3-enyl)-amide.
1-(4-Fluorophenyl)-1H-pyrazolo[3,4-c]pyridine-4-carboxylic acid [(S)-1-(5-ethanesulfonyl-pyridin-3-yl)-ethyl]-amide,
1-(4-Fluorophenyl)-1H-pyrazolo[3,4-c]pyridine-4-carboxylic acid [(S)-1-(2-ethanesulfonyl-pyridin-4-yl)-propyl]-amide,
1-(4-Fluorophenyl)-1H-pyrazolo[3,4-c]pyridine-4-carboxylic acid [(S)-1-(6-ethanesulfonyl-pyridin-3-yl)-propyl]-amide,
1-(4-Fluorophenyl)-1H-pyrazolo[3,4-c]pyridine-4-carboxylic acid [(S)-1-(6-ethanesulfonyl-pyridin-2-yl)-ethyl]-amide,
1-(4-Fluorophenyl)-1H-pyrazolo[3,4-c]pyridine-4-carboxylic acid [(S)-1-(2-ethanesulfonyl-pyridin-4-yl)-ethyl]-amide,
1-(4-Fluorophenyl)-1H-pyrazolo[3,4-c]pyridine-4-carboxylic acid [(S)-1-(6-ethanesulfonyl-pyridin-3-yl)-ethyl]-amide,
1-(4-Fluorophenyl)-1H-pyrazolo[3,4-c]pyridine-4-carboxylic acid [(S)-1-(6-ethanesulfonyl-pyridin-2-yl)-propyl]-amide.

The following methylsulfones were also prepared by methods described in Example 7 using sodium methanesulfinate and CuI in DMSO:

1-(4-Fluorophenyl)-1H-pyrazolo[3,4-c]pyridine-4-carboxylic acid [(R)-1-(5-methanesulfonyl-pyridin-3-yl)-propyl]-amide,
1-(4-Fluorophenyl)-1H-pyrazolo[3,4-c]pyridine-4-carboxylic acid [(S)-1-(5-methanesulfonyl-pyridin-3-yl)-propyl]-amide,
1-(4-Fluorophenyl)-1H-pyrazolo[3,4-c]pyridine-4-carboxylic acid [1-(6-methanesulfonyl-pyridin-3-yl)-ethyl]-amide,
1-(4-Fluorophenyl)-1H-pyrazolo[3,4-c]pyridine-4-carboxylic acid [(S)-1-(5-methanesulfonyl-pyridin-3-yl)-ethyl]-amide,
1-(4-Fluorophenyl)-1H-pyrazolo[3,4-c]pyridine-4-carboxylic acid [(S)-1-(5-methanesulfonyl-pyridin-3-yl)-butyl]-amide,
1-(4-Fluorophenyl)-1H-pyrazolo[3,4-c]pyridine-4-carboxylic acid [(S)-1-(6-methanesulfonyl-pyridin-2-yl)-ethyl]-amide,
1-(4-Fluorophenyl)-1H-pyrazolo[3,4-c]pyridine-4-carboxylic acid [(S)-1-(2-methanesulfonyl-pyridin-4-yl)-ethyl]-amide,
1-(4-Fluorophenyl)-1H-pyrazolo[3,4-c]pyridine-4-carboxylic acid [(S)-1-(6-methanesulfonyl-pyridin-2-yl)-propyl]-amide, 1-(4-Fluorophenyl)-1H-pyrazolo[3,4-c]pyridine-4-carboxylic acid [(S)-1-(4-methanesulfonyl-3-methoxy-phenyl)-propyl]-amide,
1-(4-Fluorophenyl)-1H-pyrazolo[3,4-c]pyridine-4-carboxylic acid [(S)-1-(2-methanesulfonyl-pyridin-4-yl)-but-3-enyl]-amide,
1-(4-Fluorophenyl)-1H-pyrazolo[3,4-c]pyridine-4-carboxylic acid (5-methanesulfonyl-thiophen-2-ylmethyl)-amide,
1-(4-Fluorophenyl)-1H-pyrazolo[3,4-c]pyridine-4-carboxylic acid (4-methanesulfonyl-thiophen-2-ylmethyl)-amide,
1-(4-Fluorophenyl)-1H-pyrazolo[3,4-c]pyridine-4-carboxylic acid (2-methanesulfonyl-thiazol-4-ylmethyl)-amide, and 1-(4-Fluorophenyl)-1H-pyrazolo[3,4-c]pyridine-4-carboxylic acid (2-methanesulfonyl-thiazol-5-ylmethyl)-amide.

Example 8

Synthesis of 3-[5-({[1-(4-Fluorophenyl)-1H-pyrazolo[3,4-c]pyridine-4-carbonyl]-amino}-methyl)-pyridine-2-sulfonyl]-propionic acid methyl ester (8)

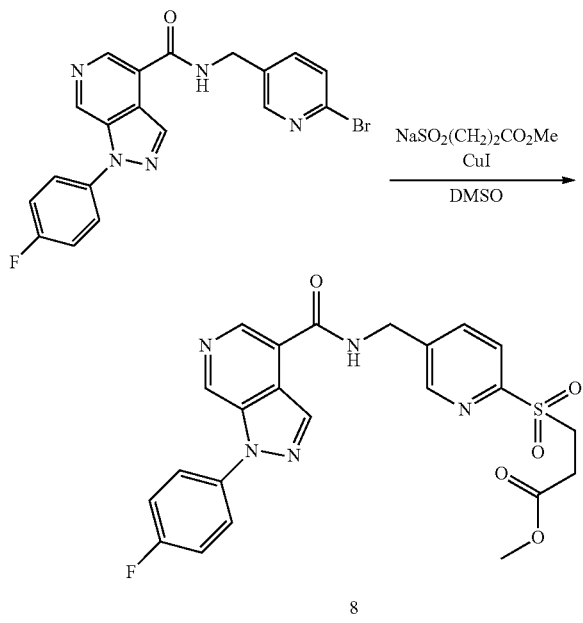

To a solution of 1-(4-fluorophenyl)-1H-pyrazolo[3,4-c]pyridine-4-carboxylic acid (6-bromopyridin-3-ylmethyl)-amide (150 mg, 0.35 mmol) in DMSO (2 mL) was added sodium 3-methoxy-3-oxopropane-1-sulfinate (125 mg, 0.717 mmol) followed by copper (I) iodide (135 mg, 0.708 mmol). The mixture was then warmed in a microwave at 110° C. for 35 minutes. The reaction was monitored by TLC (EtOAc) indicating a new slightly more polar product than starting bromide. The reaction was then diluted with brine (10 mL) and extracted with EtOAc (4×10 mL). The combined organic layers were washed with brine (5×10 mL), dried over magnesium sulfate, filtered and concentrated. The solid was dissolved in dichloromethane and purified by silica gel chromatography eluting with EtOAc-dichloromethane (25:75, then 1:1, then 75:25). The material from the column was triturated with ether to afford the title compound.

The following compound was also prepared by methods described in Example 8:
3-[4-({[1-(4-Fluorophenyl)-1H-pyrazolo[3,4-c]pyridine-4-carbonyl]-amino}-methyl)-pyridine-2-sulfonyl]-propionic acid methyl ester,
3-[5-(1-{[1-(4-Fluorophenyl)-1H-pyrazolo[3,4-c]pyridine-4-carbonyl]-amino}-butyl)-pyridine-3-sulfonyl]-propionic acid methyl ester,
3-[5-((S)-1-{[1-(4-Fluorophenyl)-1H-pyrazolo[3,4-c]pyridine-4-carbonyl]-amino}-butyl)-pyridine-3-sulfonyl]-propionic acid methyl ester,
The following two compounds were also isolated during the preparation of 3-[5-((S)-1-{[1-(4-Fluorophenyl)-1H-pyrazolo[3,4-c]pyridine-4-carbonyl]-amino}-butyl)-pyridine-3-sulfonyl]-propionic acid methyl ester from methods described in Example 8:
1-(4-Fluorophenyl)-1H-pyrazolo[3,4-c]pyridine-4-carboxylic acid ((S)-1-pyridin-3-yl-butyl)-amide, and
3-[5-((S)-1-{[1-(4-Fluorophenyl)-1H-pyrazolo[3,4-c]pyridine-4-carbonyl]-amino}-butyl)-pyridine-3-sulfonyl]-propionic acid,
3-[5-((S)-1-{[1-(4-Fluorophenyl)-1H-pyrazolo[3,4-c]pyridine-4-carbonyl]-amino}-propyl)-pyridine-3-sulfonyl]-propionic acid methyl ester,
The following two compounds were also isolated as products during the preparation of 3-[5-((S)-1-{[1-(4-Fluorophenyl)-1H-pyrazolo[3,4-c]pyridine-4-carbonyl]-amino}-propyl)-pyridine-3-sulfonyl]-propionic acid methyl ester from methods described in Example 8:
1-(4-Fluorophenyl)-1H-pyrazolo[3,4-c]pyridine-4-carboxylic acid ((S)-1-pyridin-3-yl-propyl)-amide, and
3-[5-((S)-1-{[1-(4-Fluorophenyl)-1H-pyrazolo[3,4-c]pyridine-4-carbonyl]-amino}-propyl)-pyridine-3-sulfonyl]-propionic acid,
3-[6-((S)-1-{[1-(4-Fluorophenyl)-1H-pyrazolo[3,4-c]pyridine-4-carbonyl]-amino}-ethyl)-pyridine-2-sulfonyl]-propionic acid methyl ester,
The following compound was also isolated as products during the preparation of 3-[6-((S)-1-{[1-(4-Fluorophenyl)-1H-pyrazolo[3,4-c]pyridine-4-carbonyl]-amino}-ethyl)-pyridine-2-sulfonyl]-propionic acid methyl ester from methods described in Example 8:
1-(4-Fluorophenyl)-1H-pyrazolo[3,4-c]pyridine-4-carboxylic acid ((S)-1-pyridin-2-yl-ethyl)-amide,
3-[4-((S)-1-{[1-(4-Fluorophenyl)-1H-pyrazolo[3,4-c]pyridine-4-carbonyl]-amino}-propyl)-pyridine-2-sulfonyl]-propionic acid methyl ester,
3-[4-((S)-1-{[1-(4-Fluorophenyl)-1H-pyrazolo[3,4-c]pyridine-4-carbonyl]-amino}-ethyl)-pyridine-2-sulfonyl]-propionic acid methyl ester,
The following compound was also isolated during the preparation of 3-[4-((S)-1-{[1-(4-Fluorophenyl)-1H-pyrazolo[3,4-c]pyridine-4-carbonyl]-amino}-ethyl)-pyridine-2-sulfonyl]-propionic acid methyl ester from methods described in Example 8:
3-[4-((S)-1-{[1-(4-Fluorophenyl)-1H-pyrazolo[3,4-c]pyridine-4-carbonyl]-amino}-ethyl)-pyridine-2-sulfonyl]-propionic acid,
3-[5-((S)-1-{[1-(4-Fluorophenyl)-1H-pyrazolo[3,4-c]pyridine-4-carbonyl]-amino}-ethyl)-pyridine-3-sulfonyl]-propionic acid methyl ester, and
3-[6-((S)-1-{[1-(4-Fluorophenyl)-1H-pyrazolo[3,4-c]pyridine-4-carbonyl]-amino}-propyl)-pyridine-2-sulfonyl]-propionic acid methyl ester,
The following compound was also isolated during the preparation of 3-[6-((S)-1-{[1-(4-Fluorophenyl)-1H-pyrazolo[3,4-c]pyridine-4-carbonyl]-amino}-propyl)-

239 pyridine-2-sulfonyl]-propionic acid methyl ester from methods described in Example 8
1-(4-Fluorophenyl)-1H-pyrazolo[3,4-c]pyridine-4-carboxylic acid ((S)-1-pyridin-2-yl-propyl)-amide.

Example 9

Synthesis of Acetic acid 2-{[4-({[1-(4-fluorophenyl)-1H-pyrazolo[3,4-c]pyridine-4-carbonyl]-amino}-methyl)-benzenesulfonyl]-methyl-amino}-ethyl ester (9)

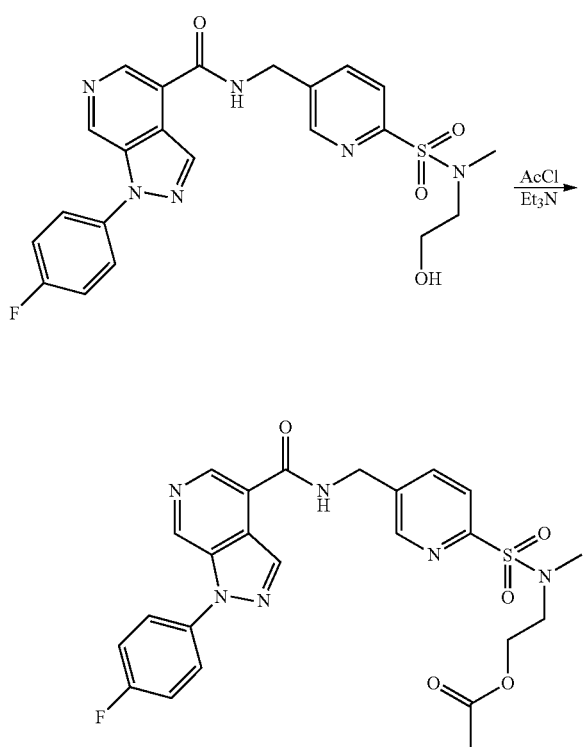

9

To a room temperature solution of 1-(4-fluorophenyl)-1H-pyrazolo[3,4-c]pyridine-4-carboxylic acid 4-[(2-hydroxyethyl)-methyl-sulfamoyl]-benzylamide (50 mg, 0.1 mmol), Et$_3$N (16 µL, 0.14 mmol) in dichloromethane was added acetyl chloride (0.010 mL, 0.11 mmol). After 4 hours, the mixture was diluted with EtOAc and the organic layer was washed with saturated aqueous sodium bicarbonate, 1 N aqueous HCl, water, brine, dried over magnesium sulfate, filtered and concentrated to afford the title compound.

The following compound was also prepared by methods described in Example 9:

1-(4-Fluorophenyl)-1H-pyrazolo[3,4-c]pyridine-4-carboxylic acid [1-(1-acetyl-piperidin-3-yl)-propyl]-amide, and
1-(4-Fluorophenyl)-1H-pyrazolo[3,4-c]pyridine-4-carboxylic acid [1-(1-acetyl-piperidin-4-yl)-propyl]-amide.

240

Example 10

Synthesis of 1-(4-Fluorophenyl)-1H-pyrazolo[3,4-c]pyridine-4-carboxylic acid [2-(3-hydroxy-propane-1-sulfonyl)-pyridin-4-ylmethyl]-amide (10)

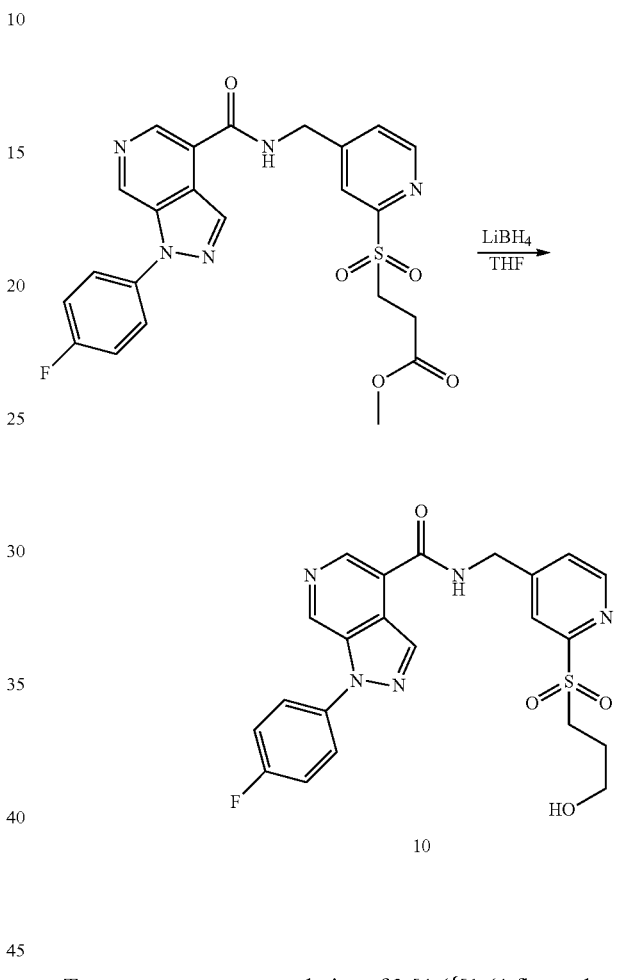

10

To a room temperature solution of 3-[4-({[1-(4-fluorophenyl)-1H-pyrazolo[3,4-c]pyridine-4-carbonyl]-amino}-methyl)-pyridine-2-sulfonyl]-propionic acid methyl ester (33 mg, 0.066 mmol) in THF (5 mL) was added lithium borohydride (8.6 mg, 0.40 mmol). The mixture was then warmed at reflux. After 1 hour, the reaction was cooled to room temperature, quenched with water (50 mL) and diluted with EtOAc (50 mL). The organic layer was separated and the aqueous layer was extracted with EtOAc (2×25 mL). The combined organic layers were washed with brine, dried over MgSO$_4$, filtered and concentrated. The residue was purified by silica gel chromatography eluting with a gradient of 0-10% MeOH in CH$_2$Cl$_2$. The residue was further purified by reversed-phase HPLC. The desired fractions were combined and lyophilized to afford the title compound as a yellow solid.

The following compound was also prepared by methods described in Example 10:

1-(4-Fluorophenyl)-1H-pyrazolo[3,4-c]pyridine-4-carboxylic acid {(S)-1-[2-(3-hydroxy-propane-1-sulfonyl)-pyridin-4-yl]-ethyl}-amide.

Example 11

Synthesis of 1-(4-Fluorophenyl)-1H-pyrazolo[3,4-c] pyridine-4-carboxylic acid [6-(2-methoxy-ethylsulfamoyl)-pyridin-3-ylmethyl]-amide (11)

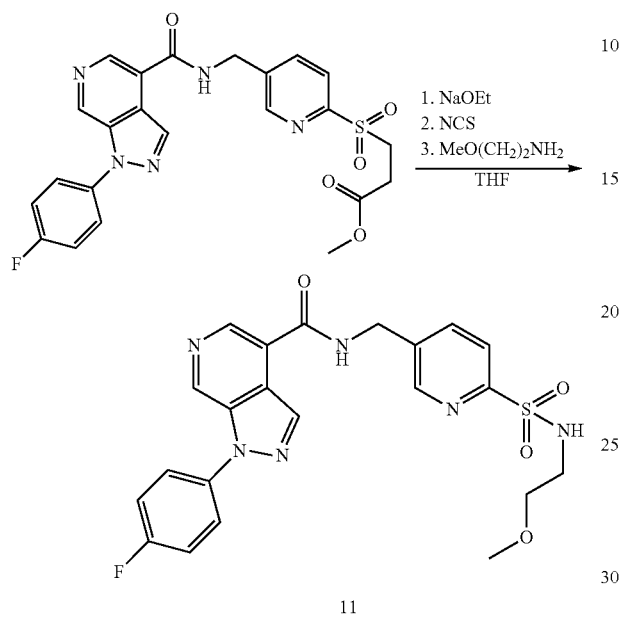

11

To a solution of 3-[5-({[1-(4-fluorophenyl)-1H-pyrazolo[3,4-c]pyridine-4-carbonyl]-amino}-methyl)-pyridine-2-sulfonyl]-propionic acid methyl ester (100 mg, 0.2 mmol) in THF (5 mL) was added a freshly prepared 8% solution of sodium ethoxide (200 μL, 0.2 mmol) in ethanol. The mixture was stirred for 15 minutes and was monitored for the disappearance of starting material by TLC (EtOAc). The mixture was then concentrated to dryness under a stream of nitrogen. The mixture was again diluted with THF and then N-chlorosuccinimide (55 mg, 0.41 mmol) was added. After 15 minutes, 2-methoxyethylamine (0.100 mL, 1.15 mmol) was added in one portion. After 15 minutes, the mixture was diluted with saturated ammonium chloride and extracted with EtOAc (3×10 mL). The combined organic layers were washed with brine (2×10 mL), dried over magnesium sulfate, filtered and concentrated. The crude material was purified by silica gel chromatography eluting with methanol-EtOAc (0:100, then 0.5:99.5, then 1:99, then 2:98). The material from the column was purified a second time by using preparative silica gel TLC eluting with methanol-EtOAc (1:9). The material from the plate was triturated with EtOAc-ether-hexanes to afford the title compound.

The following compound was also prepared by methods described in Example 11:
1-(4-Fluorophenyl)-1H-pyrazolo[3,4-c]pyridine-4-carboxylic acid [(S)-1-(6-cyclopropylsulfamoyl-pyridin-3-yl)-propyl]-amide, and
1-(4-Fluorophenyl)-1H-pyrazolo[3,4-c]pyridine-4-carboxylic acid [6-(tetrahydropyran-4-ylsulfamoyl)-pyridin-3-ylmethyl]-amide.

The following compound was also prepared by methods described in Example 11 with the following modification: N-chlorosuccinimide was replaced with Chloroamine T:
1-(4-Fluorophenyl)-1H-pyrazolo[3,4-c]pyridine-4-carboxylic acid [1-(5-methylsulfamoyl-pyridin-3-yl)-butyl]-amide, and
1-(4-Fluorophenyl)-1H-pyrazolo[3,4-c]pyridine-4-carboxylic acid [(S)-1-(5-methylsulfamoyl-pyridin-3-yl)-butyl]-amide.

The following compound was also isolated during the preparation of 1-(4-Fluorophenyl)-1H-pyrazolo[3,4-c]pyridine-4-carboxylic acid [(S)-1-(5-methylsulfamoyl-pyridin-3-yl)-butyl]-amide from methods described in Example 11:
5-((S)-1-{[1-(4-Fluorophenyl)-1H-pyrazolo[3,4-c]pyridine-4-carbonyl]-amino}-butyl)-pyridine-3-sulfonic acid.

Example 12

Synthesis of 1-(4-Fluorophenyl)-1H-pyrazolo[3,4-c] pyridine-4-carboxylic acid (2-sulfamoyl-pyridin-4-ylmethyl)-amide (12)

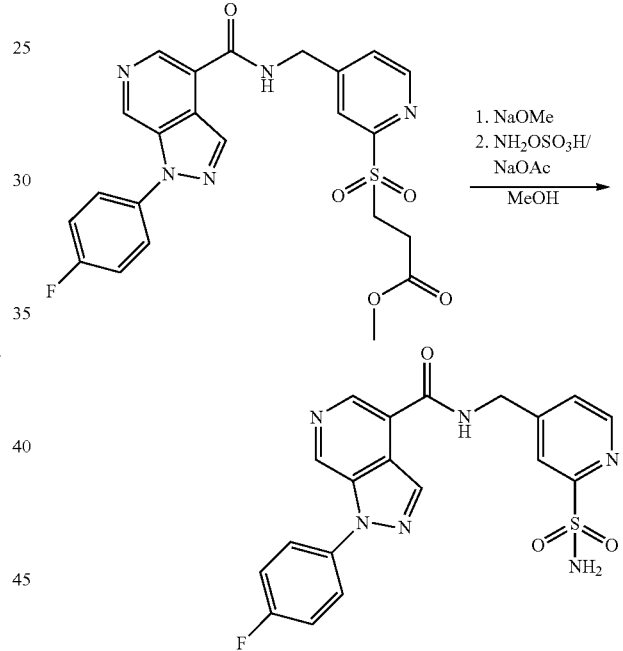

12

A solution of 3-[4-({[1-(4-fluorophenyl)-1H-pyrazolo[3,4-c]pyridine-4-carbonyl]-amino}-methyl)-pyridine-2-sulfonyl]-propionic acid methyl ester (37 mg, 0.07 mmol) in DMSO (1 mL) was added a freshly prepared 15% solution of sodium methoxide (28 μL, 0.08 mmol) in methanol. After 15 minutes, the mixture was placed in a water bath and a solution of N-hydroxylamine-O-sulfonic acid (168 mg, 1.49 mmol) and sodium acetate (97 mg, 1.2 mmol) in water (4 mL) was added. The water bath was then removed. After 60 hours, the mixture was diluted with EtOAc (20 mL) and water (20 mL) and the aqueous layer was extracted with EtOAc (3×20 mL). The combined organic layers were washed with water (4×20 mL, until the pH=5), dried over MgSO$_4$, filtered and concentrated. The residue was purified by silica gel chromatography eluting with a gradient of 0-10% methanol in dichloromethane. The material from the column was triturated with ether (3 times), filtered and dried under vacuum to afford the title compound as a white solid.

The following compound was also prepared by methods described in Example 12:
1-(4-Fluorophenyl)-1H-pyrazolo[3,4-c]pyridine-4-carboxylic acid [1-(5-sulfamoyl-pyridin-3-yl)-butyl]-amide,
1-(4-Fluorophenyl)-1H-pyrazolo[3,4-c]pyridine-4-carboxylic acid [(S)-1-(5-sulfamoyl-pyridin-3-yl)-butyl]-amide,
1-(4-Fluorophenyl)-1H-pyrazolo[3,4-c]pyridine-4-carboxylic acid [(S)-1-(5-sulfamoyl-pyridin-3-yl)-ethyl]-amide,
1-(4-Fluorophenyl)-1H-pyrazolo[3,4-c]pyridine-4-carboxylic acid [(S)-1-(5-sulfamoyl-pyridin-3-yl)-propyl]-amide,
1-(4-Fluorophenyl)-1H-pyrazolo[3,4-c]pyridine-4-carboxylic acid [(S)-1-(6-sulfamoyl-pyridin-2-yl)-propyl]-amide,
1-(4-Fluorophenyl)-1H-pyrazolo[3,4-c]pyridine-4-carboxylic acid [(S)-1-(2-sulfamoyl-pyridin-4-yl)-propyl]-amide,
1-(4-Fluorophenyl)-1H-pyrazolo[3,4-c]pyridine-4-carboxylic acid [(S)-1-(2-sulfamoyl-pyridin-4-yl)-ethyl]-amide,
1-(4-Fluorophenyl)-1H-pyrazolo[3,4-c]pyridine-4-carboxylic acid [(S)-1-(6-sulfamoyl-pyridin-2-yl)-ethyl]-amide.

Example 13

Synthesis of 1-(4-Fluorophenyl)-1H-pyrazolo[3,4-c]pyridine-4-carboxylic acid 4-(4-hydroxy-piperidine-1-sulfonyl)-benzylamide (13)

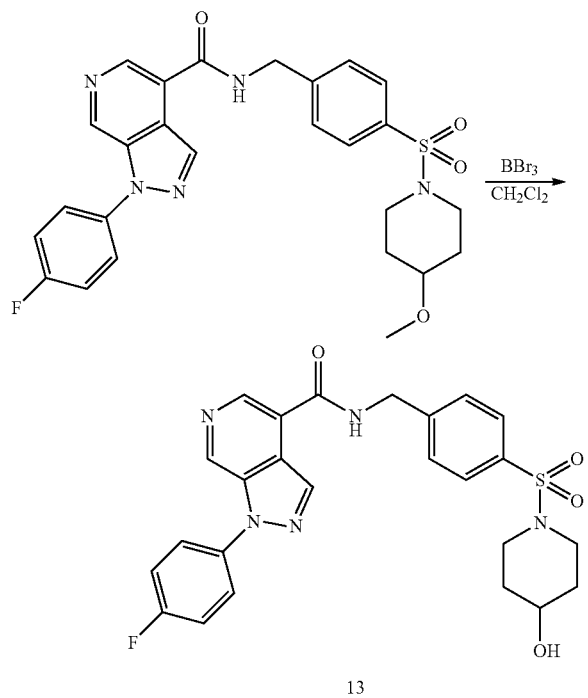

13

To a chilled (−78° C.) solution of 1-(4-fluorophenyl)-1H-pyrazolo[3,4-c]pyridine-4-carboxylic acid 4-(4-methoxy-piperidine-1-sulfonyl)-benzylamide (0.080 g, 0.15 mmol) in dichloromethane (5 mL) was added a 1 M solution of boron tribromide (0.2 mL, 0.2 mmol) in dichloromethane. The mixture was allowed to warm to room temperature. The reaction was monitored by TLC and LC-MS indicating partial conversion. Additional boron tribromide (0.4 mL, 0.4 mmol) was added. After 30 minutes, the mixture was quenched with saturated aqueous sodium bicarbonate and was then extracted with EtOAc (3×10 mL). The combined organic layers were washed with brine (3×5 mL), dried over magnesium sulfate, filtered and concentrated. The crude material was purified by silica gel chromatography using a gradient of 0-30% acetonitrile in EtOAc to afford the title compound as a colorless solid.

The following compound was also prepared by methods described in Example 13:
1-(4-Fluorophenyl)-1H-pyrazolo[3,4-c]pyridine-4-carboxylic acid [(S)-1-(4-hydroxy-3-methanesulfonyl-phenyl)-butyl]-amide,
1-(4-Fluorophenyl)-1H-pyrazolo[3,4-c]pyridine-4-carboxylic acid [(R)-1-(4-hydroxy-3-methanesulfonyl-phenyl)-butyl]-amide,
1-(4-Fluorophenyl)-1H-pyrazolo[3,4-c]pyridine-4-carboxylic acid [6-(2-hydroxy-ethylsulfamoyl)-pyridin-3-ylmethyl]-amide,
1-(4-Fluorophenyl)-1H-pyrazolo[3,4-c]pyridine-4-carboxylic acid [(S)-1-(4-hydroxy-3-methanesulfonyl-phenyl)-propyl]-amide,
1-(4-Fluorophenyl)-1H-pyrazolo[3,4-c]pyridine-4-carboxylic acid [(S)-1-(3-hydroxy-4-methanesulfonyl-phenyl)-propyl]-amide,
1-(4-Fluorophenyl)-1H-pyrazolo[3,4-c]pyridine-4-carboxylic acid 3-hydroxy-4-methanesulfonyl-benzylamide, and
1-(4-Fluorophenyl)-1H-pyrazolo[3,4-c]pyridine-4-carboxylic acid 2-hydroxy-4-methanesulfonyl-benzylamide.

Example 14

Synthesis of 1-(4-Fluorophenyl)-1H-pyrazolo[3,4-c]pyridine-4-carboxylic acid (2-methanesulfonylamino-pyridin-4-ylmethyl)-amide (14)

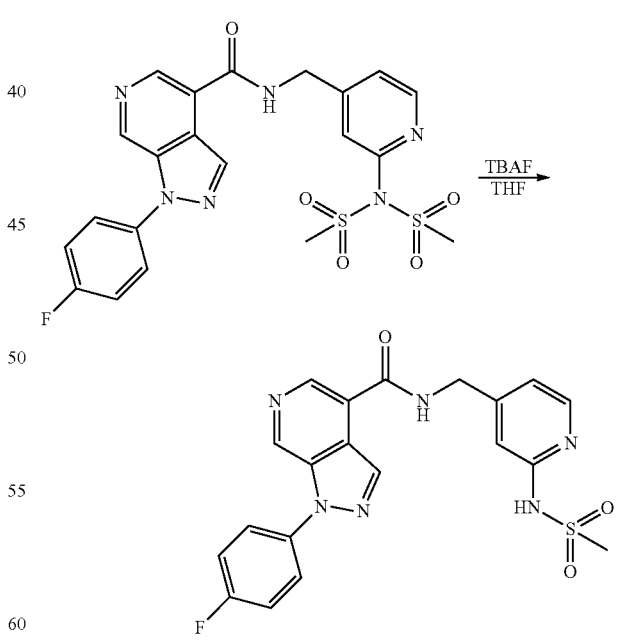

14

A solution of 1-(4-fluorophenyl)-1H-pyrazolo[3,4-c]pyridine-4-carboxylic acid (2,2-bismethanesulfonylamino-pyridin-4-ylmethyl)-amide (36 mg, 0.069 mmol) in THF (1 mL) was added a 1 M solution of tetra-n-butylammonium fluoride

Example 15

Synthesis of 1-(4-Fluorophenyl)-1H-pyrazolo[3,4-c]pyridine-4-carboxylic acid [(S)-1-(2-ethanesulfonyl-pyridin-4-yl)-butyl]-amide (15)

(347 μL, 0.347 mmol) in THF and the mixture was warmed at reflux. After 1 hour, the mixture was quenched with saturated aqueous ammonium chloride (15 mL) and diluted with EtOAc (15 mL). The organic phase was separated and washed with NaHCO$_3$ (10 mL), brine (10 mL), dried over MgSO$_4$, filtered and concentrated. The residue was purified by silica gel chromatography eluting with a gradient of 0-10% methanol in dichloromethane to afford the title compound as a solid.

A solution of 1-(4-fluorophenyl)-1H-pyrazolo[3,4-c]pyridine-4-carboxylic acid [(S)-1-(2-ethanesulfonyl-pyridin-4-yl)-but-3-enyl]-amide (136 mg, 0.284 mmol) in MeOH (30 mL) was hydrogenated over 10% Pd/C using a continuous flow hydrogenation apparatus (conditions: full H$_2$ mode, flow rate 1 mL/minute, 30° C., 1 atmosphere). The solution was concentrated in vacuo and purified by reversed-phase HPLC using a 20 minute gradient of 5-95% acetonitrile (0.1% TFA) in water (0.1% TFA) (flow rate=25 mL/min). The desired fractions were combined, neutralized with saturated aqueous sodium bicarbonate and extracted with dichloromethane (3×20 mL). The combined organic layers were dried over MgSO$_4$, filtered and concentrated to afford the title compound as an off white solid.

Example 16

Synthesis of 1-(4-Fluorophenyl)-1H-pyrazolo[3,4-c]pyridine-4-carboxylic acid [(S)-1-(2-cyano-pyridin-4-yl)-propyl]-amide (16)

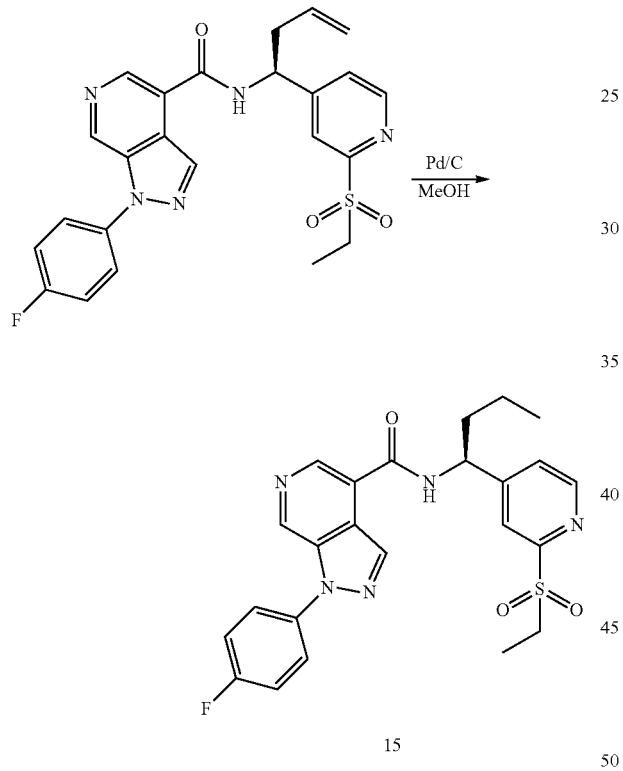

A microwave vial charged with 1-(4-fluorophenyl)-1H-pyrazolo[3,4-c]pyridine-4-carboxylic acid [(S)-1-(2-bromopyridin-4-yl)-propyl]-amide (0.10 g, 0.22 mmol), PS-triphenylphosphine (20 mg, 0.04 mmol), palladium (II) acetate (5 mg, 0.02 mmol), zinc cyanide (26 mg, 0.22 mmol) and DMF (2 mL) was warmed in a microwave at 140° C. After 30 minutes, additional zinc cyanide (25 mg, 0.22 mmol) was added and the mixture was warmed in a microwave at 140° C. After 30 minutes, the mixture was filtered washing with diethyl ether. The filtrate was diluted with ether and washed with water (2×40 mL) and brine (40 mL). The organic layer was dried over sodium sulfate and concentrated. The crude material was purified by reversed-phase HPLC. The desired fractions from the column were concentrated diluted with saturated aqueous sodium bicarbonate and extracted with dichloromethane (2×25 mL), dried with sodium sulfate and concentrated to afford the title compound.

Example 17

Synthesis of 1-(4-Fluorophenyl)-1H-pyrazolo[3,4-c]pyridine-4-carboxylic acid [(S)-1-(2-carbamoyl-pyridin-4-yl)-propyl]-amide (17a) and 4-((S)-1-{[1-(4-Fluorophenyl)-1H-pyrazolo[3,4-c]pyridine-4-carbonyl]-amino}-propyl)-pyridine-2-carboxylic acid (17b)

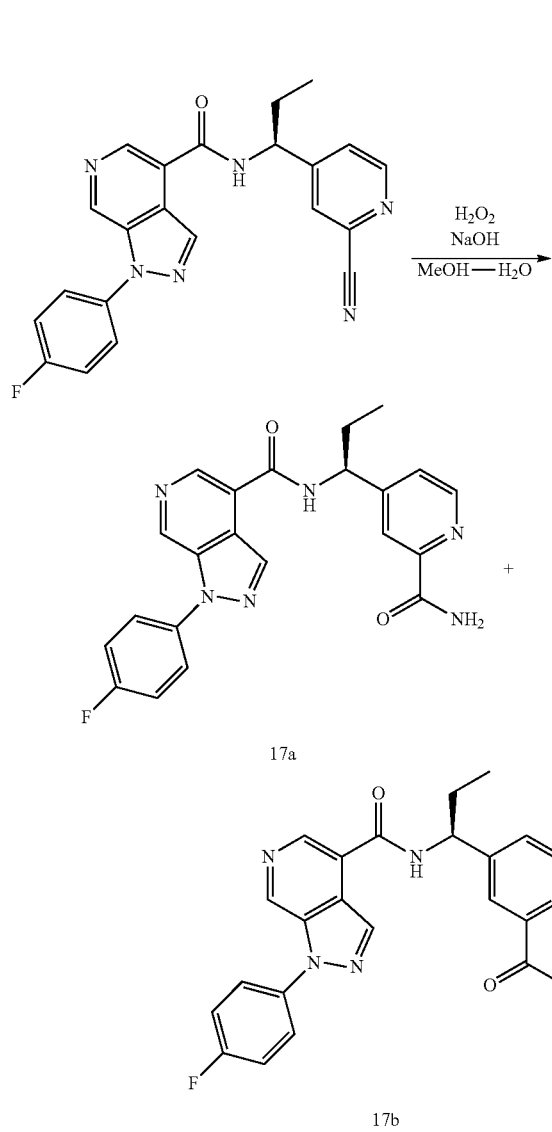

17a

17b

To a mixture of solution of 30% aqueous hydrogen peroxide (1 mL), 1 N aqueous NaOH (3 mL) and methanol (1 mL) was added 1-(4-fluorophenyl)-1H-pyrazolo[3,4-c]pyridine-4-carboxylic acid [(S)-1-(2-cyano-pyridin-4-yl)-propyl]-amide (40 mg, 0.1 mmol). After 4 hours, the reaction was concentrated and dissolved in DMSO (0.5 mL), acetonitrile-water (1 mL), filtered and purified by reversed-phase HPLC. The desired fractions containing the amide were concentrated, diluted with dichloromethane, washed with saturated aqueous sodium bicarbonate, dried over sodium sulfate, filtered and concentrated. The desired fractions containing the carboxylic acid were concentrated to afford the title compounds.

Example 18

Synthesis of [4-({[1-(4-Fluorophenyl)-1H-pyrazolo[3,4-c]pyridine-4-carbonyl]-amino}-methyl)-pyridine-2-sulfonyl]-acetic acid ethyl ester (18)

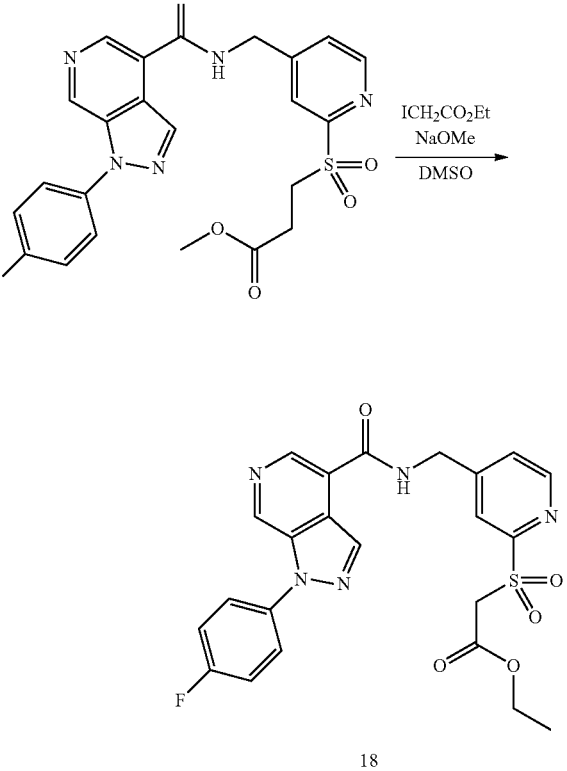

18

A solution of 3-[4-({[1-(4-fluorophenyl)-1H-pyrazolo[3,4-c]pyridine-4-carbonyl]-amino}-methyl)-pyridine-2-sulfonyl]-propionic acid methyl ester (200 mg, 0.4 mmol) in DMSO (5 mL) was treated a 15% solution of sodium methoxide in methanol (150 μL, 0.42 mmol). After 15 minutes, the mixture was cooled (water bath) and ethyl iodoacetate (50 μL, 0.42 mmol) was added followed by removal of the water bath. After 18 hours, the mixture was diluted with EtOAc (30 mL) and water (30 mL) and the organic layer was separated. The aqueous layer was extracted with EtOAc (3×20 mL). The combined organic layers were washed with water (20 mL), dried over magnesium sulfate, filtered and concentrated. The residue was purified by silica gel chromatography using a gradient of 0-6% methanol in dichloromethane. The material from the column was twice triturated with ether, filtered and dried under vacuum to afford the title compound as a tan solid.

Example 19

Synthesis of 1-(4-Fluorophenyl)-1H-pyrazolo[3,4-c]pyridine-4-carboxylic acid [(S)-1-(2-methylamino-pyridin-4-yl)-propyl]-amide (19)

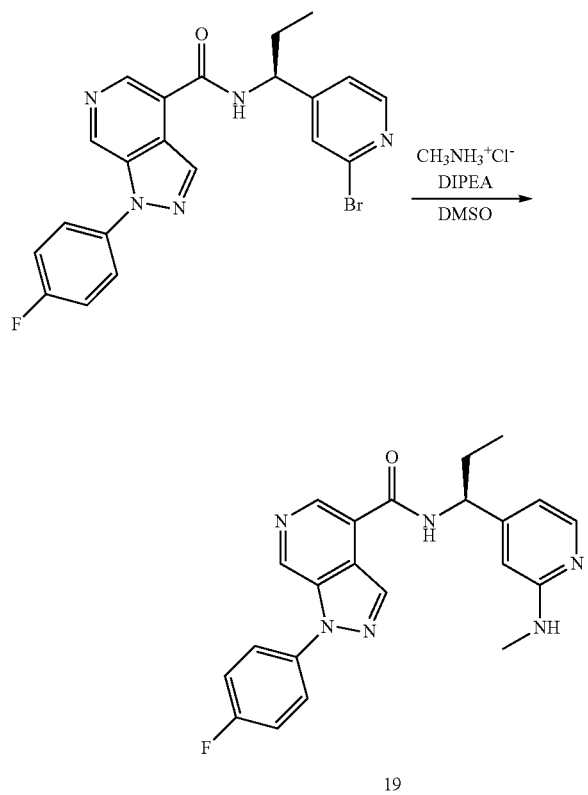

A sealed tube charged with 1-(4-fluorophenyl)-1H-pyrazolo[3,4-c]pyridine-4-carboxylic acid [(S)-1-(2-bromopyridin-4-yl)-propyl]-amide (0.10 g, 0.22 mmol), methylamine hydrochloride (45 mg, 0.67 mmol) and DIPEA (203 µL, 1.17 mmol) in DMSO (2 mL) was warmed at 160° C. After 16 hours, the reaction was diluted with saturated aqueous sodium bicarbonate (50 mL) and extracted with dichloromethane (5×10 mL). The organic layer was dried over sodium sulfate, filtered and concentrated. The crude material was purified by silica gel chromatography eluting with 10% methanol in dichloromethane to afford the title compound.

The following compound was also prepared by methods described in Example 19 with the following modification. The chloropyridine was reacted with morpholine in the absence of DIPEA:

1-(4-Fluorophenyl)-1H-pyrazolo[3,4-c]pyridine-4-carboxylic acid [(S)-1-(2-morpholin-4-yl-pyridin-4-yl)-propyl]-amide.

Example 20

Synthesis of 1-(4-Fluorophenyl)-1H-pyrazolo[3,4-c]pyridine-4-carboxylic acid {(S)-1-[2-(acetyl-methyl-amino)-pyridin-4-yl]-propyl}-amide (20)

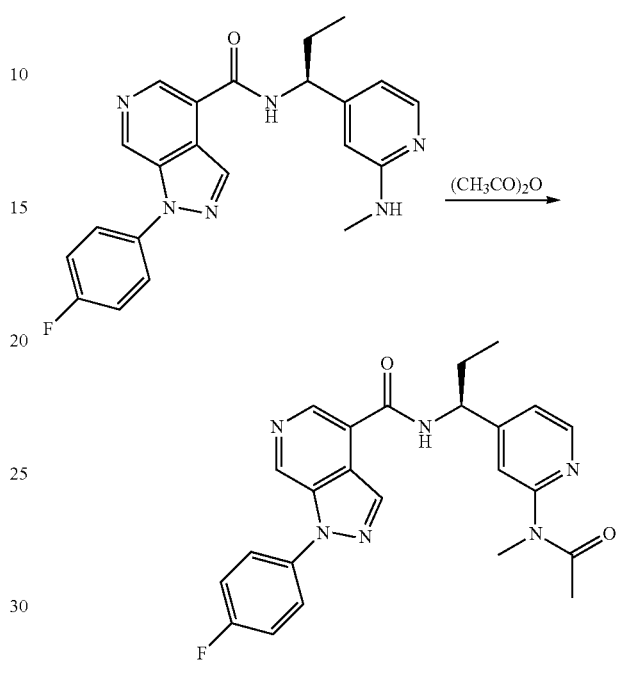

A mixture of 1-(4-fluorophenyl)-1H-pyrazolo[3,4-c]pyridine-4-carboxylic acid [(S)-1-(2-methylamino-pyridin-4-yl)-propyl]-amide (20 mg, 0.05 mmol) and acetic anhydride (2.0 mL, 21 mmol) was warmed at 60° C. After 4 hours, the mixture was diluted with 1 N aqueous NaOH. After 20 minutes, the mixture was extracted with dichloromethane, dried over sodium sulfate, filtered and concentrated. The material was purified by silica gel chromatography using a gradient of 0-10% methanol in dichloromethane to afford the title compound.

Example 21

Synthesis of 1-(4-Fluorophenyl)-1H-pyrazolo[3,4-c]pyridine-4-carboxylic acid (2-carbamoylmethane-sulfonyl-pyridin-4-ylmethyl)-amide (21)

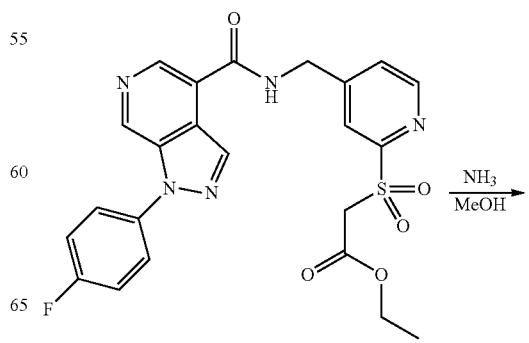

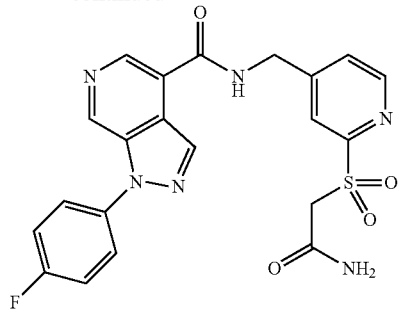

21

In a sealed tube, a solution of [4-({[1-(4-fluorophenyl)-1H-pyrazolo[3,4-c]pyridine-4-carbonyl]-amino}-methyl)-pyridine-2-sulfonyl]-acetic acid ethyl ester (40 mg, 0.08 mmol) in a 7 N solution of ammonia in methanol (345 µL, 2.41 mmol) was warmed at 100° C. After 6 hours, the mixture was cooled to room temperature, and the resulting precipitate collected by filtration. The solid was purified by reversed-phase HPLC (C18 column, flow rate=25 mL/minute) using a 20 minute gradient of 5-95% acetonitrile (0.1% TFA) in water (0.1% TFA). Desired fractions from the column were combined and neutralized with saturated aqueous sodium bicarbonate, concentrated and extracted with a 10% solution of methanol in dichloromethane (3×30 mL). The combined organic layer were dried over magnesium sulfate, filtered and concentrated. The solid was triturated with methanol (3×1 mL), filtered and dried to afford the title compound.

Example 22

Synthesis of 1-(4-Fluorophenyl)-1H-pyrazolo[3,4-c]pyridine-4-carboxylic acid (2-carbamoylmethanesulfonyl-pyridin-4-ylmethyl)-amide (22)

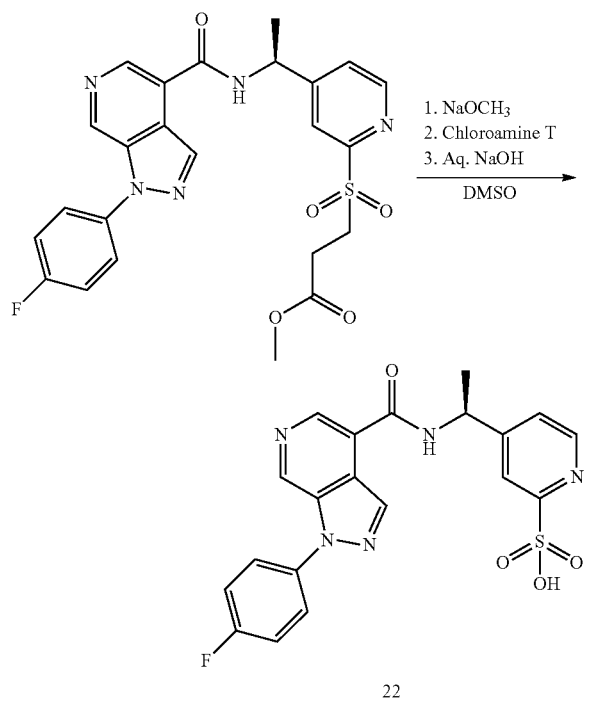

22

To a room temperature solution of 3-[4-((S)-1-{[1-(4-fluorophenyl)-1H-pyrazolo[3,4-c]pyridine-4-carbonyl]-amino}-ethyl)-pyridine-2-sulfonyl]-propionic acid methyl ester (120 mg, 0.23 mmol) in DMSO (1.7 mL) was added a freshly prepared solution of 14% sodium methoxide in methanol (90 µL, 0.23 mmol). The reaction was monitored by TLC. After 10 minutes, N-chloro-p-toluenesulfonamide sodium salt (chloramine T) (106 mg, 0.465 mmol) was added. The mixture stirred for 20 minutes and then 1 N aqueous sodium hydroxide (0.3 mL) was added. The mixture stirred overnight, HPLC-MS indicated formation of desired product and sulfonyl chloride. Additional 1 N aqueous NaOH (0.2 mL) was added. After 1 hour, the mixture was concentrated in vacuo, dissolved in DMSO (2.3 mL) followed by dilution with water (0.3 mL) and filtered. The filtrate was purified by reversed-phase HPLC (Sunfire Prep C18 OBD 5 mM, 30×150 mm column) using a gradient of 15-85% acetonitrile in water (0.1% TFA). The solid from the column was washed with ether and hexanes and collected by filtration to afford the title compound.

Example 23

Synthesis of 1-(4-Fluorophenyl)-1H-pyrazolo[3,4-c]pyridine-4-carboxylic acid ((S)-1-pyridin-4-yl-propyl)-amide (23)

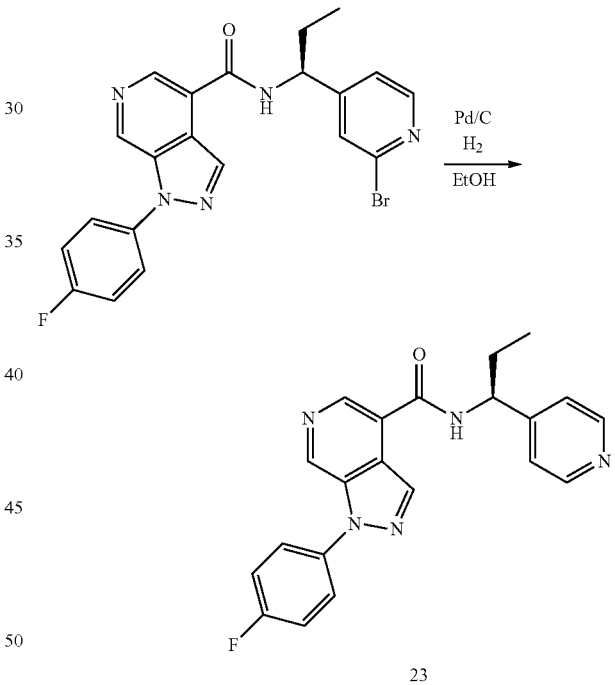

23

A mixture of 1-(4-fluorophenyl)-1H-pyrazolo[3,4-c]pyridine-4-carboxylic acid [(S)-1-(2-bromopyridin-4-yl)-propyl]-amide (165 mg, 0.363 mmol) and 10% palladium on carbon (77 mg) in ethanol (10 mL) was placed under 1 atmosphere of hydrogen (balloon). After 16 hours, diatamacous earth (300 mg) was added and the mixture and the solution was filtered through diatamacous earth and concentrated to afford an oil. The crude material was dissolved in a 4:1 mixture of acetonitrile in water and purified by reversed-phase HPLC. The desired fractions from the column were concentrated to remove the acetonitrile, diluted with saturated aqueous sodium bicarbonate and extracted with dichloromethane. The organic phase was dried over sodium sulfate and concentrated to afford the title compound.

The following compound was also prepared by methods described in Example 23 using ethanol as the reaction solvent:

1-(4-Fluorophenyl)-1H-pyrazolo[3,4-c]pyridine-4-carboxylic acid ((S)-1-thiophen-2-yl-propyl)-amide.

Example 24

Synthesis of 1-(4-Fluorophenyl)-1H-pyrazolo[3,4-c]pyridine-4-carboxylic acid (1-piperidin-3-yl-propyl)-amide (24)

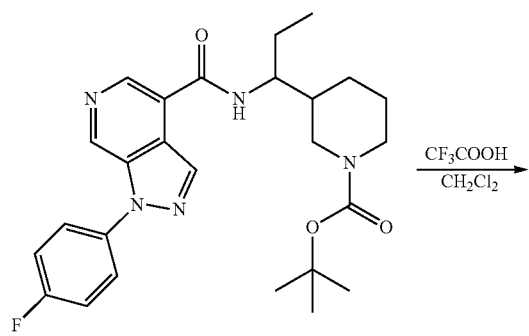

24

To 3-(1-{[1-(4-fluorophenyl)-1H-pyrazolo[3,4-c]pyridine-4-carbonyl]-amino}-propyl)-piperidine-1-carboxylic acid tert-butyl ester (1.1 g, 2.3 mmol) was added a 10% solution of trifluoroacetic acid in dichloromethane (10 mL). The mixture was stirred at room temperature overnight and the reaction was monitored by HPLC-MS indicating incomplete conversion. Additional trifluoroacetic acid (1 mL) was added. The mixture stirred until HPLC-MS indicated starting material was consumed. The mixture was concentrated in vacuo and the residue was diluted with EtOAc (100 mL), made basic with saturated aqueous sodium bicarbonate (pH=10), washed with brine, and dried over sodium sulfate, filtered and concentrated. A portion of the crude material was purified by reversed-phase HPLC (Sunfire PrepC18 OBD 5 mM 30×150 mm column) eluting with a gradient of 15-85% acetonitrile in water (0.1% TFA). The fractions from the column were concentrated to remove acetonitrile made basic with saturated aqueous sodium bicarbonate and extracted with EtOAc. The organic layers were dried and concentrated to afford the title compound as a white foam.

The following compound was also prepared by methods described in Example 24:

1-(4-Fluorophenyl)-1H-pyrazolo[3,4-c]pyridine-4-carboxylic acid (1-piperidin-4-yl-propyl)-amide.

Example 25

Synthesis of 1-(4-Fluorophenyl)-1H-pyrazolo[3,4-c]pyridine-4-carboxylic acid [1-(1-methanesulfonyl-piperidin-3-yl)-propyl]-amide (25)

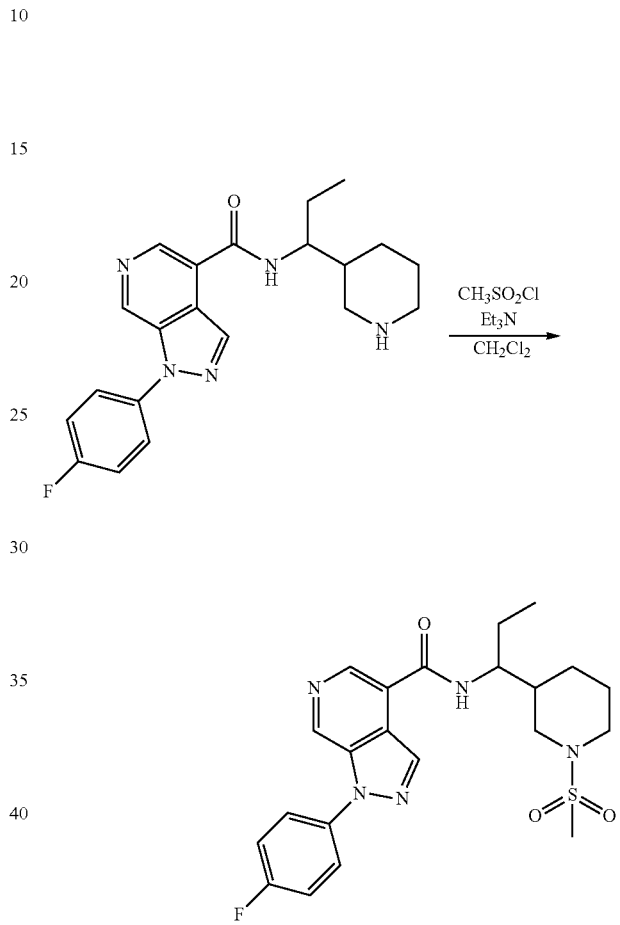

25

The solution of 1-(4-fluorophenyl)-1H-pyrazolo[3,4-c]pyridine-4-carboxylic acid (1-piperidin-3-yl-propyl)-amide (0.10 g, 0.26 mmol) and Et$_3$N (58 µL, 0.42 mmol) in dichloromethane (3 mL) was added methanesulfonyl chloride (31 µL, 0.39 mmol). After 18 hours, the cloudy mixture was quenched with saturated aqueous ammonium chloride and extracted with dichloromethane. The organic phase was dried, filtered, and concentrated. The residue was purified by silica gel chromatography eluting with a gradient of 0-95% EtOAc in hexanes to afford the title compound as a white solid.

The following compound was also prepared by methods described in Example 25:

1-(4-Fluorophenyl)-1H-pyrazolo[3,4-c]pyridine-4-carboxylic acid [1-(1-methanesulfonyl-piperidin-4-yl)-propyl]-amide.

Example 26

Synthesis of 1-(4-Fluorophenyl)-1H-pyrazolo[3,4-c]pyridine-4-carboxylic acid [1-(1-carbamoyl-piperidin-3-yl)-propyl]-amide (26)

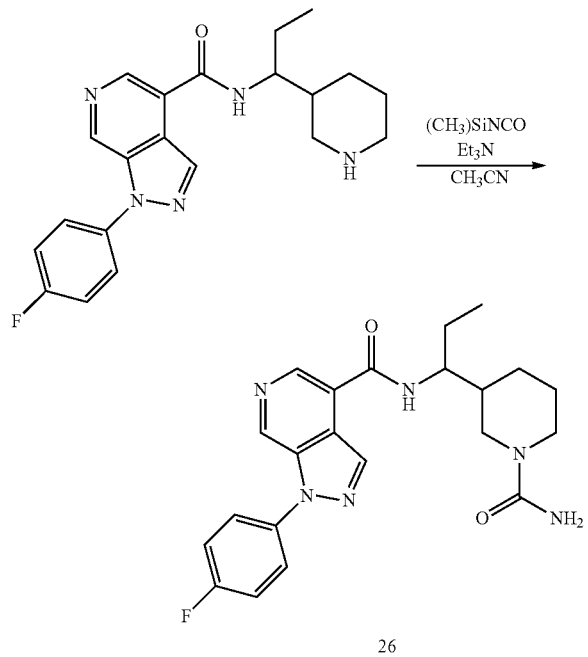

To a solution of 1-(4-fluorophenyl)-1H-pyrazolo[3,4-c]pyridine-4-carboxylic acid (1-piperidin-3-yl-propyl)-amide (0.10 g, 0.26 mmol) in acetonitrile (1 mL) was added Et₃N (79 µL, 0.79 mmol) followed by 85% trimethylsilyl isocyanate (125 µL, 0.784 mmol). After 4 hours, the cloudy mixture was filtered and attempts to crystallize the solid proved unsuccessful. The solid and filtrate was combined and diluted with water and extracted with EtOAc. The combined organic layers were dried, filtered, and concentrated. The residue was purified by silica gel chromatography eluting with a gradient of 0-10% methanol in dichloromethane to afford the title compound as a white solid.

The following compound was also prepared by methods described in Example 26:
1-(4-Fluorophenyl)-1H-pyrazolo[3,4-c]pyridine-4-carboxylic acid [1-(1-carbamoyl-piperidin-4-yl)-propyl]-amide.

Example 27

Synthesis of 1-(4-Fluorophenyl)-1H-pyrazolo[3,4-c]pyridine-4-carboxylic acid [(S)-1-(2-methanesulfinyl-pyridin-4-yl)-propyl]-amide (27)

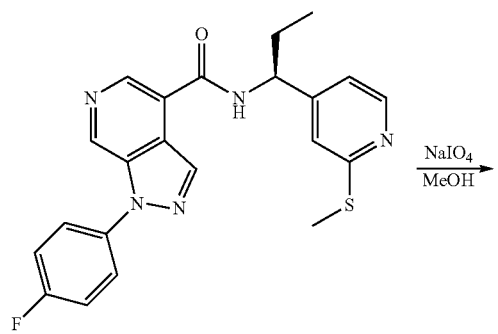

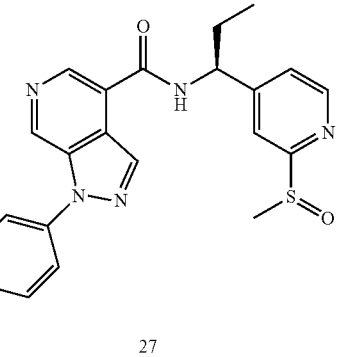

To a solution of 1-(4-fluorophenyl)-1H-pyrazolo[3,4-c]pyridine-4-carboxylic acid [(S)-1-(2-methylsulfanyl-pyridin-4-yl)-propyl]-amide (0.10 mg, 0.24 mmol) in MeOH (5 mL) was added an aqueous solution of sodium periodate (51 mg, 0.24 mmol). After 1.5 hours, a solid precipitated and additional MeOH (3 mL) was added. After 5 days, mixture was concentrated and partitioned between water (5 mL) and EtOAc (50 mL). The organic phase was separated and the aqueous layer was extracted with EtOAc (20 mL). The combined organic layers were washed with brine, dried over sodium sulfate, and concentrated. The residue was purified by reversed-phase HPLC (Sunfire PrepC18 OBD 5 mM 30×150 mm column) eluting with a gradient of 15-75% acetonitrile in water (0.1% TFA). The fractions from the column were concentrated to remove acetonitrile, made basic with saturated aqueous sodium bicarbonate and extracted with EtOAc. The organic phase was washed with brine, dried over sodium sulfate and concentrated to afford the title compound as a white solid.

Example 28

Synthesis of 1-(4-Fluorophenyl)-1H-pyrazolo[3,4-c]pyridine-4-carboxylic acid [1-(1-methyl-piperidin-4-yl)-propyl]-amide (28)

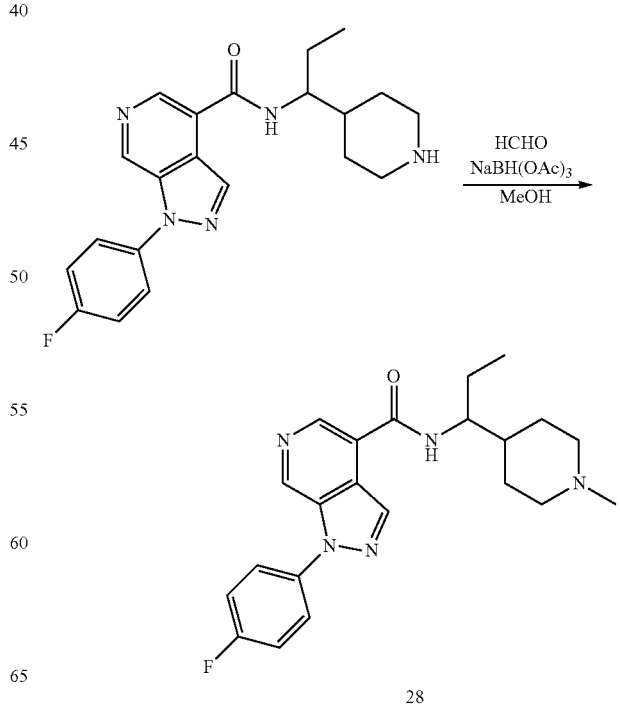

To a solution of 1-(4-fluorophenyl)-1H-pyrazolo[3,4-c]pyridine-4-carboxylic acid (1-piperidin-4-yl-propyl)-amide (0.10 mg, 0.26 mmol) and 37% aqueous formaldehyde (157 µL, 2.1 mmol) in MeOH (3 mL) was added sodium triacetoxyborohydride (83 mg, 0.39 mmol). After 2 hours, the reaction was quenched with saturated aqueous sodium bicarbonate (5 mL) and extracted with EtOAc (3×50 mL). The combined organic layers were washed with brine, dried over sodium sulfate and concentrated. The residue was purified by reversed-phase HPLC chromatography (Sunfire PrepC18 OBD 5 mM 30×150 mm column) eluting with a gradient of 5-75% acetonitrile in water (0.1% TFA). The fractions from the column were concentrated to remove acetonitrile, made basic with saturated aqueous sodium carbonate and extracted with EtOAc. The organic layer was dried and concentrated to afford the title compound.

The following compound was also prepared by methods described in Example 27:

1-(4-Fluorophenyl)-1H-pyrazolo[3,4-c]pyridine-4-carboxylic acid [1-(1-methyl-piperidin-3-yl)-propyl]-amide.

Example 29

Synthesis of 1-(4-Fluorophenyl)-1H-pyrazolo[3,4-c]pyridine-4-carboxylic acid {(S)-1-[2-(1H-tetrazol-5-yl)-pyridin-4-yl]-propyl}-amide (29)

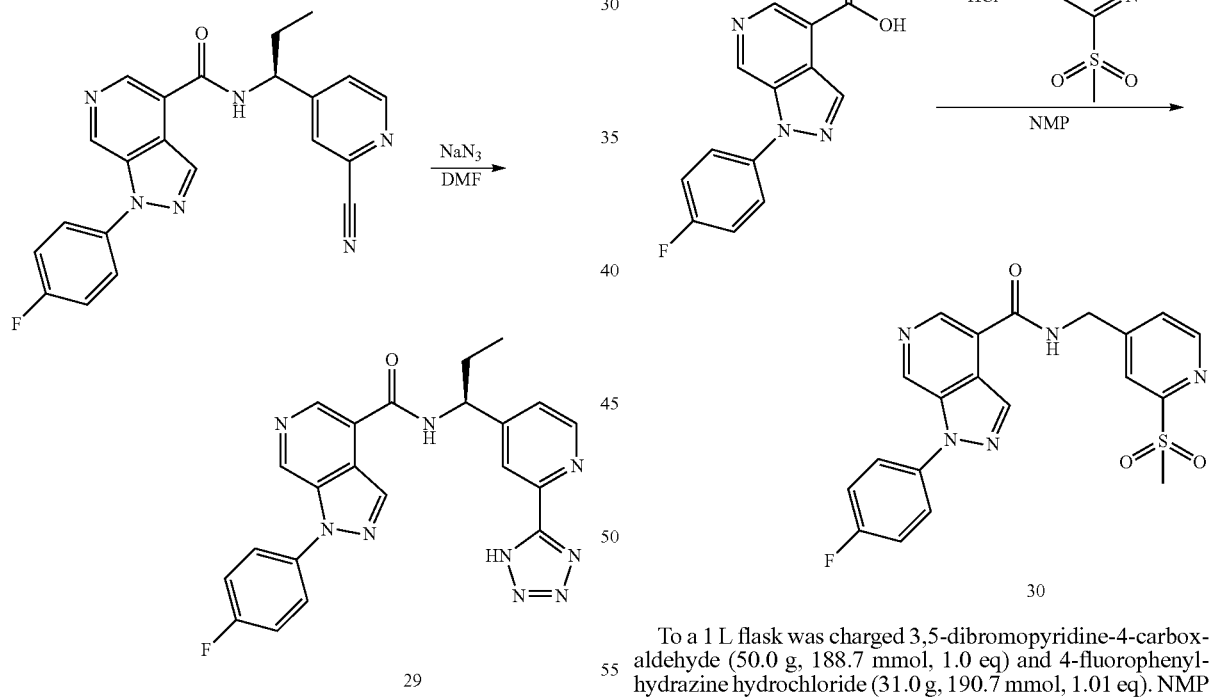

A sealed tube was charged with 1-(4-fluorophenyl)-1H-pyrazolo[3,4-c]pyridine-4-carboxylic acid [(S)-1-(2-cyanopyridin-4-yl)-propyl]-amide (75 mg, 0.19 mmol), sodium azide (37 mg, 0.58 mmol) and DMF (1 mL) and warmed at 120° C. After 16 hours, the reaction was diluted with a 4:1 mixture of acetonitrile in water, filtered and purified by reverse-phase chromatography. The desired fractions from the column were concentrated and dissolved in dichloromethane. The organic phase was washed with water, dried over sodium sulfate, filtered and concentrated to afford the title compound.

Example 30

Synthesis of 1-(4-Fluorophenyl)-1H-pyrazolo[3,4-c]pyridine-4-carboxylic acid (2-methanesulfonyl-pyridin-4-ylmethyl)-amide (30)

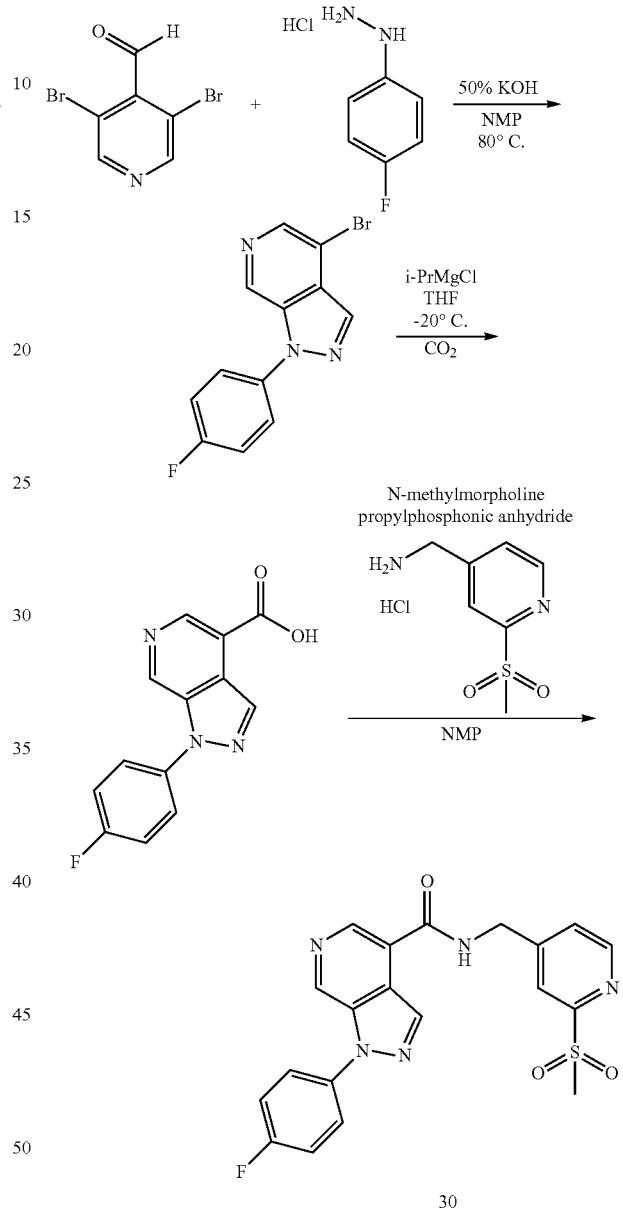

To a 1 L flask was charged 3,5-dibromopyridine-4-carboxaldehyde (50.0 g, 188.7 mmol, 1.0 eq) and 4-fluorophenylhydrazine hydrochloride (31.0 g, 190.7 mmol, 1.01 eq). NMP (250 mL) was charged, and the resulting slurry was stirred at ambient temperature for 2 hours. A solution of aqueous KOH was prepared from 85% KOH pellets (27.4 g, 415.2 mmol, 2.2 eq) and water (27.4 mL), and this KOH solution was charged to the reaction mixture. The batch was heated to 80° C. and held at this temperature for 30-60 minutes. Water (250 mL) was then charged at 80° C., and the resulting slurry was cooled to ambient temperature over 4-16 hours. The slurry was filtered, the solid was washed with water, and oven dried under vacuum to afford 4-bromo-1-(4-fluorophenyl)-1H-pyrazolo[3,4-c]pyridine as a tan colored solid, 51.5 g, 99.3 area % purity by HPLC, 93% yield.

To a 1 L flask was charged 4-bromo-1-(4-fluorophenyl)-1H-pyrazolo[3,4-c]pyridine (50.0 g, 171.1 mmol, 1 eq) and THF (300 mL). The slurry was cooled to −20° C. i-PrMgCl solution (128.2 mL, 256.4 mmol, 2.0 M in THF, 1.5 eq) was charged at a rate to keep the temperature below −10° C. The batch was held at −10° C. for 3 hours. CO$_2$ gas was then bubbled into the reaction mixture until the temperature increase peaked, and the temperature began to drop. The temperature was adjusted to 22° C., and i-PrOAc (325 mL) was added. A solution of aqueous HCl was prepared from concentrated HCl (55 mL) and water (195 mL). About 10 mL of this HCl solution was charged to the reaction mixture to achieve pH 6-7. The batch was then heated to 55° C., and the remaining ~240 mL of the HCl solution was charged. The batch was cooled to ambient temperature over 1 hour, and held at this temperature for 1 hour. The batch was then filtered, and the solid washed with water and i-PrOAc. The solid was oven dried under vacuum to afford 1-(4-fluorophenyl)-1H-pyrazolo[3,4-c]pyridine-4-carboxylic acid as a yellow solid, 38.4 g, 90 wt. % purity, 79% yield.

A 250 mL flask was charged with 1-(4-fluorophenyl)-1H-pyrazolo[3,4-c]pyridine-4-carboxylic acid (10.0 g, 33.9 mmol, 87.2 wt. %, 1.0 eq), (2-(methylsulfonyl)pyridin-4-yl)methanamine hydrochloride (8.54 g, 37.3 mmol, 97.3 wt. %, 1.10 eq), NMP (30 mL) and finally N-methylmorpholine (18.6 mL, 169.5 mmol, 5.0 eq). To the slurry was charged propylphosphonic anhydride (23.97 mL, 40.68 mmol, 50 wt. % solution in EtOAc, 1.2 eq). The batch was then heated to 60° C. and held at this temperature for 1 hour. Water (80 mL) was charged, and the batch was cooled to ambient temperature and held for 1 hour. The batch was filtered, the solid washed with water, and then oven dried under vacuum to afford the title compound as a light yellow solid, 12.7 g, >99.5 area % purity by HPLC, 88% yield.

Example 31

Synthesis of 1-(4-Fluorophenyl)-1H-pyrazolo[3,4-c]pyridine-4-carboxylic acid [(1S,3S)-3,4-dihydroxy-1-(2-methanesulfonyl-pyridin-4-yl)-butyl]-amide (31a) and 1-(4-Fluorophenyl)-1H-pyrazolo[3,4-c]pyridine-4-carboxylic acid [(1S,3R)-3,4-dihydroxy-1-(2-methanesulfonyl-pyridin-4-yl)-butyl]-amide (31b)

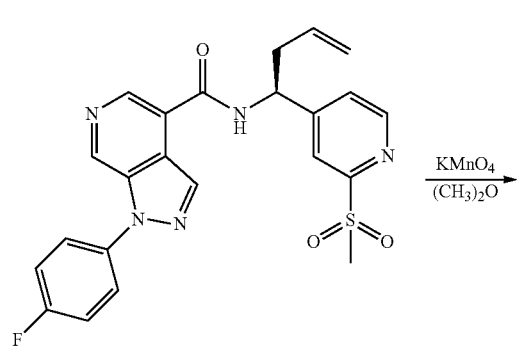

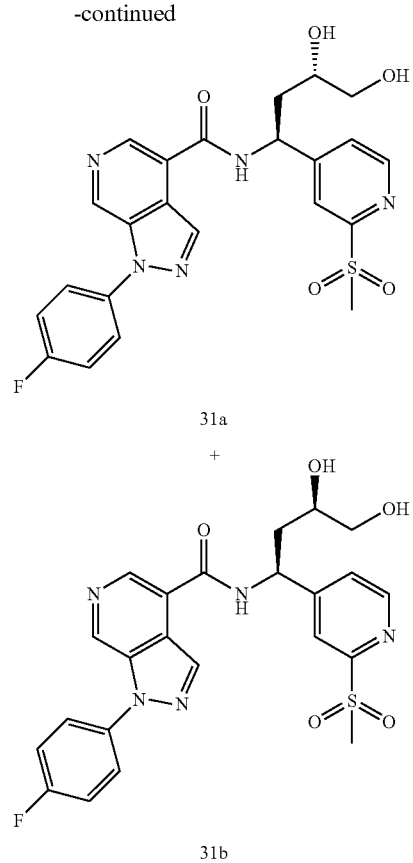

To a room temperature solution of 1-(4-fluorophenyl)-1H-pyrazolo[3,4-c]pyridine-4-carboxylic acid [(S)-1-(2-methanesulfonyl-pyridin-4-yl)-but-3-enyl]-amide (1.07 g, 2.30 mmol) in acetone (20 mL) and water (7 mL) was added KMnO$_4$ (472 mg, 2.99 mmol). After 28 hours, the mixture was diluted with acetone and filtered through diatomaceous earth and concentrated. The mixture was then dissolved in EtOAc (50 mL) and filtered through a 0.45 um nylon Acrodisc and concentrated. The crude mixture was purified by silica gel chromatography using a gradient of 0-10% methanol in dichloromethane to afford the title compounds as single diastereomer. C(3) configuration was tentatively assigned.

Example 32

Synthesis of (S)-3-{[1-(4-Fluorophenyl)-1H-pyrazolo[3,4-c]pyridine-4-carbonyl]-amino}-3-(2-methanesulfonyl-pyridin-4-yl)-propionic acid methyl ester (32)

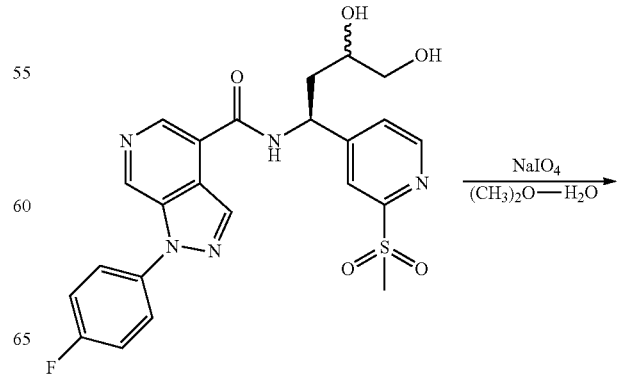

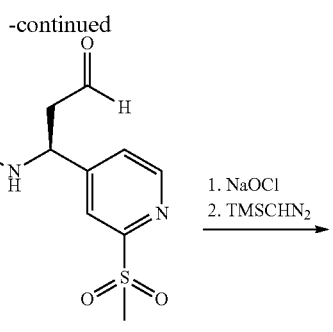

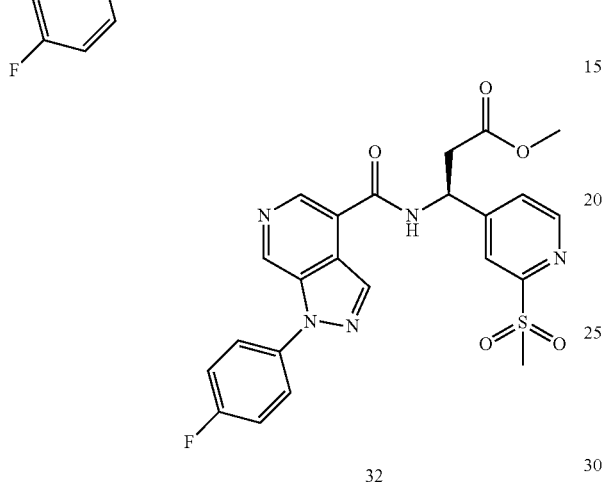

32

To a room temperature solution of 1-(4-fluorophenyl)-1H-pyrazolo[3,4-c]pyridine-4-carboxylic acid [(S)-3,4-dihydroxy-1-(2-methanesulfonyl-pyridin-4-yl)-butyl]-amide (0.710 g, 1.42 mmol) in acetone (18 mL) and water (9 mL) was added NaIO$_4$ (608 mg, 2.84 mmol). After 18 hours, the mixture was filtered through diatomaceous earth washing with acetone (3×20 mL). The acetone was removed in vacuo and the aqueous layer was diluted with brine (50 mL) and extracted with EtOAc (3×50 mL). The combined organics layers were dried over magnesium sulfate, filtered, and evaporated to afford 1-(4-fluorophenyl)-1H-pyrazolo[3,4-c]pyridine-4-carboxylic acid [(S)-1-(2-methanesulfonyl-pyridin-4-yl)-3-oxo-propyl]-amide as white solid which was used without purification.

To a room temperature solution of 1-(4-fluorophenyl)-1H-pyrazolo[3,4-c]pyridine-4-carboxylic acid [(S)-1-(2-methanesulfonyl-pyridin-4-yl)-3-oxo-propyl]-amide (0.10 g, 0.21 mmol) and 2-methyl-2-butene (147 µL, 1.39 mmol) in t-butanol (1 mL) was added a solution of 80% sodium chlorite (31 mg, 0.28 mmol) and sodium dihydrogen phosphate monohydrate (38 mg, 0.28 mmol) in water (400 µL) (addition was exothermic). The mixture stirred overnight and was then concentrated in vacuo, acidified with 1 N aqueous HCl (pH=2), diluted with brine (25 mL) and extracted with EtOAc (3×50 mL). The combined organic layers were dried over sodium sulfate, filtered and concentrated to afford (S)-3-{[1-(4-fluorophenyl)-1H-pyrazolo[3,4-c]pyridine-4-carbonyl]-amino}-3-(2-methanesulfonyl-pyridin-4-yl)-propionic acid which was used without further purification.

To a slurry of (S)-3-{[1-(4-fluorophenyl)-1H-pyrazolo[3,4-c]pyridine-4-carbonyl]-amino}-3-(2-methanesulfonyl-pyridin-4-yl)-propionic acid in methanol (1 mL) and benzene (4 mL) was added a 2 M solution of (trimethylsilyl)diazomethane in hexanes (126 µL, 0.252 mmol). After 10 minutes, the mixture became homogeneous and the resulting reaction mixture was stirred at room temperature for 30 minutes. The reaction was concentrated in vacuo and the residue was purified by silica gel chromatography using a gradient of 0-8% methanol in dichloromethane to afford the title compound as a white solid.

Example 33

Synthesis of 1-(4-Fluorophenyl)-1H-pyrazolo[3,4-c]pyridine-4-carboxylic acid [(S)-3-hydroxy-1-(2-methanesulfonyl-pyridin-4-yl)-propyl]-amide (33)

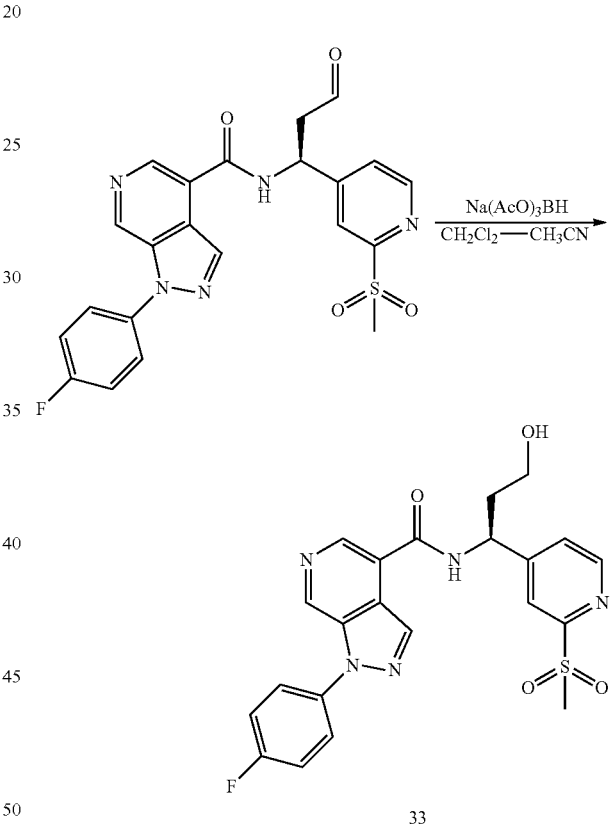

33

To a room temperature solution of 1-(4-fluorophenyl)-1H-pyrazolo[3,4-c]pyridine-4-carboxylic acid [(S)-1-(2-methanesulfonyl-pyridin-4-yl)-3-oxo-propyl]-amide (0.10 mg, 0.21 mmol) in a 9:1 mixture of dichloroethane in CH$_3$CN (5 mL) was added sodium triacetoxyborohydride (181 mg, 0.854 mmol). After 36 hours, the reaction mixture was quenched with saturated aqueous sodium bicarbonate (10 mL) and the aqueous layer was extracted with dichloromethane (3×10 mL). The combined organic layers were dried over magnesium sulfate, filtered and concentrated. The oily residue was purified by silica gel chromatography using a gradient of 0-8% methanol in dichloromethane to afford the title compound as a white solid.

Example 34

Synthesis of 1-(4-Fluorophenyl)-1H-pyrazolo[3,4-c]pyridine-4-carboxylic acid [(S)-1-(2-methanesulfonyl-pyridin-4-yl)-2-methylcarbamoyl-ethyl]-amide (34)

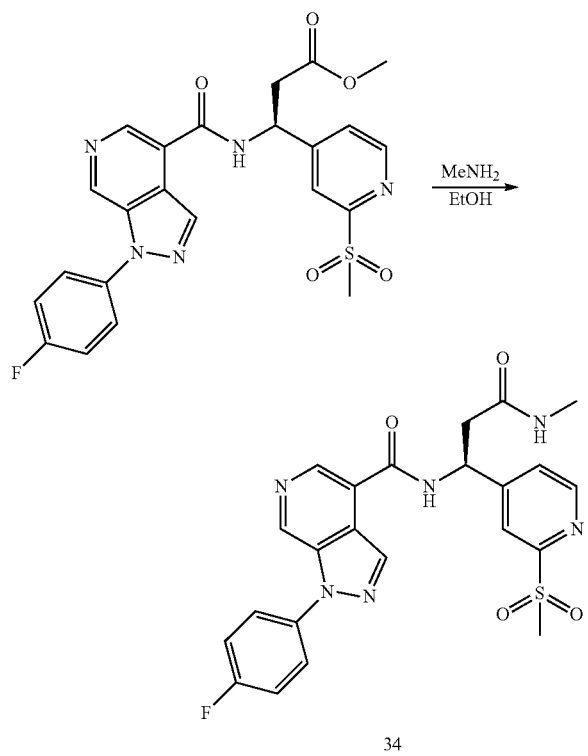

A solution of (S)-3-{[1-(4-fluorophenyl)-1H-pyrazolo[3,4-c]pyridine-4-carbonyl]-amino}-3-(2-methanesulfonyl-pyridin-4-yl)-propionic acid methyl ester (40 mg, 0.08 mmol) in 33% methylamine in ethanol (0.300 mL, 2.41 mmol) in a sealed tube was warmed at 80° C. After 16 hours, the mixture was cooled to 0° C. and filtered. The solid was washed with cold MeOH (3×0.5 mL) and dried to the title compound as a white solid.

Example 35

Synthesis of 1-(4-Fluorophenyl)-1H-pyrazolo[3,4-c]pyridine-4-carboxylic acid [(S)-1-(2-methanesulfonyl-pyridin-4-yl)-3-morpholin-4-yl-propyl]-amide (35)

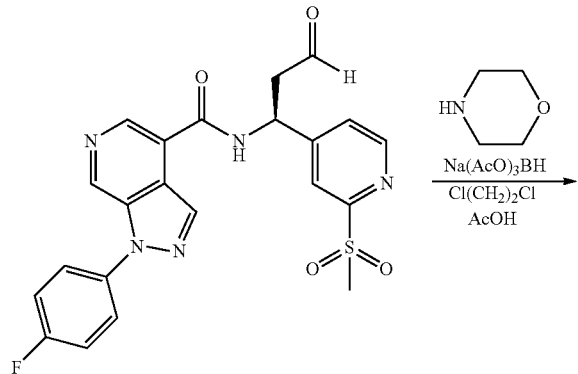

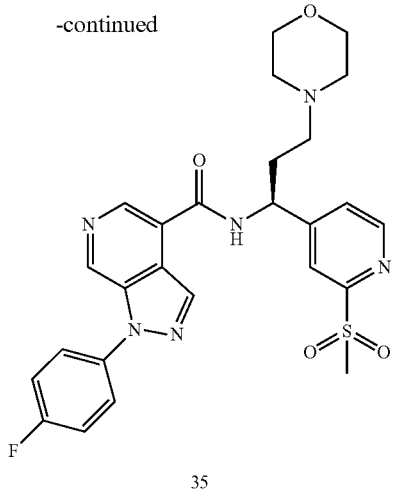

A solution of 1-(4-fluorophenyl)-1H-pyrazolo[3,4-c]pyridine-4-carboxylic acid [(S)-1-(2-methanesulfonyl-pyridin-4-yl)-3-oxo-propyl]-amide (40 mg, 0.09 mmol) and morpholine (15 µL, 0.17 mmol) in dichloroethane (2 mL) was stirred for 30 minutes. The mixture was then acidified (pH=4) with acetic acid (9 µL, 0.2 mmol) and then sodium triacetoxyborohydride (36 mg, 0.17 mmol) was added. After 2 hours, the reaction was quenched with saturated aqueous sodium bicarbonate (20 mL) and extracted with dichloromethane (3×20 mL). The combined organic layers were dried over magnesium sulfate, filtered and concentrated. The oily residue was purified by silica gel chromatography using a gradient of 0-10% methanol in EtOAc. The solid material from the column was purified a second time by reversed-phase HPLC using a 20 minute gradient of 5-95% MeCN (0.1% TFA) in $H_2O$ (0.1% TFA) (flow rate=25 mL/minute). Desired fractions from the column was made basic with saturated aqueous sodium bicarbonate (2 mL), concentrated to half of the original volume and extracted with EtOAc (3×10 mL). The combined organic layers were dried over magnesium sulfate, filtered and concentrated to afford the title compound as a white solid.

The following compound was also prepared by methods described in Example 35:
1-(4-Fluorophenyl)-1H-pyrazolo[3,4-c]pyridine-4-carboxylic acid {(S)-1-(2-methanesulfonyl-pyridin-4-yl)-3-[(2-methoxy-ethyl)-methyl-amino]-propyl}-amide

Example 36

Synthesis of 1-(4-Fluorophenyl)-1H-pyrazolo[3,4-c]pyridine-4-carboxylic acid [(S)-3-amino-1-(2-methanesulfonyl-pyridin-4-yl)-propyl]-amide (36)

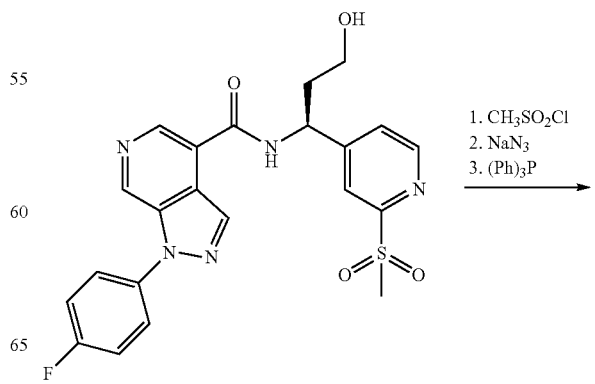

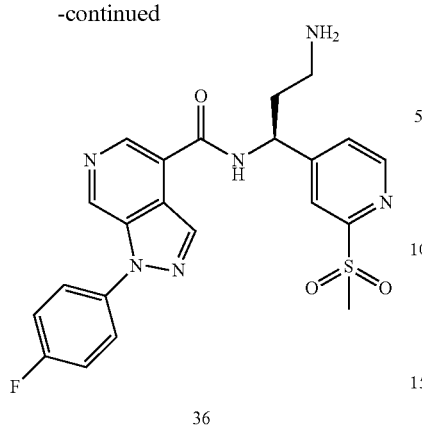

36

Example 37

Synthesis of 1-(4-Fluorophenyl)-1H-pyrazolo[4,3-c]pyridine-4-carboxylic acid (37)

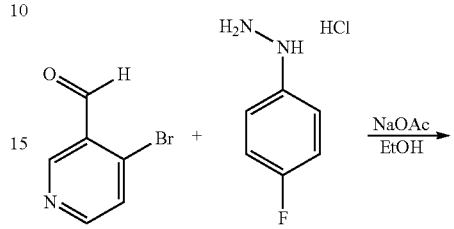

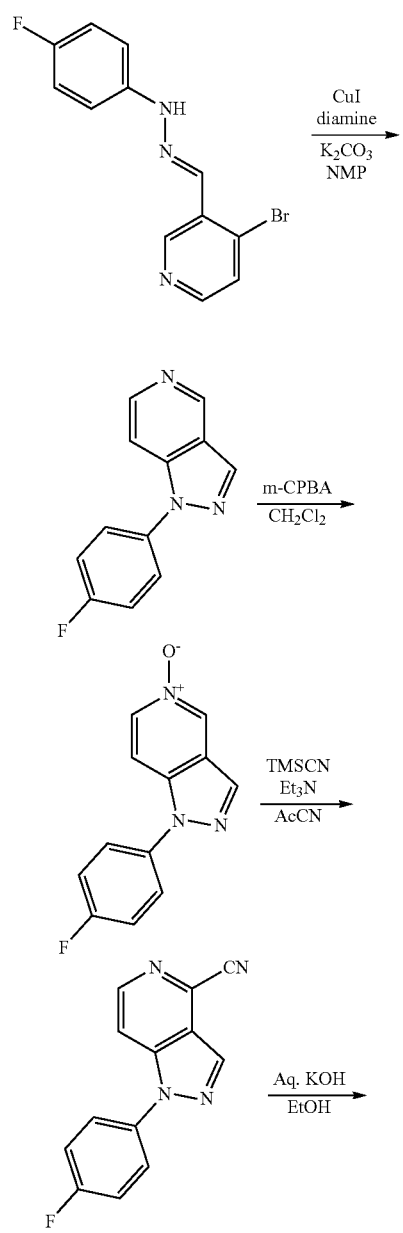

A solution of 1-(4-fluorophenyl)-1H-pyrazolo[3,4-c]pyridine-4-carboxylic acid [(S)-3-hydroxy-1-(2-methanesulfonyl-pyridin-4-yl)-propyl]-amide (0.10 g, 0.21 mmol) and N,N-diisopropylethylamine (167 µL, 0.957 mmol) in dichloromethane (20 mL) was cooled in an ice water-brine bath. After 5 minutes, methanesulfonyl chloride (25 µL, 0.32 mmol) was added and the cold bath was removed until the mixture became homogeneous. The mixture was again cooled in an ice bath. After 30 minutes, the mixture was quenched with saturated aqueous ammonium chloride (10 mL), washed with brine (10 mL), dried over magnesium sulfate and concentrated to afford methanesulfonic acid (S)-3-{[1-(4-fluorophenyl)-1H-pyrazolo[3,4-c]pyridine-4-carbonyl]-amino}-3-(2-methanesulfonyl-pyridin-4-yl)-propyl ester which was used without further purification.

To a room temperature solution of methanesulfonic acid (S)-3-{[1-(4-fluorophenyl)-1H-pyrazolo[3,4-c]pyridine-4-carbonyl]-amino}-3-(2-methanesulfonyl-pyridin-4-yl)-propyl ester (122 mg, 0.223 mmol) in DMF (2 mL) was added sodium azide (19 mg, 0.29 mmol). After 72 hours, the reaction was quenched with water (20 mL) and extracted with EtOAc (3×20 mL). The combined organic layers were washed with water (20 mL), brine (20 mL), dried over magnesium sulfate, filtered and concentrated. The mixture was passed through a plug of silica gel eluting with a gradient of 0-5% methanol in dichloromethane to afford 1-(4-fluorophenyl)-1H-pyrazolo[3,4-c]pyridine-4-carboxylic acid [(S)-3-azido-1-(2-methanesulfonyl-pyridin-4-yl)-propyl]-amide which was used without further purification.

To a room temperature solution of 1-(4-fluorophenyl)-1H-pyrazolo[3,4-c]pyridine-4-carboxylic acid [(S)-3-azido-1-(2-methanesulfonyl-pyridin-4-yl)-propyl]-amide (86 mg, 0.17 mmol) in THF (7 mL) was added triphenylphosphine (57 mg, 0.22 mmol) (gas evolved) followed by water (700 µL). After 75 hours, the mixture was concentrated acetonitrile was added and the solution was filtered through a 0.45 um nylon Acrodisc and purified by reversed-phase HPLC using a 20 minute gradient of 5-95% MeCN (0.1% TFA) in $H_2O$ (0.1% TFA) (flow rate=25 mL/minute). The desired fractions were lyophilized to afford the title compound as a yellow solid.

-continued

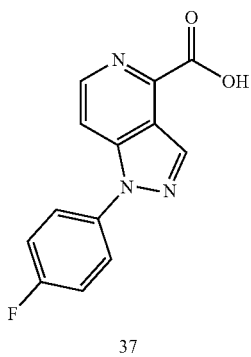

37

To a solution of 4-bromopyridine-3-carbaldehyde (2.50 g, 13.4 mmol) in ethanol (25 mL) and water (5 mL) was added 4-fluorophenyhydrazine hydrochloride (2.38 g, 14.6 mmol) (mixture turned a deep red) followed by sodium acetate (3.7 g, 27 mmol) in 5 mL of water (mixture turned a bright yellow). The mixture was warmed at 50° C. for 30 minutes to afford an orange precipitate. The mixture was cooled and diluted with water (50 mL) and the solid was collected by filtration. The filter cake was washed with water and dried to afford N-[1-(4-bromopyridin-3-yl)-meth-(E)-ylidene]-N'-(4-fluorophenyl)-hydrazine.

A mixture of N-[1-(4-bromopyridin-3-yl)-meth-(E)-ylidene]-N'-(4-fluorophenyl)-hydrazine (3.0 g, 0.010 mol), CuI (97 mg, 0.51 mmol), trans-N,N'-dimethylcyclohexane-1,2-diamine (595 µL, 3.77 mmol), and $K_2CO_3$ (2.8 g, 0.020 mol) in NMP (100 mL) was warmed at 120° C. After stifling overnight, the mixture was diluted with aqueous ammonium chloride (400 mL) and the resulting solid collected by filtration. The solid was dissolved in EtOAc, and the aqueous layer was extracted with EtOAc. The combined organics layers were dried over sodium sulfate, filtered and concentrated. The crude product was purified by silica gel chromatography to afford 1-(4-fluorophenyl)-1H-pyrazolo[4,3-c]pyridine as an orange solid.

To a solution of 1-(4-fluorophenyl)-1H-pyrazolo[4,3-c]pyridine (0.920 g, 4.31 mmol) in dichloromethane (50 mL) was added 65% m-chloroperbenzoic acid (1.26 g, 4.75 mmol). After 2 hours, the mixture was diluted with EtOAc and water. The organic layer was washed with saturated aqueous $NaHCO_3$, brine, dried over sodium sulfate, filter and concentrated to afford 1-(4-fluorophenyl)-1H-pyrazolo[4,3-c]pyridine 5-oxide.

To a solution of 1-(4-fluorophenyl)-1H-pyrazolo[4,3-c]pyridine 5-oxide (0.300 g, 1.31 mmol) in acetonitrile (10 mL) was added trimethylsilyl cyanide (TMSCN) (931 µL, 6.99 mmol) followed by $Et_3N$ (0.930 mL, 6.69 mmol) and the mixture was warmed at reflux. After 3 hours, the mixture was diluted with water and the solid collected by filtration washing with water. The flakey solid was then dissolved in methanol and concentrated to afford 1-(4-fluorophenyl)-1H-pyrazolo[4,3-c]pyridine-4-carbonitrile.

A mixture of 1-(4-fluorophenyl)-1H-pyrazolo[4,3-c]pyridine-4-carbonitrile (140 mg, 0.59 mmol) in EtOH (10 mL) and 6 N aqueous KOH (1.5 mL) was warmed at 80° C. After stirring overnight, the mixture was cooled to room temperature and diluted with water and concentrated. Additional water was added followed by acetic acid and the solid was collected by filtration to afford the title compound.

Using methods described in example 3 the following compound was prepared from 1-(4-fluorophenyl)-1H-pyrazolo[4,3-c]pyridine-4-carboxylic acid.

1-(4-Fluorophenyl)-1H-pyrazolo[4,3-c]pyridine-4-carboxylic acid 4-(4-methyl-piperazine-1-sulfonylmethyl)-benzylamide.

Example 38

Synthesis of 1-(4-Fluorophenyl)-1H-pyrazolo[3,4-c]pyridine-4-carboxylic acid (6-methanesulfonyl-2-oxo-1,2-dihydropyridin-4-ylmethyl)-amide (38)

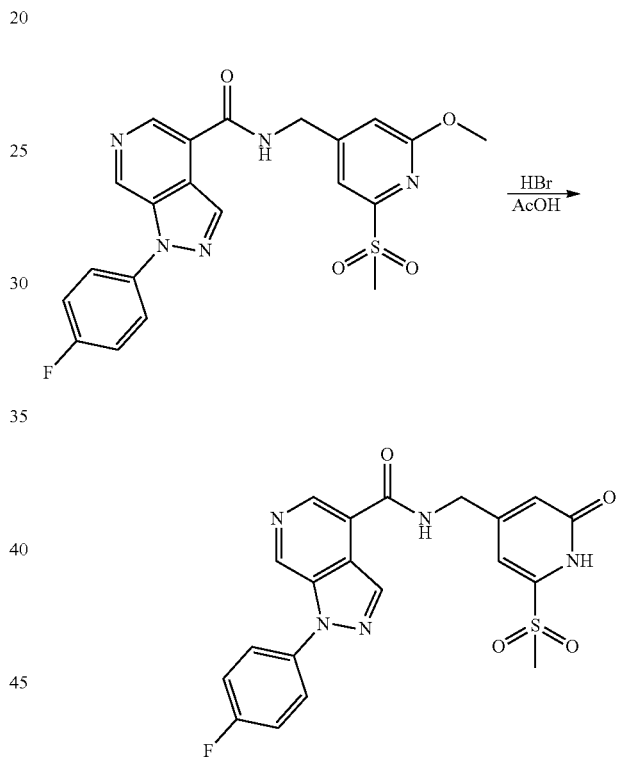

38

To a solution of 1-(4-fluorophenyl)-1H-pyrazolo[3,4-c]pyridine-4-carboxylic acid (2-methanesulfonyl-6-methoxypyridin-4-ylmethyl)-amide (58 mg, 0.13 mmol) in acetic acid (5 mL) was added 48% aqueous HBr (3 mL). After 16 hours, HPLC-MS indicated partial conversion to the desired product. The mixture was then warmed at 60° C. After 5 hours, the mixture was cooled to room temperature, diluted with water (25 mL) and extracted with EtOAc (3×20 mL). The combined organic layers were washed with saturated aqueous sodium bicarbonate (4×20 mL), brine (20 mL), dried over sodium sulfate and concentrated in vacuo. The residue was purified by silica gel chromatography using a gradient of 0-20% MeOH in EtOAc to afford the title compound as a pale yellow crystalline solid.

Example 39

Synthesis of 1-(4-Fluorophenyl)-1H-pyrazolo[3,4-c]pyridine-4-carboxylic acid [(S)-1-(1H-pyrazol-3-yl)-propyl]-amide (39)

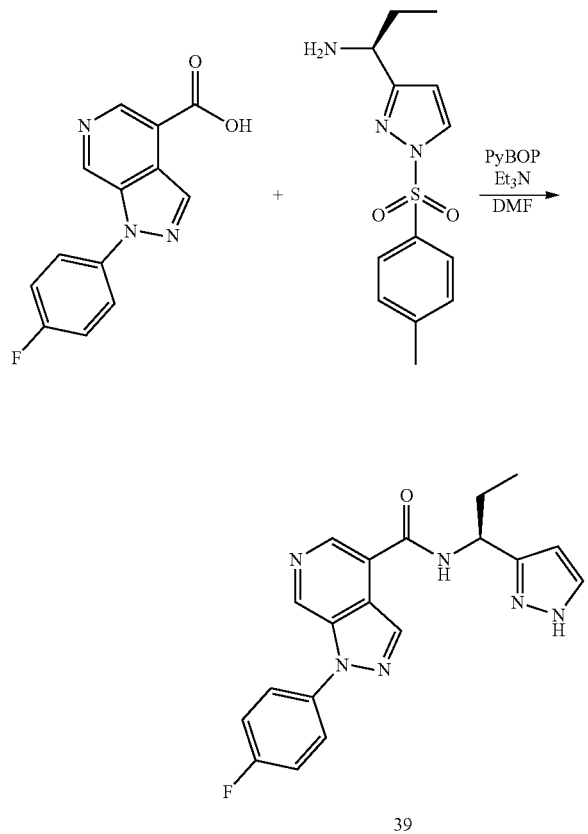

39

To a room temperature solution of 1-(4-fluorophenyl)-1H-pyrazolo[3,4-c]pyridine-4-carboxylic acid (185 mg, 0.800 mmol) in DMF was added PyBOP (360 mg, 0.72 mmol) and Et₃N (152 mg, 1.50 mmol). After 30 minutes, (S)-1-[1-(toluene-4-sulfonyl)-1H-pyrazol-3-yl]-propylamine (201 mg, 0.720 mmol) was added. After 3 hours, the reaction was diluted with water and extracted with EtOAc. The combined organic layers were washed with brine, dried over sodium sulfate and concentrated in vacuo. The residue was purified by reversed-phase HPLC. The major fractions were combined and the solvent was removed in vacuo to afford the title compound.

The following compound was also prepared by methods described in Example 38 using (S)-1-[1-(toluene-4-sulfonyl)-1H-imidazol-4-yl]-propylamine:

1-(4-Fluorophenyl)-1H-pyrazolo[3,4-c]pyridine-4-carboxylic acid [(S)-1-(1H-imidazol-4-yl)-propyl]-amide.

Example 40

Synthesis of 1-(4-Fluorophenyl)-1H-pyrazolo[3,4-c]pyridine-4-carboxylic acid [(S)-1-(1-methanesulfonyl-1H-pyrazol-3-yl)-propyl]-amide (40)

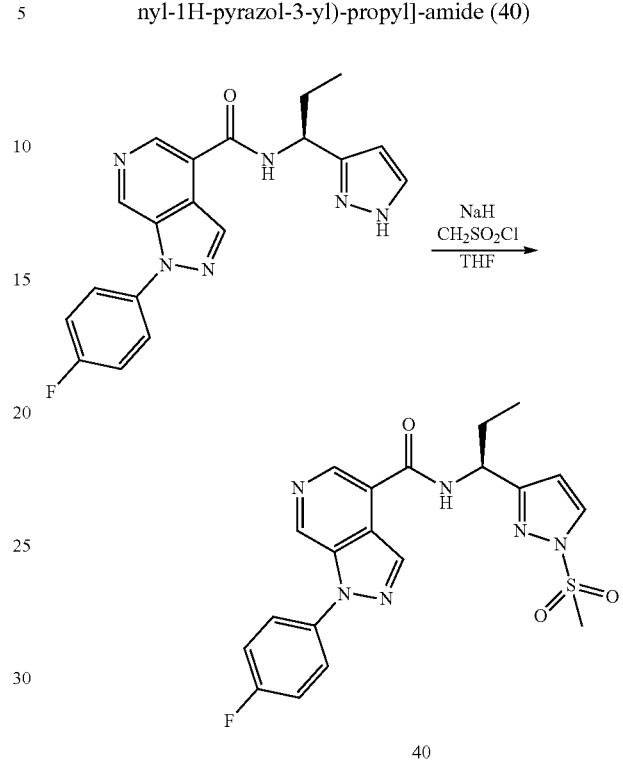

40

To a room temperature solution of 1-(4-fluorophenyl)-1H-pyrazolo[3,4-c]pyridine-4-carboxylic acid [(S)-1-(1H-pyrazol-3-yl)-propyl]-amide (0.040 g, 0.11 mmol) in THF was added 60% sodium hydride (9 mg, 0.2 mmol) in mineral oil. After 20 minutes, methansulfonyl chloride (25 mg, 0.22 mmol) was added. After 3 hours, the reaction was quenched with saturated aqueous ammonium chloride and the mixture was extracted with EtOAc. The combined organic layers were washed with brine, dried over sodium sulfate and concentrated in vacuo. The residue was purified by silica gel chromatography (the column was equilibrated with dichloromethane-Et₃N) eluting with 5% methanol in dichloromethane. Material from the column was crystallized in ether to afford the title compound.

Example 41

Synthesis of 1-(4-Fluorophenyl)-1H-pyrazolo[4,3-c]pyridine-4-carboxylic acid 3-trifluoromethyl-benzylamide (41)

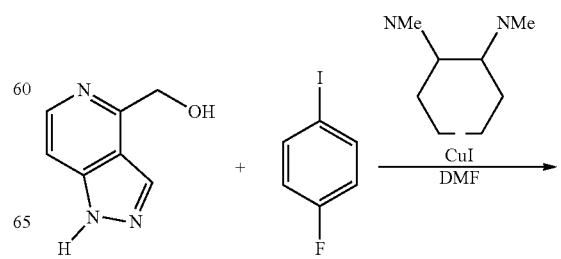

271
-continued

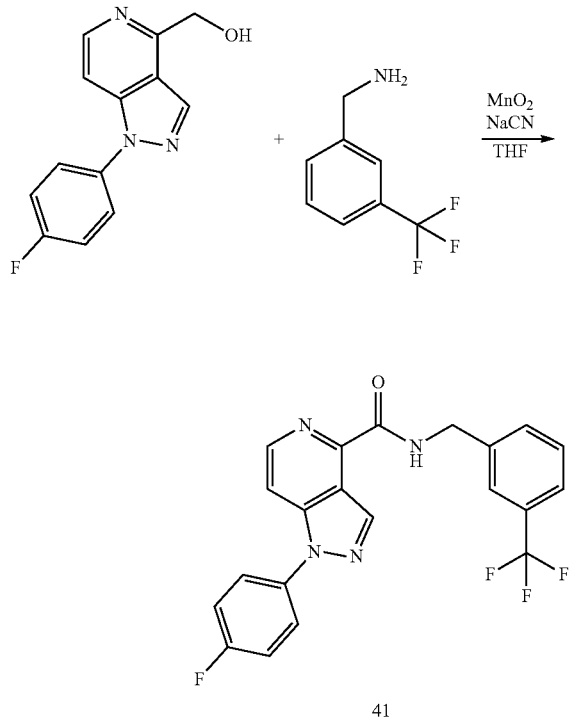

Example 42

Synthesis of (2-(Methylsulfonyl)pyridin-4-yl)methanamine hydrochloride (42)

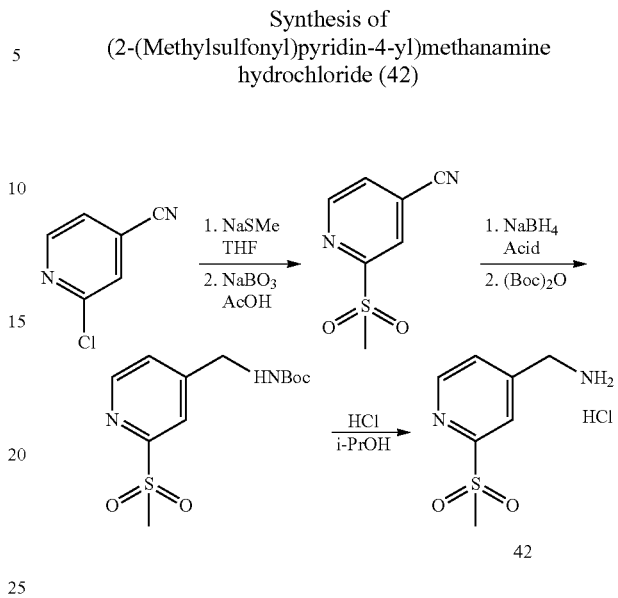

A mixture of (1H-pyrazolo[4,3-c]pyridin-4-yl)-methanol (45 mg, 0.30 mmol) (see, Michaely, W. J. et al. U.S. Pat. No. 5,300,478), copper (I) iodide (6 mg, 0.03 mmol), potassium carbonate (40 mg) was purged with nitrogen for 10 minutes and then a solution of the iodobenzene (87 mg, 0.39 mmol) and N,N'-dimethylcyclohexyl-1,2-diamine (8.6 mg, 0.06 mmol) in DMF (5 mL) was added. The mixture was warmed at 120° C. for 3 hours. The reaction was then cooled to room temperature, diluted with 1 N HCl until acidic and extracted with EtOAc (3 times). The combined organics layers were dried over magnesium sulfate, and concentrated in vacuo to afford a yellow solid which by proton NMR was a 4:1 mixture of N-1 and N-2-substituted azaindazoles. The crude material was purified by silica gel chromatography using a gradient of 0.5-10% methanol in dichloromethane to afford [1-(4-fluorophenyl)-1H-pyrazolo[4,3-c]pyridin-4-yl]-methanol.

To a mixture [1-(4-fluorophenyl)-1H-pyrazolo[4,3-c]pyridin-4-yl]-methanol (20 mg, 0.08 mmol), 3-trifluoromethylbenzylamine (71 mg, 0.41 mmol) and sodium cyanide (4 mg, 0.08 mmol) in THF (2 mL) was added manganese (IV) oxide (107 mg, 1.23 mmol). After 30 minutes, additional manganese (IV) oxide (107 mg, 1.23 mmol) was added. After 18 hours, the reaction was filtered through a pad of diatomaceous earth and concentrated in vacuo. The mixture was purified by silica gel chromatography eluting with a gradient of 0-5% methanol in dichloromethane to afford the title compound as a yellow solid.

NaSMe (6.74 g, 90 wt. %, 1.2 eq) was charged to a flask followed by THF (10 mL). To the slurry was charged a solution of 2-chloro-4-cyanopyridine (10.0 g, 72.2 mmol, 1.0 eq) in THF (20 mL). The reaction mixture was heated at 50° C. for 2 hours. The batch was then treated with $NaBO_3 \cdot 4H_2O$ (33.31 g, 3.0 eq) followed by AcOH (50 mL). The reaction mixture was heated at 55° C. for 16 hours. The THF was distilled out under slight vacuum at 55° C., and the resulting white slurry was treated with water (120 mL) and cooled to ambient temperature and held for 1 hour. The batch was filtered, the solid washed well with water, and then oven dried under vacuum to afford 2-(methylsulfonyl)isonicotinonitrile as a white solid, 7.65 g, >99.5 area % purity by HPLC, 58% yield.

2-(Methylsulfonyl)isonicotinonitrile (10.93 g, 60.0 mmol, 1.0 eq), $NaBH_4$ (3.41 g, 90.0 mmol, 1.5 eq) and zinc bromide (1.35 g, 6.0 mmol, 0.1 eq) were charged to a 250 mL flask. THF (60 mL) was charged, and the slurry cooled to 0-5° C. TFA (6.69 mL, 90.0 mmol, 1.5 eq) was charged at a rate to keep the temperature below 20° C. and to control hydrogen evolution. After the addition, the batch was stirred at ambient temperature for 1-2 hours. The reaction mixture was then cooled to 0-5° C. and treated with methanol (10 mL) followed by water (40 mL) and finally a solution of di-tert-butyl dicarbonate (15.06 g, 69.0 mmol, 1.15 eq) in THF (10 mL). The batch was stirred at ambient temperature for 2 hours, and then the THF and MeOH was removed by distillation under vacuum at 55° C. To the resulting slurry was added water (40 mL), toluene (20 mL) and heptane (40 mL). The slurry was stirred for 1 hour at ambient temperature and filtered. The solid was washed with water and heptane, and then oven dried under vacuum to afford tert-butyl (2-(methylsulfonyl)pyridin-4-yl)methylcarbamate as an off-white solid, 13.25 g, 97.9 wt. % purity, 76% yield.

To a 500 mL reactor was charged tert-butyl (2-(methylsulfonyl)pyridin-4-yl)methylcarbamate (20.0 g, 65.65 mmol, 94.0 wt. %) followed by i-PrOH (140 mL). The slurry was stirred and treated with concentrated HCl (16.4 mL, 196.96 mmol, 3.0 eq), and then heated to 65° C. and held at this temperature for 3 hours. The batch was cooled to 20-25° C., held at this temperature for at least 2 hours, and then filtered.

Example 43

Synthesis of (S)-1-(5-methanesulfonyl-furan-2-yl)-propylamine hydrochloride (43)

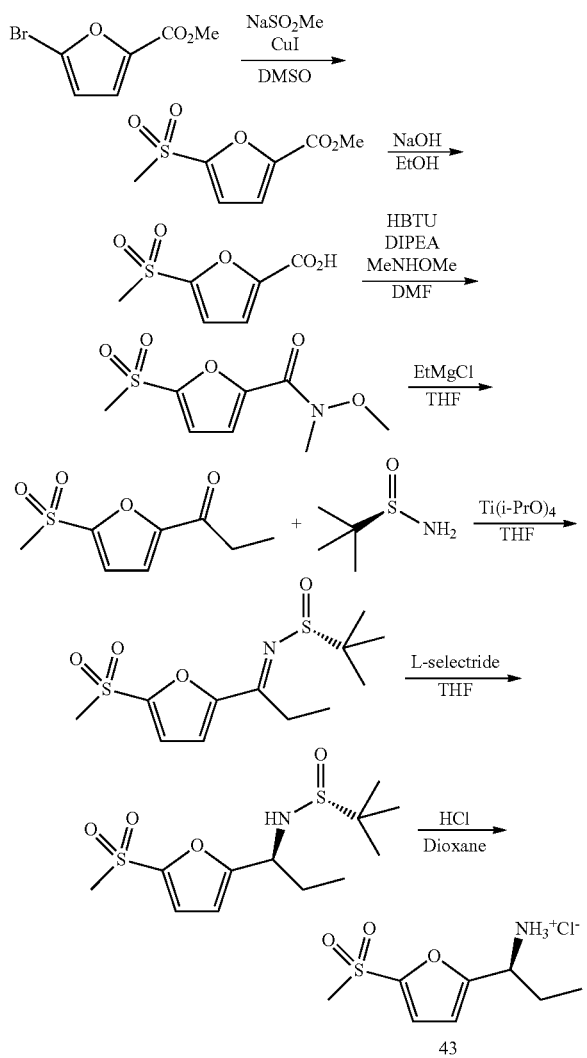

43

To a solution of 5-bromo-furan-2-carboxylic acid methyl ester (4.7 g, 23 mmol) in DMSO (25 mL) was added the sodium methanesulfinate (5.5 g, 46 mmol) followed by copper (I) iodide (4.4 g, 23 mmol). The mixture was then heated to 110° C. for 2 hours. The reaction was diluted with water (100 mL) and ethyl acetate (100 mL) and filtered through diatomaceous earth. The aqueous layer was separated and extracted with ethyl acetate (3×50 mL). The combined organic layers were washed with brine (2×50 mL), dried over sodium sulfate, filtered and concentrated to afford 5-methanesulfonyl-furan-2-carboxylic acid methyl ester.

To a solution of 5-methanesulfonyl-furan-2-carboxylic acid methyl ester (2.94 g, 14.4 mmol) in EtOH (100 mL) was added a 2 N aqueous solution of sodium hydroxide (40 mL, 80 mmol). The mixture was warmed at 80° C. for 4 hours and then concentrated in vacuo to remove ethanol. The mixture was then acidified with 1 N aqueous HCl and extracted with ethyl acetate (4×30 mL). The combined organic layers were washed with brine (2×100 mL), dried over sodium sulfate, filtered and concentrated to afford 5-methanesulfonyl-furan-2-carboxylic acid.

To a solution of 5-methanesulfonyl-furan-2-carboxylic acid (1.1 g, 5.8 mmol) in DMF (20 mL) was added HBTU (2.8 g, 8.7 mmol) and DIPEA (3.2 mL, 17.4 mmol). After stirring for 10 minutes, N,O-dimethylhydroxylamine hydrochloride (0.85 g, 0.71 mmol) was added. After 18 hours, the mixture was diluted with saturated aqueous sodium bicarbonate solution (50 mL) and extracted with ethyl acetate (4×25 mL). The combined organic layers were washed with brine (30 mL), dried over sodium sulfate, filtered and concentrated in vacuo to afford 5-methanesulfonyl-furan-2-carboxylic acid methoxy-methyl-amide.

To a chilled (0° C.) solution of 5-methanesulfonyl-furan-2-carboxylic acid methoxy-methyl-amide (1.48 g, 6.36 mmol) in THF (30 mL) was added a 2 M solution of ethylmagnesium chloride in THF (7.0 mL, 14 mmol). The mixture was then slowly warmed to with stifling. After 18 hours, the mixture was quenched with saturated aqueous ammonium chloride (50 mL) and then diluted with ethyl acetate (50 mL). The aqueous phase was separated and extracted with ethyl acetate (3×30 mL). The combined organic layers were dried over sodium sulfate, filtered and concentrated to afford 1-(5-methanesulfonyl-furan-2-yl)-propan-1-one.

To a solution of 1-(5-methanesulfonyl-furan-2-yl)-propan-1-one (1.1 g, 5.5 mmol) in THF (30 mL) was added (R)-(+)-2-methyl-2-propanesulfinamide (0.750 g, 6.06 mmol) and titanium (IV) isopropoxide (6 mL, 25 mmol) and the mixture was warmed at reflux. After 18 hours, the mixture was cooled to room temperature, and diluted with diethyl ether (100 mL) and water (6 mL). The mixture was stirred for 10 minutes, dried over sodium sulfate, filtered and concentrated. The crude product was purified by silica gel chromatography, eluting with a gradient of 0-80% EtOAc-hexanes to afford (R)-2-methyl-propane-2-sulfinic acid[1-(5-methanesulfonyl-furan-2-yl)-prop-(E)-ylidene]-amide.

To a chilled (−78° C.) solution of (R)-2-methyl-propane-2-sulfinic acid[1-(5-methanesulfonyl-furan-2-yl)-prop-(E)-ylidene]-amide (0.360 g, 1.18 mmol) in THF (15 mL) was added a 1 M solution of L-Selectride (2.4 mL, 2.4 mmol) in THF in several portions. After stifling for 2 hours, the mixture was quenched with saturated aqueous ammonium chloride (100 mL) and extracted with ethyl acetate (3×20 mL). The combined organic layers were washed with brine (10 mL), dried over sodium sulfate, filtered and concentrated. The crude residue was purified by silica gel chromatography eluting with a gradient of 0-100% ethyl acetate in hexanes to afford (R)-2-methyl-propane-2-sulfinic acid [(S)-1-(5-methanesulfonyl-furan-2-yl)-propyl]-amide.

To a solution of (R)-2-methyl-propane-2-sulfinic acid [(S)-1-(5-methanesulfonyl-furan-2-yl)-propyl]-amide (0.530 g, 1.72 mmol) in methanol (5 mL) was added 4 N HCl in dioxane (2 mL, 8 mmol). After 1 hour, the mixture was concentrated in vacuo to afford (S)-1-(5-methanesulfonyl-furan-2-yl)-propylamine hydrochloride.

Example 44

Synthesis of (S)-1-(2-Chloro-6-methanesulfonyl-pyridin-4-yl)-propylamine (44)

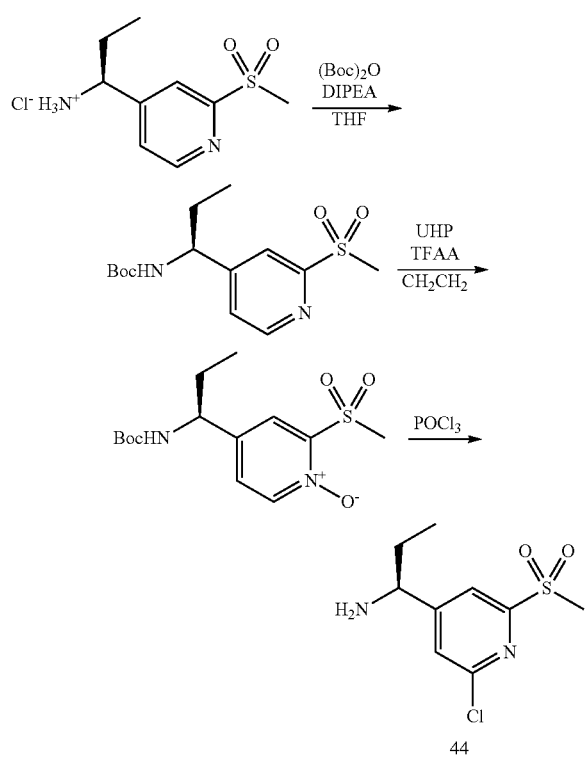

To a suspension of (S)-1-(2-methanesulfonyl-pyridin-4-yl)-propylamine hydrochloride (3.47 g, 13.9 mmol) in THF (50 mL) was added DIPEA (7.3 mL, 42 mmol) and di-tert-butyl dicarbonate (3.2 g, 15 mmol). The mixture was then washed with saturated aqueous ammonium chloride (50 mL), brine (50 mL), dried over sodium sulfate, filtered and concentrated to afford [(S)-1-(2-methanesulfonyl-pyridin-4-yl)-propyl]-carbamic acid tert-butyl ester.

To a solution of [(S)-1-(2-methanesulfonyl-pyridin-4-yl)-propyl]-carbamic acid tert-butyl ester (2 g, 6 mmol) in dichloromethane (50 mL) was added urea hydrogen peroxide (UHP) (1.26 g, 13.4 mmol). The mixture was then cooled to 0° C. and trifluoroacetic anhydride (1.8 mL, 13 mmol) was added slowly. The mixture was slowly warmed to room temperature and stirred for 16 hours. The reaction was quenched with saturated aqueous sodium sulfite (20 mL) and stirred for 15 minutes. The mixture was then extracted with ethyl acetate (3×30 mL), dried over sodium sulfate, filtered and concentrated to afford [(S)-1-(2-methanesulfonyl-1-oxy-pyridin-4-yl)-propyl]-carbamic acid tert-butyl ester.

A solution of [(S)-1-(2-methanesulfonyl-1-oxy-pyridin-4-yl)-propyl]-carbamic acid tert-butyl ester (1.7 g, 5.2 mmol) in phosphorous oxychloride (10 mL) was warmed at reflux for 10 minutes. The mixture was then added in portions to ice water (100 mL) and vigorously stirred for 30 minutes. The solution was then made basic with saturated sodium carbonate and extracted then with ethyl acetate (4×30 mL). The combined organic layers were washed with brine (2×50 mL), dried over sodium sulfate and concentrated in vacuo to afford the title compound.

Example 45

Synthesis of (S)-1-(2-Methanesulfonyl-oxazol-5-yl)-propylamine hydrochloride (45)

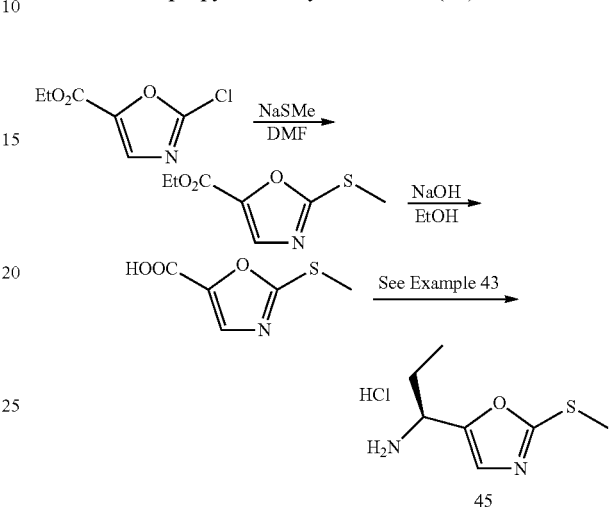

To a solution of 2-chloro-oxazole-5-carboxylic acid ethyl ester (4 g, 22 mmol) in DMF (75 mL) was added sodium thiomethoxide (1.8 g, 25.7 mmol). The mixture was heated to 50° C. to afford a yellow solution. After 18 hours, the mixture was diluted with saturated aqueous ammonium chloride (50 mL) and extracted with ethyl acetate (3×50 mL). The combined organic layers were washed with brine (50 mL), dried over sodium sulfate and concentrated in vacuo to afford 2-ethylsulfanyl-oxazole-5-carboxylic acid ethyl ester.

To a solution of 2-ethylsulfanyl-oxazole-5-carboxylic acid ethyl ester (4.6 g, 24.57 mmol) in ethanol (100 mL) was added a 2 N solution of sodium hydroxide (37 mL, 74 mmol) in water. The mixture was heated at 80° C. for 4 hours and then concentrated in vacuo to remove the ethanol. The remaining aqueous solution was then acidified with 1 N HCl and extracted with ethyl acetate (4×30 mL). The combined organic layers were washed with brine (2×100 mL), dried over sodium sulfate and concentrated to afford 2-methylsulfanyl-oxazole-5-carboxylic acid.

2-Methylsulfanyl-oxazole-5-carboxylic acid was converted to (S)-1-(2-methanesulfanyl-oxazol-5-yl)-propylamine hydrochloride (45) via the Weinreb amide using the same methods as described in Example 43.

2-Methylsulfanyl-oxazole-5-carboxylic acid was converted to (S)-1-(2-methanesulfanyl-oxazol-5-yl)-ethylamine hydrochloride via the Weinreb amide using the same methods as described in Example 43 except methyl magnesium bromide was substituted for ethyl magnesium chloride.

2-Methylsulfanyl-oxazole-4-carboxylic acid was converted to (S)-1-(2-methylsulfanyl-oxazol-4-yl)-propylamine hydrochloride via the Weinreb amide using the same methods as described in Example 43.

2-Methylsulfanyl-oxazole-4-carboxylic acid was converted to (S)-1-(2-methylsulfanyl-oxazol-4-yl)-ethylamine hydrochloride via the Weinreb amide using the same methods as described in Example 43 except methyl magnesium bromide was substituted for ethyl magnesium chloride.

Example 46

Synthesis of 1-(4-Fluorophenyl)-1H-pyrazolo[3,4-c]pyridine-4-carboxylic acid [(S)-1-(2-methanesulfonyl-oxazol-5-yl)-propyl]-amide (46)

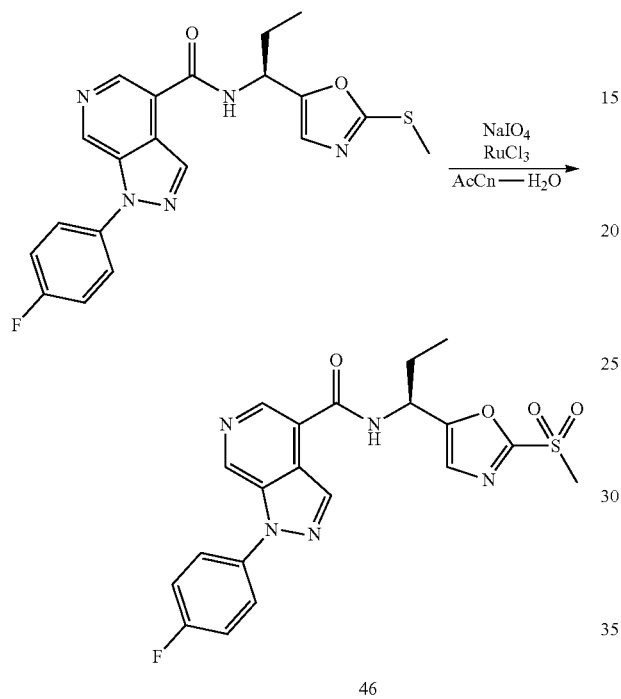

46

To a solution of 1-(4-fluorophenyl)-1H-pyrazolo[3,4-c]pyridine-4-carboxylic acid [(S)-1-(2-methylsulfanyl-oxazol-5-yl)-propyl]-amide (0.1 g, 0.2 mmol) in a mixture of acetonitrile (25 mL) and water (5 mL) was added sodium periodate (0.155 g, 0.725 mmol) followed by ruthenium trichloride (5 mg, 0.02 mmol). After 6 hours, the mixture was filtered and the filtrate was diluted with water (50 mL) and extracted with ethyl acetate (3×50 mL). The combined organic layers were dried over sodium sulfate, filtered, and concentrated. The crude material was dissolved in ethyl acetate and passed through a pad of silica. The material from the pad was crystallized from ethyl acetate-hexanes to afford the title compound.

1-(4-Fluorophenyl)-1H-pyrazolo[3,4-c]pyridine-4-carboxylic acid [(S)-1-(2-methanesulfanyl-oxazol-5-yl)-ethyl]-amide was converted to 1-(4-fluorophenyl)-1H-pyrazolo[3,4-c]pyridine-4-carboxylic acid [(S)-1-(2-methanesulfonyl-oxazol-5-yl)-ethyl]-amide using the same methods as described in Example 46.

1-(4-Fluorophenyl)-1H-pyrazolo[3,4-c]pyridine-4-carboxylic acid [(S)-1-(2-methylsulfanyl-oxazol-4-yl)-propyl]-amide was converted to 1-(4-fluorophenyl)-1H-pyrazolo[3,4-c]pyridine-4-carboxylic acid [(S)-1-(2-methanesulfonyl-oxazol-4-yl)-propyl]-amide using the same methods as described in Example 46.

1-(4-Fluorophenyl)-1H-pyrazolo[3,4-c]pyridine-4-carboxylic acid [(S)-1-(2-methylsulfanyl-oxazol-4-yl)-ethyl]-amide was converted to 1-(4-fluorophenyl)-1H-pyrazolo[3, 4-c]pyridine-4-carboxylic acid [(S)-1-(2-methanesulfonyl-oxazol-4-yl)-ethyl]-amide using the same methods as described in Example 46.

Example 47

Synthesis of (S)-1-(2-Methanesulfonyl-6-methoxy-pyridin-4-yl)-propylamine hydrochloride

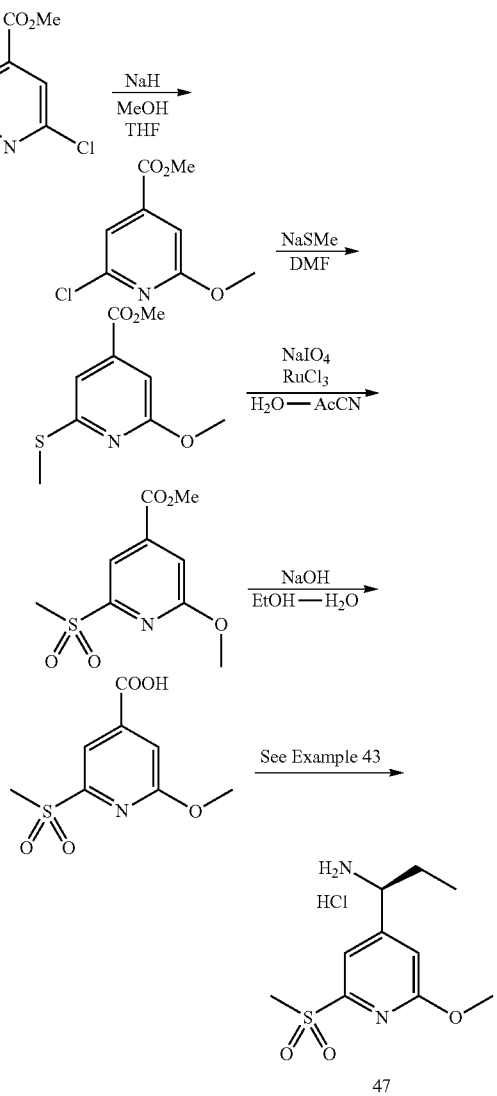

47

To a solution of dry methanol (2.2 mL, 53 mmol) in THF (200 mL) was added sodium hydride (2.12 g, 53 mmol) in portions under a stream of nitrogen. When gas evolution ceased, 2,6-dichloro-isonicotinic acid methyl ester (10.0 g, 48.5 mmol) was added. After stirring for 2 hours, the reaction was diluted with saturated aqueous ammonium chloride (100 mL) and extracted with ethyl acetate (4×50 mL). The combined organics were washed with brine, dried over sodium sulfate, and concentrated to afford 2-chloro-6-methoxy-isonicotinic acid methyl ester.

To a stirred solution of 2-chloro-6-methoxy-isonicotinic acid methyl ester (8.5 g, 42 mmol) in DMF (100 mL) was added sodium thiomethoxide (3.22 g, 41.6 mmol), resulting in a yellow colored solution. After 18 hours, the mixture was quenched with saturated aqueous ammonium chloride (100 mL) and extracted with ethyl acetate (4×50 mL). The combined organic layers were washed with brine (50 mL), dried over sodium sulfate and concentrated in vacuo to afford 2-methoxy-6-methylsulfanyl-isonicotinic acid methyl ester.

To a solution of 2-methoxy-6-methylsulfanyl-isonicotinic acid methyl ester (4.7 g, 22 mmol) in acetonitrile (180 mL) and water (40 mL) was added sodium periodate (14.15 g, 16.16 mmol) followed by ruthenium trichloride (20 mg, 0.1 mmol). After 6 hours, the mixture was filtered and the filtrate was diluted with water (50 mL) and extracted with ethyl acetate (4×50 mL). The combined organic layers were dried over sodium sulfate, filtered, and concentrated to afford 2-methanesulfonyl-6-methoxy-isonicotinic acid methyl ester.

To a solution of 2-methanesulfonyl-6-methoxy-isonicotinic acid methyl ester (4.3 g, 17.5 mmol) in ethanol (75 mL) was added 2 N aqueous sodium hydroxide (35 mL, 70 mmol). The mixture was warmed at 80° C. for 4 hours and then concentrated in vacuo to remove the ethanol. The remaining aqueous solution was acidified with 1 N aqueous HCl and extracted with ethyl acetate (4×30 mL). The combined organic layers were washed with brine (2×100 mL), dried over sodium sulfate and concentrated to afford 2-methanesulfonyl-6-ethoxy-isonicotinic acid.

2-Methanesulfonyl-6-ethoxy-isonicotinic acid was converted to (S)-1-(2-methanesulfonyl-6-methoxy-pyridin-4-yl)-propylamine hydrochloride (47) via the Weinreb amide using the same methods as described in Example 43.

The Weinreb amide of 2-methanesulfonyl-6-ethoxy-isonicotinic acid was also converted to (S)-1-(2-methanesulfonyl-6-methoxy-pyridin-4-yl)-ethylamine hydrochloride according to methods described in Example 43 except during the Grignard addition methyl magnesium bromide was added to the Weinreb amide instead of ethyl magnesium chloride to afford the corresponding methyl ketone.

Example 48

Synthesis of 1-(4-Fluorophenyl)-1H-pyrazolo[3,4-c] pyridine-4-carboxylic acid [(S)-1-(6-methanesulfonyl-2-oxo-1,2-dihydropyridin-4-yl)-propyl]-amide (48)

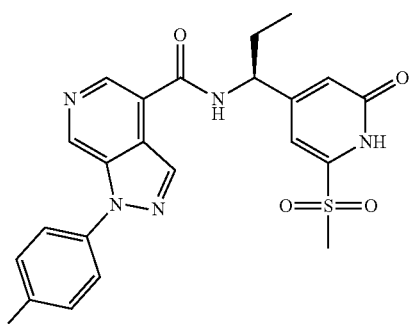

48

A solution of 1-(4-fluorophenyl)-1H-pyrazolo[3,4-c]pyridine-4-carboxylic acid [(S)-1-(2-methanesulfonyl-6-methoxy-pyridin-4-yl)-propyl]-amide (0.150 g, 310 mmol) in 48% aqueous hydrobromic acid (7.0 mL, 42 mmol) was warmed at 60° C. After 5 hours, the mixture was cooled to room temperature, diluted with water (25 mL) and extracted with ethyl acetate (4×20 mL). The combined organic layers were washed with saturated sodium bicarbonate (4×20 mL), brine (20 mL), dried over sodium sulfate and concentrated in vacuo. The crude material was triturated with ethyl acetate-ether to afford the title compound.

The following compound was also prepared by methods described in Example 48:

1-(4-Fluorophenyl)-1H-pyrazolo[3,4-c]pyridine-4-carboxylic acid [(S)-1-(6-methanesulfonyl-2-oxo-1,2-dihydropyridin-4-yl)-ethyl]-amide Example 49

Synthesis of 1-(4-Fluorophenyl)-1H-pyrazolo[3,4-c] pyridine-4-carboxylic acid [(S)-1-(2-methanesulfonyl-6-methylamino-pyridin-4-yl)-propyl]-amide (49)

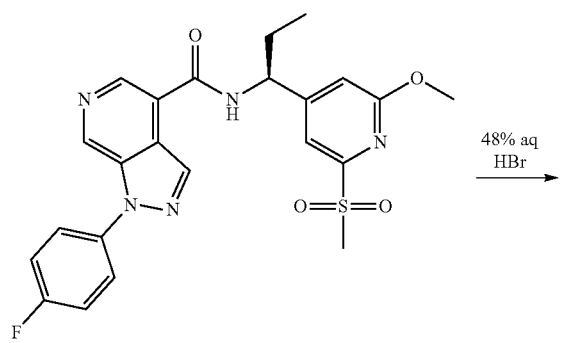

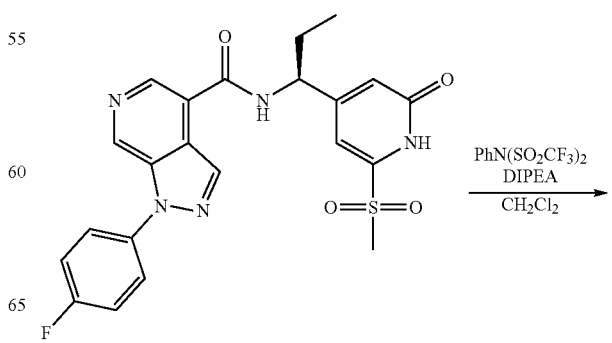

-continued

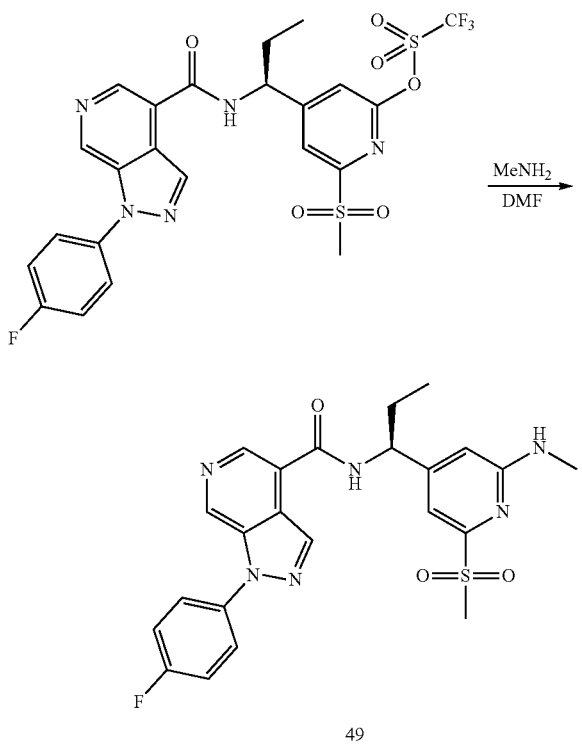

49

To a solution of 1-(4-fluorophenyl)-1H-pyrazolo[3,4-c]pyridine-4-carboxylic acid [(S)-1-(6-methanesulfonyl-2-oxo-1,2-dihydropyridin-4-yl)-propyl]-amide (0.800 g, 1.70 mmol) in dichloromethane (30 mL) was added N-phenyltrifluoromethane sulfonimide (0.930, 2.57 mmol) followed by DIPEA (0.45 mL, 2.6 mmol). The mixture was stirred at overnight. LC-MS indicated that approximately 70% of the starting material had been converted. Additional N-phenyltrifluoromethanesulfonimide (0.5 eq.) and DIPEA (0.5 eq.) was added. After 6 hours, the mixture was diluted with saturated aqueous ammonium chloride (30 mL) and extracted with ethyl acetate (4×15 mL). The combined organic layers were washed with brine (30 mL), dried over sodium sulfate and concentrated in vacuo. The crude material was purified by silica gel chromatography eluting with a gradient of 0-100% ethyl acetate in hexanes to afford trifluoromethanesulfonic acid 4-((S)-1-{[1-(4-fluorophenyl)-1H-pyrazolo[3,4-c]pyridine-4-carbonyl]-amino}-propyl)-6-methanesulfonyl-pyridin-2-yl ester.

To a stirred solution of trifluoromethanesulfonic acid 4-((S)-1-{[1-(4-fluorophenyl)-1H-pyrazolo[3,4-c]pyridine-4-carbonyl]-amino}-propyl)-6-methanesulfonyl-pyridin-2-yl ester (0.08 g, 0.13 mmol) in DMF (2 mL) was added a 2.0 M solution of methylamine in THF (0.150 mL, 0.30 mmol) followed by DIPEA (0.05 mL, 0.3 mmol). After 16 hours, the mixture was diluted with saturated aqueous ammonium chloride (5 mL) and extracted with ethyl acetate (3×5 mL). The combined organic layers were dried over sodium sulfate and concentrated onto silica gel. The crude material was purified by silica gel chromatography eluting with a gradient of 0-100% ethyl acetate in hexanes to afford the title compound.

The following compounds were also prepared from the intermediate methanesulfonic acid 4-((S)-1-{[1-(4-fluorophenyl)-1H-pyrazolo[3,4-c]pyridine-4-carbonyl]-amino}-propyl)-6-methanesulfonyl-pyridin-2-yl ester by methods described in Example 49:

1-(4-Fluorophenyl)-1H-pyrazolo[3,4-c]pyridine-4-carboxylic acid [(S)-1-(2-methanesulfonyl-6-methylamino-pyridin-4-yl)-ethyl]-amide, 1-(4-Fluorophenyl)-1H-pyrazolo[3,4-c]pyridine-4-carboxylic acid [(S)-1-(2-dimethylamino-6-methanesulfonyl-pyridin-4-yl)-ethyl]-amide, 1-(4-Fluorophenyl)-1H-pyrazolo[3,4-c]pyridine-4-carboxylic acid [(S)-1-(2-dimethylamino-6-methanesulfonyl-pyridin-4-yl)-propyl]-amide, 1-(4-Fluorophenyl)-1H-pyrazolo[3,4-c]pyridine-4-carboxylic acid [(S)-1-(2-isopropylamino-6-methanesulfonyl-pyridin-4-yl)-propyl]-amide, 1-(4-Fluorophenyl)-1H-pyrazolo[3,4-c]pyridine-4-carboxylic acid {(S)-1-[2-(carbamoylmethyl-amino)-6-methanesulfonyl-pyridin-4-yl]-propyl}-amide, 1-(4-Fluorophenyl)-1H-pyrazolo[3,4-c]pyridine-4-carboxylic acid {(S)-1-[2-(carbamoylmethyl-methyl-amino)-6-methanesulfonyl-pyridin-4-yl]-propyl}-amide, 1-(4-Fluorophenyl)-1H-pyrazolo[3,4-c]pyridine-4-carboxylic acid [2-(carbamoylmethyl-methyl-amino)-6-methanesulfonyl-pyridin-4-ylmethyl]-amide, 1-(4-Fluorophenyl)-1H-pyrazolo[3,4-c]pyridine-4-carboxylic acid [2-(carbamoylmethyl-amino)-6-methanesulfonyl-pyridin-4-ylmethyl]-amide, 1-(4-Fluorophenyl)-1H-pyrazolo[3,4-c]pyridine-4-carboxylic acid {(S)-1-[2-(carbamoylmethyl-methyl-amino)-6-methanesulfonyl-pyridin-4-yl]-ethyl}-amide, and 1-(4-Fluorophenyl)-1H-pyrazolo[3,4-c]pyridine-4-carboxylic acid {(S)-1-[2-(carbamoylmethyl-amino)-6-methanesulfonyl-pyridin-4-yl]-ethyl}-amide.

The following compound was also prepared according to the procedure in example 49:

1-(4-Fluorophenyl)-1H-pyrazolo[3,4-c]pyridine-4-carboxylic acid (6-methanesulfonyl-2-oxo-1,2-dihydropyridin-4-ylmethyl)-amide was converted to 1-(4-fluorophenyl)-1H-pyrazolo[3,4-c]pyridine-4-carboxylic acid [2-(2-hydroxy-2-methyl-propylamino)-6-methanesulfonyl-pyridin-4-ylmethyl]-amide using amino-2-methyl-propan-2-ol instead of methylamine in the final step.

Example 50

Synthesis of 1-(4-Fluorophenyl)-1H-pyrazolo[3,4-c]pyridine-4-carboxylic acid (2-methoxy-thiazol-5-ylmethyl)-amide (50)

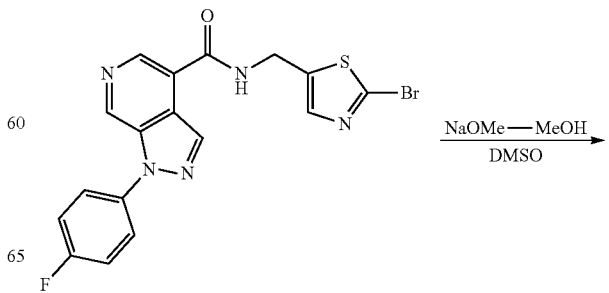

-continued

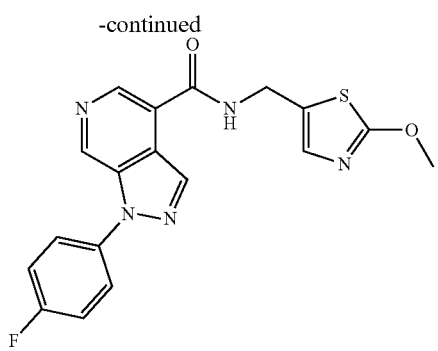

50

To a solution of 1-(4-fluorophenyl)-1H-pyrazolo[3,4-c]pyridine-4-carboxylic acid (2-bromo-thiazol-5-ylmethyl)-amide (30 mg, 0.07 mmol) in DMSO (5 mL) was added a 0.5 M solution of NaOMe in MeOH (2.0 mL, 1.0 mmol). The solution was warmed at 50° C. and after 48 hours, was partitioned between saturated aqueous sodium bicarbonate (50 mL) and EtOAc (50 mL). The organic phase was separated and washed with brine (50 mL), dried over sodium sulfate, filtered and concentrated. The crude material was purified by silica gel chromatography eluting with a gradient of 0-10% methanol in dichloromethane. The material was further purified by preparative thin layer silica gel chromatography eluting with methanol-dichloromethane (2:98) to afford the title compound.

Example 51

Synthesis of 1-(4-Fluorophenyl)-1H-pyrazolo[3,4-c]pyridine-4-carboxylic acid (2-methylamino-thiazol-5-ylmethyl)-amide (51)

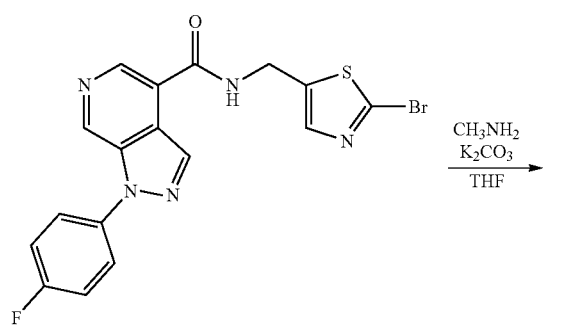

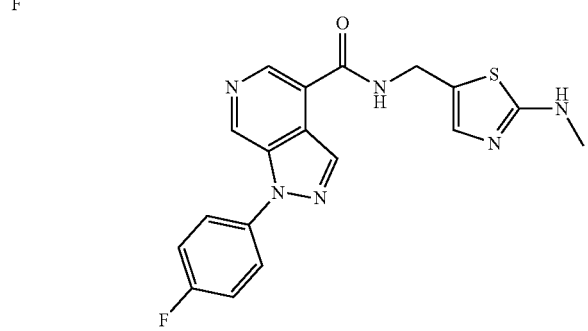

51

1-(4-Fluorophenyl)-1H-pyrazolo[3,4-c]pyridine-4-carboxylic acid (2-bromo-thiazol-5-ylmethyl)-amide (50 mg, 0.10 mmol) was treated with a 2 M solution of methylamine in THF (2.0 mL, 4.0 mmol) in a microwave tube. To this solution was added solid $K_2CO_3$ (19 mg, 0.14 mmol), and the microwave tube was sealed and heated at 100° C. for 1 hour in a microwave. The mixture was then heated at 160° C. in a microwave for 4 hours, and the mixture was diluted with saturated aqueous ammonium chloride (40 mL) and EtOAc (20 mL). The layers were separated and the organics layer was washed with brine (50 mL), dried over sodium sulfate, filtered and concentrated. The crude material was purified by silica gel chromatography eluting with a gradient of 0-10% methanol in dichloromethane to afford the title compound.

Example 52

Synthesis of 1-(4-Fluorophenyl)-1H-pyrazolo[3,4-c]pyridine-4-carboxylic acid [2-(acetyl-methyl-amino)-thiazol-5-ylmethyl]-amide (52)

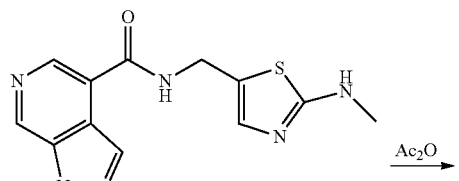

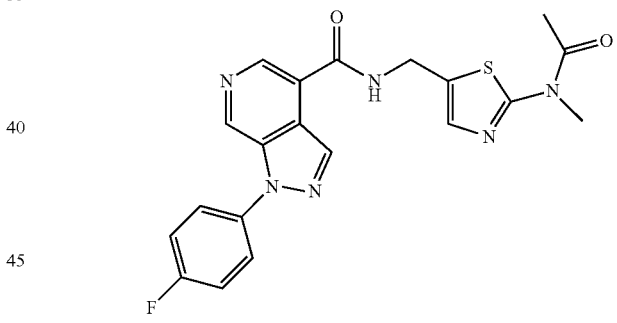

52

A solution of 1-(4-fluorophenyl)-1H-pyrazolo[3,4-c]pyridine-4-carboxylic acid (2-bromo-thiazol-5-ylmethyl)-amide (80 mg, 0.2 mmol) in acetic anhydride (2 mL) was heated at 60° C. for 18 hours. The solution was diluted with 10 mL of a 1 N solution of aqueous NaOH and stirred for 10 minutes. The solution was then extracted with dichloromethane (20 mL). The organic layers were dried over sodium sulfate, filtered and concentrated. The crude material was purified by silica gel chromatography eluting with a gradient of 0-10% methanol in dichloromethane. The purification was repeated eluting with a gradient of 0-7% methanol in dichloromethane. The material from the purification was diluted with dichloromethane (1 mL) followed by hexanes (5 mL). The solid was collected by filteration to afford the title compound.

Example 53

Synthesis of 1-(4-Fluorophenyl)-1H-pyrazolo[3,4-c]pyridine-4-carboxylic acid (2-morpholin-4-yl-thiazol-5-ylmethyl)-amide (53)

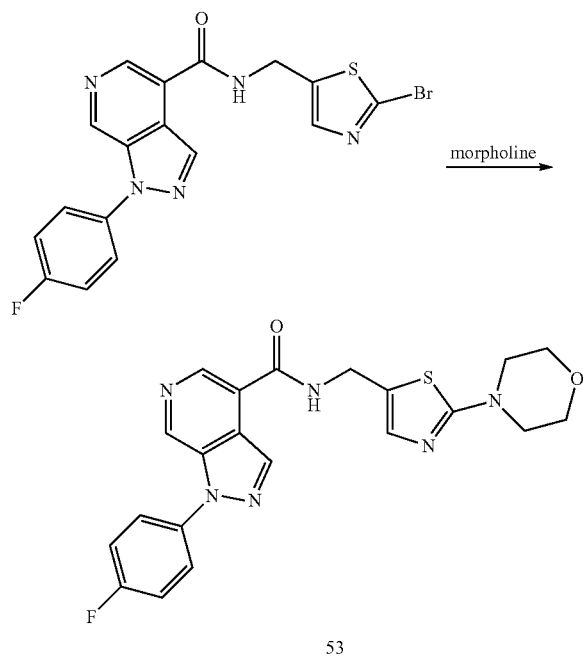

A solution of 1-(4-fluorophenyl)-1H-pyrazolo[3,4-c]pyridine-4-carboxylic acid (2-bromo-thiazol-5-ylmethyl)-amide (80 mg, 0.21 mmol) in morpholine (2 mL) was heated at 140° C. for 72 hours in a sealed tube. The mixture was partitioned between EtOAc (20 mL) and saturated aqueous ammonium chloride (20 mL). The organic layer was separated and washed with brine (20 mL), dried over sodium sulfate, filtered and concentrated. The crude material was purified by silica gel chromatography eluting with a gradient of 0-10% methanol in dichloromethane. The purification was repeated using the same conditions listed above. The material from the purification was diluted with dichloromethane (1 mL) followed by hexanes (5 mL) and filtered to afford the title compound.

Example 54

Synthesis of 1-(4-Fluorophenyl)-1H-pyrazolo[3,4-c]pyridine-4-carboxylic acid (5-methylamino-1,3,4-thiadiazol-2-ylmethyl)-amide (54)

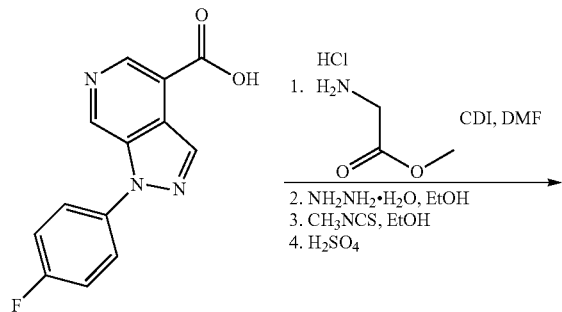

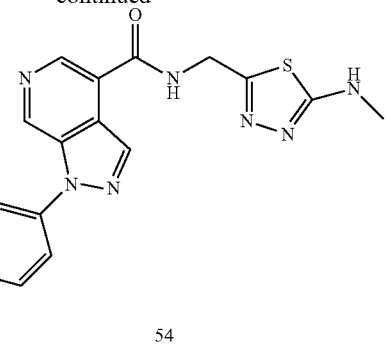

54

A suspension of 1-(4-fluorophenyl)-1H-pyrazolo[3,4-c]pyridine-4-carboxylic acid (2.95 g, 11.5 mmol) in DMF (25 mL) was treated with CDI (1.51 g, 12.0 mmol). The mixture turned to a dark brown clear solution in 5 minutes, and then a solid precipitate formed. Additional DMF (10 mL) was added to assist stirring. The mixture was stirred for 1 hour. A solution of glycine methyl ester hydrochloride (2.42 g, 14.9 mmol) in DMF (5 mL) was added. After 18 hours, the mixture was poured into water (200 mL) and diluted with saturated aqueous ammonium bicarbonate (50 mL). The solid was collected by filtration to afford {[1-(4-fluorophenyl)-1H-pyrazolo[3,4-c]pyridine-4-carbonyl]-amino}-acetic acid methyl ester as a light brown solid.

To a solution of {[1-(4-fluorophenyl)-1H-pyrazolo[3,4-c]pyridine-4-carbonyl]-amino}-acetic acid methyl ester (0.50 g, 1.5 mmol) in EtOH (6 mL) was added hydrazine hydrate (2 mL) and the mixture was warmed at 60° C. After 18 hours, the mixture was cooled to room temperature and poured into water (100 mL). The solid was collected by filtration to afford 1-(4-fluorophenyl)-1H-pyrazolo[3,4-c]pyridine-4-carboxylic acid hydrazinocarbonylmethyl-amide (purity 90%).

To a mixture of 1-(4-fluorophenyl)-1H-pyrazolo[3,4-c]pyridine-4-carboxylic acid hydrazinocarbonylmethyl-amide (104 mg, 0.32 mmol) in EtOH (4 mL) was added methyl isothiocyanate (50 mg, 0.7 mmol). The mixture was warmed at reflux for 6 days, and was then cooled to room temperature, and the product was collected by filtration. The crude material was suspended in concentrated sulfuric acid (1 mL) and stirred for 10 minutes. After standing for 10 minutes, the mixture was poured into ice water. The solution was made basic by addition of aqueous ammonia followed by a minimal amount of saturated aqueous sodium bicarbonate to pH=8 and the solid collected by filtration to afford title compound.

The following compounds were prepared using the CDI coupling method described in example 54:

1-(4-Fluorophenyl)-1H-pyrazolo[3,4-c]pyridine-4-carboxylic acid [(S)-1-(4-methanesulfonyl-furan-2-yl)-propyl]-amide, 1-(4-Fluorophenyl)-1H-pyrazolo[3,4-c]pyridine-4-carboxylic acid [(S)-1-(2-methylsulfanyl-oxazol-5-yl)-propyl]-amide, 1-(4-Fluorophenyl)-1H-pyrazolo[3,4-c]pyridine-4-carboxylic acid [(S)-1-(2-methanesulfonyl-6-methoxy-pyridin-4-yl)-ethyl]-amide, 1-(4-Fluorophenyl)-1H-pyrazolo[3,4-c]pyridine-4-carboxylic acid [(S)-1-(2-methanesulfonyl-thiazol-4-yl)-ethyl]-amide, and 1-(4-Fluorophenyl)-1H-pyrazolo[3,4-c]pyridine-4-carboxylic acid [(S)-1-(2-methanesulfonyl-thiazol-5-yl)-ethyl]-amide.

Example 55

Synthesis of (S)-1-(2-Methanesulfonyl-thiazol-5-yl)-propylamine hydrochloride (55)

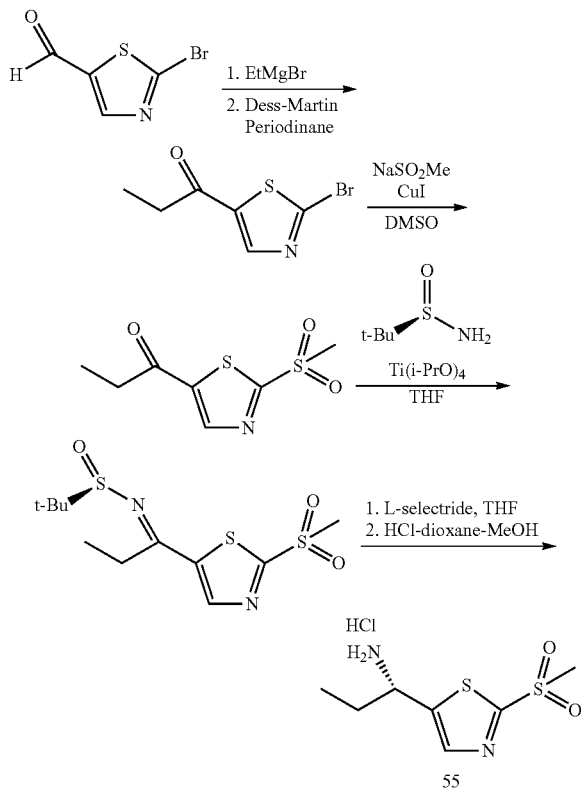

To a solution of 2-bromo-thiazole-5-carbaldehyde (1.00 g, 5.21 mmol) in THF (10 mL) was added a 3 M solution of ethylmagnesium bromide (5.00 mL, 15.0 mmol) in diethyl ether. The mixture was stirred for 18 hours. The reaction was poured into saturated aqueous ammonium chloride (100 mL) containing crushed ice and diluted with EtOAc (100 mL). The organic phase was separated, washed with saturated aqueous sodium bicarbonate solution (100 mL), dried over sodium sulfate, filtered and concentrated. The compound was purified by silica gel chromatography eluting with a gradient of 0-100% ethyl acetate in hexanes provided 1-(2-bromo-thiazol-5-yl)-propan-1-ol.

To a solution of 1-(2-bromo-thiazol-5-yl)-propan-1-ol (180 mg, 0.79 mmol) in dichloromethane (10 mL) was added Dess-Martin periodinane (DMP) (330 mg, 0.79 mmol). The reaction was stirred for 2 hours, then diluted with dichloromethane (50 mL), washed with saturated aqueous sodium bicarbonate solution (50 mL) and brine (50 mL), dried over sodium sulfate, filtered and concentrated. The compound was purified by silica gel chromatography eluting with a gradient of 0-100% ethyl acetate in hexanes to afford 1-(2-bromo-thiazol-5-yl)-propan-1-one.

To a solution of 1-(2-bromo-thiazol-5-yl)-propan-1-one (75 mg, 0.34 mmol) in dimethyl sulfoxide (3 mL) was added the sodium methanesulfonate (41 mg, 0.34 mmol) followed by copper (I) iodide (65 mg, 0.34 mmol). The mixture was heated in a microwave at 120° C. for 1 hour. The reaction was diluted with EtOAc (20 mL) and washed with saturated aqueous sodium bicarbonate solution (50 mL) and brine (10 mL). The aqueous phase was extracted with EtOAc (2×10 mL). The combined organic extracts were dried over magnesium sulfate, filtered and concentrated to afford 1-(2-methanesulfonyl-thiazol-5-yl)-propan-1-one which was used without further purification.

A mixture of 1-(2-methanesulfonyl-thiazol-5-yl)-propan-1-one (110 mg, 0.50 mmol), (R)-2-methyl-2-propanesulfinamide (70 mg, 0.6 mmol) and titanium (IV) isopropoxide (0.29 mL, 1.0 mmol) in THF (10 mL) was warmed at reflux for 18 hours. The mixture was cooled to room temperature and diluted with diethyl ether (100 mL) and water (6 mL). After 10 minutes with stifling, the solution was dried over sodium sulfate, filtered and concentrated. The crude product was purified by silica gel chromatography eluting with a gradient of 0-100% EtOAc in hexanes to afford 2-methyl-propane-2-sulfinic acid [1-(2-methanesulfonyl-thiazol-5-yl)-prop-(Z)-ylidene]-amide.

To a chilled (−78° C.) solution of 2-methyl-propane-2-sulfinic acid [1-(2-methanesulfonyl-thiazol-5-yl)-prop-(Z)-ylidene]-amide (93 mg, 0.29 mmol) in THF (5 mL) was added a 1 M solution of lithium tri-sec-butylborohydride (L-Selectride) (0.58 mL, 0.58 mmol) in THF dropwise. After 2.5 hours, the reaction mixture was quenched with saturated aqueous ammonium chloride solution (100 mL), and the aqueous layer was separated. The aqueous layer was extracted with ethyl acetate (2×10 mL). The combined organic layers were washed with brine (10 mL), dried over sodium sulfate, filtered and concentrated. The residue was purified by silica gel chromatography eluting with a gradient of 0-100% ethyl acetate in hexanes to afford 2-methyl-propane-2-sulfinic acid [(S)-1-(2-methanesulfonyl-thiazol-5-yl)-propyl]-amide.

To a solution of 2-methyl-propane-2-sulfinic acid [(S)-1-(2-methanesulfonyl-thiazol-5-yl)-propyl]-amide (80 mg, 0.3 mmol) in methanol (5 mL) was added a 4 N solution of hydrochloric acid (1 mL, 4 mmol) in dioxane. After 1 hour, the mixture was concentrated and diluted with dichloromethane (2 mL) followed by hexanes (10 mL), and concentrated to afford (S)-1-(2-methanesulfonyl-thiazol-5-yl)-propylamine hydrochloride.

The following intermediates were prepared according to methods described in example 55:
(S)-1-(2-Methanesulfonyl-thiazol-4-yl)-ethylamine, and
(S)-1-(2-Methanesulfonyl-thiazol-4-yl)-propylamine.

The following intermediate were synthesized in a similar fashion, except the methyl sulfone functionality was introduced via displacement of the halide with sodium thiomethoxide followed by an oxidation as described in example 47 (steps 2 and 3 of example 47:
(S)-1-(2-Methanesulfonyl-thiazol-5-yl)-ethylamine.

The following intermediate were synthesized as described above, except the intermediate ketone was accessed via an ethyl Grignard addition to the appropriate Weinreb amide (method is described in example 43, steps 3 and 4). The corresponding starting material, 2-bromothiophene-4-carboxylic acid, was synthesized as described in *J. Am. Chem. Soc.*, 1954, 76, 2445.
(S)-1-(5-Methanesulfonyl-thiophen-3-yl)-propylamine.

The following intermediates were synthesized as described above, except the intermediate 4-bromothiazoles were carried through without introduction of the methyl sulfone functionality. The 4-bromo-2-formylthiazole starting material was synthesized from the 2,4-dibromothiazole as described in *Bioorg. Med. Chem.*, 1999, 7, 665-697.
(S)-1-(4-Bromo-thiazol-2-yl)-propylamine, and
(5)-1-(4-Bromo-thiazol-2-yl)-ethylamine.

Example 56

Synthesis of (S)-1-Thiazol-2-yl-propylamine (56)

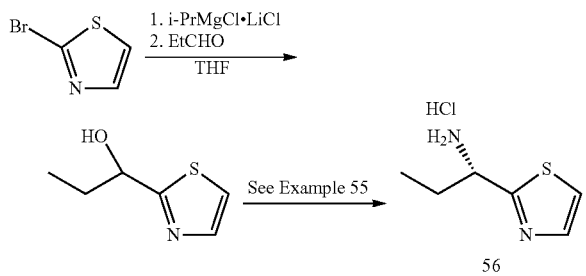

A 1.3 M solution of i-PrMgCl.LiCl (2.65 mL, 3.44 mmol) under an atmosphere of argon was cooled to −15° C. and treated with a solution of 2-bromothiazole (0.56 g, 3.4 mmol) in anhydrous THF (1 mL). The reaction mixture was then allowed to warm to 0° C. over 15 minutes. Propionaldehyde (0.25 mL, 3.4 mmol) was added and the solution was allowed to warm to room temperature over 18 hours. The solution was poured into saturated aqueous ammonium chloride (50 mL) containing crushed ice. The aqueous layer was extracted with EtOAc (50 mL) and washed with saturated aqueous sodium bicarbonate (100 mL). The aqueous layer was again extracted with EtOAc (50 mL). The combined organic layers were dried over sodium sulfate, filtered and concentrated. The material was purified by silica gel chromatography eluting with a gradient of 0-10% methanol in dichloromethane to afford 1-thiazol-2-yl-propan-1-ol.

1-Thiazol-2-yl-propan-1-ol was converted to the title compound according to methods described in example 55.

Example 57

Synthesis of (S)-1-(3-Methyl-3H-imidazol-4-yl)-propylamine (57)

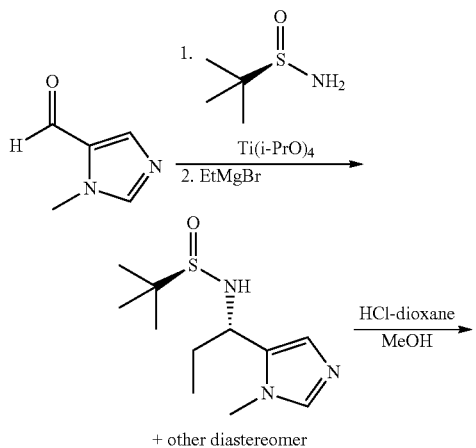

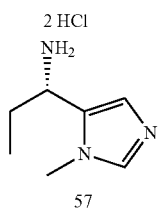

A mixture of 3-methyl-3H-imidazole-4-carbaldehyde (1.40 g, 12.7 mmol), (R)-(+)-2-methyl-2-propanesulfinamide (2.36 g, 19.1 mmol) and titanium (IV) isopropoxide (11.2 mL, 38.1 mmol) in THF (10 mL) was warmed at reflux for 18 hours. The mixture was cooled to room temperature, and diluted with ether (100 mL) and water (6 mL). The mixture was stirred for 10 minutes and then dried over sodium sulfate, filtered and concentrated. The crude product was purified by silica gel chromatography eluting with a gradient of 0-100% EtOAc in hexanes, and concentrated to afford 2-methyl-propane-2-sulfinic acid [1-(3-methyl-3H-imidazol-4-yl)-prop-(E)-ylidene]-amide as a yellow solid.

To a chilled (−78° C.) solution of 2-methyl-propane-2-sulfinic acid [1-(3-methyl-3H-imidazol-4-yl)-prop-(E)-ylidene]-amide (1.22 g, 5.72 mmol) in 10 mL of THF was added a 1 M solution of ethylmagnesium bromide in ether (11.4 mL, 11.4 mmol). The reaction mixture was stirred for 18 hours, while gradually warming to room temperature. The mixture was poured into saturated aqueous ammonium chloride on ice (100 mL), and diluted with EtOAc (100 mL). The organic layer was washed with saturated aqueous sodium bicarbonate (100 mL), dried over sodium sulfate, filtered and concentrated. The material was purified by silica gel chromatography eluting with a gradient of 0-10% methanol in dichloromethane. Two fractions were obtained that both match the desired by mass, indicating two diastereomers. The first eluting diastereomer corresponded to the R,S-diastereomer, and the second eluting distereomer corresponded to the R,R-diastereomer in a 1:3 ratio, respectively. Each diastereomer was carried on separately without further purification.

To a solution of the R,S-diastereomer in methanol (5 mL) was added a 4 N solution of HCl in dioxane (1 mL, 4 mmol). After 18 hours, the mixture was concentrated and diluted with diethyl ether. The solid was collected by filtration to afford the title compound.

Example 58

Synthesis of 2-(1-{[1-(4-Fluorophenyl)-1H-pyrazolo[3,4-c]pyridine-4-carbonyl]-amino}-propyl)-5-methyl-oxazole-4-carboxylic acid methyl ester (58)

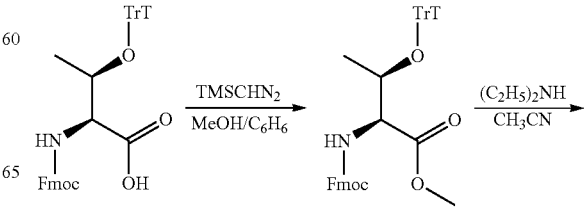

-continued

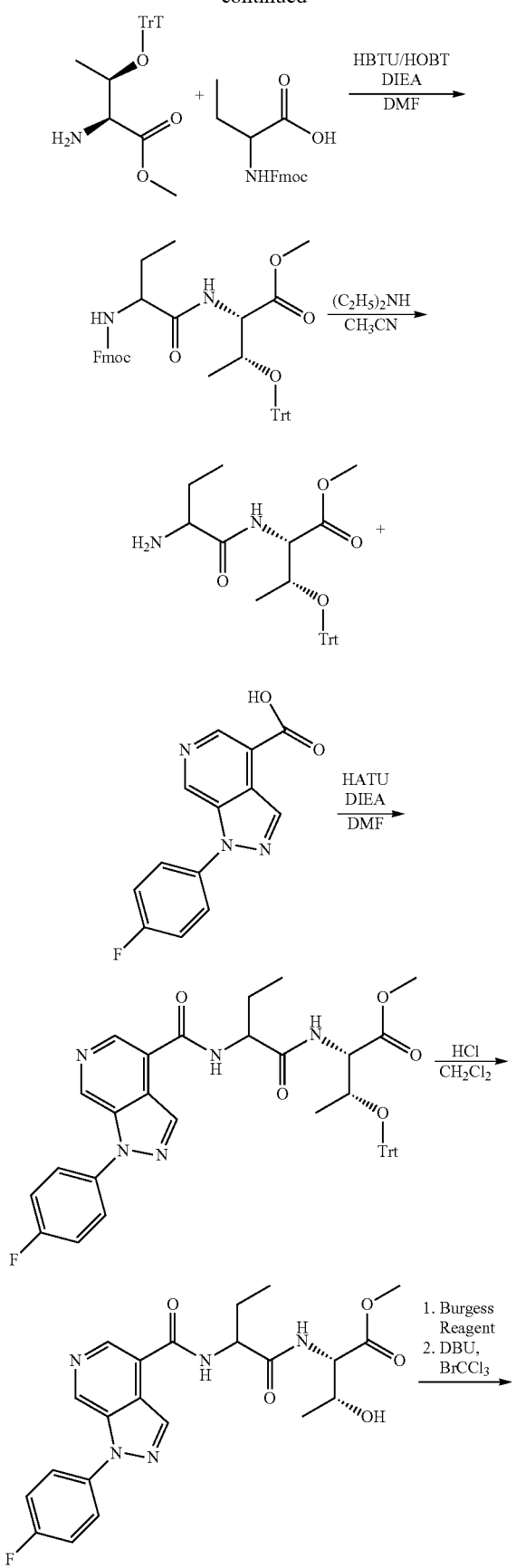

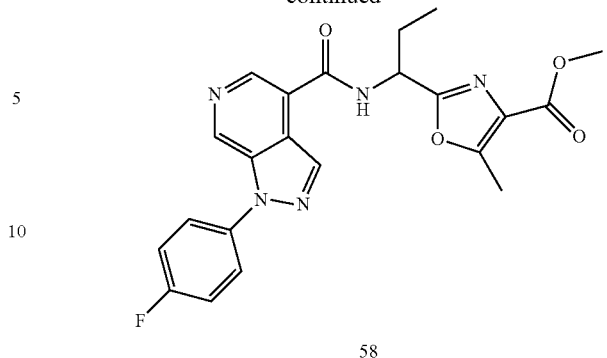

58

To a stirred solution of Fmoc-L-Thr(Trt)-OH (2.33 g, 4.00 mmol) in methanol (4.0 mL) and benzene (16 mL) was added TMS-diazomethane (2.40 mL, 4.80 mmol). After 1 hour, the mixture was concentrated in vacuo to afford Fmoc-L-Thr(Trt)-OMe which was used without purification.

To a solution of Fmoc-L-Thr(Trt)-OMe (2.40 g, 4.00 mmol) in acetonitrile (20.0 mL) was added diethylamine (20.0 mL). After 30 minutes, the mixture was concentrated in vacuo and the residue was diluted with acetonitrile (3×10 mL) and azeotroped in vacuo to afford L-Thr(Trt)-OMe which was used without further purification.

To a solution of Fmoc-DL-2-aminobutyric acid (Fmoc-DL-ABU-OH) (1.30 g, 4.00 mmol) in DMF (15.0 mL) was added HOBT (0.594 g, 4.40 mmol) and HBTU (1.67 g, 4.40 mmol). After 10 minutes, a solution of L-Thr(Trt)-OMe (2.48 g, 65% pure, 4.30 mmol) and DIPEA (1.46 mL, 8.39 mmol) in DMF (5 mL) was added. After 20 hours, the mixture was concentrated in vacuo, reconstituted in ethyl acetate (100 mL) and washed with saturated aqueous sodium bicarbonate (100 mL) and brine (100 mL). The organic layer was dried over $MgSO_4$, filtered and concentrated. The resulting residue was purified by silica gel chromatography eluting with a gradient of 0-50% ethyl acetate in hexanes to afford Fmoc-DL-ABU-L-Thr(Trt)-OMe as white solid.

To a stirred solution of Fmoc-DL-ABU-L-Thr(Trt)-OMe (1.80 g, 2.64 mmol) in acetonitrile (15.0 mL) was added diethylamine (13.8 mL). After 30 minutes, the mixture was concentrated in vacuo and the residue was diluted with acetonitrile (3×20 mL) and azeotroped in vacuo to afford DL-ABU-L-Thr(Trt)-OMe which was used without further purification.

A suspension of 1-(4-fluorophenyl)-1H-pyrazolo[3,4-c]pyridine-4-carboxylic acid (0.600 g, 2.33 mmol) in DMF (10 mL) was stirred for 10 minutes (until it became a fine slurry) and then HATU (0.976 g, 2.56 mmol) was added. After 30 minutes, DIPEA (0.850 mL, 4.90 mmol) and a solution of DL-ABU-L-Thr(Trt)-OMe (1.84 g, 65% purity, 2.59 mmol) in DMF (5 mL) was added. After 18 hours, the mixture was concentrated in vacuo and dissolved in ethyl acetate (100 mL). The solution was washed with saturated aqueous sodium bicarbonate (2×100 mL) and brine (50 mL), dried over $MgSO_4$, filtered and concentrated. The residue was purified by silica gel chromatography eluting with a gradient of 0-70% ethyl acetate in heptane to afford (2S,3R)-2-(2-{[1-(4-fluorophenyl)-1H-pyrazolo[3,4-c]pyridine-4-carbonyl]-amino}-butyrylamino)-3-trityloxy-butyric acid methyl ester. MS m/z 700.82 (MH+).

To a chilled (0° C.) solution of (2S,3R)-2-(2-{[1-(4-fluorophenyl)-1H-pyrazolo[3,4-c]pyridine-4-carbonyl]-amino}-butyrylamino)-3-trityloxy-butyric acid methyl ester (1.47 g, 2.10 mmol) in CH₂Cl₂ (100 mL) was added a 1 M solution of HCl (6.30 mL, 6.30 mmol) in ether. After 30 minutes, the reaction was quenched with saturated aqueous sodium bicarbonate (100 mL) and warmed to room temperature. After 30 minutes, the aqueous layer was extracted with CH₂Cl₂ (2×50 mL). The combined organic layers were dried over MgSO₄, filtered and passed through a pad of silica gel eluting with a gradient of 0-10% methanol in methylene chloride to afford (2S,3R)-2-(2-{[1-(4-fluorophenyl)-1H-pyrazolo[3,4-c]pyridine-4-carbonyl]-amino}-butyrylamino)-3-hydroxy-butyric acid methyl ester as white solid. MS m/z 458.76 (MH+).

To a solution of (2S,3R)-2-(2-{[1-(4-fluorophenyl)-1H-pyrazolo[3,4-c]pyridine-4-carbonyl]-amino}-butyrylamino)-3-hydroxy-butyric acid methyl ester (0.900 g, 1.96 mmol) in THF (20.0 mL) was added Burgess reagent (0.586 g, 2.46 mmol). The mixture was warmed at reflux for 23 hours. The mixture was then concentrated in vacuo, dissolved in ethyl acetate (100 mL) and washed with saturated aqueous sodium bicarbonate (50 mL) and brine (50 mL). The organic layer was dried over MgSO₄, filtered and concentrated. The residue was purified by silica gel chromatography eluting with a gradient of 0-10% methanol in ethyl acetate to afford (4S,5S)-2-(1-{[1-(4-fluorophenyl)-1H-pyrazolo[3,4-c]pyridine-4-carbonyl]-amino}-propyl)-5-methyl-4,5-dihydro-oxazole-4-carboxylic acid methyl ester as white foam.

To a chilled (0° C.) solution of (4S,5S)-2-(1-{[1-(4-fluorophenyl)-1H-pyrazolo[3,4-c]pyridine-4-carbonyl]-amino}-propyl)-5-methyl-4,5-dihydro-oxazole-4-carboxylic acid methyl ester (0.529 g, 1.20 mmol) and DBU (360 μL, 2.40 mmol) in CH₂Cl₂ (10.0 mL) was added BrCCl₃ (125 μL, 1.26 mmol). The mixture was then warmed to room temperature. After 18 hours, the mixture was diluted with CH₂Cl₂ (50 mL) and extracted with saturated aqueous ammonium chloride (2×50 mL). The organic layer was washed with saturated aqueous sodium bicarbonate (50 mL) and brine (50 mL), dried over MgSO₄, filtered and concentrated. The residue was purified by silica gel chromatography eluting with a gradient of 0-100% ethyl acetate in heptane to afford the title compound as white solid. MS m/z 438.74 (MH+).

2-((S)-1-{[1-(4-Fluorophenyl)-1H-pyrazolo[3,4-c]pyridine-4-carbonyl]-amino}-propyl)-oxazole-4-carboxylic acid methyl ester was also prepared from Fmoc-L-Ser(Trt)-OH according to the method described above. MS m/z 424.74 (MH+).

Example 59

Synthesis of 2-(1-{[1-(4-Fluorophenyl)-1H-pyrazolo[3,4-c]pyridine-4-carbonyl]-amino}-propyl)-thiazole-4-carboxylic acid methyl ester (59)

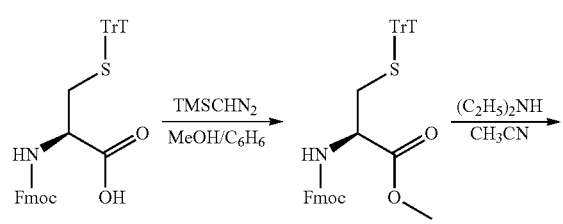

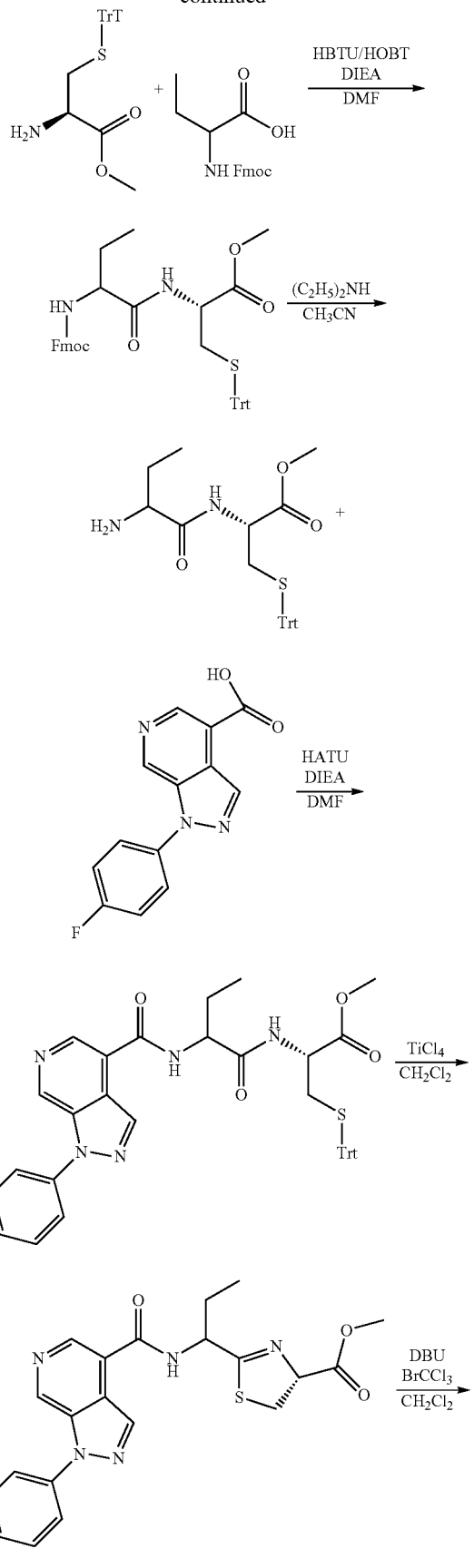

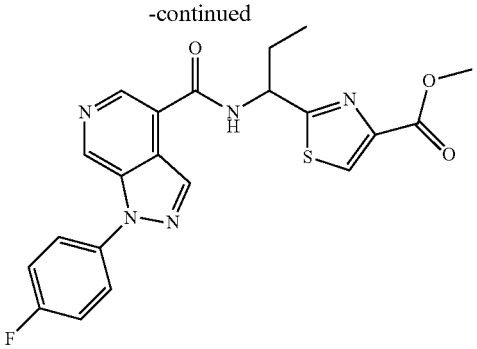

59

To a stirred solution of Fmoc-L-Cys(Trt)-OH (2.34 g, 4.00 mmol) in methanol (4.0 mL) and benzene (16 mL) was added TMS-diazomethane (2.40 mL, 4.80 mmol). After 1 hour, the mixture was concentrated in vacuo to afford Fmoc-L-Cys(Trt)-OMe which was used in the next step without purification.

To a solution of Fmoc-L-Cys(Trt)-OMe (2.58 g, 4.30 mmol) in acetonitrile (20.0 mL) was added diethylamine (20.0 mL). After 30 minutes, the mixture was concentrated in vacuo. The residue was dissolved in acetonitrile (3×10 mL) and concentrated in vacuo to afford L-Cys(Trt)-OMe as crude product which was used without purification.

To a solution of Fmoc-DL-2-aminobutyric acid (Fmoc-DL-ABU-OH) (1.30 g, 4.00 mmol) in DMF (15.0 mL) was added HOBT (0.594 g, 4.40 mmol) and HBTU (1.67 g, 4.40 mmol). After 10 minutes, a solution of the crude L-Cys(Trt)-OMe (2.63 g, 65% purity, 4.53 mmol) and DIPEA (1.46 mL, 8.39 mmol) in DMF (5 mL). After 18 hours, the mixture was concentrated in vacuo, dissolved in ethyl acetate (100 mL) and washed with saturated aqueous sodium bicarbonate (100 mL) and brine (100 mL). The organic layer was dried over MgSO$_4$, filtered and concentrated. The resulting residue was purified by silica gel chromatography eluting with a gradient of 0-50% ethyl acetate in hexanes to afford Fmoc-DL-ABU-L-Cys(Trt)-OMe as white foam.

A stirred solution of Fmoc-DL-ABU-L-Cys(Trt)-OMe (2.60 g, 3.80 mmol) in acetonitrile (20 mL) was treated with diethylamine (20 mL). After 30 minutes, the mixture was concentrated in vacuo and the residue was dissolved in acetonitrile (10 mL) and concentrated in vacuo (this process was repeated three times) to afford DL-ABU-L-Cys(Trt)-OMe as crude product which was used without purification.

A suspension of 1-(4-fluorophenyl)-1H-pyrazolo[3,4-c]pyridine-4-carboxylic acid (0.905 g, 3.52 mmol) in DMF (15 mL) was stirred for 10 minutes (until it became a fine slurry) and treated with HATU (1.47 g, 3.87 mmol). After 30 minutes, the resulting mixture was treated with DIPEA (1.29 mL, 7.39 mmol) and a solution of DL-ABU-L-Cys(Trt)-OMe (2.76 g, 65% purity, 3.87 mmol) in DMF (5 mL). After 18 hours, the mixture was concentrated in vacuo and dissolved in ethyl acetate (100 mL). The solution was washed with saturated aqueous sodium bicarbonate (2×100 mL) and brine (50 mL), dried over MgSO$_4$, filtered and concentrated. The residue was purified by silica gel chromatography eluting with a gradient of 0-80% ethyl acetate in heptane to afford (R)-2-(2-{[1-(4-fluorophenyl)-1H-pyrazolo[3,4-c]pyridine-4-carbonyl]-amino}-butyrylamino)-3-tritylsulfanyl-propionic acid methyl ester.

To a solution of (R)-2-(2-{[1-(4-fluorophenyl)-1H-pyrazolo[3,4-c]pyridine-4-carbonyl]-amino}-butyrylamino)-3-tritylsulfanyl-propionic acid methyl ester (0.560 g, 0.798 mmol) in CH$_2$Cl$_2$ (24.0 mL) was added a 1 M solution of TiCl$_4$ (2.40 mL, 2.40 mmol) in CH$_2$Cl$_2$. After 2 hours, the resulting mixture was quenched with saturated aqueous sodium bicarbonate (10 mL). The aqueous layer was separated and extracted with CH$_2$Cl$_2$ (2×10 mL). The combined organic layers were washed with brine (10 mL), dried over MgSO$_4$, filtered and concentrated. The mixture was purified by silica gel chromatography eluting with a gradient of 0-80% ethyl acetate in heptane to afford (R)-2-(1-{[1-(4-fluorophenyl)-1H-pyrazolo[3,4-c]pyridine-4-carbonyl]-amino}-propyl)-4,5-dihydro-thiazole-4-carboxylic acid methyl ester.

To a chilled (0° C.) solution of (R)-2-(1-{[1-(4-fluorophenyl)-1H-pyrazolo[3,4-c]pyridine-4-carbonyl]-amino}-propyl)-4,5-dihydro-thiazole-4-carboxylic acid methyl ester (0.296 g, 0.670 mmol) and DBU (200 µL, 1.34 mmol) in CH$_2$Cl$_2$ (8.0 mL) was added BrCCl$_3$ (69.0 µL, 0.700 mmol). The mixture was then warm to room temperature. After 18 hours, the reaction mixture was diluted with CH$_2$Cl$_2$ (20 mL) and washed with saturated aqueous ammonium chloride (3×10 mL). The organic layer was washed with saturated aqueous sodium bicarbonate (10 mL) and brine (10 mL), dried over MgSO$_4$, filtered and concentrated. The mixture was purified by silica gel chromatography eluting with a gradient of 0-80% ethyl acetate in heptane to afford the title compound. MS m/z 440.77 (MH+).

Example 60

Synthesis of 1-(4-Fluorophenyl)-1H-pyrazolo[3,4-c]pyridine-4-carboxylic acid [1-(4-carbamoyl-5-methyl-oxazol-2-yl)-propyl]-amide (60)

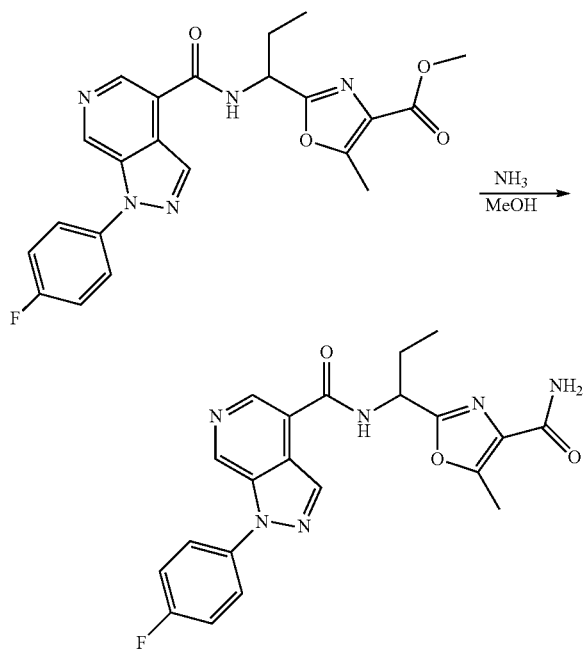

60

A mixture of 2-(1-{[1-(4-fluorophenyl)-1H-pyrazolo[3,4-c]pyridine-4-carbonyl]-amino}-propyl)-5-methyl-oxazole-4-carboxylic acid methyl ester (40 mg, 0.091 mmol) in a 7 M solution of ammonia in methanol (525 µL, 3.66 mmol) was stirred at 90° C. in a sealed tube. After 34 hours, the reaction was cooled to room temperature, vented, opened and concentrated. The resulting residue was purified by silica gel chromatography eluting with a gradient of 0-10% methanol in methylene chloride to afford the title compound as white solid. MS m/z 423.89 (MH+).

The following compounds were also prepared by the methods described in Example 60:

1-(4-Fluorophenyl)-1H-pyrazolo[3,4-c]pyridine-4-carboxylic acid [(S)-1-(4-carbamoyl-thiazol-2-yl)-propyl]-amide, 1-(4-Fluorophenyl)-1H-pyrazolo[3,4-c]pyridine-4-carboxylic acid [1-(4-carbamoyl-oxazol-2-yl)-propyl]-amide, and 1-(4-Fluorophenyl)-1H-pyrazolo[3,4-c]pyridine-4-carboxylic acid {1-[4-(carbamoylmethyl-carbamoyl)-5-methyl-oxazol-2-yl]-propyl}-amide.

Example 61

Synthesis of 1-(4-Fluorophenyl)-1H-pyrazolo[3,4-c]pyridine-4-carboxylic acid [1-(5-methyl-4-methylcarbamoyl-oxazol-2-yl)-propyl]-amide (61)

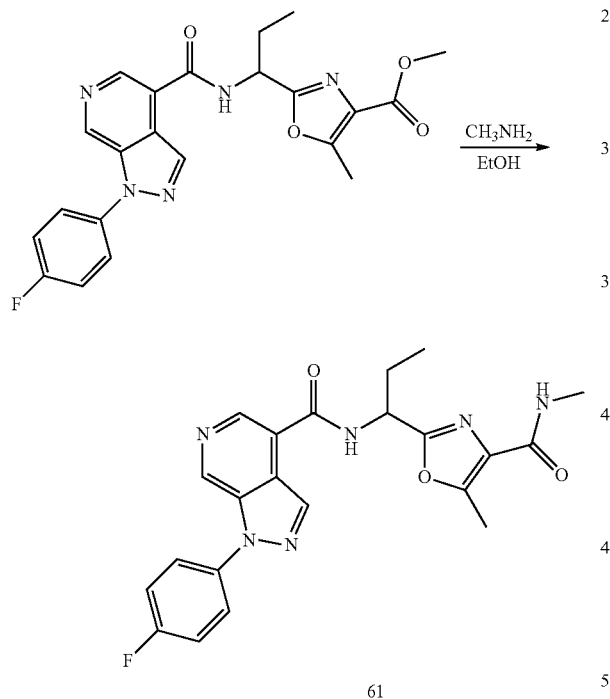

61

A mixture of 2-(1-{[1-(4-fluorophenyl)-1H-pyrazolo[3,4-c]pyridine-4-carbonyl]-amino}-propyl)-5-methyl-oxazole-4-carboxylic acid methyl ester (40 mg, 0.091 mmol) in a solution of methyl amine in ethanol (455 μL, 33% solution, 3.66 mmol) was stirred at 100° C. in a sealed tube. After 16 hours, the reaction was cooled to room temperature, vented, opened and concentrated. The residue was purified by silica gel chromatography eluting with a gradient of 0-8% methanol in methylene chloride to afford the title compound as white solid. MS m/z 437.63 (MH+).

The following compounds were also prepared by the methods described in Example 61:

1-(4-Fluorophenyl)-1H-pyrazolo[3,4-c]pyridine-4-carboxylic acid [(S)-1-(4-methylcarbamoyl-thiazol-2-yl)-propyl]-amide, 1-(4-Fluorophenyl)-1H-pyrazolo[3,4-c]pyridine-4-carboxylic acid [1-(4-methylcarbamoyl-oxazol-2-yl)-propyl]-amide, and 1-(4-Fluorophenyl)-1H-pyrazolo[3,4-c]pyridine-4-carboxylic acid {1-[5-methyl-4-(methylcarbamoylmethyl-carbamoyl)-oxazol-2-yl]-propyl}-amide.

Example 62

Synthesis of 2-(1-{[1-(4-Fluorophenyl)-1H-pyrazolo[3,4-c]pyridine-4-carbonyl]-amino}-propyl)-5-methyl-oxazole-4-carboxylic acid (62)

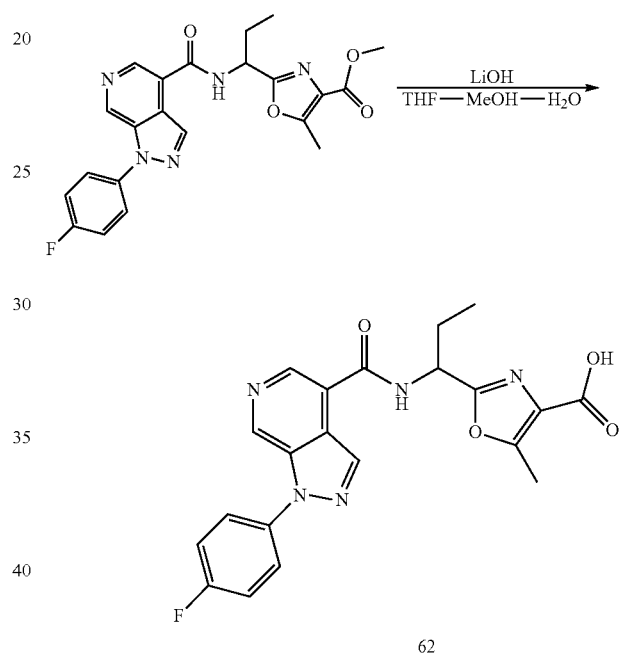

62

To a solution of 2-(1-{[1-(4-fluorophenyl)-1H-pyrazolo[3,4-c]pyridine-4-carbonyl]-amino}-propyl)-5-methyl-oxazole-4-carboxylic acid methyl ester (95.0 mg, 0.217 mmol) in a mixture of THF/Methanol/water (3 mL, 3:1:1) was added LiOH.H$_2$O (36.5 mg, 0.869 mmol). After 3 hours, the reaction mixture was acidified to pH 3-4 with 2 M aqueous hydrochloric acid and concentrated. The mixture was diluted with ethyl acetate (25 mL) and water (25 mL) and stirred vigorously. After 5 hours, the heterogeneous mixture was filtered and the solid was washed with water (until the pH of the filtrate was 5), ethyl acetate (3×10 mL), and air dried to afford the title compound as a white solid. MS m/z 424.74 (MH+).

The following compounds were also prepared by the methods described in Example 62:

2-(1-{[1-(4-Fluorophenyl)-1H-pyrazolo[3,4-c]pyridine-4-carbonyl]-amino}-propyl)-thiazole-4-carboxylic acid, and 2-(1-{[1-(4-Fluorophenyl)-1H-pyrazolo[3,4-c]pyridine-4-carbonyl]-amino}-propyl)-oxazole-4-carboxylic acid.

Example 63

Synthesis of 1-(4-Fluorophenyl)-1H-pyrazolo[3,4-c]pyridine-4-carboxylic acid {1-[4-(carbamoylmethyl-carbamoyl)-5-methyl-oxazol-2-yl]-propyl}-amide (63)

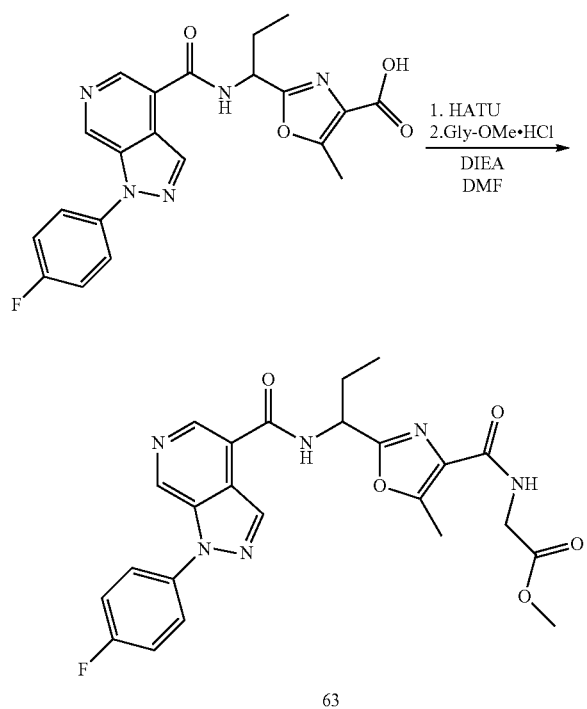

63

To a solution of 2-(1-{[1-(4-Fluorophenyl)-1H-pyrazolo[3,4-c]pyridine-4-carbonyl]-amino}-propyl)-5-methyl-oxazole-4-carboxylic acid (0.130 g, 0.307 mmol) in DMF (3 mL) was added HATU (0.140 g, 0.368 mmol). After 10 minutes, DIPEA (215 µL, 1.22 mmol) and Gly-OMe.HCl (46.2 mg, 0.368 mmol) was added. After 18 hours, the mixture was concentrated in vacuo. The residue was dissolved in ethyl acetate (30 mL) and washed with 2 N sodium hydroxide (3×10 mL), saturated aqueous ammonium chloride (2×10 mL), saturated aqueous sodium bicarbonate (10 mL) and brine (10 mL). The organic layer was dried over MgSO₄, filtered and concentrated. The resulting residue was purified by silica gel chromatography eluting with a gradient of 0-4% methanol in ethyl acetate to afford the title compound. MS m/z 495.71 (MH+).

The following compounds were also prepared by the methods described in Example 63:

1-(4-Fluorophenyl)-1H-pyrazolo[3,4-c]pyridine-4-carboxylic acid {1-[4-(cyanomethyl-carbamoyl)-oxazol-2-yl]-propyl}-amide, and 1-(4-Fluorophenyl)-1H-pyrazolo[3,4-c]pyridine-4-carboxylic acid {1-[4-(cyanomethyl-carbamoyl)-5-methyl-oxazol-2-yl]-propyl}-amide.

Example 64

Synthesis of 1-(4-Fluorophenyl)-1H-pyrazolo[3,4-c]pyridine-4-carboxylic acid [(S)-2-cyano-1-(2-methanesulfonyl-pyridin-4-yl)-ethyl]-amide (64)

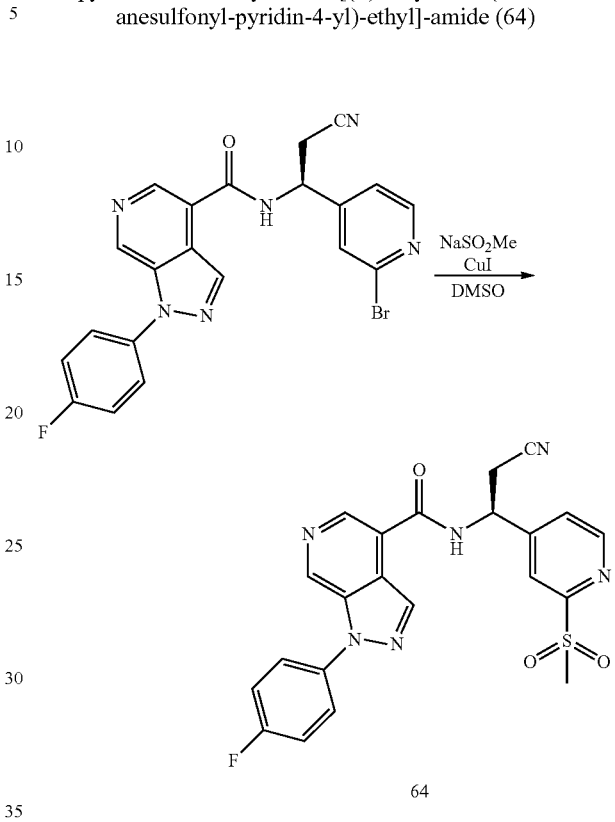

64

A solution of 1-(4-fluorophenyl)-1H-pyrazolo[3,4-c]pyridine-4-carboxylic acid [(S)-1-(2-bromo-pyridin-4-yl)-2-cyano-ethyl]-amide (122 mg, 0.262 mmol), sodium methanesulfinate (53.5 mg, 0.524 mmol) and copper (I) iodine (99.8 mg, 0.524 mmol) in DMSO (2.5 mL) was evacuated and purged with argon three times and warmed at 130° C. After 45 minutes, the reaction was cooled to room temperature and N,N'-dimethylethylenediamine (112 µL, 1.05 mmol) was added. The mixture stirred for 30 minutes and was then diluted with ethyl acetate (20 mL), stirred for 15 minutes, and saturated aqueous ammonium chloride (20 mL) was added. The mixture was sonicated for 30 minutes, and was then diluted with ethyl acetate (100 mL). The aqueous layer was separated and extracted with ethyl acetate (2×20 mL). The combined organic layers were washed with saturated aqueous ammonium chloride (2×50 mL), saturated aqueous sodium bicarbonate (50 mL), brine (50 mL), dried over MgSO₄, filtered and concentrated. The resulting residue was purified by silica gel chromatography eluting with a gradient of 0-8% methanol in CH₂Cl₂. The solid was further purified by HPLC using a C18 column and a gradient of 5-95% acetonitrile+0.1% TFA and water+0.1% TFA to afford the title compound. MS m/z 465.68 (MH+).

The following compounds were also prepared by the method described in Example 64:

1-(4-Fluorophenyl)-1H-pyrazolo[3,4-c]pyridine-4-carboxylic acid [(R)-2-hydroxy-1-(2-methanesulfonyl-pyridin-4-yl)-ethyl]-amide, 1-(4-Fluorophenyl)-1H-pyrazolo[3,4-c]pyridine-4-carboxylic acid (2-methanesulfonyl-6-methyl-pyridin-4-ylmethyl)-amide, 1-(4-Fluorophenyl)-1H-pyrazolo[3,4-c]pyridine-4-carboxylic acid [1-(2-methanesulfonyl-pyridin-4-yl)-1-methyl-ethyl]-amide, 1-(4-Fluorophenyl)-1H-pyrazolo[3,4-c]pyridine-4-carboxylic acid [1-(2-methanesulfonyl-pyridin-4-yl)-1-methyl-propyl]-amide, 1-(4-Fluorophenyl)-1H-pyrazolo[3,4-c]pyridine-4-carboxylic acid [1-ethyl-1-(2-methanesulfonyl-pyridin-4-yl)-propyl]-amide, and 1-(4-Fluorophenyl)-1H-pyrazolo[3,4-c]pyridine-4-carboxylic acid [(R)-1-(2-methanesulfonyl-pyridin-4-yl)-2-methoxy-ethyl]-amide.

Example 65

Synthesis of C-(2-Bromo-6-methyl-pyridin-4-yl)-methylamine hydrochloride salt (65)

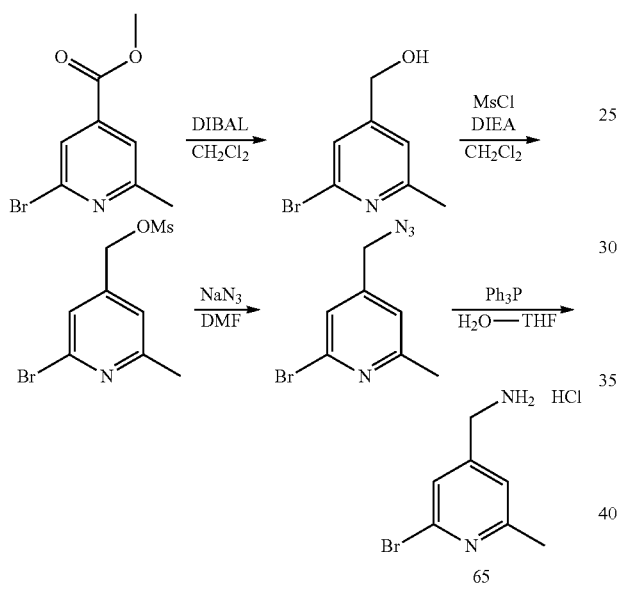

To a chilled (−78° C.) solution of 2-bromo-6-methyl-isonicotinic acid methyl ester (1.90 g, 8.26 mmol) in CH$_2$Cl$_2$ (200 mL) was added a 1 M solution of DIBAH (24.8 mL, 24.8 mmol) in CH$_2$Cl$_2$. The mixture was allowed to warm to room temperature. After 12 hours, the reaction was quenched with saturated aqueous sodium bicarbonate (100 mL). After 5 hours, phases were separated and the aqueous layer was extracted with CH$_2$Cl$_2$ (3×100 mL). The combined organic layers were washed with brine (100 mL), dried over MgSO$_4$, filtered and concentrated. The resulting residue was purified by silica gel chromatography eluting with a gradient of 0-100% ethyl acetate in heptane to afford (2-bromo-6-methyl-pyridin-4-yl)-methanol as white solid. MS m/z 202.45 (M+), 204.44 (M+2).

To a solution of (2-bromo-6-methyl-pyridin-4-yl)-methanol (0.300 g, 1.48 mmol) in dichloromethane (2.0 mL) was added DIPEA (776 µL, 4.45 mmol). The resulting mixture was cooled to 0° C. and methanesulfonyl chloride (120 µL, 1.56 mmol) was added. After 1 hour, the reaction mixture was diluted CH$_2$Cl$_2$ (20 mL) and washed with saturated aqueous ammonium chloride (3×10 mL), saturated aqueous sodium bicarbonate (10 mL) and brine (10 mL). The organic layer was dried over MgSO$_4$, filtered and concentrated to afford methanesulfonic acid 2-bromo-6-methyl-pyridin-4-ylmethyl ester as crude product which was used in the next step without purification.

To a solution of methanesulfonic acid 2-bromo-6-methyl-pyridin-4-ylmethyl ester (410 mg, 1.46 mmol) in DMF (2.0 mL) was added sodium azide (238 mg, 3.66 mmol). After 15 hours, the reaction was quenched with water (10 mL) and extracted with ethyl acetate (3×10 mL). The combined organic layers were washed with water (10 mL) and brine (10 mL), dried over MgSO$_4$, filtered and concentrated. The residue was passed through a pad of silica gel eluting with 30% ethyl acetate in heptane to afford 4-azidomethyl-2-bromo-6-methyl-pyridine.

To a solution of 4-azidomethyl-2-bromo-6-methyl-pyridine (309 mg, 1.36 mmol) in THF (4.0 mL) was added triphenylphosphine (446 mg, 1.70 mmol) followed by water (400 µL). After 17 hours, the reaction mixture was concentrated. The residue was partitioned between 1 M hydrochloric acid (50 mL) and CH$_2$Cl$_2$ (50 mL). The aqueous phase was separated and extracted with CH$_2$Cl$_2$ (3×50 mL). The aqueous layer was evaporated under high vacuum to afford the title compound as off-white solid. MS m/z 201.40 (M+), 203.38 (M+2).

Example 66

Synthesis of C-(1H-Pyrrolo[2,3-b]pyridin-4-yl)-methylamine trifluoroacetic acid salt (66)

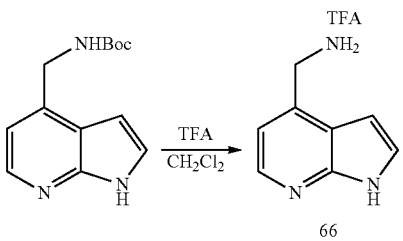

To a solution of (1H-pyrrolo[2,3-b]pyridin-4-ylmethyl)-carbamic acid tert-butyl ester (200 mg, 0.809 mmol) in CH$_2$Cl$_2$ (6 mL) was added trifluoroacetic acid (1.58 mL, 20.6 mmol). After 14 hours, the reaction was concentrated in vacuo to afford the title compound which was used in the without purification.

Example 67

Synthesis of C-(1-Methanesulfonyl-1H-pyrrolo[2,3-b]pyridin-4-yl)-methylamine ditrifloroacetic acid salt (67)

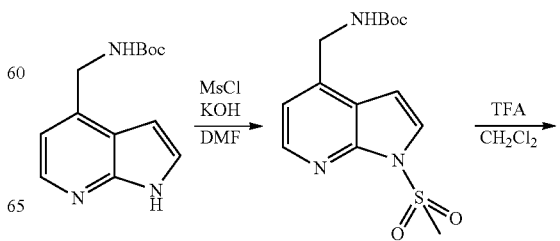

-continued

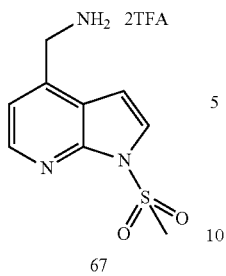
67

To a stirred solution of (1H-pyrrolo[2,3-b]pyridin-4-ylmethyl)-carbamic acid tert-butyl ester (400 mg, 1.62 mmol) in DMF (10.0 mL) was added powdered KOH (143 mg, 1.88 mmol). After 15 minutes, methanesulfonyl chloride (137 µL, 1.78 mmol) was added. After 15 hours, the mixture was diluted with water (30 mL) and extracted with ethyl acetate (3×50 mL). The combined organic layers were washed with brine (25 mL), dried over magesium sulfate, filtered and concentrated. The residue was purified by silica gel chromatography eluting with a gradient of 0-50% ethyl acetate in heptane to afford (1-methanesulfonyl-1H-pyrrolo[2,3-b]pyridin-4-ylmethyl)-carbamic acid tert-butyl ester.

To a solution of (1-methanesulfonyl-1H-pyrrolo[2,3-b]pyridin-4-ylmethyl)-carbamic acid tert-butyl ester (100 mg, 0.307 mmol) in $CH_2Cl_2$ (2 mL) was added trifluoroacetic acid (0.600 mL, 7.80 mmol). After 14 hours, the reaction was concentrated in vacuo to afford the title compound which was used in the without purification. MS m/z 226.42 (MH+).

Example 68

Synthesis of (S)-1-(2-Methanesulfonyl-pyridin-4-yl)-ethyl-2,2,2-D3-amine hydrochloride salt (68)

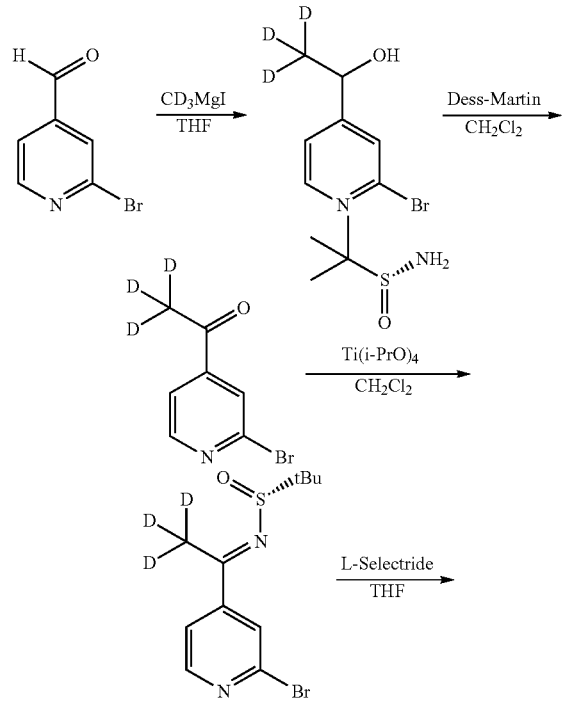

-continued

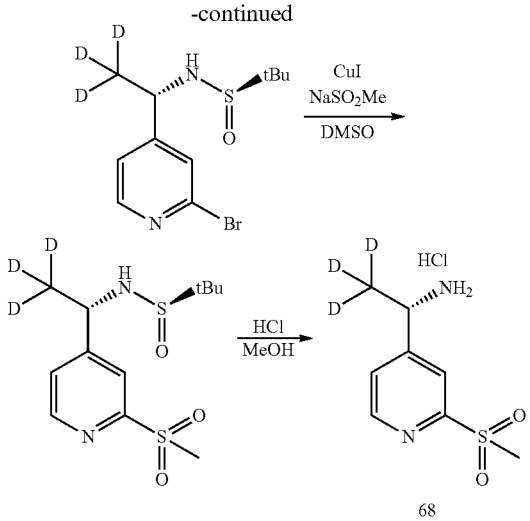
68

A 1.0 M solution of methyl(D3)magnesium iodide in ether (30.0 mL, 30.0 mmol) was added over 20 minutes to a chilled (−78° C.) solution of 2-bromo-pyridine-4-carbaldehyde (5.00 g, 26.8 mmol) in anhydrous THF (50.0 mL). After 1 hour, the mixture was warmed to room temperature over a 3 hours period. The reaction was quenched with saturated aqueous ammonium chloride (200 mL). The aqueous layer was separated and extracted with ethyl acetate (200 mL). The combined organic layers were washed with saturated aqueous sodium bicarbonate (200 mL) and brine (200 mL), dried over $MgSO_4$, filtered and concentrated. The residue was purified by silica gel chromatography eluting with a gradient of 0-50% ethyl acetate in heptane to afford 1-(2-bromo-pyridin-4-yl)-ethan-2,2,2-D3-ol as a colorless oil.

To a chilled (0° C.) solution of 1-(2-bromo-pyridin-4-yl)-ethan-2,2,2-D3-ol (5.50 g, 26.8 mmol) in anhydrous $CH_2Cl_2$ (50.0 mL) was added Dess-Martin periodinane (11.4 g, 26.8 mmol). The mixture was stirred for 30 minutes at room temperature and then quenched with saturated aqueous sodium bicarbonate (100 mL). After 30 minutes, the resulting mixture was filtered through a pad of diatomaceous earth and washing with ethyl acetate (3×100 mL). The organic layer was washed with saturated aqueous sodium bicarbonate (100 mL) and brine (100 mL), dried over $MgSO_4$, filtered and concentrated. The residue was purified by silica gel chromatography eluting with a gradient of 0-25% ethyl acetate in heptane to afford 1-(2-bromo-pyridin-4-yl)-ethan-2,2,2-D3-one as white solid.

A solution of 1-(2-bromo-pyridin-4-yl)-ethan-2,2,2-D3-one (3.00 g, 14.8 mmol) and R-(+)-2-methylpropane-2-sulfinamide (2.14 g, 17.7 mmol) and Ti(OiPr)$_4$ (4.62 g, 16.3 mmol) in anhydrous dichoromethane (30 mL) was warmed at 40° C. After 18 hours, the mixture was cooled to room temperature, concentrated in vacuo and dissolved in ethyl acetate (50 mL). The stirred solution was slowly treated with water (50 mL). After 45 minutes, the mixture was filtered through a pad of diatomaceous earth and the pad was washed with ethyl acetate (3×50 mL). The organic layer was dried over $MgSO_4$, filtered and concentrated. The residue was purified by silica gel chromatography eluting with a gradient of 30-50% ethyl acetate in heptane to afford (R)-2-methyl-propane-2-sulfinic acid [1-(2-bromo-pyridin-4-yl)-eth-2,2,2-D3-ylidene]-amide as yellow oil.

To a chilled (−78° C.) solution of (R)-2-methyl-propane-2-sulfinic acid [1-(2-bromo-pyridin-4-yl)-eth-2,2,2-D3-ylidene]-amide (1.00 g, 3.26 mmol) in THF (30.0 mL) was added a 1 M solution of L-Selectride in THF (6.53 mL, 6.53 mmol). After 3 hours, the mixture was quenched with aqueous ammonium chloride (10 mL). The aqueous phase was separated and extracted with ethyl acetate (2×30 mL). The combined organic layers were washed with brine (50 mL), dried over MgSO$_4$, filtered and concentrated. The residue was purified by silica gel chromatography eluting with a gradient of 0-5% methanol in CH$_2$Cl$_2$ to afford (R)-2-methyl-propane-2-sulfinic acid [(S)-1-(2-bromo-pyridin-4-yl)-ethyl-2,2,2-D3]-amide as a clear oil.

(R)-2-Methyl-propane-2-sulfinic acid [(S)-1-(2-methanesulfonyl-pyridin-4-yl)-ethyl-2,2,2-D3]-amide was prepared from (R)-2-methyl-propane-2-sulfinic acid [(S)-1-(2-bromo-pyridin-4-yl)-ethyl-2,2,2-D3]-amide (200 mg, 0.649 mmol) according to the procedure described in example 64.

To a solution of (R)-2-methyl-propane-2-sulfinic acid [(S)-1-(2-methanesulfonyl-pyridin-4-yl)-ethyl-2,2,2-D3]-amide (82.0 mg, 0.267 mmol) in methanol (1.0 mL) was added a solution of 4 N HCl in dioxane (70.0 µL, 0.280 mmol). After 1 hour, the mixture was concentrated in vacuo to half the volume, diluted with toluene (4 mL) and concentrated to dryness (the process was repeated three times) to afford the title compound as an off-white solid which was used without purification.

Example 69

Synthesis of (S)-1-(2-Methanesulfonyl-pyridin-4-yl)-ethyl-1,2,2,2-D4-amine hydrochloride salt (69)

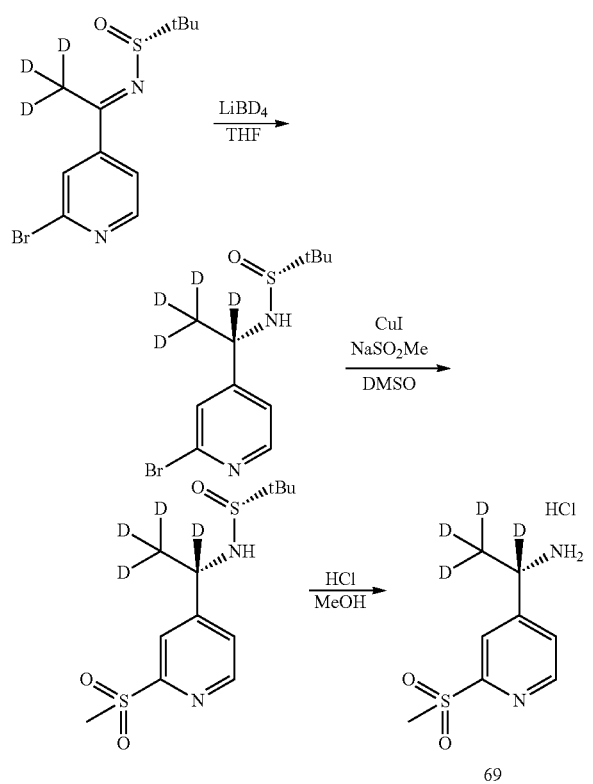

hours and then quenched with aqueous ammonium chloride (30 mL). The aqueous layer was separated and extracted with ethyl acetate (2×50 mL). The combined organic layers were washed with brine (50 mL), dried over MgSO$_4$, filtered and concentrated. The residue was purified by silica gel chromatography eluting with a gradient of 0-5% methanol in CH$_2$Cl$_2$ to afford (R)-2-methyl-propane-2-sulfinic acid [(S)-1-(2-bromo-pyridin-4-yl)-ethyl-1,2,2,2-D4]-amide as a clear oil.

(R)-2-Methyl-propane-2-sulfinic acid [(S)-1-(2-methanesulfonyl-pyridin-4-yl)-ethyl-1,2,2,2-D4]-amide was prepared from (R)-2-methyl-propane-2-sulfinic acid [(S)-1-(2-bromo-pyridin-4-yl)-ethyl-1,2,2,2-D4]-amide (175 mg, 0.566 mmol) according to the procedure described in example 64.

To a solution of (R)-2-methyl-propane-2-sulfinic acid [(S)-1-(2-methanesulfonyl-pyridin-4-yl)-ethyl-1,2,2,2-D4]-amide (93.6 mg, 0.303 mmol) in methanol (1.0 mL) was added a solution of 4 N HCl in dioxane (79.6 µL, 0.319 mmol). After 1 hour, the mixture was concentrated in vacuo to half the volume, diluted with toluene (4 mL) and concentrated to dryness (the process was repeated three times) to afford the title compound as off white solid which was used without further manipulation.

Example 70

Synthesis of 1-(4-Fluorophenyl)-1H-pyrazolo[3,4-c]pyridine-4-carboxylic acid [(S)-1-(2-methanesulfonyl-pyridin-4-yl)-2-(2-oxo-1,3-dioxolan-4-yl)-ethyl]-amide (70)

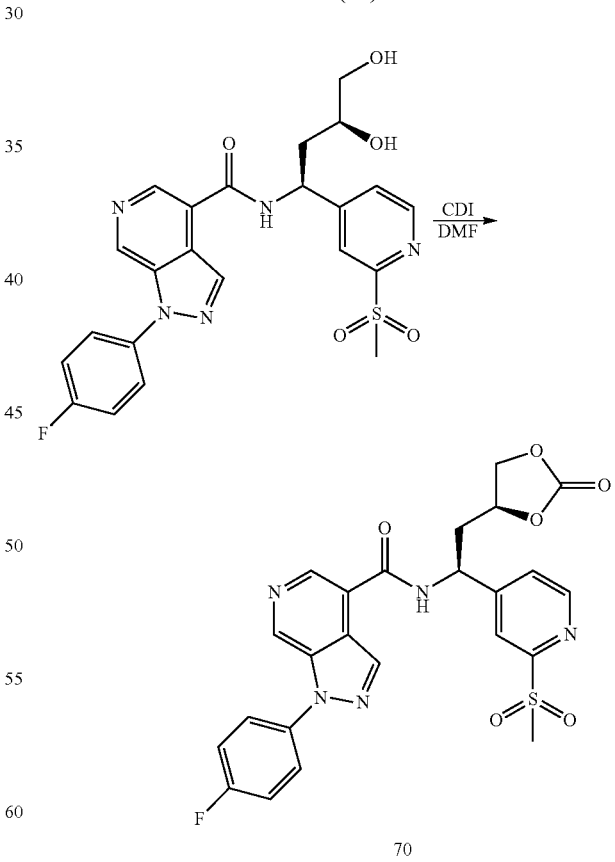

To a chilled (−78° C.) solution of (R)-2-methyl-propane-2-sulfinic acid [1-(2-bromo-pyridin-4-yl)-eth-2,2,2-D3-ylidene]-amide (1.00 g, 3.26 mmol) in THF (30 mL) was added lithium (D4)-borohydride (168 mg, 6.53 mmol). After 1 hour, the mixture was warmed to room temperature over 2

To a chilled (0° C.) solution of 1-(4-fluorophenyl)-1H-pyrazolo[3,4-c]pyridine-4-carboxylic acid [(1S,3S)-3,4-dihydroxy-1-(2-methanesulfonyl-pyridin-4-yl)-butyl]-amide (50.0 mg, 0.100 mmol) in DMF (1 mL) was added CDI (32.4 mg, 0.200 mmol). The mixture was then allowed to warm to room temperature. After 12 hours, the reaction was poured in to water (10 mL) and extracted with ethyl acetate (3×10 mL). The combined organic layers were washed with aqueous ammonium chloride (3×10 mL) and brine (10 mL), dried over MgSO₄, filtered and concentrated. The residue was purified by silica gel chromatography eluting with a gradient of 0-6% methanol in methylene chloride. The solid from the column chromatography was crystallized from methylene chloride to afford the title compound as white needle-shaped crystals. MS m/z 526.64 (MH+).

Example 71

Synthesis of (S)-1-(3-bromo-isoxazol-5-yl)-propylamine hydrochloride salt (71)

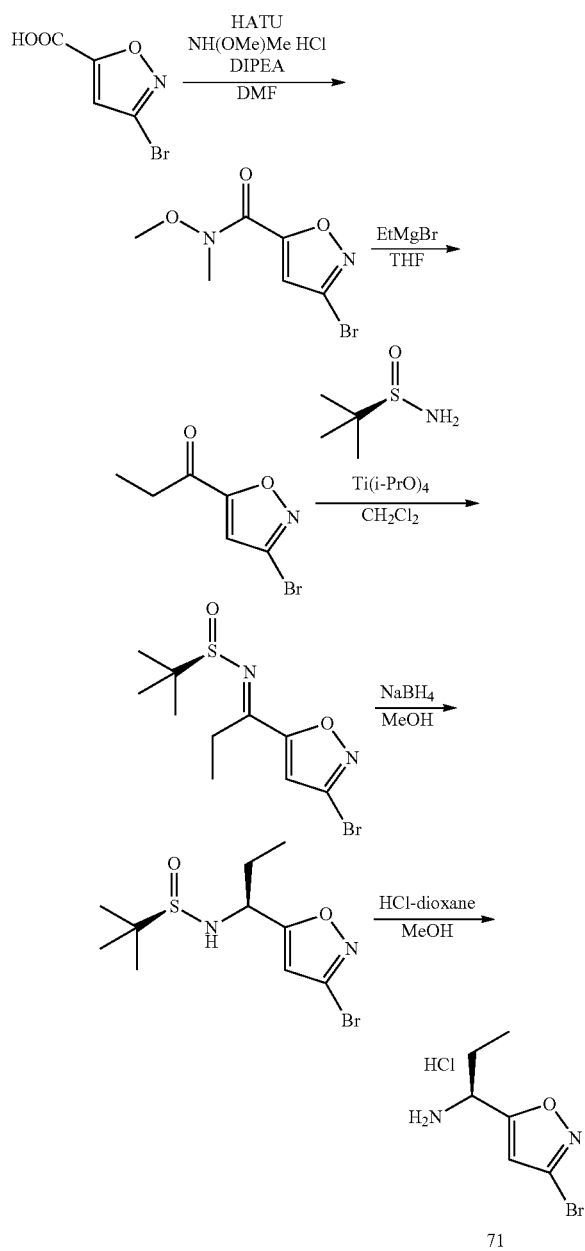

To a solution of 3-bromoisoxazole-5-carboxylic acid (2.85 g, 14.8 mmol) in DMF (74 mL) was added 2-(7-aza-1H-benzotriazole-1-yl)-1,1,3,3-tetramethyluronium hexafluorophosphate (HATU) (6.89 g, 18.1 mmol). The solution was cooled (0° C.) and DIPEA (10.5 mL, 60.3 mmol) was added followed by N,O-dimethylhydroxylamine hydrochloride (1.81 g, 18.6 mmol) and the reaction was maintained at room temperature. After 25 hours, DMAP (183 mg, 1.50 mmol) was added. After 38 hours, the mixture was diluted with EtOAc and washed with saturated aqueous NaHCO₃, saturated aqueous NH₄Cl, water, brine, dried over Na₂SO₄, filtered and concentrated in vacuo. The crude material was purified by silica gel chromatography eluting with a gradient of 0%-100% EtOAc in heptane to afford 3-bromo-isoxazole-5-carboxylic acid methoxy-methyl-amide as a pale yellow solid. MS m/z 235 (M), 237 (M+2).

To a chilled (−78° C.) solution of 3-bromo-isoxazole-5-carboxylic acid methoxy-methyl-amide (1.20 g, 5.11 mmol) in THF (56 mL) was added a 1 M solution of ethylmagnesium bromide (13.0 mL, 13.0 mmol) in THF dropwise over a 5 minutes period. The reaction was monitored by TLC (hexanes-EtOAc 4:1). After 5 hours, the reaction was transferred via a 16 gauge cannula to a 0° C. solution of saturated aqueous NH₄Cl (75 mL). The resultant heterogeneous mixture was warmed to room temperature and maintained at this temperature for 15 hours. The aqueous phase was then extracted with Et₂O (2×) and EtOAc (2×). The combined organic extracts were washed with brine, dried over Na₂SO₄, filtered and concentrated in vacuo to afford 1-(3-bromo-isoxazol-5-yl)-propan-1-one as an orange solid which was used without further purification.

To a solution of 1-(3-bromo-isoxazol-5-yl)-propan-1-one (452 mg, 2.22 mmol) and (R)-(+)-2-methyl-2-propanesulfinamide (342 mg, 2.82 mmol) in CH₂Cl₂ (5 mL) was added titanium (IV) isopropoxide (1.4 mL, 4.9 mmol) and the mixture was warmed at 45° C. After 24 hours, the reaction was monitored by LC-MS, and the solvent was concentrated in vacuo and the remaining residue was diluted with EtOAc (32 mL) and saturated aqueous NaCl (8 mL) was added. The heterogeneous mixture was filtered through a pad of diatomaceous earth. The EtOAc layer was dried over Na₂SO₄, filtered and concentrated in vacuo. The crude material was purified by silica gel chromatography eluting with a gradient of 0-100% EtOAc in heptane to afford 2-methyl-propane-2-sulfinic acid [1-(3-bromo-isoxazol-5-yl)-prop-(E)-ylidene]-amide. MS m/z 307 (M), 309 (M+2).

To a chilled (0° C.) solution of 2-methyl-propane-2-sulfinic acid [1-(3-bromo-isoxazol-5-yl)-prop-(E)-ylidene]-amide (208 mg, 0.677 mmol) in MeOH (11 mL) was added sodium borohydride (9.1 mg, 0.24 mmol) in three portions. After 2 hours, the mixture was warmed to room temperature over a 1 hour period. The mixture was then quenched with saturated aqueous NH₄Cl (21 mL) and extracted with EtOAc (3×). The combined organic extracts were dried over Na₂SO₄, filtered and concentrated in vacuo. The ¹H NMR of the crude material revealed a 7:3 ratio of diastereomers, 2-methyl-propane-2-sulfinic acid [(S)-1-(3-bromo-isoxazol-5-yl)-propyl]-amide and 2-methyl-propane-2-sulfinic acid [(R)-1-(3-bromo-isoxazol-5-yl)-propyl]-amide, respectively. The mixture was purified by silica gel chromatography eluting with a gradient of 20-100% EtOAc in heptane. MS m/z 309.41 (M), 311.38 (M+2).

To a solution of 2-methyl-propane-2-sulfinic acid [(S)-1-(3-bromo-isoxazol-5-yl)-propyl]-amide (17.5 mg, 0.0566 mmol) in MeOH (1 mL) was added a 4 M solution of HCl in dioxane (0.70 mL, 0.28 mmol) dropwise. After 2.5 hours, the mixture was concentrated in vacuo to afford the title compound which was used with out purification. MS m/z 188.24 (M−53), 190.20 (M+2−53).

Example 72

Synthesis of C-(3-bromo-isoxazol-5-yl)-methylamine hydrochloride salt (72)

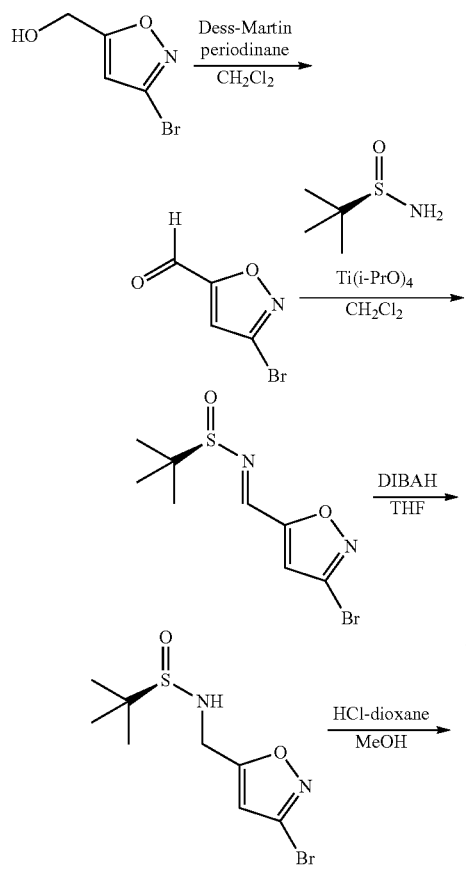

To a chilled (0° C.) solution of 3-bromo-isoxazol-5-yl)-methanol (560 mg, 3.15 mmol) in CH₂Cl₂ (31 mL) was added Dess-Martin periodinane (2.00 g, 4.72 mmol) in 3 portions and the mixture was warmed to room temperature. After 4 hours, the mixture was diluted with Et₂O (40 mL) and 1:1 mixture of aqueous solution of saturated aqueous NaHCO₃ (20 mL) and saturated aqueous Na₂S₂O₃ (20 mL) was added. After 15 hours, the aqueous layer was separated and extracted with Et₂O (2×) and EtOAc (2×). The combined organic layers were washed with brine, dried over Na₂SO₄, filtered and concentrated in vacuo to afford 3-bromo-isoxazole-5-carbaldehyde as a yellowish/orange solid. MS m/z 194.00 (M+H₂O); 195.97 (M+2).

To a solution of 3-bromo-isoxazole-5-carbaldehyde (182 mg, 1.03 mmol) and (R)-(+)-2-methyl-2-propanesulfinamide (150 mg, 121 mmol) in CH₂Cl₂ (2 mL) was added titanium (IV) isopropoxide (0.667 mL, 2.28 mmol) and the mixture was warmed at reflux. After 22 hours, the solvent was concentrated in vacuo and the remaining solution was diluted with EtOAc (33 mL) and saturated aqueous NaCl (6 mL) was added. The resultant heterogeneous mixture was stir at room temperature. After 30 minutes, the mixture was filtered through a pad of diatomaceous earth. The EtOAc layer was dried over Na₂SO₄, filtered and concentrated in vacuo. The crude material was purified by silica gel chromatography eluting with a gradient of 0-100% EtOAc in heptane to afford 2-methyl-propane-2-sulfinic acid 1-(3-bromo-isoxazol-5-yl)-meth-(E)-ylideneamide.

To a chilled (−78° C.) yellow solution of 2-methyl-propane-2-sulfinic acid 1-(3-bromo-isoxazol-5-yl)-meth-(E)-ylideneamide (129 mg, 0.462 mmol) in THF (7 mL) was added a 1 M solution of DIBAH (1.2 mL, 1.2 mmol) in hexanes dropwise. After 1.5 hours, the reaction was quenched with MeOH (4 mL) and the cold bath was removed. The mixture was concentrated in vacuo and the residue was treated with 1 N aqueous NaOH (10 mL) and extracted with EtOAc (3×). The combined organic layers were washed with brine, dried over Na₂SO₄, filtered and concentrated in vacuo to afford 2-methyl-propane-2-sulfinic acid (3-bromo-isoxazol-5-ylmethyl)-amide which was used without further purification. MS m/z 281.35 (M), 283.32 (M+2).

To a solution of 2-methyl-propane-2-sulfinic acid (3-bromo-isoxazol-5-ylmethyl)-amide (128 mg, 0.455 mmol) in MeOH (5 mL) was added a 4 M solution of HCl in dioxane (0.350 mL, 1.40 mmol) dropwise. After 2 hours and 10 minutes, the reaction mixture was concentrated in vacuo to afford the title compound which was used without further purification.

Example 73

(S)-1-[1-(toluene-4-sulfonyl)-1H-pyrazol-3-yl]-propylamine (73)

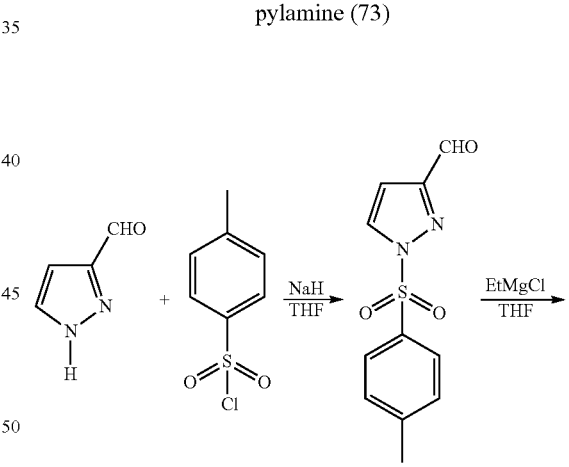

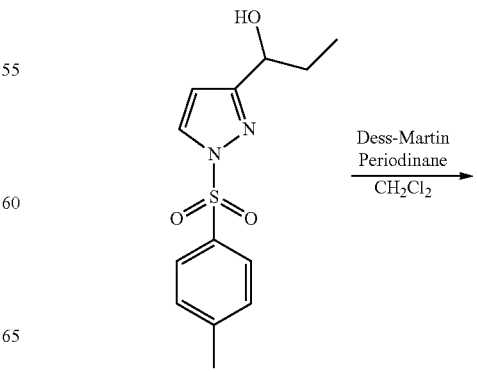

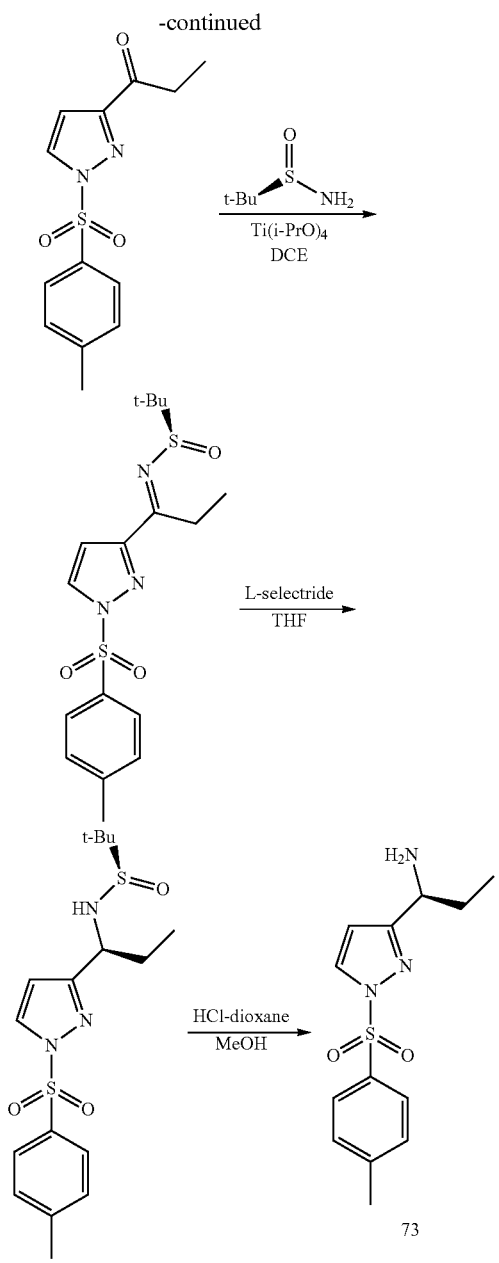

73

To a solution of 1H-pyrazole-3-carbaldehyde (3.00 g, 31.22 mmol) in THF was added 60% NaH (1.64 g, 41.00 mmol) in mineral oil. After 20 minutes, p-toluenesulfonyl chloride (7.82 g, 41.00 mmol) was added. After 2 hours, the reaction was diluted with water and extracted with EtOAc. The combined organic layers were washed with brine, dried over sodium sulfate and concentrated in vacuo. The residue was purified by silica gel chromatography eluting with a gradient of 10-50% EtOAc in heptane. The major fractions were combined and the solvent was concentrated in vacuo to afford (1-(toluene-4-sulfonyl)-1H-pyrazole-3-carbaldehyde) as a white solid.

To a chilled (−40° C.) solution of 1-(toluene-4-sulfonyl)-1H-pyrazole-3-carbaldehyde (1.50 g, 5.99 mmol) in THF was added a 2 M solution of ethylmagnesium chloride (3.00 mL, 6.00 mmol) in THF. After 3 hours, the mixture was diluted with saturated aqueous ammonia chloride and extracted with EtOAc. The combined organic layers were washed with brine, dried over sodium sulfate and the concentrated in vacuo. The residue was purified by reversed-phase HPLC. The major fractions were combined and the solvent was concentrated in vacuo to afford 1-[1-(toluene-4-sulfonyl)-1H-pyrazol-3-yl]-propan-1-ol.

To a solution of 1-[1-(toluene-4-sulfonyl)-1H-pyrazol-3-yl]-propan-1-ol (2.20 g, 7.85 mmol) in $CH_2Cl_2$ was added the Dess-Martin periodinane (4.24 g, 10.00 mmol). After 12 hours, the reaction was quenched with saturated aqueous sodium bicarbonate and filtered through diatomaceous earth and concentrated in vacuo. The residue was purified by silica gel chromatography eluting with 30% EtOAc in heptane. The major fractions were combined and the solvent was concentrated in vacuo to afford 1-[1-(toluene-4-sulfonyl)-1H-pyrazol-3-yl]-propan-1-one.

To a solution of 1-[1-(toluene-4-sulfonyl)-1H-pyrazol-3-yl]-propan-1-one (2.10 g, 7.55 mmol) in dichloroethane was added (R)-(+)-2-methyl-2-propanesulfinamide (1.45 g, 12.00 mmol) and titanium (IV) isopropoxide (4.26 g, 15.00 mmol) and the mixture was warmed at reflux overnight. After cooling, the solvent was concentrated in vacuo. The residue was diluted with EtOAc and saturated aqueous NaCl was added dropwise. After 20 minutes, the solution was passed through diatomaceous earth. The combined organics were washed with brine and dried over sodium sulfate. The solvent was concentrated in vacuo to afford 2-methyl-propane-2-sulfinic acid [1-[1-(toluene-4-sulfonyl)-1H-pyrazol-3-yl]-prop-(E)-ylidene]-amide.

To a chilled (−78° C.) solution of 2-methyl-propane-2-sulfinic acid [1-[1-(toluene-4-sulfonyl)-1H-pyrazol-3-yl]-prop-(E)-ylidene]-amide (2.00 g, 5.24 mmol) in THF was added a 1 M solution of L-Selectride (5.27 mL, 5.27 mmol) in THF. After 6 hours, the reaction was quenched with saturated aqueous $NH_4Cl$ and extracted with EtOAc. The combined organic layers were washed with saturated aqueous $NH_4Cl$, brine, dried over sodium sulfate, and concentrated in vacuo. The residue was purified by silica gel chromatography eluting with 20-40% ethyl acetate in heptane. The major fraction (with one diastereomer) were combined and the solvent was removed in vacuo to afford 2-methyl-propane-2-sulfinic acid {(S)-1-[1-(toluene-4-sulfonyl)-1H-pyrazol-3-yl]-propyl}-amide.

To a solution of 2-methyl-propane-2-sulfinic acid {(S)-1-[1-(toluene-4-sulfonyl)-1H-pyrazol-3-yl]-propyl}-amide (1.00 g, 2.61 mmol) in MeOH was added a 4 M solution of HCl in dioxane (1 mL, 4 mmol). After 2 hours, the solvent was concentrated in vacuo. The residue was made basic with saturated aqueous $NaHCO_3$ and extracted with EtOAc. The combined organic layers were washed with brine, dried over sodium sulfate and concentrated in vacuo to afford the title compound.

(S)-1-[1-(Toluene-4-sulfonyl)-1H-imidazol-4-yl]-propylamine was also prepared from 1H-imidazole-4-carbaldehyde, and (S)-1-(4-bromo-2-methyl-2H-pyrazol-3-yl)-propylamine was prepared from 4-bromo-2-methyl-2H-pyrazole-3-carbaldehyde according to the method described in experiment 73.

Example 74

5-Bromo-1H-pyrrole-3-carboxylic acid ethyl ester (74)

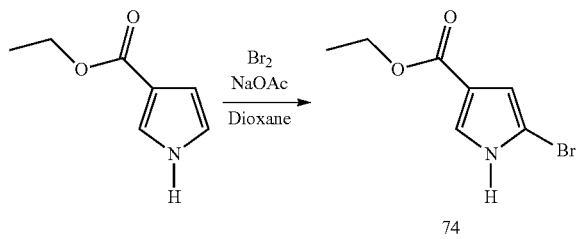

To a solution of methyl 1H-pyrrolecarboxylate (4.00 g, 32.00 mmol) in dioxane was added anhydrous sodium acetate (4.92 g, 60.00 mmol) followed by a solution of bromine (32.00 mmol) in dioxane (150 mL) dropwise. After 4 hours, the solvent was concentrated in vacuo and the residue was poured into an ice cold solution of 5% aqueous sodium carbonate (100 mL) and extracted with ethyl acetate. The combined organic layers were washed with brine, dried over sodium sulfate and concentrated in vacuo. The residue was purified by silica gel chromatography eluting with 10-40% ethyl acetate in heptane. The major fractions were combined and the solvent was concentrated in vacuo to afford the title compound.

Example 75

(S)-1-(1H-Pyrazol-4-yl)-propylamine (75)

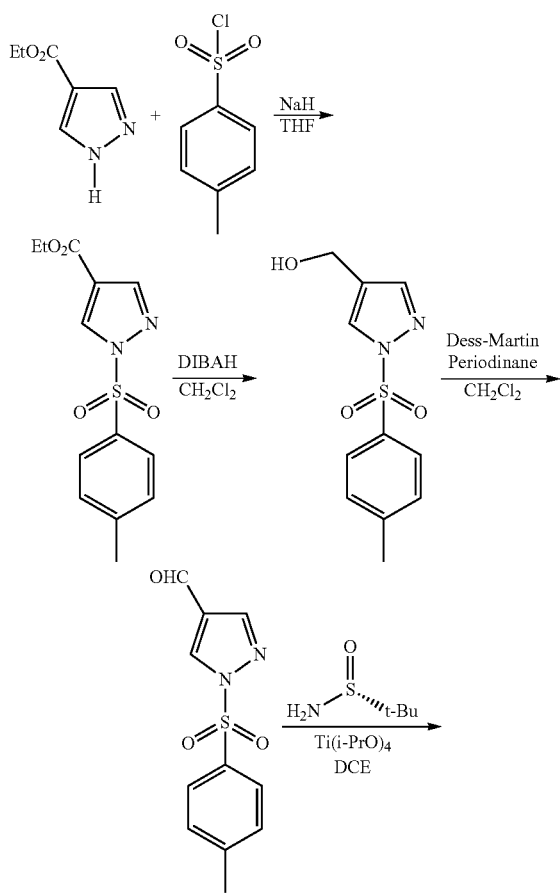

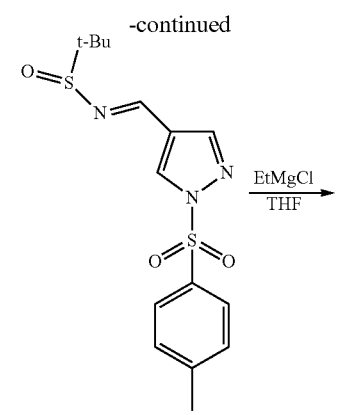

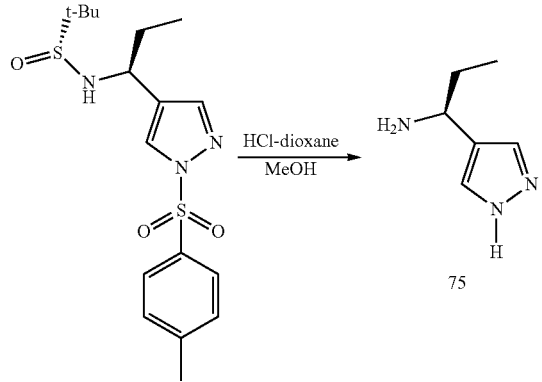

To a solution of ethyl 1H-pyrazole-4-carboxylate (4.50 g, 32.11 mmol) in THF was added 60% NaH (1.60 g, 40.00 mmol) in mineral oil. After 20 minutes, p-toluenesulfonyl chloride was added. After 3 hours, the mixture was diluted with saturated aqueous $NH_4Cl$ and extracted with ethyl acetate. The combined organic layers were washed with brine, dried over sodium sulfate and concentrated in vacuo. The residue was purified by silica gel chromatography eluting with 30-50% ethyl acetate in heptane. The major fractions were combined and the solvent was concentrated in vacuo to afford 1-(toluene-4-sulfonyl)-1H-pyrazole-4-carboxylic acid ethyl ester.

To a chilled (−78° C.) solution of 1-(toluene-4-sulfonyl)-1H-pyrazole-4-carboxylic acid ethyl ester (0.90 g, 3.06 mmol) in $CH_2Cl_2$ was added a 1 M solution of DIBAH (11.00 mL, 11.00 mmol) in $CH_2Cl_2$ dropwise. After 4 hours, the reaction was warmed to room temperature. After 8 hours, the mixture was diluted with saturated aqueous $NaHCO_3$. After 2 hours, the solution was passed through the diatomaceous earth. The combined organic layers were washed with brine, dried over sodium sulfate and concentrated in vacuo to afford the [1-(toluene-4-sulfonyl)-1H-pyrazol-4-yl]-methanol.

To a solution of [1-(toluene-4-sulfonyl)-1H-pyrazol-4-yl]-methanol (5.20 g, 20.61 mmol) in THF was added Dess-Martin periodinane (15.00 g, 35.37 mmol). After 3 hours, the mixture was diluted with saturated aqueous $NaHCO_3$ and filtered through diatomaceous earth. The combined organic layers were washed with brine, dried over sodium sulfate and concentrated in vacuo. The residue was purified by silica gel chromatography eluting with a gradient of 20-50% ethyl acetate in heptane. The major fractions were combined and the solvent was concentrated in vacuo to afford 1-(toluene-4-sulfonyl)-1H-pyrazole-4-carbaldehyde.

To a solution of 1-(toluene-4-sulfonyl)-1H-pyrazole-4-carbaldehyde (5.20 g, 20.78 mmol) in dichloroethane was added (R)-(+)-2-methyl-2-propanesulfinamide (4.24 g, 35.00 mmol) and titanium (IV) isopropoxide (12.00 g, 42.00 mmol)

and the mixture was warmed at reflux. After 12 hours, the mixture was cooled, concentrated in vacuo, diluted with ethyl acetate and saturated aqueous NaCl was added dropwise. After 20 minutes, the solution was filtered through diatomaceous earth. The organic layer was washed with brine, dried over sodium sulfate and concentrated in vacuo to afford 2-methyl-propane-2-sulfinic acid 1-[1-(toluene-4-sulfonyl)-1H-pyrazol-4-yl]-methyl-(E)-ylideneamine.

To a chilled (−40° C.) solution of 2-methyl-propane-2-sulfinic acid 1-[1-(toluene-4-sulfonyl)-1H-pyrazol-4-yl]-methyl-(E)-ylideneamine (7.00 g, 19.80 mmol) in THF was added a 2 M solution of ethylmagnesium chloride (12.50 ml, 25.00 mmol) in THF dropwise. After 3 hours, the reaction was quenched with saturated aqueous $NH_4Cl$ and extracted with ethyl acetate. The combined organic layers were washed with brine, dried over sodium sulfate and concentrated in vacuo. The residue was purified by silica gel chromatography eluting with 10-40% ethyl acetate in heptane. The major fractions were combined and the solvent was concentrated in vacuo to afford 2-methyl-propane-2-sulfinic acid {(S)-1-[1-(toluene-4-sulfonyl)-1H-pyrazol-4-yl]-propyl}-amide.

To a solution of 2-methyl-propane-2-sulfinic acid {(S)-1-[1-(toluene-4-sulfonyl)-1H-pyrazol-4-yl]-propyl}-amide (2.00 g, 5.22 mmol) in MeOH was added a 4 M solution of HCl (5.0 mL, 20 mmol) in dioxane. After 12 hours, the solvent was concentrated in vacuo. The residue was made basic with saturated aqueous $NaHCO_3$ and extracted with ethyl acetate. The combined organic layers were washed with brine, dried over sodium sulfate and concentrated in vacuo to afford the title compound.

The following chiral intermediates were also prepared by the method described in Example 75.
(S)-1-[4-Bromo-1-(toluene-4-sulfonyl)-1H-pyrrol-2-yl]-propylamine, and
(S)-1-[5-Bromo-1-(toluene-4-sulfonyl)-1H-pyrrol-2-yl]-propylamine.

Example 76

N-(5-Aminomethyl-pyrimidin-2-yl)-N-methyl-acetamide (76)

was diluted with water and extracted with ethyl acetate. The combined organic layers were washed with brine, dried over sodium sulfate and concentrated in vacuo. The residue was purified by silica gel chromatography eluting with 30% ethyl acetate in heptane. The major fractions were combined and the solvent was concentrated in vacuo to afford N-(5-bromo-pyrimidin-2-yl)-N-methyl-acetamide.

In a sealed tube was added N-(5-bromo-pyrimidin-2-yl)-N-methyl-acetamide (0.70 g, 3.04 mmol), $Zn(CN)_2$ (0.59 g, 5.00 mmol) and tetrakis(triphenylphosphine)palladium(0) (0.35 g, 0.30 mmol) in anhydrous DMF was degassed with Argon for 5 minutes and then warmed at 120° C. After 5 hours, the mixture was cooled and diluted with saturated aqueous $NH_4Cl$ and extracted with EtOAc. The combined organic layers were washed with brine, dried over sodium sulfate and concentrated in vacuo. The residue was purified by silica gel chromatography eluting with 20% ethyl acetate in heptane. The major fractions were combined and the solvent was concentrated in vauco to afford N-(5-cyano-pyrimidin-2-yl)-N-methyl-acetamide.

A solution of N-(5-cyano-pyrimidin-2-yl)-N-methyl-acetamide (0.08 g, 0.45 mmol) in MeOH and 28% aqueous ammonia hydroxide (0.80 mL, 0.45 mmol) was hydrogenated over Raney-Ni catalyst using a continuous flow hydrogenation apparatus (conditions: flow rate 1 mL/minute, 25° C., 10 bar). After 2 hours, the solvent was concentrated in vacuo. The residue was purified by silica gel chromatography eluting with 5% MeOH in $CH_2Cl_2$. The major fractions were combined and the solvent was concentrated in vacuo to afford the title compound.

The following intermediates were also prepared by the method described in Example 76:
N-(5-Aminomethyl-pyrimidin-2-yl)-N-methyl-methanesulfonamide, and
C— (2-Morpholin-4-yl-pyrimidin-5-yl)-methylamine.

Example 77

N-(4-Aminomethyl-pyrimidin-2-yl)-N-methyl-methanesulfonamide (77)

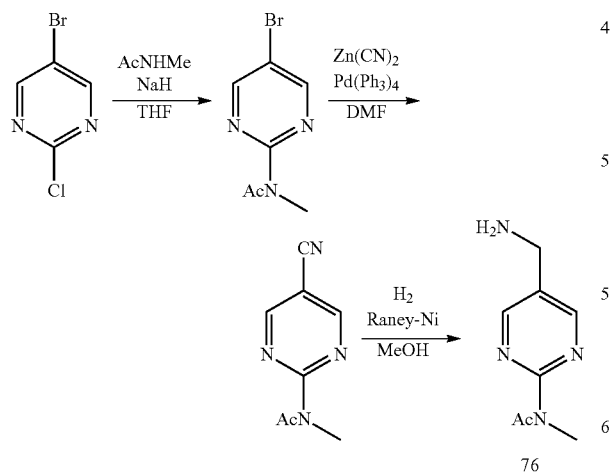

76

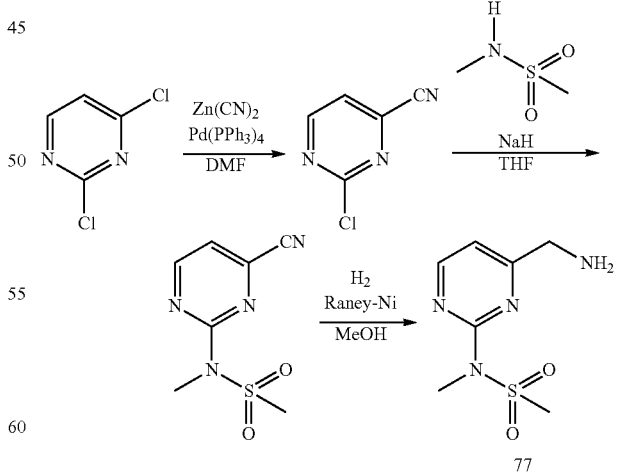

77

To a solution of 5-bromo-2-chloroprimidine (2.00 g, 10.34 mmol) in THF was added 60% NaH (0.34 g, 14.00 mmol) in mineral oil. After 20 minutes, N-methylacetamide (0.80 g, 11.00 mmol) was added dropwise. After 2 hours, the reaction In a sealed tube a mixture of 2,4-dichloropyrimide (3.00 g, 20.14 mmol), $Zn(CN)_2$ (2.46 g, 21.00 mmol) and tetrakis(triphenylphosphine)palladium(0) (2.32 g, 2.00 mmol) in anhydrous DMF was degassed with argon for 10 minutes and then warmed at 120° C. for 2 hours. After cooling, the reaction was diluted with saturated aqueous NH₄Cl and extracted with ethyl acetate. The combined organic layers were washed with brine, dried over sodium sulfate and concentrated in vacuo. The residue was purified by silica gel chromatography eluting with 20% ethyl acetate in heptane. The major fractions were combined and the solvent was concentrated in vacuo to afford 2-chloropyrimidine-4-carbonitrile.

To a solution of 2-chloropyrimidine-4-carbonitrile (0.20 g, 1.43 mmol) in THF was 60% NaH (0.05 g, 2.00 mmol) in mineral oil. After 20 minutes, N-methylmethanesulfonamide (0.22 g, 2.00 mmol) was added. After 3 hours, the reaction was diluted with water and extracted with ethyl acetate. The combined organic layers were washed with brine, dried over sodium sulfate and concentrated in vacuo. The residue was purified by silica gel chromatography eluting with 30% ethyl acetate in heptane. The major fractions were combined and the solvent was concentrated in vacuo to afford N-(4-cyano-pyrimidin-2-yl)-N-methyl-methanesulfonamide.

A solution of N-(4-cyano-pyrimidin-2-yl)-N-methyl-methanesulfonamide (0.15 g, 0.71 mmol) in MeOH and 28% aqueous ammonia hydroxide (1.2 mL, 0.70 mmol) was hydrogenated over Raney-Ni catalyst using a continuous flow hydrogenation apparatus (conditions: 1 mL/minute, 25° C., 10 bar). After 2 hours, the solvent was concentrated in vacuo. The residue was purified by silica gel chromatography eluting with 5% MeOH in CH₂Cl₂. The major fractions were combined and the solvent was concentrated in vacuo to afford the title compound.

Example 78

C-(2-Morpholin-4-yl-pyrimidin-4-yl)-methylamine (78)

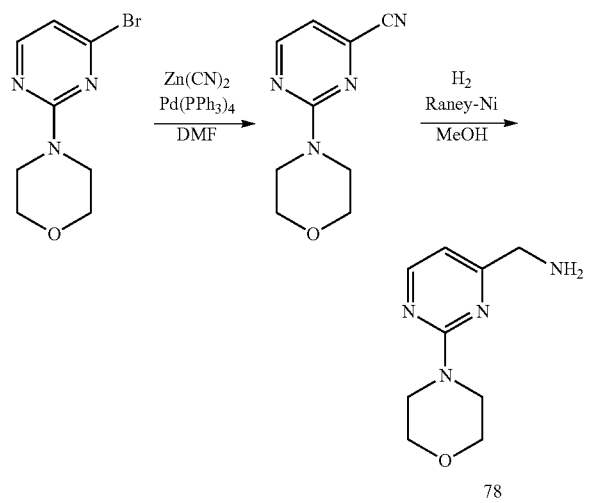

In a sealed tube a mixture of 4-(4-bromopyrimidin-2-yl)morpholine (0.40 g, 1.64 mmol), Zn(CN)₂ (0.35 g, 3.00 mmol) and tetrakis(triphenylphosphine)palladium(0) (0.23 g, 0.20 mmol) in anhydrous DMF was degassed with argon for 10 minutes and then warmed at 120° C. After 2 hours, the mixture was cooled and diluted with saturated aqueous NH₄Cl and extracted with ethyl acetate. The combined organic layers were washed with brine, dried over sodium sulfate and concentrated in vacuo. The residue was purified by silica gel chromatography eluting with 20% ethyl acetate in heptane. The major fractions were combined and the solvent was concentrated in vacuo to afford 2-morpholin-4-yl-pyrimidine-4-carbonitrile.

A solution of 2-morpholin-4-yl-pyrimidine-4-carbonitrile (0.28 g, 1.47 mmol) in MeOH and 28% aqueous ammonia hydroxide (2.0 mL, 1.40 mmol) was hydrogenated over Raney-Ni catalyst using a continuous flow apparatus (conditions: 1 mL/minute, 25° C., 10 bar). After 2 hours, the solvent was concentrated in vacuo. The residue was purified by silica gel chromatography eluting with 5% MeOH in CH₂Cl₂. The major fractions were combined and the solvent was concentrated in vacuo to afford the title compound.

Example 79

1-(4-Fluorophenyl)-1H-pyrazolo[3,4-c]pyridine-4-carboxylic acid [(S)-1-(2-carbamoyl-piperidin-4-yl)-propyl]-amide (79)

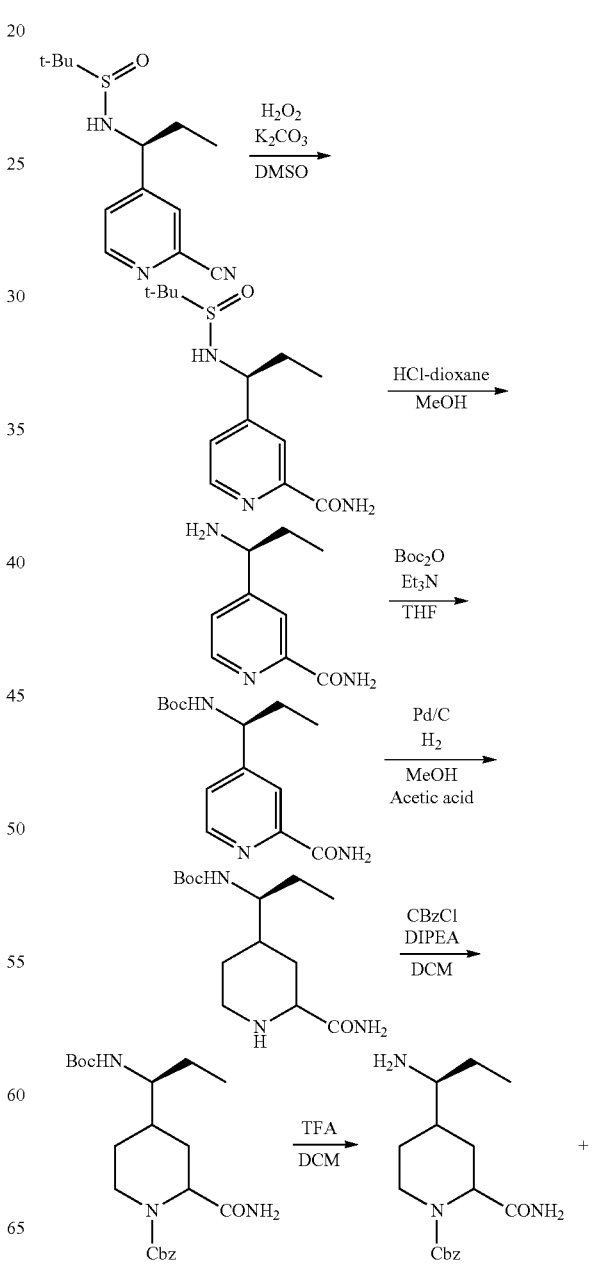

-continued

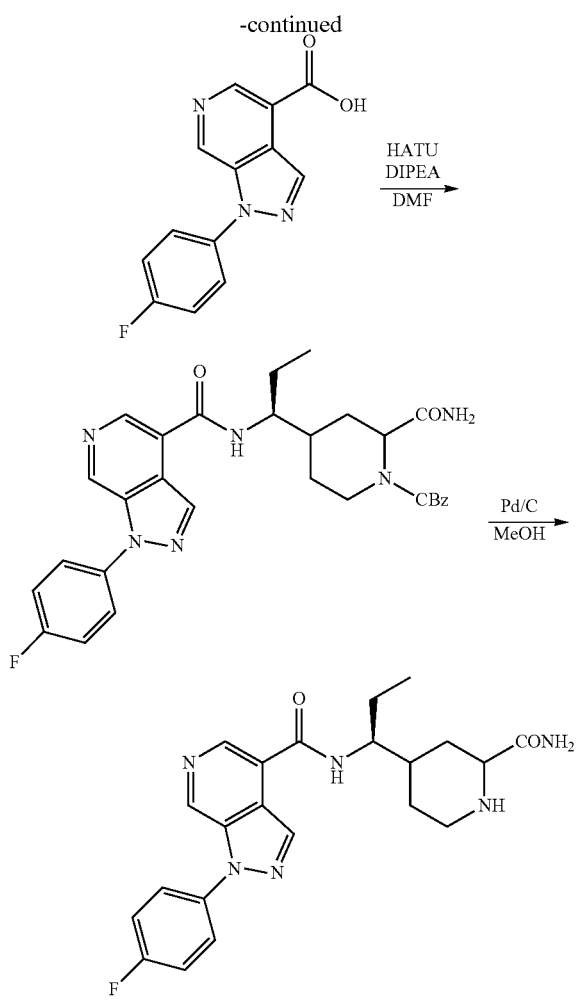

79

To a chilled (10° C.) rapidly stirred solution of 2-methyl-propane-2-sulfinic acid [(S)-1-(2-cyano-pyridin-4-yl)-propyl]-amide (4.4 g, 16.58 mmol) in DMSO (70 mL) was added potassium carbonate (3 g, 21.72 mmol) portionwise followed by a 30% aqueous solution of hydrogen peroxide (6.16 mL, 54.38 mmol) dropwise. The reaction was stirred at room temperature for 3.5 hours. The reaction was cooled to 5° C., diluted with EtOAc (100 mL), quenched with 10% aqueous sodium thiosulfate solution (25 mL), and stirred for 1 hour. The organic layer was separated, and the aqueous layer was extracted with EtOAc (4×100 mL). The combined organic layers were washed with water (3×50 mL), brine (20 mL), dried over sodium sulfate, filtered and concentrated to afford 4-[(S)-1-(2-methyl-propane-2-sulfinylamino)-propyl]pyridine-2-carboxylic acid amide as a thick colorless oil.

To a solution of 85% 4-[(S)-1-(2-methyl-propane-2-sulfinylamino)-propyl]-pyridine-2-carboxylic acid amide (5.5 g, 16.5 mmol) in methanol (50 mL) was added a 4 N solution of HCl in dioxane (4.33 mL, 17.32 mmol). After 2 hour, additional 4 N HCl in dioxane (0.5 mL) was added. The reaction was monitored by TLC (eluting with EtOAc). After 1.5 hours, the mixture was concentrated in vacuo to remove MeOH and EtOAc (400 mL) was added. The mixture was washed with saturated sodium carbonate solution (100 mL) and the aqueous layer was extracted with EtOAc (4×100 mL). The combined organic layers were washed with brine, dried over sodium sulfate, filtered and concentrated to afford 4-((S)-1-amino-propyl)-pyridine-2-carboxylic acid amide.

To a solution of 4-((S)-1-amino-propyl)-pyridine-2-carboxylic acid amide (1 g, 5.58 mmol) in THF (30 mL) was added triethylamine (2.33 mL, 16.74 mmol) followed by a solution of di-tert-butyl dicarbonate (1.34 g, 6.14 mmol) in THF (10 mL). The reaction was stirred overnight and was then diluted with EtOAc (100 mL). The organic layer was washed with saturated aqueous NH₄Cl (20 mL), brine (20 mL), dried over sodium sulfate, filtered, and concentrated. The residue was purified by silica gel chromatography eluting with a gradient of 0-75% EtOAc in heptane to afford [(S)-1-(2-carbamoyl-pyridin-4-yl)-propyl]-carbamic acid tert-butyl ester as a white foam.

A solution of [(S)-1-(2-carbamoyl-pyridin-4-yl)-propyl]-carbamic acid tert-butyl ester (1 g, 3.58 mmol) in MeOH (16.6 mL) and glacial acetic acid (3.3 mL) was added to a flask containing 10% palladium on carbon (0.38 g, 0.36 mmol) under nitrogen. The reaction was stirred at 60° C. under hydrogen at 400 psi using a Biotage Endeavour Argonaut instrument. After 20 hours, the reaction was filtered and concentrated. The crude material was diluted with EtOAc (100 mL), washed with saturated sodium carbonate solution (20 mL), brine, dried over sodium sulfate, filtered and concentrated to afford [(S)-1-(2-carbamoyl-piperidin-4-yl)-propyl]carbamic acid tert-butyl ester as a white solid.

To a chilled (0° C.) solution of [(S)-1-(2-carbamoyl-piperidin-4-yl)-propyl]-carbamic acid tert-butyl ester (780 mg, 2.73 mmol) in methylene chloride (25 mL) was added DIPEA (0.41 mL, 2.9 mmol) followed by benzylchloroformate (723 µL, 4.1 mmol). After 1 hour, the reaction was diluted with dichloromethane (200 mL), washed with saturated ammonium chloride, brine, dried over sodium sulfate, filtered and concentrated to afford 4-((S)-1-tert-butoxycarbonylamino-propyl)-2-carbamoyl-piperidine-1-carboxylic acid benzyl ester.

To a solution of 84% 4-((S)-1-tert-butoxycarbonylamino-propyl)-2-carbamoyl-piperidine-1-carboxylic acid benzyl ester (0.7 g, 1.4 mmol) in methylene chloride (20 mL) was added trifluoroacetic acid (2 mL). After 1 hour, the reaction was monitored by HPLC-MS. Additional TFA (1 mL) was added. After 30 minutes, the reaction was concentrated to afford 4-((S)-1-amino-propyl)-2-carbamoyl-piperidine-1-carboxylic acid benzyl ester.

To a suspension of 1-(4-fluorophenyl)-1H-pyrazolo[3,4-c]pyridine-4-carboxylic acid (360 mg, 1.4 mmol) in DMF (4 mL) was added DIPEA (487 µL, 2.8 mmol). After 10 minutes, HATU (638 mg, 1.68 mmol) was added to the brown solution. After 10 minutes, a solution of 4-((S)-1-amino-propyl)-2-carbamoyl-piperidine-1-carboxylic acid benzyl ester (0.45 g, 1.4 mmol) in DMF (4 mL) and DIPEA (244 µL, 1.4 mmol) was added resulting in a clear solution. After 18 hours, the reaction was diluted with EtOAc (200 mL), washed with NH₄Cl (50 mL), water (50 mL), brine, dried over sodium sulfate, filtered and concentrated. The residue was purified by silica gel chromatography eluting with a gradient of 0-6% MeOH in DCM to afford 2-carbamoyl-4-((S)-1-{[1-(4-fluorophenyl)-1H-pyrazolo[3,4-c]pyridine-4-carbonyl]-amino}-propyl)-piperidine-1-carboxylic acid benzyl ester as a light brown foam.

A solution of 2-carbamoyl-4-((S)-1-{[1-(4-fluorophenyl)-1H-pyrazolo[3,4-c]pyridine-4-carbonyl]-amino}-propyl)-piperidine-1-carboxylic acid benzyl ester (340 mg, 0.61 mmol) in MeOH (10 mL) was added to a flask containing 10% palladium on carbon (52 mg, 0.05 mmol) under nitrogen and then the mixture was placed under 1 atmosphere of hydrogen. The reaction was monitored by HPLC-MS indicating 50% conversion. After stirring overnight, the mixture was filtered, and concentrated. The reaction was re-subjected to the above condition for an additional 5 hours at which time the mixture was filtered through diatomaceous earth, rinsed with MeOH, filtered and concentrated. The crude material was purified by reversed-phase HPLC (Sunfire PrepC18 OBD 5 uM 30×150 mm column, eluted with 15-85% acetonitrile in water, with 0.1% TFA). Fractions containing the desired product were concentrated in vacuo, made basic with a few drops of saturated sodium bicarbonate solution and extracted with EtOAc. The organic layer was washed with brine, dried over sodium sulfate, filtered, and concentrated to afford the title compound as a white solid.

Example 80

Synthesis of 1-(4-Fluorophenyl)-1H-pyrazolo[3,4-c]pyridine-4-carboxylic acid [(S)-1-(2S,4R)-2-carbamoyl-1-methanesulfonyl-piperidin-4-yl)-propyl]-amide (80a) and 1-(4-Fluorophenyl)-1H-pyrazolo[3,4-c]pyridine-4-carboxylic acid [(S)-1-(2R,4S)-2-carbamoyl-1-methanesulfonyl-piperidin-4-yl)-propyl]-amide (80b)

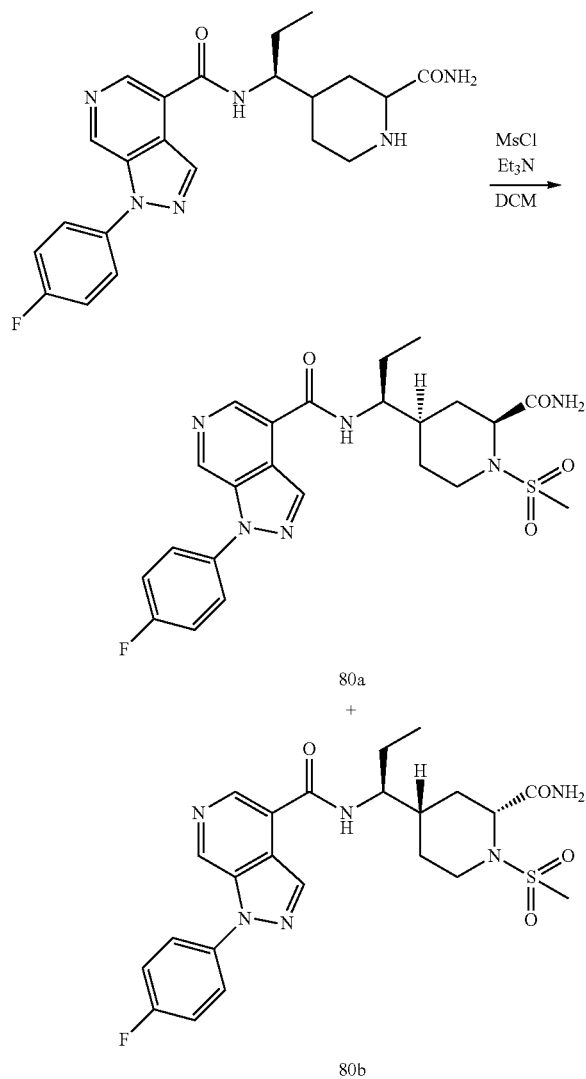

The solution of 1-(4-fluorophenyl)-1H-pyrazolo[3,4-c]pyridine-4-carboxylic acid [(S)-1-(2-carbamoyl-piperidin-4-yl)-propyl]-amide (150 mg, 0.35 mmol) and triethyl amine (78.8 µL, 0.57 mmol) in dichloromethane (8 mL) was added methanesulfonyl chloride (42.6 µL, 0.53 mmol). After 3 hours, the reaction was quenched with saturated aqueous ammonium chloride (10 mL) and extracted with dichloromethane (2×30 mL). The combined organic layers were dried over sodium sulfate, filtered, and concentrated. The mixture (containing two major cis-isomers and two minor trans-isomers) was purified by silica gel chromatography eluting with a gradient of 0-5% methanol in dichloromethane to afford the title compounds as white solids. The absolute stereocenters on the piperidine ring were assigned tentatively.

Example 81

Synthesis of 1-(4-Fluorophenyl)-1H-pyrazolo[3,4-c]pyridine-4-carboxylic acid [(S)-1-(2-hydroxymethyl-pyridin-4-yl)-propyl]-amide (81)

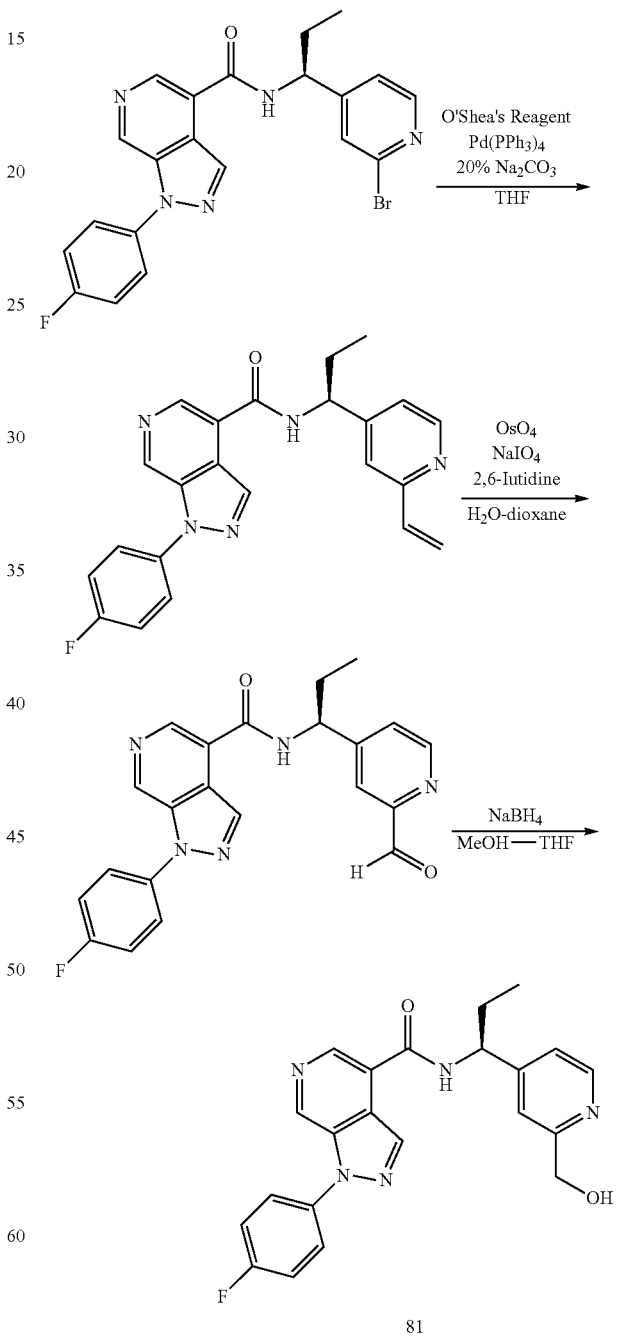

A solution of 1-(4-fluorophenyl)-1H-pyrazolo[3,4-c]pyridine-4-carboxylic acid [(S)-1-(2-bromo-pyridin-4-yl)-propyl]-amide (1.1 g, 2.42 mmol), vinylboranic anhydride pyridine complex (O'shea's reagent) (582 mg, 2.42 mmol), and tetrakistriphenylphosphinepalladium(0) (279 mg, 0.24 mmol) in THF (7 mL) and 20% aqueous sodium carbonate (2.5 mL) was warmed at 70° C. After 18 hours, the mixture was cooled to room temperature, diluted with EtOAc (200 mL), washed with saturated aqueous sodium bicarbonate (2×100 mL), dried with MgSO$_4$, filtered, and concentrated. The mixture was purified by silica gel chromatography eluting with a gradient of 70-100% EtOAc in hexanes to afford 1-(4-fluorophenyl)-1H-pyrazolo[3,4-c]pyridine-4-carboxylic acid [(S)-1-(2-vinyl-pyridin-4-yl)-propyl]-amide.

A solution of 1-(4-fluorophenyl)-1H-pyrazolo[3,4-c]pyridine-4-carboxylic acid [(S)-1-(2-vinyl-pyridin-4-yl)-propyl]-amide (200 mg, 0.5 mmol) in dioxane (10 mL) and water (3.3 mL) was treated with 2,6-lutidine (116 µL, 1 mmol), 2.5% osmium tetroxide in tert-butanol (125 µL, 0.01 mmol), and sodium periodate (426 mg, 2 mmol). After 5 hours, the reaction mixture was diluted with water (5 mL) and EtOAc (20 mL) and filtered. The organic layer was separated and washed with brine, dried over MgSO$_4$, filtered and concentrated. The mixture was purified by silica gel chromatography eluting with a gradient of 0-100% EtOAc in heptane to afford 1-(4-fluorophenyl)-1H-pyrazolo[3,4-c]pyridine-4-carboxylic acid [(S)-1-(2-formyl-pyridin-4-yl)-propyl]-amide as a white solid.

To a chilled (0° C.) solution of 1-(4-fluorophenyl)-1H-pyrazolo[3,4-c]pyridine-4-carboxylic acid [(S)-1-(2-formyl-pyridin-4-yl)-propyl]-amide (95 mg, 0.24 mmol) in THF (2 mL) and methanol (2 mL) was added sodium borohydride (17.8 mg, 0.47 mmol). The mixture was then warmed to room temperature. After 1.5 hours, the mixture was quenched with water (5 mL) and extracted with EtOAc (20 mL). The organic layer was washed with brine, dried over sodium sulfate, filtered and concentrated. The mixture was purified by silica gel chromatography eluting with a gradient of 0-10% methanol in dichloromethane to afford the title compound as a white solid.

Example 82

Synthesis of (S)-1-(2-Methanesulfonyl-pyridin-4-yl)-propylamine hydrochloride salt (82)

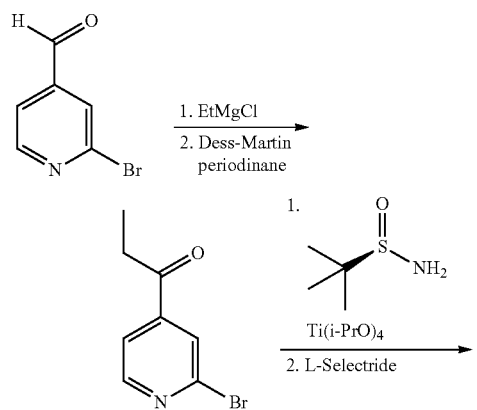

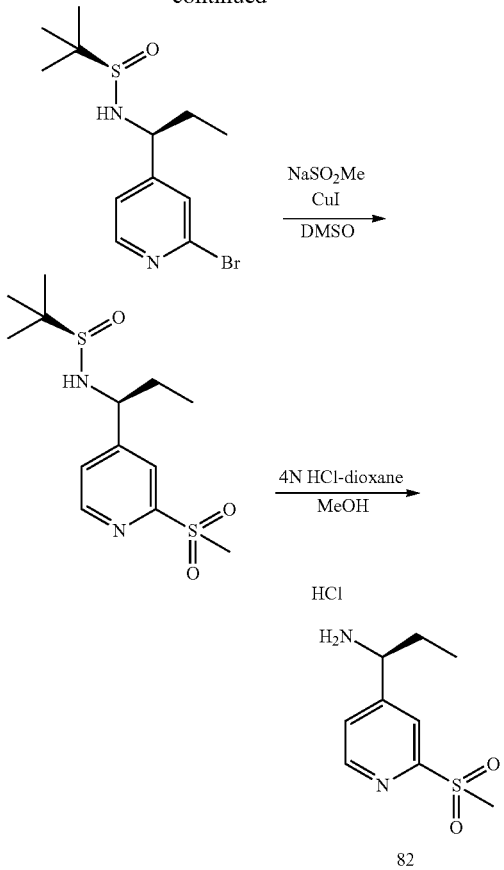

To a chilled (−78° C.) solution of 2-bromo-pyridine-4-carbaldehyde (7.0 g, 38 mmol) in THF (200 mL) was added a 2 M solution of ethylmagnesium chloride in ether (23.5 mL, 47.0 mmol) over a 10 minute period. After 15 minutes, the mixture was gradually warmed to room temperature over 1 hour. The reaction was quenched by the slow addition of saturated aqueous NH$_4$Cl (100 mL) and extracted with EtOAc (2×200 mL). The combined organic layers were washed with brine, dried over sodium sulfate, and concentrated to afford a brown oil. The crude material was purified by silica gel chromatography eluting with a gradient of 20-40% EtOAc in hexanes to afford 1-(2-bromo-pyridin-4-yl)-propan-1-ol.

To a solution of 1-(2-bromo-pyridin-4-yl)-propan-1-ol (2.20 g 10.2 mmol) in dichloromethane (55 mL) was added Dess-Martin periodinane (5.6 g, 13 mmol). After 30 hours, and was diluted with saturated aqueous sodium carbonate (40 mL) and partially concentrated to remove the dichloromethane. The crude material was filtered through diatomaceous earth and washed with EtOAc (100 mL). The aqueous layer was separated and extracted with EtOAc (40 mL). The combined organic layers were washed with saturated aqueous sodium carbonate (40 mL) and brine (40 mL). The material was dried over magnesium sulfate, filtered and concentrated to afford 1-(2-bromo-pyridin-4-yl)-propan-1-one as a clear oil which was used without further purification.

Alternatively, the intermediate ketone, 1-(2-bromo-pyridin-4-yl)-propan-1-one, can be prepared via a Grignard addition to a Weinreb amide derived from commercially available 2-bromo-isonicotinic acid.

A solution of 1-(2-bromo-pyridin-4-yl)-propan-1-one (8.9 g, 42 mmol), R-(+)-2-methylpropane-2-sulfinamide (6 g, 50 mmol) and titanium (IV) isopropoxide (26 g, 91 mmol) in anhydrous dichloromethane (50 mL) was heated to 40° C. for 18 hours. After cooling, the solution was concentrated and the residue was taken up in EtOAc (100 mL). The solution was stirred and brine (100 mL) was added slowly. After 15 minutes, the mixture was filtered through a pad of diatomaceous earth and washed with EtOAc (100 mL). The organic layers were separated, dried over sodium sulfate, and concentrated. The product was purified by silica gel chromatography eluting with a gradient of 0-50% EtOAc in hexanes to afford 2-methyl-propane-2-sulfinic acid [1-(2-bromo-pyridin-4-yl)-prop-(E)-ylidene]-amide.

To a chilled (−78° C.) solution of 2-methyl-propane-2-sulfinic acid [1-(2-bromo-pyridin-4-yl)-prop-(E)-ylidene]-amide (6.0 g, 19 mmol) in THF (280 mL) was added a 1 M solution of L-Selectride in THF (37.8 ml, 37.8 mmol) dropwise. After 2.5 hours, the reaction mixture was quenched with saturated aqueous NH$_4$Cl (100 mL). The layers were separated and the aqueous layer was extracted with EtOAc (2×400 mL). The combined organic layers were washed with brine, and concentrated. The residue was purifed by silica gel chromatography eluting with a gradient of 0-100% EtOAc in hexanes to afford an oily solid, which after further drying provided 2-methyl-propane-2-sulfinic acid [(R)-1-(2-bromo-pyridin-4-yl)-propyl]-amide as a crystalline solid.

To a solution of 2-methyl-propane-2-sulfinic acid [(R)-1-(2-bromo-pyridin-4-yl)-propyl]-amide (6.00 g, 18.8 mmol) in DMSO (240 ml) was added sodium methanesulfinate (6.77 g, 56.4 mmol) and copper (I) iodide (10.7 g, 56.4 mmol) The mixture was then heated at 130° C. for 45 minutes. The reaction was diluted with saturated aqueous NH$_4$Cl (90 mL), saturated NaHCO$_3$ (10 mL), and EtOAc (150 mL), and sonicated for 10 minutes to dissolve all the solids. The phases were separated and the organic layer was washed with a 9:1 mixture of saturated NH$_4$Cl-saturated NaHCO$_3$ (100 mL). The combined aqueous phases were extracted with EtOAc (150 mL). Combined organic layers were washed with brine, dried over sodium sulfate, filtered and concentrated. The crude material was purified by silica gel chromatography eluting with a gradient of 0-100% EtOAc in hexanes to afford 2-methyl-propane-2-sulfinic acid [(S)-1-(2-methanesulfonyl-pyridin-4-yl)-propyl]-amide as a clear thick oil.

Alternatively, (1-(2-bromo-pyridin-4-yl)-propan-1-one could be converted to the corresponding methyl sulfone via the above procedure to afford 1-(2-methanesulfonyl-pyridin-4-yl)-propan-1-one. 1-(2-Methanesulfonyl-pyridin-4-yl)-propan-1-one can be converted to the title compound by methods described in example 82.

To a solution of 2-methyl-propane-2-sulfinic acid [(S)-1-(2-methanesulfonyl-pyridin-4-yl)-propyl]-amide (26 g, 82 mmol) in methanol (150 mL) was added a solution of 4 N HCl in dioxane (22.5 ml, 89.8 mmol) and stirred for 1 hour. The solution was concentrated to half the original volume and diluted with toluene (100 mL), and concentrated. The crude material was co-evaporated from toluene (3×100 mL) and dried in vacuo for 18 hours to afford the title compound as an off-white solid.

Example 83

Synthesis of 1-(4-Fluorophenyl)-1H-pyrazolo[3,4-c]pyridine-4-carboxylic acid [(S)-1-(2-methanesulfonyl-pyridin-4-yl)-propyl]-amide (83)

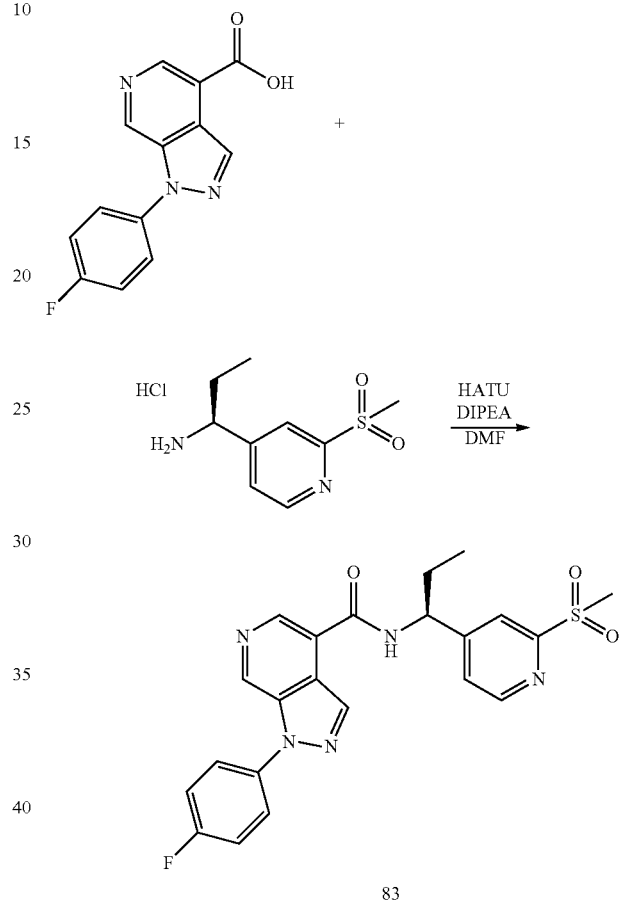

To a mixture of 1-(4-fluorophenyl)-1H-pyrazolo[3,4-c]pyridine-4-carboxylic acid (1.08 g, 4.20 mmol) and DIPEA (2.19 ml, 12.6 mmol) in DMF (20 mL) was added HATU (3.19 g, 8.39 mmol). After 30 minutes, a solution of (S)-1-(2-methanesulfonyl-pyridin-4-yl)-propylamine hydrochloride salt (0.90 g, 4.2 mmol) in DCM (1 mL) was added, and the reaction mixture became homogeneous. After 16 hours, the mixture was poured into saturated aqueous NaHCO$_3$, and extracted with dichloromethane (3×100 mL). The combined organic layers were washed with brine and dried over sodium sulfate, filtered and concentrated. The crude material was twice purified by silica gel chromatography eluting with a gradient of 0-100% EtOAc in hexanes to afford a yellow solid. The solid was dissolved in a minimal amount of dichloromethane and diluted with hexanes, and the collected by filtration washing with diethyl ether to afford the title compound as an off-white solid.

Example 84

Synthesis of 1-(4-Fluorophenyl)-1H-pyrazolo[3,4-c]pyridine-4-carboxylic acid [(R)-1-(2-bromo-pyridin-4-yl)-2-methoxy-ethyl]-amide (84)

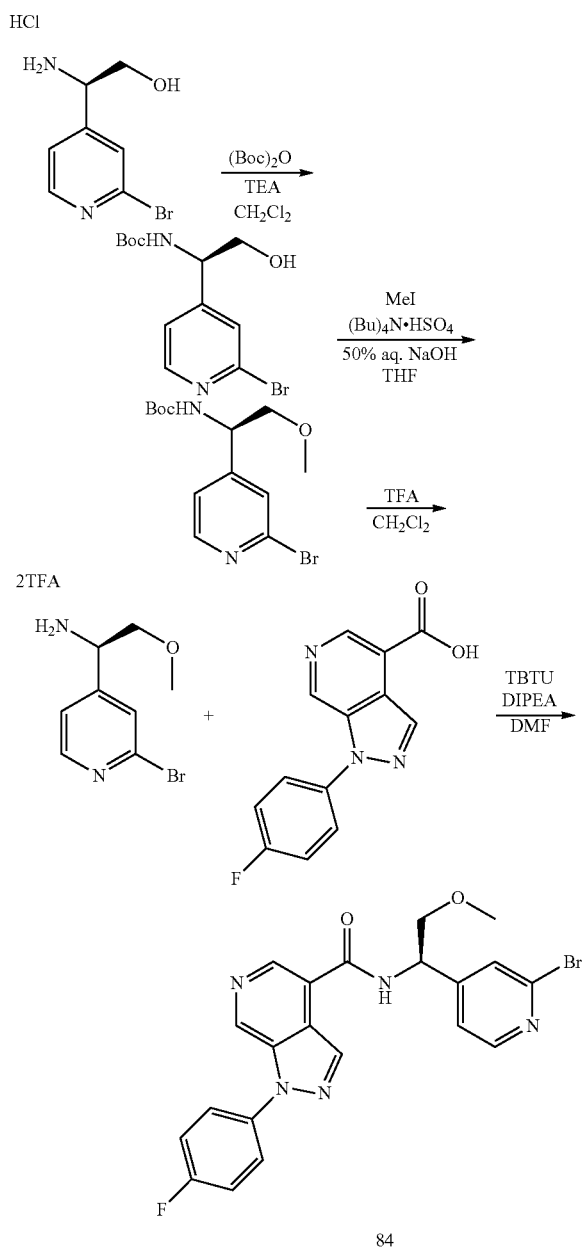

84

To a suspension of (R)-2-amino-2-(2-bromo-pyridin-4-yl)-ethanol hydrochloride salt (180 mg, 0.710 mmol) in methylene chloride (5 mL) was added triethylamine (370 µL, 2.13 mmol) and di-tert-butyl dicarbonate (186 mg, 0.852 mmol). After 16 hours, the mixture was diluted with methylene chloride (20 mL), washed with saturated aqueous ammonium chloride (20 mL), saturated aqueous sodium bicarbonate (20 mL) and brine (20 mL), dried over MgSO₄, filtered and concentrated in vacuo. The resulting residue was purified by silica gel chromatography eluting with a gradient of 0-10% methanol in methylene chloride to afford [(R)-1-(2-bromo-pyridin-4-yl)-2-hydroxy-ethyl]-carbamic acid tert-butyl ester as foam. MS m/z 317.1 (M+), 319.0 (M+2).

To a solution of [(R)-1-(2-bromo-pyridin-4-yl)-2-hydroxy-ethyl]-carbamic acid tert-butyl ester (180 mg, 0.568 mmol), methyl iodide (177 µL, 2.84 mmol) and tetrabutylammonium hydrogen sulfate (192 mg, 0.568 mmol) in THF (4.0 mL) was added 50% aqueous solution of sodium hydroxide (2.5 mL). After 1 hour, the reaction mixture was diluted with water (50 mL) and extracted with ethyl ether (3×50 mL). The combined organic layers were dried over MgSO₄, filtered and concentrated in vacuo. The residue was purified by silica gel chromatography eluting with a gradient of 0-30% ethyl acetate in heptane to afford [(R)-1-(2-bromo-pyridin-4-yl)-2-methoxy-ethyl]-carbamic acid tert-butyl ester as oil which solidified upon standing.

To a solution of [(R)-1-(2-bromo-pyridin-4-yl)-2-methoxy-ethyl]-carbamic acid tert-butyl ester (150 mg, 0.453 mmol) in CH₂Cl₂ (3 mL) was added trifluoroacetic acid (872 µL, 11.3 mmol). After 14 hours, the mixture was concentrated in vacuo to afford (R)-1-(2-bromo-pyridin-4-yl)-2-methoxy-ethylamine ditrifloroacetic acid salt which was used without purification. MS m/z 231.01 (M+), 232.99 (M+2).

To a solution of 1-(4-fluorophenyl)-1H-pyrazolo[3,4-c]pyridine-4-carboxylic acid (110 mg, 0.428 mmol), (R)-1-(2-bromo-pyridin-4-yl)-2-methoxy-ethylamine ditrifloroacetic acid salt (205 mg, 0.447 mmol) and DIPEA (380 µL, 2.14 mmol) in DMF (4.0 mL) was added TBTU (172 mg, 0.535 mmol). After 2 hours, the mixture was concentrated in vacuo, dissolved in ethyl acetate (100 mL), and washed with 2 N sodium hydroxide (100 mL), saturated aqueous ammonium chloride (2×100 mL), saturated aqueous sodium bicarbonate (100 mL) and brine (100 mL). The organic layer was dried over MgSO₄, filtered and concentrated in vacuo. The crude residue was purified by silica gel chromatography eluting with a gradient of 0-4% methanol in methylene chloride to afford the title compound as off-white solid.

The following compound was also prepared using the above coupling procedure:

1-(4-Fluorophenyl)-1H-pyrazolo[3,4-c]pyridine-4-carboxylic acid [1-(2-bromo-pyridin-4-yl)-1-methyl-ethyl]-amide,
1-(4-Fluorophenyl)-1H-pyrazolo[3,4-c]pyridine-4-carboxylic acid [1-(2-bromo-pyridin-4-yl)-1-methyl-propyl]-amide,
1-(4-Fluorophenyl)-1H-pyrazolo[3,4-c]pyridine-4-carboxylic acid [1-(2-bromo-pyridin-4-yl)-1-ethyl-propyl]-amide, and
1-(4-Fluorophenyl)-1H-pyrazolo[4,3-c]pyridine-4-carboxylic acid [(S)-1-(2-methanesulfonyl-pyridin-4-yl)-propyl]-amide

Example 85

1-(4-Fluorophenyl)-1H-pyrazolo[3,4-c]pyridine-4-carboxylic acid {(S)-1-[2-(4-methyl-piperazin-1-yl)-pyridin-4-yl]-propyl}-amide (85)

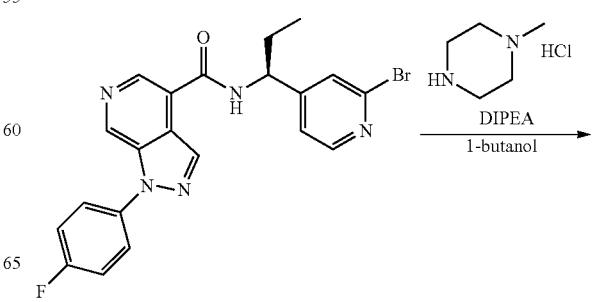

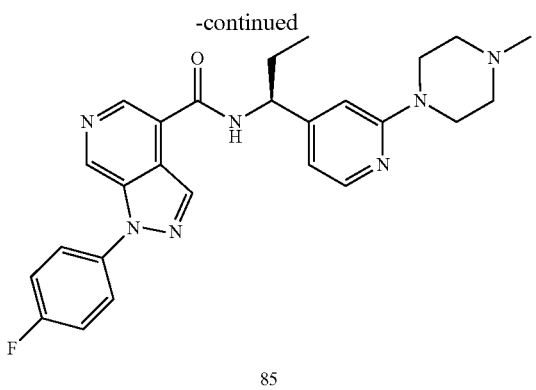

85

A microwave vessel charged with 1-(4-fluorophenyl)-1H-pyrazolo[3,4-c]pyridine-4-carboxylic acid [(S)-1-(2-bromopyridin-4-yl)-propyl]-amide (0.05 g, 0.11 mmol), 1-methylpiperazine (33.1 mg, 0.33 mmol) and DIPEA (115 µL, 0.66 mmol) in 1-butanol (1.5 mL) was irradiated at 200° C. After 4 hours, the reaction was cooled, evaporated to dryness and the residue was purified with reverse phase liquid chromatography to afford the title compound.

The following compounds were also prepared by methods described in Example 85 by using the appropriate amine (0.33 mmol).

1-(4-Fluorophenyl)-1H-pyrazolo[3,4-c]pyridine-4-carboxylic acid [(S)-1-(4-methanesulfonyl-3,4,5,6-tetrahydro-2H-[1,2']bipyridinyl-4'-yl)-propyl]-amide, 1-(4-Fluorophenyl)-1H-pyrazolo[3,4-c]pyridine-4-carboxylic acid [(S)-1-(4,4-difluoro-3,4,5,6-tetrahydro-2H-[1,2'] bipyridinyl-4'-yl)-propyl]-amide, 1-(4-Fluorophenyl)-1H-pyrazolo[3,4-c]pyridine-4-carboxylic acid ((S)-1-{2-[(2-methoxy-ethyl)-methyl-amino]-pyridin-4-yl}-propyl)-amide, 1-(4-Fluorophenyl)-1H-pyrazolo[3,4-c]pyridine-4-carboxylic acid {(S)-1-[2-(4-acetyl-piperazin-1-yl)-pyridin-4-yl]-propyl}-amide, and 1-(4-Fluorophenyl)-1H-pyrazolo[3,4-c]pyridine-4-carboxylic acid {(S)-1-[2-(1,1-dioxo-1λ$^6$-thiomorpholin-4-yl)-pyridin-4-yl]-propyl}-amide.

Example 86

Synthesis of (S)-1-(2-Methanesulfonyl-pyridin-4-yl)-ethylamine hydrochloride (86)

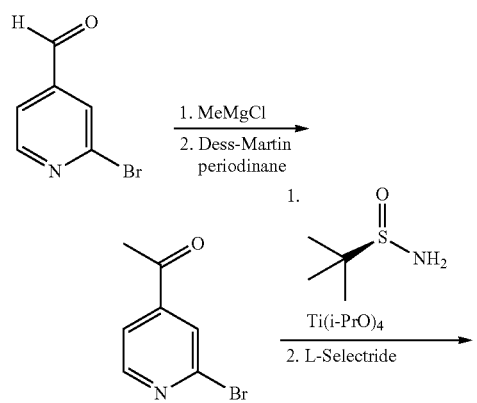

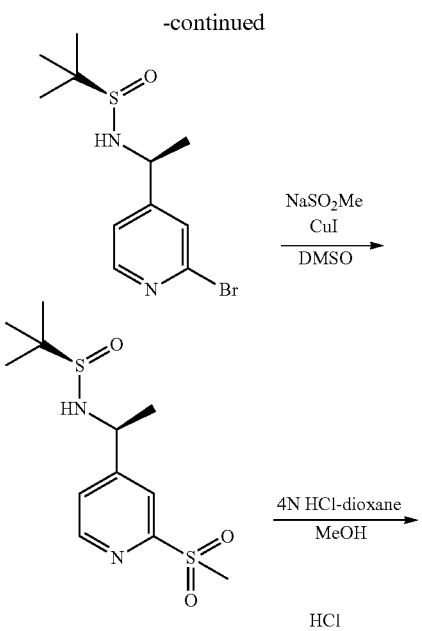

86

To a chilled (−78° C.) solution of 2-bromo-pyridine-4-carbaldehyde (10.0 g, 53.8 mmol) in THF (100 mL) was added a 3 M solution of methylmagnesium chloride in THF (18 mL, 54 mmol) over a 10 minute period. After 1 hour, the yellow solution was allowed to warm gradually to room temperature over a 3 hour period. The reaction was quenched by the slow addition of saturated aqueous NH$_4$Cl (50 mL) and extracted with EtOAc (2×200 mL). The combined organic layers were washed with brine, dried over sodium sulfate, and concentrated to afford a brown oil. The crude material was purified by silica gel chromatography eluting with a gradient of 10-45% EtOAc in hexanes to afford 1-(2-bromo-pyridin-4-yl)-ethanol.

To a chilled (ice water bath) solution of 1-(2-bromo-pyridin-4-yl)-ethanol (27.5 g, 132 mmol) in dichloromethane (200 mL) was added Dess-Martin periodinane (56.0 g, 132 mmol). The cold bath was then removed and the mixture was stirred at room temperature. After 2 hours, the mixture was diluted with saturated sodium carbonate (100 mL) and partially concentrated to remove the dichloromethane. The crude material was filtered through diatomaceous earth and washed with EtOAc (200 mL). The aqueous layer was separated and extracted with EtOAc (100 mL). The combined organic layers were washed with saturated aqueous sodium carbonate (100 mL), brine (100 mL), dried over magnesium sulfate, filtered and concentrated. The crude material was purified by silica gel chromatography eluting with a gradient of 5-30% EtOAc in hexanes to afford 1-(2-bromo-pyridin-4-yl)-ethanone as white needles.

Alternatively, the intermediate ketone (1-(2-bromo-pyridin-4-yl)-ethanone) can be accessed via a Grignard addition to a Weinreb amide derived from commercially available 2-bromo-isonicotinic acid.

A solution of 1-(2-bromo-pyridin-4-yl)-ethanone (8.0 g, 40 mmol), R-(+)-2-methylpropane-2-sulfinamide (5.8 g, 48 mmol) and titanium (IV) isopropoxide (25.7 mL, 87.8 mmol) in anhydrous dichloromethane (10 mL) was heated at 60° C. After 18 hours, the mixture was cooled and concentrated. The residue was diluted with EtOAc (300 mL) and brine (50 mL) was added slowly to the stirred mixture. After 15 minutes, the mixture was filtered through diatomaceous earth and washed with EtOAc (100 mL). The organic phase was separated, dried over sodium sulfate, and concentrated. The product was purified by silica gel chromatography eluting with a gradient of 0-50% EtOAc in hexanes to afford 2-methyl-propane-2-sulfinic acid [1-(2-bromo-pyridin-4-yl)-eth-(E)-ylidene]-amide.

To a chilled (−78° C.) solution of 2-methyl-propane-2-sulfinic acid [1-(2-bromo-pyridin-4-yl)-eth-(E)-ylidene]-amide (9.3 g, 31 mmol) in THF (280 mL) was added a 1 M solution of L-Selectride in THF (61.3 ml, 61.3 mmol) dropwise. After 2.5 hours, the chilled mixture was quenched with saturated aqueous NH$_4$Cl (100 mL). The layers were separated and the aqueous layer was extracted with EtOAc (2×400 mL). The combined organic layers were washed with brine, and concentrated. The residue was purified by silica gel chromatography eluting with a gradient of 50-90% EtOAc in hexanes to afford 2-methyl-propane-2-sulfinic acid [(S)-1-(2-bromo-pyridin-4-yl)-ethyl]amide as a light yellow oil which contained 5% of the opposite diastereomer.

To a solution of 2-methyl-propane-2-sulfinic acid [(S)-1-(2-bromo-pyridin-4-yl)-ethyl]-amide (3.10 g, 10.2 mmol) (containing 5 wt % of the other diastereomer) in DMSO (120 mL) was added sodium methanesulfinate (3.7 g, 31 mmol) and copper (I) iodide (5.8 g, 31 mmol) The mixture was warmed at 130° C. for 45 minutes. The reaction was diluted with saturated aqueous NH$_4$Cl (90 mL), saturated aqueous NaHCO$_3$ (10 mL), and EtOAc (150 mL), and sonicated for 10 minutes to dissolve all the solids. The aqueous phase was separated and the organic layer was washed with a mixture of saturated aqueous NH$_4$Cl (90 mL) in saturated aqueous NaHCO$_3$ (10 mL). The combined aqueous layers were extracted with EtOAc (150 mL). The combined organic layers were washed with brine, dried over sodium sulfate, filtered and concentrated. The crude material was purified by silica gel chromatography eluting with a gradient of 75-100% EtOAc in hexanes to afford 2-methyl-propane-2-sulfinic acid [(S)-1-(2-methanesulfonyl-pyridin-4-yl)-ethyl]-amide as a clear thick oil as a single diastereomer.

Alternatively, (1-(2-bromo-pyridin-4-yl)-ethanone) could be converted to the corresponding methyl sulfone via the above procedure to afford 1-(2-methanesulfonyl-pyridin-4-yl)-ethanone. 1-(2-Methanesulfonyl-pyridin-4-yl)-ethanone can be converted to the title compound by methods described in example 86.

To a solution of 2-methyl-propane-2-sulfinic acid [(S)-1-(2-methanesulfonyl-pyridin-4-yl)-ethyl]-amide (29.9 g, 98.2 mmol) in methanol (160 mL) was added a solution of 4 N HCl in dioxane (25.8 mL, 103 mmol). After 1 hour, the solution was concentrated to half the original volume and diluted with toluene (100 mL), and concentrated. The crude material was diluted with toluene (3×100 mL) and concentrated in vacuo and dried in vacuo for 18 hours to afford the title compound as an off-white solid which was used without further purification.

Example 87

Synthesis of 1-(4-Fluorophenyl)-1H-pyrazolo[3,4-c] pyridine-4-carboxylic acid [(S)-1-(2-methanesulfonyl-pyridin-4-yl)-ethyl]-amide (87)

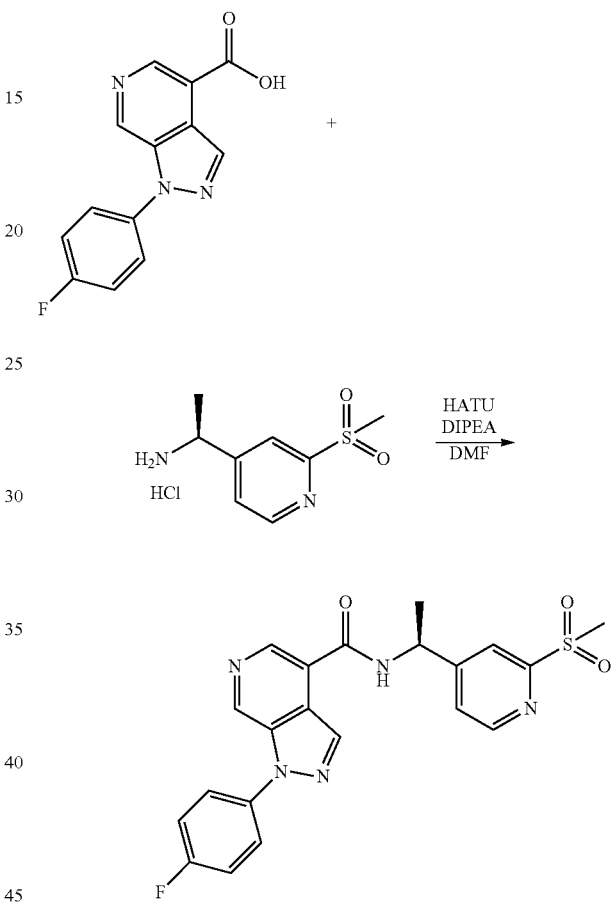

87

To a suspension of 1-(4-fluorophenyl)-1H-pyrazolo[3,4-c] pyridine-4-carboxylic acid (17.74 g, 68.98 mmol) in DMF (200 mL) was added DIPEA (30 mL, 170 mmol) followed by HATU (27.37 g, 71.98 mmol). After 5 minutes, a light brown precipitate formed and additional DMF (50 mL) was added to aid stifling. After 1.5 hours, (S)-1-(2-methanesulfonyl-pyridin-4-yl)-ethylamine hydrochloride (14.20 g, 59.99 mmol) was added, followed by additional DIPEA (10 mL, 55 mmol). After 18 hours, the mixture was poured into water (1.5 L) containing sodium bicarbonate (25 g). The solid was collected by filtration and washed with aqueous sodium carbonate (1 L), water (1 L) and dried by pulling vacuum through the filter cake. The crude product was passed through a pad of silica gel eluting with EtOAc in dichloromethane (1:9, then 2:8, then 5:5, then 100:0). The material from the pad was concentrated and triturated with diethylether to afford the title compound as an off-white solid.

Example 88

Synthesis of 6-(Dimethylaminosulfonylamino)-pyridin-3-ylmethyl amine dihydrochloride salt (88)

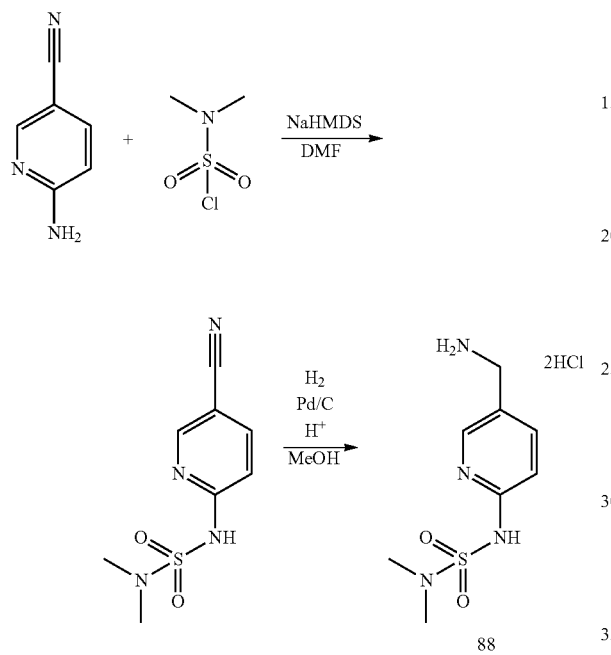

Example 89

Synthesis of (S)-1-(4-Bromo-pyridin-2-yl)-propylamine hydrochloride salt (89)

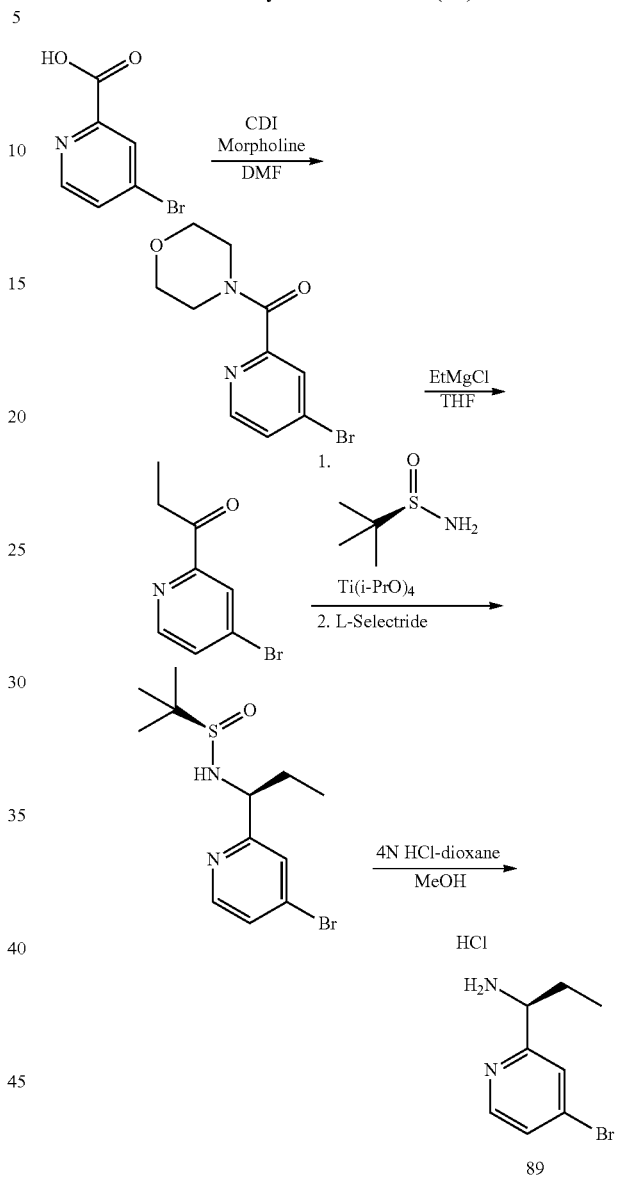

To a solution of 6-amino-nicotinonitrile (2.4 g, 20.15 mmol) in DMF (40 mL) was added a 1 M solution of NaHMDS (22.0 mL, 22.0 mmol) in THF followed by sulfamoyl chloride (3.0 mL, 27.9 mmol). The mixture was stirred overnight and was then diluted with 1 N aqueous sodium hydroxide and a mixture of ether-hexanes. The aqueous layer was separated. The organic layer was extracted with 1 N aqueous sodium hydroxide (2×30 mL). The combined aqueous layers were washed with ether (3×30 mL), made acidic with 1 N aqueous HCl and extracted with ethyl acetate (3×40 mL). The combined organic phases were washed with brine (3×30 mL), dried over magnesium sulfate, treated with activated carbon, filtered through diatomaceous earth and concentrated in vacuo. The solid was adsorbed onto silica gel and purified by silica gel chromatography eluting with a gradient of 10-50% ethyl acetate in hexanes (compound precipitated on the column but dissolved over time at high ethyl acetate concentration) to afford 6-(dimethylaminosulfonylamino)-3-cyanopyridine as a white solid A solution of 6-(dimethylaminosulfonylamino)-3-cyanopyridine (250 mg, 1.1 mmol) in a mixture of MeOH (25 mL) and 4 N HCl in dioxane (1 mL) was hydrogenated over 10% Pd/C catalyst using a continuous flow hydrogenation apparatus (conditions: flow rate 1.0 mL/minute, 25° C., 1 atmosphere). The reaction was monitored by TLC (ethyl acetate). The methanol was concentrated in vacuo to afford the title compound.

To a solution of 4-bromo-pyridine-2-carboxylic acid (2.0 g, 9.9 mmol) in DMF (15 mL) was added CDI. After 15 minutes, morpholine (3.0 mL, 34.4 mmol) was added. The reaction was monitored by HPLC-MS indicating a single peak with the desired mass and the mixture was diluted with saturated aqueous ammonium chloride (60 mL) and extracted with ethyl acetate (5×50 mL). The combined organic layers were washed with brine (2×30 mL), dried over magnesium sulfate, filtered and concentrated. The crude mixture was passed through a silica gel column using dichloromethane to load the sample and then eluting with a gradient of 10-100% ethyl acetate in hexanes to afford 4-bromo-pyridin-2-yl)-morpholin-4-yl-methanone To a chilled (−78° C.) solution of 4-bromo-pyridin-2-yl)-morpholin-4-yl-methanone (1.5 g, 5.53 mmol) in THF (30 mL) was added of a 2 M solution of ethyl magnesium chloride (3.5 mL, 7.0 mmol) in THF dropwise. The reaction was monitored by TLC (ethyl acetate-hexanes 2:8). The mixture was diluted with saturated aqueous ammonium chloride (40 mL) and extracted with ethyl acetate (3×50 mL). The combined organic layers were washed with brine (2×30 mL), dried over magnesium sulfate, filtered and concentrated. The crude material was passed through a pad of silica gel eluting with 5% ethyl acetate in hexanes to afford 1-(4-bromo-pyridin-2-yl)-propan-1-one.

A mixture of 1-(4-bromo-pyridin-2-yl)-propan-1-one (1.0 g, 4.67 mmol), R-(+)-2-methylpropane-2-sulfinamide (711 mg, 5.87 mmol) and titanium (IV) isopropoxide (2 mL, 6.8 mmol) in dichloroethane (10 mL) was warmed at reflux. After 1 hour, the mixture was cooled to room temperature and stirred for 2 days. The reaction was monitored by TLC (ethyl acetate-hexanes 2:8). The mixture was then diluted with dichloromethane (50 mL) and water (2 mL) was added. The mixture was stirred for 10 minutes and then dried over magnesium sulfate, filtered through diatomaceous earth and concentrated in vacuo. The residue was purified by silica gel chromatography eluting with ethyl acetate in hexanes (1:99, then 5:95) to afford 2-methyl-propane-2-sulfinic acid [(S)-1-(4-bromo-pyridin-2-yl)-propyl]-amide.

To a chilled (−78° C.) solution of 2-methyl-propane-2-sulfinic acid [(S)-1-(4-bromo-pyridin-2-yl)-propyl]-amide (985 mg, 3.10 mmol) in THF (25 mL) was added a 1 M solution of L-Selectride (3.2 mL, 3.2 mmol) in THF. The reaction was monitored by TLC (ethyl acetate-ether 3:7) indicating a single diastereomer when compared to a mixture of diastereomers prepared by reduction of 2-methyl-propane-2-sulfinic acid [(S)-1-(4-bromo-pyridin-2-yl)-propyl]-amide with lithium borohydride in THF. After 3 hours, the mixture was quenched with saturated aqueous ammonium chloride (30 mL) and extracted with ethyl acetate (3×25 mL). The combined organic layers were washed with brine (3×30 mL), dried over magnesium sulfate, filtered and concentrated. The crude material was purified by silica gel chromatography eluting with a gradient of 0-100% ethyl acetate in dichloromethane. The material from the column was crystallized from hexanes to afford (S)-1-(4-bromo-pyridin-2-yl)-propylamine.

A mixture of (S)-1-(4-bromo-pyridin-2-yl)-propylamine (600 mg, 1.88 mmol) in 3 N aqueous HCl was stirred for 16 hours. The reaction was monitored by TLC for the disappearance of starting material (ethyl acetate-ether 3:7). The mixture was then added to a solution of saturated aqueous sodium bicarbonate (15 mL) and extracted with ethyl acetate (5×15 mL). The combined organic layers were dried over sodium sulfate, filtered and concentrated in vacuo to afford title compound which was used without purification

Example 90

Synthesis of C-(5-Methanesulfonyl-pyridin-2-yl)-methylamine (90)

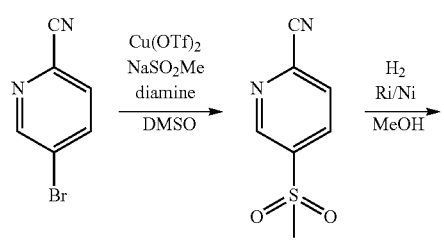

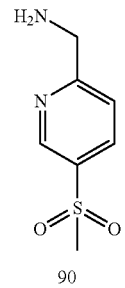

To a solution of 5-bromo-pyridine-2-carbonitrile (500 mg, 2.73 mmol) in DMSO (10 mL) in a microwave tube was added 85% sodium methanesulfinate (525 mg, 4.37 mmol) followed by copper (II) triflate (990 mg, 2.74 mmol) and dimethylethylene diamine (890 µL, 8.36 mmol). The mixture was warmed in a microwave reactor at 115° C. After 30 minutes, the mixture was diluted with saturated aqueous ammonium chloride (100 mL) and extracted with ethyl acetate (3×20 mL). The combined organic layers were washed with saturated aqueous ammonium chloride (2×15 mL), brine (3×15 mL), dried over magnesium sulfate, filtered and concentrated. The crude material was triturated with ether to afford 5-methanesulfonyl-pyridine-2-carbonitrile.

A solution of 5-methanesulfonyl-pyridine-2-carbonitrile (120 mg, 0.66 mmol) in methanol was hydrogenated over 10% Pd/C catalyst using a continuous flow hydrogenation apparatus (conditions: flow rate 1 mL/minute, 10 bars, 25° C.). The reaction was monitored by HPLC-MS and TLC (ethyl acetate) indicating the disappearance of starting material. The mixture was concentrated in vacuo and then twice diluted with ether-hexanes and concentrated to afford the title compound.

Example 91

Synthesis of (S)-1-(6-Bromo-pyridin-3-yl)-propylamine dihydrochloride salt (91)

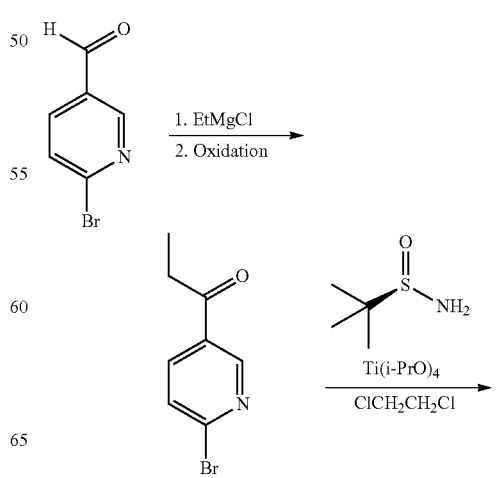

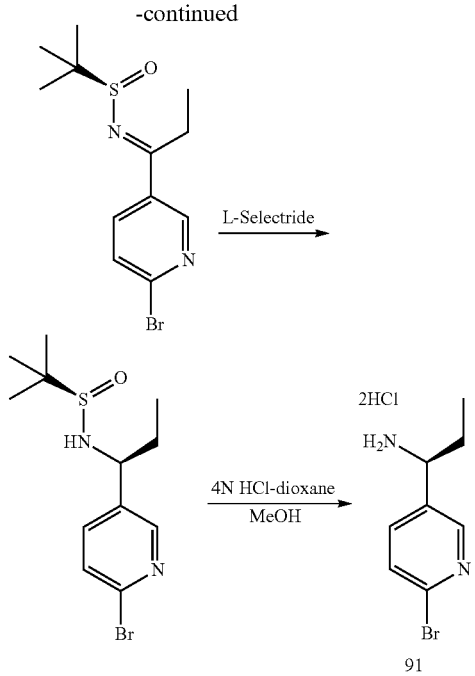

To a chilled (ice bath) solution of 6-bromo-pyridine-3-carbaldehyde (15.0 g, 80.64 mmol) in a 1:1 mixture of ether:toluene (400 mL) was added a 2 M solution of ethylmagnesium chloride (40.0 mL, 80.0 mmol) in THF over a 15 minute period. The reaction was monitored by TLC (ethyl acetate-hexanes 3:7). After 4 hours, the mixture was diluted with saturated aqueous ammonium chloride (300 mL) and the organic phase separated. The aqueous layer was extracted with ethyl acetate (2×100 mL). The combined organic layers were washed with brine (2×50 mL), dried over magnesium sulfate, filtered and concentrated. The crude material was passed through a pad of silica gel eluting with dichloromethane-hexanes (0-100%). The material from the pad was purified by silica gel chromatography eluting with ethyl acetate-hexanes (2:98, then 4:96, then 6:94, then 8:92, then 1:9, then 12:88, then 15:85) to afford 1-(6-bromo-pyridin-3-yl)-propan-1-ol as a clear oil.

Reacting 6-bromo-pyridine-3-carbaldehyde with propylmagnesium chloride according to the above method gave the following analog:
1-(6-bromo-pyridin-3-yl)-butan-1-ol.

To a solution of 1-(6-bromo-pyridin-3-yl)-propan-1-ol (12.9 g, 59.93 mmol) in THF (200 mL) was added 85% activated MnO$_2$ (6.4 g, 62.57 mmol) and the mixture was stirred overnight. The reaction was monitored by TLC (ethyl acetate-hexanes 4:6) indicating starting material and a new less polar product. To the mixture was added additional 85% activated MnO$_2$ (6.0 g, 58.66 mmol) and the mixture stirred for 2 days. The reaction was monitored by TLC (ethyl acetate-hexanes 3:7) indicting starting material was still present. The mixture was warmed at reflux for 6 hours. The mixture was filtered through diatomaceous earth and concentrated. The residue was diluted with dichloromethane and Dess-Martin periodinane (19 g, 44.8 mmol) was added. After 1 hour, the mixture was diluted with saturated aqueous potassium carbonate (200 mL) and concentrated. The resulting solid was collected by filtration washing with water and dried by pulling vacuum through the filter cake. The solid was then suspended in dichloromethane and filtered and the filtrate was passed through a pad of silica gel eluting with ether to afford 1-(6-bromo-pyridin-3-yl)-propan-1-one as a white solid.

Reacting (1-(6-bromo-pyridin-3-yl)-butan-1-ol according to the above method gave the following analog:
1-(6-Bromo-pyridin-3-yl)-butan-1-one.

A mixture of 1-(6-bromo-pyridin-3-yl)-propan-1-one (11.8 g, 55.12 mmol), R-(+)-2-methylpropane-2-sulfinamide (8.0 g, 66.01 mmol) and titanium (IV) isopropoxide (18.0 mL, 61.43 mmol) in dichloroethane (65 mL) was warmed at reflux. The reaction was monitored by TLC (ethyl acetate-hexanes 2:8). After 2 days, the mixture was diluted with dichloromethane (600 mL) and water (15 mL) was added. After 10 minutes of stirring, the mixture was dried over magnesium sulfate, filtered through diatomaceous earth and concentrated. The residue was purified by silica gel chromatography eluting with a gradient of 0-40% ethyl acetate in hexanes and then a gradient of 0-40% ethyl acetate in dichloromethane to afford 2-methyl-propane-2-sulfinic acid [1-(6-bromo-pyridin-3-yl)-prop-(E)-ylidene]-amide.

Reacting 1-(6-bromo-pyridin-3-yl)-butan-1-one according to the above method gave the following analog:
2-Methyl-propane-2-sulfinic acid [1-(6-bromo-pyridin-3-yl)-but-(E)-ylidene]-amide.

To a chilled (−78° C.) solution of 2-methyl-propane-2-sulfinic acid [1-(6-bromo-pyridin-3-yl)-prop-(E)-ylidene]-amide (10.4 g, 32.78 mmol) in THF (150 mL) was added a 1 M solution of L-Selectride (33.0 mL, 33.0 mmol) in THF. The reaction was monitored by TLC (ethyl acetate-ether 3:7) indicating a single diastereomer (when compared to a mixture of diastereomers prepared by a reduction of 2-methyl-propane-2-sulfinic acid [1-(6-bromo-pyridin-3-yl)-prop-(E)-ylidene]-amide with lithium borohydride in THF). After 6 hours, the mixture was quenched with saturated aqueous ammonium chloride (100 mL) and extracted with ethyl acetate (3×100 mL). The combined organic layers were washed with saturated aqueous ammonium chloride (2×50 mL), brine (50 mL), dried over magnesium sulfate, filtered and concentrated. The crude material was purified by silica gel chromatography eluting with ether-dichloromethane (0:100, then 5:95, then 1:9, then 2:8). The material from the chromatography was triturated with ether to afford in two crops material which by $^1$H NMR is consistent with a single diastereomer however an impurity is present by TLC (ethyl acetate-ether 3:7). This material and the filtrate was purified by silica gel chromatography separately using ethyl acetate-dichloromethane (0:100, then 4:96, then 8:98, then 12:88, then 2:8, then 3:7, then 4:6). The material from the two purifications was combined and crystallized from dichloromethane-hexanes-ether to afford in 3 crops 2-methyl-propane-2-sulfinic acid [(S)-1-(6-bromo-pyridin-3-yl)-propyl]-amide.

Reacting 2-methyl-propane-2-sulfinic acid [1-(6-bromo-pyridin-3-yl)-but-(E)-ylidene]-amide according to the above method gave the following analog:
2-Methyl-propane-2-sulfinic acid [(S)-1-(6-bromo-pyridin-3-yl)-butyl]-amide.

To a mixture of 2-methyl-propane-2-sulfinic acid [(S)-1-(6-bromo-pyridin-3-yl)-propyl]-amide (5.35 g, 16.76 mmol) in methanol (25 mL) was added a solution of 4 N HCl in dioxane (10 mL, 40.0 mmol). The mixture was monitored by TLC (ethyl acetate-hexanes 3:7). After 2 hour, the mixture was concentrated to near dryness to afford a white solid. The solid was diluted with ether and collected by filtration to afford the title compound.

Reacting 2-methyl-propane-2-sulfinic acid [(S)-1-(6-bromo-pyridin-3-yl)-butyl]-amide according to the above method gave the following analog:
(S)-1-(6-Bromo-pyridin-3-yl)-butylamine.

Example 92

Synthesis of 1-(6-Bromo-pyridin-3-yl)-2,2,2-trifluoro-ethylamine (92)

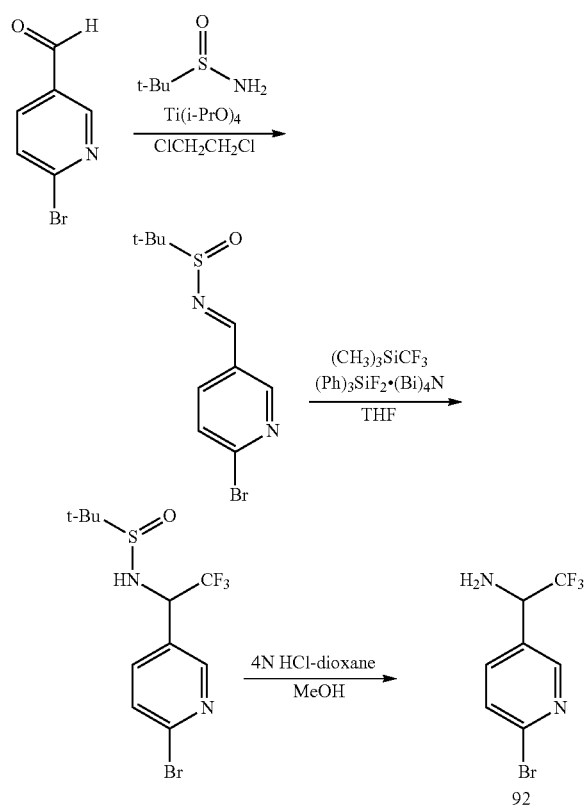

A mixture of 6-bromo-pyridine-3-carbaldehyde (1.0 g, 5.38 mmol), 2-methylpropane-2-sulfinamide (715 mg, 5.90 mmol) and titanium (IV) isopropoxide (2.5 mL, 8.53 mmol) in dichloroethane (10 mL) was warmed at 110° C. in the microwave for 15 minutes. The reaction was monitored by TLC (ethyl acetate-hexanes 2:8). The mixture was diluted with dichloromethane (100 mL) and water (5 mL) was added. The mixture was stirred for 10 minutes and then dried over magnesium sulfate. The crude material was purified by silica gel chromatography eluting with a gradient of 0-20% ethyl acetate in hexanes to afford 2-methyl-propane-2-sulfinic acid 1-(6-bromo-pyridin-3-yl)-meth-(E)-ylideneamide To a chilled (−20° C.) solution of 2-methyl-propane-2-sulfinic acid 1-(6-bromo-pyridin-3-yl)-meth-(E)-ylideneamide (1.25 g, 4.32 mmol) and tetrabutylammonium triphenyldifluorosilicate (2.6 g, 4.82 mmol) in THF (20 mL) was added a solution of trimethyl(trifluoromethyl)silane (1 g, 7.0 mmol) in THF (10 mL) in several portions. After 30 minutes, the mixture was warmed to room temperature. The reaction was monitored by TLC (ethyl acetate-hexanes 2:8). The mixture was diluted with saturated aqueous ammonium chloride (30 mL) and extracted with ethyl acetate (3×25 mL). The combined organic layers were washed with brine (2×20 mL), dried over sodium sulfate, filtered and concentrated. The crude residue was purified by silica gel chromatography eluting with a gradient of 0-20% ethyl acetate in hexanes. The material from the column was triturated with ether-hexanes to afford 2-methyl-propane-2-sulfinic acid [146-bromo-pyridin-3-yl)-2,2,2-trifluoro-ethyl]-amide.

To a solution of 2-methyl-propane-2-sulfinic acid [1-(6-bromo-pyridin-3-yl)-2,2,2-trifluoro-ethyl]-amide (1.17 g, 3.26 mmol) in methanol (15 mL) was added a 4 N solution of HCl in dioxane (2 mL, 8.0 mmol). The reaction was monitored by TLC (ethyl acetate-hexanes 3:7). The mixture was diluted with saturated aqueous potassium carbonate and extracted with ethyl acetate (3×25 mL). The combined organic layers were washed with brine (3×15 mL), dried over magnesium sulfate, filtered and concentrated. The crude material was purified by silica gel chromatography eluting with ethyl acetate-hexanes (1:9, then 2:8) to afford the title compound as a clear oil.

Example 93

Synthesis of (S)-1-(6-Methanesulfonyl-pyridin-3-yl)-propylamine hydrochloride (93)

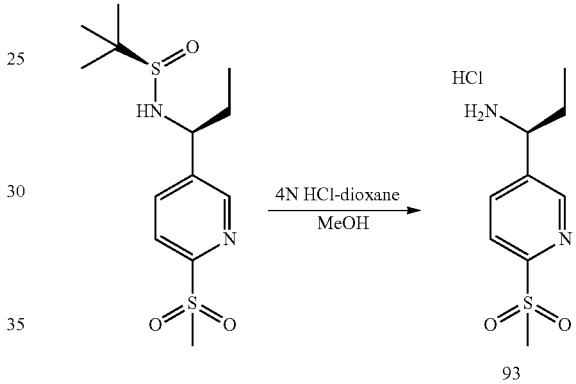

To a solution of 2-methyl-propane-2-sulfinic acid [(S)-1-(6-methanesulfonyl-pyridin-3-yl)-propyl]-amide (50.0 g, 157.0 mmol) in methanol (500 mL) was added a 4 N solution of HCl in dioxane (40.0 mL, 160.0 mmol). After 1 hour, the mixture was concentrated to near dryness (about 40 mL) and the resulting mixture was diluted with ether (500 mL) to afford the title compound.

Example 94

Synthesis of 1-(4-Fluorophenyl)-1H-pyrazolo[3,4-c]pyridine-4-carboxylic acid [(S)-1-(6-methanesulfonyl-pyridin-3-yl)-propyl]-amide (94)

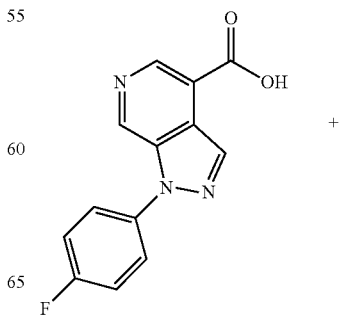

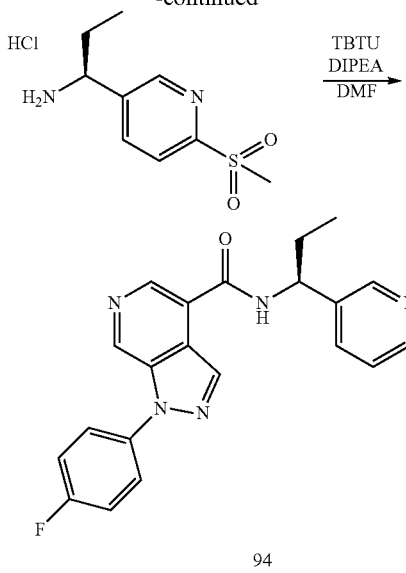

To a suspension of 1-(4-fluorophenyl)-1H-pyrazolo[3,4-c]pyridine-4-carboxylic acid (37.8 g, 146.9 mmol) in DMF (400 mL) was added DIPEA (50 mL, 287.0 mmol) followed by TBTU (49.5 g, 154.1 mmol). The mixture stirred for 1 hour, to afford a precipitate. To the mixture was added (S)-1-(6-methanesulfonyl-pyridin-3-yl)-propylamine hydrochloride (32.0 g, 127.6 mmol) followed by DIPEA (30 mL, 172.2 mmol). The mixture stirred overnight and was then poured into water (2.5 L) with sodium bicarbonate (50 g) added. The solid was collected by filtration washing with aqueous sodium carbonate (2 L) and then water (3 L). The solid was dried by pulling vacuum through the filter cake. The crude material was dissolved in dichloromethane and passed through a pad of silica gel (2000 mL funnel) using ethyl acetate-dichloromethane (1:9, then 2:8, then 100:0). The material from the pad was triturated with ether and the solid was collected by filtration. The solid was then dissolved in hot acetonitrile (1 L) and diluted with water (1 L). The product crystallized from the light yellow solution upon cooling overnight. The solid was collected by filtration washing with a 1:1 mixture of acetonitrile-water and then dried by pulling vacuum through the filter cake for 4 hours and then at 90° C. under house vacuum for approximately 11 hours (until a constant weight) to afford the title compound as a crystalline solid.

Example 95

Synthesis of 1-(4-Fluorophenyl)-1H-pyrazolo[3,4-c]pyridine-4-carboxylic acid {(S)-1-[2-(1-hydroxy-1-methyl-ethyl)-pyridin-4-yl]-propyl}-amide (95)

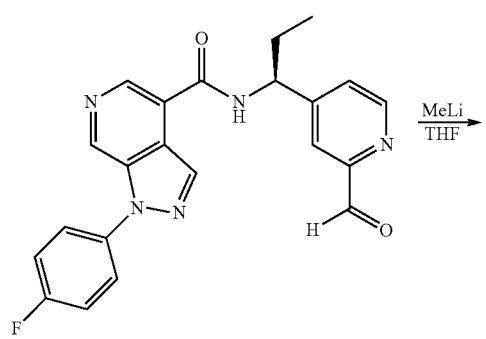

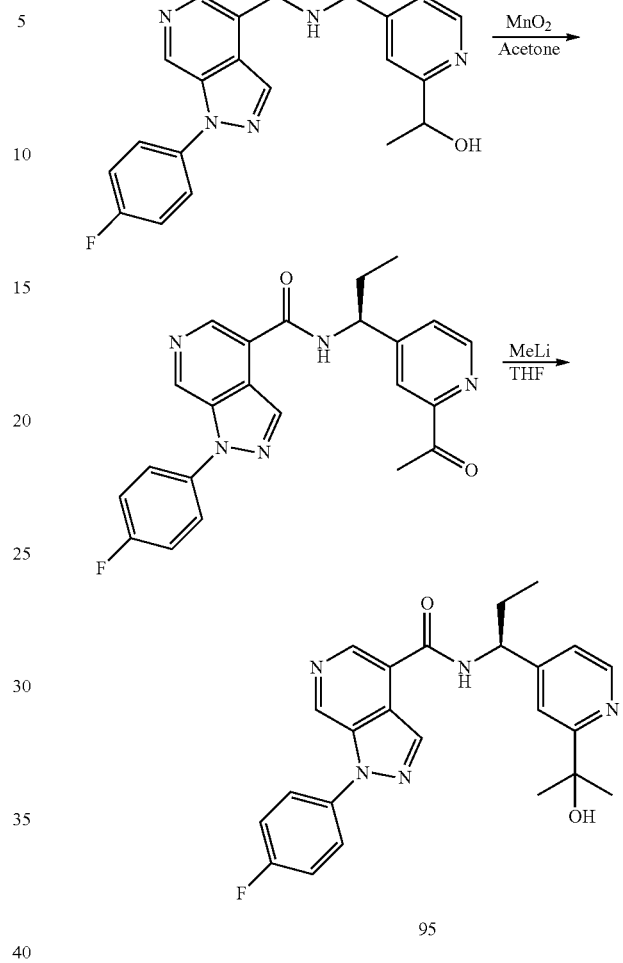

To a chilled (−78° C.) solution of 1-(4-fluorophenyl)-1H-pyrazolo[3,4-c]pyridine-4-carboxylic acid [(S)-1-(2-formyl-pyridin-4-yl)-propyl]-amide (368 mg, 0.91 mmol) in anhydrous THF (8 mL) was added a solution of 1.6 N methyl lithium (2.28 mL, 3.65 mmol) in diethyl ether and the mixture was slowly warmed to room temperature. After 3.5 hours, the reaction mixture was cooled to −78° C., quenched with saturated aqueous ammonium chloride and extracted with EtOAc (4×60 mL). The combined organic layers were washed with brine, dried over $Na_2SO_4$, and concentrated in vacuo. The residue was purified by silica gel chromatography eluting with a gradient of 0-10% MeOH in DCM to afford 1-(4-fluorophenyl)-1H-pyrazolo[3,4-c]pyridine-4-carboxylic acid {(S)-1-[2-(1-hydroxy-ethyl)-pyridin-4-yl]-propyl}-amide as a light yellow foam.

To a solution of 1-(4-fluorophenyl)-1H-pyrazolo[3,4-c]pyridine-4-carboxylic acid {(S)-1-[2-(1-hydroxy-ethyl)-pyridin-4-yl]-propyl}-amide (71 mg, 0.17 mmol) in acetone (4 mL) was added $MnO_2$ (147 mg, 1.69 mmol). After 18 hours, the reaction was monitored by HPLC-MS indicating a 1:3 mixture of product to starting material. The mixture was filtered through diatomaceous earth rinsing with acetone (200 mL) and the filtrate was concentrated in vacuo. The residue was diluted with acetone (4 mL) and $MnO_2$ (147 mg, 1.69 mmol) was added. After 5 hours, the reaction was filtered through diatomaceous earth, rinsed with acetone and the filtrate was concentrated in vacuo. The residue was purified by silica gel chromatography eluting with using a gradient of 10-100% EtOAc in heptane to afford 1-(4-fluorophenyl)-1H-pyrazolo[3,4-c]pyridine-4-carboxylic acid [(S)-1-(2-acetyl-pyridin-4-yl)-propyl]-amide as a white solid.

To a chilled (−78°) solution of 1-(4-fluorophenyl)-1H-pyrazolo[3,4-c]pyridine-4-carboxylic acid [(S)-1-(2-acetyl-pyridin-4-yl)-propyl]-amide (32 mg, 0.08 mmol) in anhydrous THF (2 mL) was added a solution of 1.6 N methyl lithium (0.29 mL, 0.46 mmol) in diethyl ether. The reaction mixture was slowly warmed to room temperature. After 18 hours, the mixture was cooled to −78° C., quenched with saturated aqueous ammonium chloride and extracted with EtOAc (4×60 mL). The combined organic layers were washed with brine, dried over sodium sulfate, and concentrated. The residue was purified by reversed-phase HPLC (Sunfire PrepC18 OBD 5 μM 30×150 mm column) using a gradient of 15-65% acetonitrile in water with 0.1% TFA. Fractions from the chromatography were concentrated, made basic by saturated aqueous NaHCO$_3$ solution and extracted with EtOAc. The organic layer was washed with brine, dried over Na$_2$SO$_4$, filtered, and concentrated. The solid was triturated with EtOAc-hexanes to afford the title.

Example 96

Synthesis of 1-Ethyl-1-(2-methanesulfonyl-thiazol-5-yl)-propylamine hydrochloride (96)

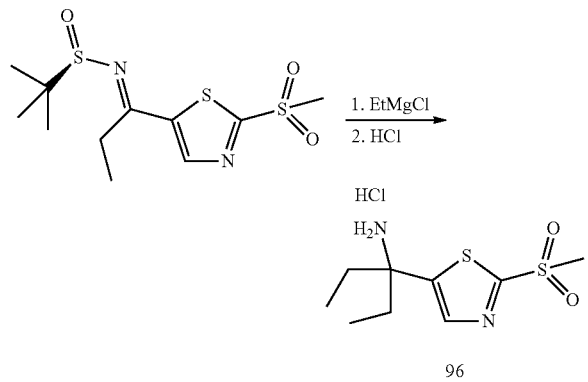

To a chilled (0° C.) solution of 2-methyl-propane-2-sulfinic acid [1-(2-methanesulfonyl-thiazol-5-yl)-prop-(Z)-ylidene]-amide (100 mg, 0.3 mmol) in THF (5 mL) was added a 2 M solution of ethylmagnesium chloride (0.19 mL, 0.38 mmol) in diethyl ether. After 2.5 hours, the reaction mixture was quenched with saturated aqueous ammonium chloride (10 mL) and extracted with EtOAc (2×10 mL). The combined organic layers were washed with brine (10 mL), dried over sodium sulfate, filtered and concentrated. The residue was purified by silica gel chromatography eluting with a gradient of 0-10% methanol in dichloromethane to yield an oil. The oil was dissolved in methanol (5 mL) and a 4 N solution of HCl in dioxane (0.5 mL, 2 mmol) was added. After 1 hour, the solution was concentrated to obtain the title compound.

The following compounds were prepared according to methods described in Example 96:

1-(2-Bromo-pyridin-4-yl)-1-methyl-ethylamine was prepared from 2-methyl-propane-2-sulfinic acid [1-(2-bromo-pyridin-4-yl)-eth-(E)-ylidene]-amide using methyl magnesium bromide as the Grignard reagent and toluene as solvent;

1-(2-Bromo-pyridin-4-yl)-1-methyl-propylamine was prepared from 2-methyl-propane-2-sulfinic acid [1-(2-bromo-pyridin-4-yl)-eth-(E)-ylidene]-amide using toluene as solvent; and 1-(2-Bromo-pyridin-4-yl)-1-ethyl-propylamine was prepared from 2-methyl-propane-2-sulfinic acid [1-(2-bromo-pyridin-4-yl)-prop-(E)-ylidene]-amide using toluene as solvent.

Assessment of Biological Properties

Compounds are assessed for the ability to block the interaction of CCR1 and MIP-1α in a functional cellular assay measuring calcium flux in CCR1 transfected cells.

Method A: Non-adherent cells purchased from Chemicon Corporation (HTS005C), stably expressing recombinant CCR1 and G-alpha-16 are grown in RPMI 1640 medium (Mediatech 10-080-CM) supplemented with 10% heat-inactivated FBS, 0.4 mg/mL Geneticin and penicillin/streptomycin. On the day of the assay, the cells are transferred to a beaker and dye-loaded in bulk using a Fluo-4 NW Calcium Assay Kit with probenecid (Invitrogen F36205) at 0.8E6 cells/mL for 1 hour at room temperature. After 1 hour, they are seeded in a 384-well tissue culture-treated plate at a density of 20,000 cells/well. Appropriately diluted test compound is added to the well to achieve a top concentration of 3,000 nM (diluted 4-fold with 10 doses total). The final concentration of DMSO is 1%. The buffer is HBSS (Invitrogen 14025) with 20 mM HEPES at pH 7.4. The cells are allowed to incubate 1 hour in the dark at room temperature. The plates are transferred to the FLIPR TETRA where MIP-1 alpha in 1% BSA is added at the EC80 final concentration. Wells +/−MIP-1 alpha containing diluted DMSO instead of compound serve as the controls. Intracellular calcium flux is recorded on the FLIPR TETRA, using excitation at 470/495 nm and emission at 515/575 nm. Data are analyzed using Activity Base software.

Method B: Non-adherent cells purchased from Chemicon Corporation (HTS005C), stably expressing recombinant CCR1 and G-alpha-16 are grown in RPMI 1640 medium (Mediatech 10-080-CM) supplemented with 10% FBS, 0.4 mg/mL Geneticin and penicillin/streptomycin. On the day of the assay, the cells are loaded with Calcium 4 dye (Molecular Devices R7448) with Probenecid (Invitrogen P346400) at 8E5 cells/mL for 1 hour at room temperature. After 1 hour, they are seeded in a 384-well tissue culture-treated plate at a density of 20,000 cells/well. Appropriately diluted test compound is added to the well to achieve a top concentration of 3,000 nM (diluted 4-fold with 10 doses total). The final concentration of DMSO is 1%. The buffer is HBSS (Invitrogen 14025) with 20 mM HEPES at pH 7.4. The cells incubate 30 minutes at 37 C. and then 30 minutes at room temperature. The plates are transferred to the HAMAMATSU FDSS6000 where MIP-1alpha in 1% BSA is added at the EC80 final concentration. All plates must be read within 4 hours of the start of dye-loading. Wells +/−MIP-1alpha containing diluted DMSO instead of compound serve as the controls. Data are analyzed using Activity Base software.

In general, the preferred potency range (IC$_{50}$) of compounds in one or both of the above assays is between 0.1 nM to 3 μM, and the most preferred potency range is 0.1 nM to 50 nM. Results from both assays were comparable as shown by selected compounds. Representative compounds of the invention have been tested in one or both of the above assay variations and have shown activity as CCR1 antagonists, this represents another embodiment of the invention.

TABLE II

| Name | Method A IC$_{50}$ (nM) | Method B IC$_{50}$ (nM) |
|---|---|---|
| 1-(4-Fluorophenyl)-1H-pyrazolo[3,4-c]pyridine-4-carboxylic acid 3-trifluoromethyl-benzylamide | 1 | |
| 1-(4-Fluorophenyl)-6-oxy-1H-pyrazolo[3,4-c]pyridine-4-carboxylic acid 3-trifluoromethyl-benzylamide | 6 | |
| 1-(4-Fluorophenyl)-1H-pyrazolo[3,4-c]pyridine-4-carboxylic acid (6-methanesulfonyl-pyridin-3-ylmethyl)-amide | 26 | |
| 1-(4-Fluorophenyl)-1H-pyrazolo[3,4-c]pyridine-4-carboxylic acid 3-methanesulfonyl-benzylamide | 7 | |
| 1-(4-Fluorophenyl)-1H-pyrazolo[3,4-c]pyridine-4-carboxylic acid 2-chloro-4-methylsulfamoyl-benzylamide | 0.2 | |
| 1-(4-Fluorophenyl)-1H-pyrazolo[3,4-c]pyridine-4-carboxylic acid 4-methylsulfamoyl-benzylamide | 1 | |
| 1-(4-Fluorophenyl)-1H-pyrazolo[3,4-c]pyridine-4-carboxylic acid 4-methanesulfonyl-benzylamide | 14 | |
| 1-(4-Fluorophenyl)-1H-pyrazolo[3,4-c]pyridine-4-carboxylic acid 4-(isopropylsulfamoyl-methyl)-benzylamide | 3 | |
| 1-(4-Fluorophenyl)-1H-pyrazolo[3,4-c]pyridine-4-carboxylic acid (6-methanesulfonylamino-pyridin-3-ylmethyl)-amide | 25 | |
| 1-(4-Fluorophenyl)-1H-pyrazolo[3,4-c]pyridine-4-carboxylic acid (6-ethanesulfonyl-pyridin-3-ylmethyl)-amide | 31 | |
| 1-(4-Fluorophenyl)-1H-pyrazolo[3,4-c]pyridine-4-carboxylic acid (5-bromopyridin-3-ylmethyl)-amide | 13 | |
| 1-(4-Fluorophenyl)-1H-pyrazolo[3,4-c]pyridine-4-carboxylic acid 4-(piperidine-1-sulfonylmethyl)-benzylamide | 6 | |
| 1-(4-Fluorophenyl)-1H-pyrazolo[3,4-c]pyridine-4-carboxylic acid 4-(morpholine-4-sulfonylmethyl)-benzylamide | 20 | |
| 1-(4-Fluorophenyl)-1H-pyrazolo[3,4-c]pyridine-4-carboxylic acid 4-cyclohexylsulfamoylmethyl-benzylamide | 11 | |
| 1-(4-Fluorophenyl)-1H-pyrazolo[3,4-c]pyridine-4-carboxylic acid 4-(4-methyl-piperazine-1-sulfonylmethyl)-benzylamide | 39 | |
| 1-(4-Fluorophenyl)-1H-pyrazolo[3,4-c]pyridine-4-carboxylic acid 4-(4-methyl-piperazine-1-sulfonyl)-benzylamide | 1 | |
| 1-(4-Fluorophenyl)-1H-pyrazolo[3,4-c]pyridine-4-carboxylic acid 4-(morpholine-4-sulfonyl)-benzylamide | 2 | |
| 1-(4-Fluorophenyl)-1H-pyrazolo[3,4-c]pyridine-4-carboxylic acid 3,5-dichloro-benzylamide | 7 | |
| 1-(4-Fluorophenyl)-1H-pyrazolo[3,4-c]pyridine-4-carboxylic acid 4-[(2-hydroxy-ethyl)-methyl-sulfamoyl]-benzylamide | 1 | |
| [4-({[1-(4-Fluorophenyl)-1H-pyrazolo[3,4-c]pyridine-4-carbonyl]-amino}-methyl)-benzenesulfonylamino]-acetic acid methyl ester | 3 | |
| 1-(4-Fluorophenyl)-1H-pyrazolo[3,4-c]pyridine-4-carboxylic acid (2-methoxy-pyridin-4-ylmethyl)-amide | 2 | |
| 1-(4-Fluorophenyl)-1H-pyrazolo[3,4-c]pyridine-4-carboxylic acid (2-bromopyridin-4-ylmethyl)-amide | 2 | |
| 1-(4-Fluorophenyl)-1H-pyrazolo[3,4-c]pyridine-4-carboxylic acid (2-methanesulfonyl-pyridin-4-ylmethyl)-amide | 7 | 5 |
| 1-(4-Fluorophenyl)-1H-pyrazolo[3,4-c]pyridine-4-carboxylic acid (2-ethanesulfonyl-pyridin-4-ylmethyl)-amide | 19 | |
| 1-(4-Fluorophenyl)-1H-pyrazolo[3,4-c]pyridine-4-carboxylic acid (2-cyclopropanesulfonyl-pyridin-4-ylmethyl)-amide | 41 | |
| Acetic acid 2-{[4-({[1-(4-fluorophenyl)-1H-pyrazolo[3,4-c]pyridine-4-carbonyl]-amino}-methyl)-benzenesulfonyl]-methyl-amino}-ethyl ester | 2 | |
| 1-(4-Fluorophenyl)-1H-pyrazolo[3,4-c]pyridine-4-carboxylic acid 4-(carbamoylmethyl-sulfamoyl)-benzylamide | 22 | |
| 1-(4-Fluorophenyl)-1H-pyrazolo[3,4-c]pyridine-4-carboxylic acid 4-[methyl-(1-methyl-piperidin-4-yl)-sulfamoyl]-benzylamide | 5 | |
| 1-(4-Fluorophenyl)-1H-pyrazolo[3,4-c]pyridine-4-carboxylic acid [6-(methanesulfonyl-methyl-amino)-pyridin-3-ylmethyl]-amide | 5 | |
| 1-(4-Fluorophenyl)-1H-pyrazolo[3,4-c]pyridine-4-carboxylic acid [6-(dimethylamino-sulfonylamino)-pyridin-3-ylmethyl]-amide | 24 | |

TABLE II-continued

| Name | Method A IC$_{50}$ (nM) | Method B IC$_{50}$ (nM) |
|---|---|---|
| 1-(4-Fluorophenyl)-1H-pyrazolo[3,4-c]pyridine-4-carboxylic acid 4-(2-hydroxy-ethylsulfamoyl)-benzylamide | 1 | |
| 1-(4-Fluorophenyl)-1H-pyrazolo[3,4-c]pyridine-4-carboxylic acid 4-(3-oxo-piperazine-1-sulfonyl)-benzylamide | 3 | |
| 1-(4-Fluorophenyl)-1H-pyrazolo[3,4-c]pyridine-4-carboxylic acid 3,5-bis-trifluoromethyl-benzylamide | 3 | |
| 1-(4-Fluorophenyl)-1H-pyrazolo[3,4-c]pyridine-4-carboxylic acid 3-methanesulfonyl-5-trifluoromethyl-benzylamide | 1 | |
| 1-(4-Fluorophenyl)-1H-pyrazolo[3,4-c]pyridine-4-carboxylic acid {6-[(2-dimethylamino-ethyl)-methanesulfonyl-amino]-pyridin-3-ylmethyl}-amide | 22 | |
| 1-(4-Fluorophenyl)-1H-pyrazolo[3,4-c]pyridine-4-carboxylic acid [6-(2-methoxy-ethylsulfamoyl)-pyridin-3-ylmethyl]-amide | 9 | |
| 1-(4-Fluorophenyl)-1H-pyrazolo[3,4-c]pyridine-4-carboxylic acid [6-(tetrahydropyran-4-ylsulfamoyl)-pyridin-3-ylmethyl]-amide | 17 | |
| 1-(4-Fluorophenyl)-1H-pyrazolo[3,4-c]pyridine-4-carboxylic acid 4-{[methyl-(1-methyl-piperidin-4-yl)-sulfamoyl]-methyl}-benzylamide | 33 | |
| 1-(4-Fluorophenyl)-1H-pyrazolo[3,4-c]pyridine-4-carboxylic acid (6-dimethylsulfamoyl-pyridin-3-ylmethyl)-amide | 1 | |
| 1-(4-Fluorophenyl)-1H-pyrazolo[3,4-c]pyridine-4-carboxylic acid {6-[methanesulfonyl-(2-methoxy-ethyl)-amino]-pyridin-3-ylmethyl}-amide | 1 | |
| 1-(4-Fluorophenyl)-1H-pyrazolo[3,4-c]pyridine-4-carboxylic acid [6-(dimethylamino-sulfonylmethylamino)-pyridin-3-ylmethyl]-amide | 1 | |
| 1-(4-Fluorophenyl)-1H-pyrazolo[3,4-c]pyridine-4-carboxylic acid (2-sulfamoyl-pyridin-4-ylmethyl)-amide | 13 | |
| 1-(4-Fluorophenyl)-1H-pyrazolo[3,4-c]pyridine-4-carboxylic acid 4-(4-dimethylamino-piperidine-1-sulfonyl)-benzylamide | 3 | |
| 1-(4-Fluorophenyl)-1H-pyrazolo[3,4-c]pyridine-4-carboxylic acid 4-(methyl-piperidin-4-yl-sulfamoyl)-benzylamide | 2 | |
| 1-(4-Fluorophenyl)-1H-pyrazolo[3,4-c]pyridine-4-carboxylic acid 4-(4-amino-piperidine-1-sulfonyl)-benzylamide | 0.3 | |
| 1-(4-Fluorophenyl)-1H-pyrazolo[3,4-c]pyridine-4-carboxylic acid (6-methanesulfonyl-pyridin-2-ylmethyl)-amide | 39 | |
| 1-(4-Fluorophenyl)-1H-pyrazolo[3,4-c]pyridine-4-carboxylic acid 4-(2-hydroxy-1-methyl-ethylsulfamoyl)-benzylamide | 2 | |
| 1-(4-Fluorophenyl)-1H-pyrazolo[3,4-c]pyridine-4-carboxylic acid 4-methanesulfonyl-2-methoxy-benzylamide | 10 | |
| 1-(4-Fluorophenyl)-1H-pyrazolo[3,4-c]pyridine-4-carboxylic acid 4-methanesulfonyl-3-methoxy-benzylamide | 4 | |
| 1-(4-Fluorophenyl)-1H-pyrazolo[3,4-c]pyridine-4-carboxylic acid [6-(morpholine-4-sulfonyl)-pyridin-3-ylmethyl]-amide | 18 | |
| 1-(4-Fluorophenyl)-1H-pyrazolo[3,4-c]pyridine-4-carboxylic acid 4-(4-methoxy-piperidine-1-sulfonyl)-benzylamide | 0.7 | |
| 1-(4-Fluorophenyl)-1H-pyrazolo[3,4-c]pyridine-4-carboxylic acid [1-(6-methanesulfonyl-pyridin-3-yl)-butyl]-amide | 0.8 | |
| 1-(4-Fluorophenyl)-1H-pyrazolo[3,4-c]pyridine-4-carboxylic acid 4-(3-hydroxy-pyrrolidine-1-sulfonyl)-benzylamide | 0.9 | |
| 1-(4-Fluorophenyl)-1H-pyrazolo[3,4-c]pyridine-4-carboxylic acid 4-(4-hydroxy-piperidine-1-sulfonyl)-benzylamide | 2 | |
| 1-(4-Fluorophenyl)-1H-pyrazolo[3,4-c]pyridine-4-carboxylic acid 3-hydroxy-4-methanesulfonyl-benzylamide | 24 | |
| 1-(4-Fluorophenyl)-1H-pyrazolo[3,4-c]pyridine-4-carboxylic acid 4-[methyl-(tetrahydropyran-4-yl)-sulfamoyl]-benzylamide | 2 | |
| 1-(4-Fluorophenyl)-1H-pyrazolo[3,4-c]pyridine-4-carboxylic acid 4-(2-hydroxy-propylsulfamoyl)-benzylamide | 2 | |
| 1-(4-Fluorophenyl)-1H-pyrazolo[3,4-c]pyridine-4-carboxylic acid 4-methanesulfonylamino-benzylamide | 7 | |

TABLE II-continued

| Name | Method A IC$_{50}$ (nM) | Method B IC$_{50}$ (nM) |
| --- | --- | --- |
| 1-(4-Fluorophenyl)-1H-pyrazolo[3,4-c]pyridine-4-carboxylic acid 3-methoxy-4-methylsulfamoyl-benzylamide | 3 | |
| 1-(4-Fluorophenyl)-1H-pyrazolo[3,4-c]pyridine-4-carboxylic acid [1-(2-bromopyridin-4-yl)-butyl]-amide | 0.4 | |
| 1-(4-Fluorophenyl)-1H-pyrazolo[3,4-c]pyridine-4-carboxylic acid [6-(1,1-dioxo-1λ6-perhydro-1,2-thiazin-2-yl)-pyridin-3-ylmethyl]-amide | 9 | |
| 1-(4-Fluorophenyl)-1H-pyrazolo[3,4-c]pyridine-4-carboxylic acid 4-methoxy-3-methylsulfamoyl-benzylamide | 12 | |
| 1-(4-Fluorophenyl)-1H-pyrazolo[3,4-c]pyridine-4-carboxylic acid [1-(2-methanesulfonyl-pyridin-4-yl)-butyl]-amide | 0.3 | |
| 1-(4-Fluorophenyl)-1H-pyrazolo[3,4-c]pyridine-4-carboxylic acid [1-(2-ethanesulfonyl-pyridin-4-yl)-butyl]-amide | 0.8 | |
| 1-(4-Fluorophenyl)-1H-pyrazolo[3,4-c]pyridine-4-carboxylic acid 3-fluoro-4-methylsulfamoyl-benzylamide | 1 | |
| 1-(4-Chlorophenyl)-1H-pyrazolo[3,4-c]pyridine-4-carboxylic acid (6-methanesulfonyl-pyridin-3-ylmethyl)-amide | 34 | |
| 1-(4-Chlorophenyl)-1H-pyrazolo[3,4-c]pyridine-4-carboxylic acid {6-[methanesulfonyl-(2-methoxy-ethyl)-amino]-pyridin-3-ylmethyl}-amide | 5 | |
| 1-(4-Chlorophenyl)-1H-pyrazolo[3,4-c]pyridine-4-carboxylic acid [1-(6-methanesulfonyl-pyridin-3-yl)-butyl]-amide | 1 | |
| 1-(4-Chlorophenyl)-1H-pyrazolo[3,4-c]pyridine-4-carboxylic acid 4-(3-hydroxy-pyrrolidine-1-sulfonyl)-benzylamide | 2 | |
| 1-(4-Chlorophenyl)-1H-pyrazolo[3,4-c]pyridine-4-carboxylic acid 3-methanesulfonyl-benzylamide | 7 | |
| 1-(4-Chlorophenyl)-1H-pyrazolo[3,4-c]pyridine-4-carboxylic acid [6-(morpholine-4-sulfonyl)-pyridin-3-ylmethyl]-amide | 3 | |
| 1-(4-Fluorophenyl)-1H-pyrazolo[3,4-c]pyridine-4-carboxylic acid [1-(5-bromopyridin-3-yl)-butyl]-amide | 0.4 | |
| 1-(4-Fluorophenyl)-1H-pyrazolo[3,4-c]pyridine-4-carboxylic acid [(S)-1-(5-bromopyridin-3-yl)-propyl]-amide | 0.2 | |
| 1-(4-Chlorophenyl)-1H-pyrazolo[3,4-c]pyridine-4-carboxylic acid [1-(2-bromopyridin-4-yl)-butyl]-amide | 2 | |
| 1-(4-Chlorophenyl)-1H-pyrazolo[3,4-c]pyridine-4-carboxylic acid [1-(2-methanesulfonyl-pyridin-4-yl)-butyl]-amide | 0.4 | |
| 1-(4-Fluorophenyl)-1H-pyrazolo[3,4-c]pyridine-4-carboxylic acid 4-((R)-2-hydroxy-1-methyl-ethylsulfamoyl)-benzylamide | 2 | |
| 1-(4-Fluorophenyl)-1H-pyrazolo[3,4-c]pyridine-4-carboxylic acid 4-((S)-2-hydroxy-1-methyl-ethylsulfamoyl)-benzylamide | 2 | |
| 1-(4-Fluorophenyl)-1H-pyrazolo[3,4-c]pyridine-4-carboxylic acid 4-(2-hydroxy-1,1-dimethyl-ethylsulfamoyl)-benzylamide | 0.9 | |
| 1-(4-Fluorophenyl)-1H-pyrazolo[3,4-c]pyridine-4-carboxylic acid [1-(5-methanesulfonyl-pyridin-3-yl)-butyl]-amide | 0.6 | |
| 1-(4-Fluorophenyl)-1H-pyrazolo[3,4-c]pyridine-4-carboxylic acid [1-(6-methanesulfonyl-pyridin-3-yl)-propyl]-amide | 3 | |
| 3-[5-(1-{[1-(4-Fluorophenyl)-1H-pyrazolo[3,4-c]pyridine-4-carbonyl]-amino}-butyl)-pyridine-3-sulfonyl]-propionic acid methyl ester | 3 | |
| 1-(4-Fluorophenyl)-1H-pyrazolo[3,4-c]pyridine-4-carboxylic acid [(S)-1-(5-methanesulfonyl-pyridin-3-yl)-propyl]-amide | 0.5 | 0.2 |
| 1-(4-Fluorophenyl)-1H-pyrazolo[3,4-c]pyridine-4-carboxylic acid [1-(5-methylsulfamoyl-pyridin-3-yl)-butyl]-amide | 0.5 | |
| 1-(4-Fluorophenyl)-1H-pyrazolo[3,4-c]pyridine-4-carboxylic acid [1-(5-sulfamoyl-pyridin-3-yl)-butyl]-amide | 0.4 | |
| 1-(4-Fluorophenyl)-1H-pyrazolo[3,4-c]pyridine-4-carboxylic acid [1-(2-bromopyridin-4-yl)-propyl]-amide | 0.4 | |
| 1-(4-Chlorophenyl)-1H-pyrazolo[3,4-c]pyridine-4-carboxylic acid [(S)-1-(5-bromopyridin-3-yl)-ethyl]-amide | 2 | |
| 1-(4-Chlorophenyl)-1H-pyrazolo[3,4-c]pyridine-4-carboxylic acid [(S)-1-(5-bromopyridin-3-yl)-propyl]-amide | 0.6 | |

TABLE II-continued

| Name | Method A IC$_{50}$ (nM) | Method B IC$_{50}$ (nM) |
|---|---|---|
| 1-(4-Chlorophenyl)-1H-pyrazolo[3,4-c]pyridine-4-carboxylic acid [(S)-1-(5-methanesulfonyl-pyridin-3-yl)-ethyl]-amide | 4 | |
| 1-(4-Chlorophenyl)-1H-pyrazolo[3,4-c]pyridine-4-carboxylic acid [(S)-1-(5-methanesulfonyl-pyridin-3-yl)-propyl]-amide | 0.4 | |
| 1-(4-Fluorophenyl)-1H-pyrazolo[3,4-c]pyridine-4-carboxylic acid [(S)-1-(5-bromopyridin-3-yl)-ethyl]-amide | 1 | |
| 1-(4-Fluorophenyl)-1H-pyrazolo[3,4-c]pyridine-4-carboxylic acid [1-(6-methanesulfonyl-pyridin-3-yl)-ethyl]-amide | 9 | |
| 1-(4-Fluorophenyl)-1H-pyrazolo[3,4-c]pyridine-4-carboxylic acid [1-(6-bromopyridin-3-yl)-ethyl]-amide | 30 | |
| 1-(4-Fluorophenyl)-1H-pyrazolo[3,4-c]pyridine-4-carboxylic acid [(S)-1-(5-methanesulfonyl-pyridin-3-yl)-ethyl]-amide | 3 | |
| 1-(4-Fluorophenyl)-1H-pyrazolo[3,4-c]pyridine-4-carboxylic acid [1-(2-methanesulfonyl-pyridin-4-yl)-propyl]-amide | 0.2 | |
| 1-(4-Fluorophenyl)-1H-pyrazolo[3,4-c]pyridine-4-carboxylic acid [(R)-1-(2-bromopyridin-4-yl)-but-3-enyl]-amide | 17 | |
| 1-(4-Fluorophenyl)-1H-pyrazolo[3,4-c]pyridine-4-carboxylic acid [(R)-1-(2-methanesulfonyl-pyridin-4-yl)-but-3-enyl]-amide | 1 | |
| 1-(4-Fluorophenyl)-1H-pyrazolo[3,4-c]pyridine-4-carboxylic acid [(S)-1-(6-bromopyridin-2-yl)-ethyl]-amide | 5 | |
| 1-(4-Fluorophenyl)-1H-pyrazolo[3,4-c]pyridine-4-carboxylic acid [(S)-1-(5-bromopyridin-3-yl)-butyl]-amide | 0.2 | |
| 1-(4-Fluorophenyl)-1H-pyrazolo[3,4-c]pyridine-4-carboxylic acid [(S)-1-(5-methanesulfonyl-pyridin-3-yl)-butyl]-amide | 0.3 | |
| 1-(4-Fluorophenyl)-1H-pyrazolo[3,4-c]pyridine-4-carboxylic acid ((S)-1-pyridin-3-yl-butyl)-amide | 5 | |
| 3-[5-((S)-1-{[1-(4-Fluorophenyl)-1H-pyrazolo[3,4-c]pyridine-4-carbonyl]-amino}-butyl)-pyridine-3-sulfonyl]-propionic acid methyl ester | 2 | |
| 3-[5-((S)-1-{[1-(4-Fluorophenyl)-1H-pyrazolo[3,4-c]pyridine-4-carbonyl]-amino}-butyl)-pyridine-3-sulfonyl]-propionic acid | 17 | |
| 1-(4-Fluorophenyl)-1H-pyrazolo[3,4-c]pyridine-4-carboxylic acid [(S)-1-(6-methanesulfonyl-pyridin-2-yl)-ethyl]-amide | 6 | |
| 1-(4-Fluorophenyl)-1H-pyrazolo[3,4-c]pyridine-4-carboxylic acid [(S)-1-(2-methanesulfonyl-pyridin-4-yl)-butyl]-amide | 0.2 | 0.1 |
| 1-(4-Fluorophenyl)-1H-pyrazolo[3,4-c]pyridine-4-carboxylic acid [1-(2-bromopyridin-4-yl)-ethyl]-amide | 1 | |
| 5-((S)-1-{[1-(4-Fluorophenyl)-1H-pyrazolo[3,4-c]pyridine-4-carbonyl]-amino}-butyl)-pyridine-3-sulfonic acid | 4 | |
| 1-(4-Fluorophenyl)-1H-pyrazolo[3,4-c]pyridine-4-carboxylic acid [(S)-1-(5-methylsulfamoyl-pyridin-3-yl)-butyl]-amide | 0.2 | |
| 1-(4-Fluorophenyl)-1H-pyrazolo[3,4-c]pyridine-4-carboxylic acid [(S)-1-(5-sulfamoyl-pyridin-3-yl)-butyl]-amide | 0.3 | |
| 1-(4-Fluorophenyl)-1H-pyrazolo[3,4-c]pyridine-4-carboxylic acid [(S)-1-(2-bromopyridin-4-yl)-but-3-enyl]-amide | 0.3 | |
| 1-(4-Fluorophenyl)-1H-pyrazolo[3,4-c]pyridine-4-carboxylic acid [(S)-1-(6-methanesulfonyl-pyridin-3-yl)-ethyl]-amide | 9 | 3 |
| 1-(4-Fluorophenyl)-1H-pyrazolo[3,4-c]pyridine-4-carboxylic acid [(S)-1-(5-ethanesulfonyl-pyridin-3-yl)-propyl]-amide | 0.4 | 0.3 |
| 1-(4-Fluorophenyl)-1H-pyrazolo[3,4-c]pyridine-4-carboxylic acid [(S)-1-(5-sulfamoyl-pyridin-3-yl)-ethyl]-amide | 2 | 0.9 |
| 1-(4-Fluorophenyl)-1H-pyrazolo[3,4-c]pyridine-4-carboxylic acid [1-(2-methanesulfonyl-pyridin-4-yl)-ethyl]-amide | 2 | 1 |
| 1-(4-Fluorophenyl)-1H-pyrazolo[3,4-c]pyridine-4-carboxylic acid 4-((R)-2-hydroxy-propylsulfamoyl)-benzylamide | 2 | 1 |
| 1-(4-Fluorophenyl)-1H-pyrazolo[3,4-c]pyridine-4-carboxylic acid 4-((S)-2-hydroxy-propylsulfamoyl)-benzylamide | 1 | 0.8 |

TABLE II-continued

| Name | Method A IC$_{50}$ (nM) | Method B IC$_{50}$ (nM) |
|---|---|---|
| 1-(4-Fluorophenyl)-1H-pyrazolo[3,4-c]pyridine-4-carboxylic acid ((S)-1-pyridin-3-yl-propyl)-amide | 15 | 8 |
| 3-[5-((S)-1-{[1-(4-Fluorophenyl)-1H-pyrazolo[3,4-c]pyridine-4-carbonyl]-amino}-propyl)-pyridine-3-sulfonyl]-propionic acid | 35 | 14 |
| 3-[5-((S)-1-{[1-(4-Fluorophenyl)-1H-pyrazolo[3,4-c]pyridine-4-carbonyl]-amino}-propyl)-pyridine-3-sulfonyl]-propionic acid methyl ester | | 6.3 |
| 1-(4-Fluorophenyl)-1H-pyrazolo[3,4-c]pyridine-4-carboxylic acid [(S)-1-(2-ethanesulfonyl-pyridin-4-yl)-but-3-enyl]-amide | 0.6 | 0.4 |
| 1-(4-Fluorophenyl)-1H-pyrazolo[3,4-c]pyridine-4-carboxylic acid ((S)-1-pyridin-4-yl-but-3-enyl)-amide | | 32 |
| 1-(4-Fluorophenyl)-1H-pyrazolo[3,4-c]pyridine-4-carboxylic acid [(S)-1-(2-ethanesulfonyl-pyridin-4-yl)-butyl]-amide | | 0.1 |
| 1-(4-Fluorophenyl)-1H-pyrazolo[3,4-c]pyridine-4-carboxylic acid [(S)-1-(5-sulfamoyl-pyridin-3-yl)-propyl]-amide | | 0.3 |
| 3-[6-((S)-1-{[1-(4-Fluorophenyl)-1H-pyrazolo[3,4-c]pyridine-4-carbonyl]-amino}-ethyl)-pyridine-2-sulfonyl]-propionic acid methyl ester | | 35 |
| 1-(4-Fluorophenyl)-1H-pyrazolo[3,4-c]pyridine-4-carboxylic acid [(S)-1-(6-methanesulfonyl-pyridin-3-yl)-propyl]-amide | | 1 |
| 1-(4-Fluorophenyl)-1H-pyrazolo[3,4-c]pyridine-4-carboxylic acid [(S)-1-(5-ethanesulfonyl-pyridin-3-yl)-ethyl]-amide | | 4 |
| 1-(4-Fluorophenyl)-1H-pyrazolo[3,4-c]pyridine-4-carboxylic acid [(S)-1-(2-methanesulfonyl-pyridin-4-yl)-propyl]-amide | | 0.2 |
| 1-(4-Fluorophenyl)-1H-pyrazolo[3,4-c]pyridine-4-carboxylic acid [(S)-1-(2-ethanesulfonyl-pyridin-4-yl)-propyl]-amide | | 0.2 |
| 1-(4-Fluorophenyl)-1H-pyrazolo[3,4-c]pyridine-4-carboxylic acid [(S)-1-(6-sulfamoyl-pyridin-2-yl)-ethyl]-amide | | 15 |
| 1-(4-Fluorophenyl)-1H-pyrazolo[3,4-c]pyridine-4-carboxylic acid [(S)-1-(2-chloropyridin-4-yl)-propyl]-amide | | 0.2 |
| 3-[4-((S)-1-{[1-(4-Fluorophenyl)-1H-pyrazolo[3,4-c]pyridine-4-carbonyl]-amino}-propyl)-pyridine-2-sulfonyl]-propionic acid methyl ester | | 1 |
| 1-(4-Fluorophenyl)-1H-pyrazolo[3,4-c]pyridine-4-carboxylic acid [(S)-1-(2-bromopyridin-4-yl)-ethyl]-amide | | 0.4 |
| 1-(4-Fluorophenyl)-1H-pyrazolo[3,4-c]pyridine-4-carboxylic acid [(S)-1-(2-methanesulfonyl-pyridin-4-yl)-ethyl]-amide | | 0.9 |
| 3-[4-((S)-1-{[1-(4-Fluorophenyl)-1H-pyrazolo[3,4-c]pyridine-4-carbonyl]-amino}-ethyl)-pyridine-2-sulfonyl]-propionic acid methyl ester | | 37 |
| 1-(4-Fluorophenyl)-1H-pyrazolo[3,4-c]pyridine-4-carboxylic acid [(S)-1-(6-methanesulfonyl-pyridin-3-yl)-butyl]-amide | | 0.4 |
| 1-(4-Fluorophenyl)-1H-pyrazolo[3,4-c]pyridine-4-carboxylic acid [(S)-1-(2-cyano-pyridin-4-yl)-propyl]-amide | | 0.3 |
| 1-(4-Fluorophenyl)-1H-pyrazolo[3,4-c]pyridine-4-carboxylic acid [(S)-1-(3-bromo-4-methoxy-phenyl)-propyl]-amide | | 7 |
| 1-(4-Fluorophenyl)-1H-pyrazolo[3,4-c]pyridine-4-carboxylic acid [(S)-1-(2-carbamoyl-pyridin-4-yl)-propyl]-amide | | 1 |
| 4-((S)-1-{[1-(4-Fluorophenyl)-1H-pyrazolo[3,4-c]pyridine-4-carbonyl]-amino}-propyl)-pyridine-2-carboxylic acid | | 12 |
| 1-(4-Fluorophenyl)-1H-pyrazolo[3,4-c]pyridine-4-carboxylic acid [(R)-1-(3-bromo-4-methoxy-phenyl)-propyl]-amide | | 0.2 |
| 1-(4-Fluorophenyl)-1H-pyrazolo[3,4-c]pyridine-4-carboxylic acid [(R)-1-(3-methanesulfonyl-4-methoxy-phenyl)-propyl]-amide | | 0.2 |
| 1-(4-Fluorophenyl)-1H-pyrazolo[3,4-c]pyridine-4-carboxylic acid [(S)-1-(3-methanesulfonyl-4-methoxy-phenyl)-propyl]-amide | | 6 |
| 1-(4-Fluorophenyl)-1H-pyrazolo[3,4-c]pyridine-4-carboxylic acid [(S)-1-(6-ethanesulfonyl-pyridin-3-yl)-propyl]-amide | | 0.3 |

TABLE II-continued

| Name | Method A IC$_{50}$ (nM) | Method B IC$_{50}$ (nM) |
| --- | --- | --- |
| 1-(4-Fluorophenyl)-1H-pyrazolo[3,4-c]pyridine-4-carboxylic acid [(R)-1-(3-bromo-4-methoxy-phenyl)-butyl]-amide | | 0.3 |
| 1-(4-Fluorophenyl)-1H-pyrazolo[3,4-c]pyridine-4-carboxylic acid [(R)-1-(3-methanesulfonyl-4-methoxy-phenyl)-butyl]-amide | | 0.2 |
| 1-(4-Fluorophenyl)-1H-pyrazolo[3,4-c]pyridine-4-carboxylic acid [(S)-1-(6-ethanesulfonyl-pyridin-2-yl)-ethyl]-amide | | 14 |
| 1-(4-Fluorophenyl)-1H-pyrazolo[3,4-c]pyridine-4-carboxylic acid [(R)-1-(4-hydroxy-3-methanesulfonyl-phenyl)-butyl]-amide | | 0.2 |
| 1-(4-Fluorophenyl)-1H-pyrazolo[3,4-c]pyridine-4-carboxylic acid [(S)-1-(2-sulfamoyl-pyridin-4-yl)-propyl]-amide | | 0.4 |
| 1-(4-Fluorophenyl)-1H-pyrazolo[3,4-c]pyridine-4-carboxylic acid 4-(2-hydroxy-2-methyl-propylsulfamoyl)-benzylamide | | 1 |
| [4-({[1-(4-Fluorophenyl)-1H-pyrazolo[3,4-c]pyridine-4-carbonyl]-amino}-methyl)-pyridine-2-sulfonyl]-acetic acid ethyl ester | | 4 |
| 1-(4-Fluorophenyl)-1H-pyrazolo[3,4-c]pyridine-4-carboxylic acid [(S)-1-(2-methylamino-pyridin-4-yl)-propyl]-amide | | 4 |
| 1-(4-Fluorophenyl)-1H-pyrazolo[3,4-c]pyridine-4-carboxylic acid [(S)-1-(2-ethanesulfonyl-pyridin-4-yl)-ethyl]-amide | | 2 |
| 1-(4-Fluorophenyl)-1H-pyrazolo[3,4-c]pyridine-4-carboxylic acid [(S)-1-(2-sulfamoyl-pyridin-4-yl)-ethyl]-amide | | 3 |
| 1-(4-Fluorophenyl)-1H-pyrazolo[3,4-c]pyridine-4-carboxylic acid {(S)-1-[2-(acetyl-methyl-amino)-pyridin-4-yl]-propyl}-amide | | 5 |
| 1-(4-Fluorophenyl)-1H-pyrazolo[3,4-c]pyridine-4-carboxylic acid {(S)-1-[2-(3-hydroxy-propane-1-sulfonyl)-pyridin-4-yl]-ethyl}-amide | | 38 |
| 1-(4-Fluorophenyl)-1H-pyrazolo[3,4-c]pyridine-4-carboxylic acid [(S)-1-(6-ethanesulfonyl-pyridin-3-yl)-ethyl]-amide | | 6 |
| 1-(4-Fluorophenyl)-1H-pyrazolo[3,4-c]pyridine-4-carboxylic acid [(S)-1-(3-chlorophenyl)-propyl]-amide | | 0.4 |
| 1-(4-Fluorophenyl)-1H-pyrazolo[3,4-c]pyridine-4-carboxylic acid [(S)-1-(3-methanesulfonyl-phenyl)-propyl]-amide | | 0.3 |
| 1-(4-Fluorophenyl)-1H-pyrazolo[3,4-c]pyridine-4-carboxylic acid [(S)-1-(3-chlorophenyl)-ethyl]-amide | | 5 |
| 1-(4-Fluorophenyl)-1H-pyrazolo[3,4-c]pyridine-4-carboxylic acid [(S)-1-(6-ethanesulfonyl-pyridin-2-yl)-propyl]-amide | | 0.5 |
| 1-(4-Fluorophenyl)-1H-pyrazolo[3,4-c]pyridine-4-carboxylic acid [(S)-1-(6-bromopyridin-2-yl)-propyl]-amide | | 0.2 |
| 1-(4-Fluorophenyl)-1H-pyrazolo[3,4-c]pyridine-4-carboxylic acid [(S)-1-(3-methanesulfonyl-phenyl)-ethyl]-amide | | 1 |
| 1-(4-Fluorophenyl)-1H-pyrazolo[3,4-c]pyridine-4-carboxylic acid [(S)-1-(6-methanesulfonyl-pyridin-2-yl)-propyl]-amide | | 0.2 |
| 1-(4-Fluorophenyl)-1H-pyrazolo[3,4-c]pyridine-4-carboxylic acid ((S)-1-pyridin-2-yl-propyl)-amide | | 23 |
| 3-[6-((S)-1-{[1-(4-Fluorophenyl)-1H-pyrazolo[3,4-c]pyridine-4-carbonyl]-amino}-propyl)-pyridine-2-sulfonyl]-propionic acid methyl ester | | 3 |
| 1-(4-Fluorophenyl)-1H-pyrazolo[3,4-c]pyridine-4-carboxylic acid [(S)-1-(4-methanesulfonyl-pyridin-2-yl)-propyl]-amide | | 0.8 |
| 1-(4-Fluorophenyl)-1H-pyrazolo[3,4-c]pyridine-4-carboxylic acid [(S)-1-(6-sulfamoyl-pyridin-2-yl)-propyl]-amide | | 0.3 |
| 1-(4-Fluorophenyl)-1H-pyrazolo[3,4-c]pyridine-4-carboxylic acid [(S)-1-(2-methyl-pyridin-4-yl)-propyl]-amide | | 0.9 |
| 3-(1-{[1-(4-Fluorophenyl)-1H-pyrazolo[3,4-c]pyridine-4-carbonyl]-amino}-propyl)-piperidine-1-carboxylic acid tert-butyl ester | | 26 |
| 4-(1-{[1-(4-Fluorophenyl)-1H-pyrazolo[3,4-c]pyridine-4-carbonyl]-amino}-propyl)-piperidine-1-carboxylic acid tert-butyl ester | | 4 |

TABLE II-continued

| Name | Method A IC$_{50}$ (nM) | Method B IC$_{50}$ (nM) |
| --- | --- | --- |
| 1-(4-Fluorophenyl)-1H-pyrazolo[3,4-c]pyridine-4-carboxylic acid ((S)-1-pyridin-4-yl-propyl)-amide | | 6 |
| 1-(4-Fluorophenyl)-1H-pyrazolo[3,4-c]pyridine-4-carboxylic acid [(S)-1-(2-methylsulfanyl-pyridin-4-yl)-propyl]-amide | | 0.2 |
| 1-(4-Fluorophenyl)-1H-pyrazolo[3,4-c]pyridine-4-carboxylic acid [(S)-1-(5-bromo-thiophen-2-yl)-propyl]-amide | | 0.6 |
| 1-(4-Fluorophenyl)-1H-pyrazolo[3,4-c]pyridine-4-carboxylic acid [1-(6-methanesulfonyl-1-oxy-pyridin-3-yl)-propyl]-amide | | 9 |
| 1-(4-Fluorophenyl)-1H-pyrazolo[3,4-c]pyridine-4-carboxylic acid [(S)-1-(4-hydroxy-3-methanesulfonyl-phenyl)-propyl]-amide | | 0.2 |
| 1-(4-Fluorophenyl)-1H-pyrazolo[3,4-c]pyridine-4-carboxylic acid [(S)-1-(6-cyclopropylsulfamoyl-pyridin-3-yl)-propyl]-amide | | 0.2 |
| 1-(4-Fluorophenyl)-1H-pyrazolo[3,4-c]pyridine-4-carboxylic acid [1-(1-methanesulfonyl-piperidin-3-yl)-propyl]-amide | | 2 |
| 1-(4-Fluorophenyl)-1H-pyrazolo[3,4-c]pyridine-4-carboxylic acid [1-(1-methanesulfonyl-piperidin-4-yl)-propyl]-amide | | 2 |
| 1-(4-Fluorophenyl)-1H-pyrazolo[3,4-c]pyridine-4-carboxylic acid [1-(1-carbamoyl-piperidin-4-yl)-propyl]-amide | | 16 |
| 1-(4-Fluorophenyl)-1H-pyrazolo[3,4-c]pyridine-4-carboxylic acid [(S)-1-(2-methanesulfinyl-pyridin-4-yl)-propyl]-amide | | 0.5 |
| 1-(4-Fluorophenyl)-1H-pyrazolo[3,4-c]pyridine-4-carboxylic acid [(S)-1-(5-methanesulfonyl-thiophen-2-yl)-propyl]-amide | | 0.2 |
| 1-(4-Fluorophenyl)-1H-pyrazolo[3,4-c]pyridine-4-carboxylic acid [(S)-1-(1-methyl-1H-pyrazol-4-yl)-propyl]-amide | | 11 |
| 1-(4-Fluorophenyl)-1H-pyrazolo[3,4-c]pyridine-4-carboxylic acid [1-(1-acetyl-piperidin-4-yl)-propyl]-amide | | 10 |
| 1-(4-Fluorophenyl)-1H-pyrazolo[3,4-c]pyridine-4-carboxylic acid [(S)-1-(4-bromo-3-methoxy-phenyl)-propyl]-amide | | 0.5 |
| 1-(4-Fluorophenyl)-1H-pyrazolo[3,4-c]pyridine-4-carboxylic acid [(S)-1-(4-methanesulfonyl-3-methoxy-phenyl)-propyl]-amide | | 0.2 |
| 1-(4-Fluorophenyl)-1H-pyrazolo[3,4-c]pyridine-4-carboxylic acid [(S)-1-(3-hydroxy-4-methanesulfonyl-phenyl)-propyl]-amide | | 0.6 |
| 1-(4-Fluorophenyl)-1H-pyrazolo[3,4-c]pyridine-4-carboxylic acid [(S)-1-(2-morpholin-4-yl-pyridin-4-yl)-propyl]-amide | | 0.7 |
| 1-(4-Fluorophenyl)-1H-pyrazolo[3,4-c]pyridine-4-carboxylic acid {(S)-1-[2-(1H-tetrazol-5-yl)-pyridin-4-yl]-propyl}-amide | | 3 |
| 1-(4-Fluorophenyl)-1H-pyrazolo[3,4-c]pyridine-4-carboxylic acid [(S)-1-(2-methanesulfonyl-pyridin-4-yl)-but-3-enyl]-amide | | 0.3 |
| 1-(4-Fluorophenyl)-1H-pyrazolo[3,4-c]pyridine-4-carboxylic acid (2-methanesulfonyl-6-methoxy-pyridin-4-ylmethyl)-amide | | 1 |
| 1-(4-Fluorophenyl)-1H-pyrazolo[3,4-c]pyridine-4-carboxylic acid [(1S)-3,4-dihydroxy-1-(2-methanesulfonyl-pyridin-4-yl)-butyl]-amide (single diastereomer) | | 11 |
| 1-(4-Fluorophenyl)-1H-pyrazolo[3,4-c]pyridine-4-carboxylic acid (6-methanesulfonyl-2-oxo-1,2-dihydropyridin-4-ylmethyl)-amide | | 17 |
| (S)-3-{[1-(4-Fluorophenyl)-1H-pyrazolo[3,4-c]pyridine-4-carbonyl]-amino}-3-(2-methanesulfonyl-pyridin-4-yl)-propionic acid methyl ester | | 4 |
| 1-(4-Fluorophenyl)-1H-pyrazolo[3,4-c]pyridine-4-carboxylic acid [(S)-3-hydroxy-1-(2-methanesulfonyl-pyridin-4-yl)-propyl]-amide | | 12 |
| 1-(4-Fluorophenyl)-1H-pyrazolo[3,4-c]pyridine-4-carboxylic acid [(S)-1-(2-methanesulfonyl-thiazol-5-yl)-propyl]-amide | | 0.6 |
| 1-(4-Fluorophenyl)-1H-pyrazolo[3,4-c]pyridine-4-carboxylic acid [(S)-1-(4-methanesulfonyl-thiophen-2-yl)-propyl]-amide | | 0.1 |

TABLE II-continued

| Name | Method A IC$_{50}$ (nM) | Method B IC$_{50}$ (nM) |
|---|---|---|
| 1-(4-Fluorophenyl)-1H-pyrazolo[3,4-c]pyridine-4-carboxylic acid [(S)-1-(1-methanesulfonyl-1H-pyrazol-3-yl)-propyl]-amide | | 3 |
| [3-((S)-1-{[1-(4-Fluorophenyl)-1H-pyrazolo[3,4-c]pyridine-4-carbonyl]-amino}-propyl)-pyrazol-1-yl]-acetic acid ethyl ester | | 11 |
| 1-(4-Fluorophenyl)-1H-pyrazolo[3,4-c]pyridine-4-carboxylic acid [(S)-1-(5-methanesulfonyl-furan-2-yl)-propyl]-amide | | 0.4 |
| 1-(4-Fluorophenyl)-1H-pyrazolo[3,4-c]pyridine-4-carboxylic acid ((S)-1-{2-[(2-hydroxy-ethyl)-methyl-amino]-pyridin-4-yl}-propyl)-amide | | 2 |
| 2-((S)-1-{[1-(4-Fluorophenyl)-1H-pyrazolo[3,4-c]pyridine-4-carbonyl]-amino}-propyl)-thiazole-4-carboxylic acid methyl ester | | 5 |
| 1-(4-Fluorophenyl)-1H-pyrazolo[3,4-c]pyridine-4-carboxylic acid [(S)-1-(4-carbamoyl-thiazol-2-yl)-propyl]-amide | | 8 |
| 1-(4-Fluorophenyl)-1H-pyrazolo[3,4-c]pyridine-4-carboxylic acid [(S)-1-(4-methylcarbamoyl-thiazol-2-yl)-propyl]-amide | | 3 |
| 1-(4-Fluorophenyl)-1H-pyrazolo[3,4-c]pyridine-4-carboxylic acid [(S)-1-(2-chloro-6-methanesulfonyl-pyridin-4-yl)-propyl]-amide | | 0.3 |
| 2-((S)-1-{[1-(4-Fluorophenyl)-1H-pyrazolo[3,4-c]pyridine-4-carbonyl]-amino}-propyl)-oxazole-4-carboxylic acid methyl ester | | 38 |
| 1-(4-Fluorophenyl)-1H-pyrazolo[3,4-c]pyridine-4-carboxylic acid [1-(4-carbamoyl-oxazol-2-yl)-propyl]-amide | | 36 |
| 1-(4-Fluorophenyl)-1H-pyrazolo[3,4-c]pyridine-4-carboxylic acid [1-(4-methylcarbamoyl-oxazol-2-yl)-propyl]-amide | | 16 |
| 1-(4-Fluorophenyl)-1H-pyrazolo[3,4-c]pyridine-4-carboxylic acid {(S)-1-[2-(methyl-piperidin-4-yl-amino)-pyridin-4-yl]-propyl}-amide | | 11 |
| 1-(4-Fluorophenyl)-1H-pyrazolo[3,4-c]pyridine-4-carboxylic acid [(S)-1-(2-methylsulfanyl-oxazol-5-yl)-propyl]-amide | | 1 |
| 1-(4-Fluorophenyl)-1H-pyrazolo[3,4-c]pyridine-4-carboxylic acid [(S)-1-(4-methanesulfonyl-furan-2-yl)-propyl]-amide | | 6 |
| 1-(4-Fluorophenyl)-1H-pyrazolo[3,4-c]pyridine-4-carboxylic acid [(S)-1-(2-methanesulfonyl-oxazol-5-yl)-propyl]-amide | | 3 |
| 1-(4-Fluorophenyl)-1H-pyrazolo[3,4-c]pyridine-4-carboxylic acid (5-bromo-thiophen-2-ylmethyl)-amide | | 19 |
| 1-(4-Fluorophenyl)-1H-pyrazolo[3,4-c]pyridine-4-carboxylic acid (4-bromo-thiophen-2-ylmethyl)-amide | | 7 |
| 1-(4-Fluorophenyl)-1H-pyrazolo[3,4-c]pyridine-4-carboxylic acid (2-bromo-thiazol-5-ylmethyl)-amide | | 25 |
| 1-(4-Fluorophenyl)-1H-pyrazolo[3,4-c]pyridine-4-carboxylic acid (5-methanesulfonyl-thiophen-2-ylmethyl)-amide | | 5 |
| 1-(4-Fluorophenyl)-1H-pyrazolo[3,4-c]pyridine-4-carboxylic acid (4-methanesulfonyl-thiophen-2-ylmethyl)-amide | | 5 |
| 1-(4-Fluorophenyl)-1H-pyrazolo[3,4-c]pyridine-4-carboxylic acid {(S)-1-[2-((S)-methanesulfinyl)-pyridin-4-yl]-propyl}-amide | | 0.5 |
| 1-(4-Fluorophenyl)-1H-pyrazolo[3,4-c]pyridine-4-carboxylic acid {(S)-1-[2-((R)-methanesulfinyl)-pyridin-4-yl]-propyl}-amide | | 0.6 |
| 1-(4-Fluorophenyl)-1H-pyrazolo[3,4-c]pyridine-4-carboxylic acid [(S)-1-(2-methylsulfanyl-oxazol-5-yl)-ethyl]-amide | | 6 |
| 1-(4-Fluorophenyl)-1H-pyrazolo[3,4-c]pyridine-4-carboxylic acid [(S)-1-(2-methanesulfonyl-6-methoxy-pyridin-4-yl)-propyl]-amide | | 0.1 |
| 1-(4-Fluorophenyl)-1H-pyrazolo[3,4-c]pyridine-4-carboxylic acid [(S)-1-(2-methanesulfonyl-oxazol-5-yl)-ethyl]-amide | | 19 |
| 1-(4-Fluorophenyl)-1H-pyrazolo[3,4-c]pyridine-4-carboxylic acid (2-methanesulfonyl-thiazol-4-ylmethyl)-amide | | 29 |

TABLE II-continued

| Name | Method A IC$_{50}$ (nM) | Method B IC$_{50}$ (nM) |
|---|---|---|
| 1-(4-Fluorophenyl)-1H-pyrazolo[3,4-c]pyridine-4-carboxylic acid [(S)-1-(6-methanesulfonyl-2-oxo-1,2-dihydropyridin-4-yl)-propyl]-amide | | 0.3 |
| 1-(4-Fluorophenyl)-1H-pyrazolo[3,4-c]pyridine-4-carboxylic acid {1-[4-(cyanomethyl-carbamoyl)-oxazol-2-yl]-propyl}-amide | | 25 |
| 1-(4-Fluorophenyl)-1H-pyrazolo[3,4-c]pyridine-4-carboxylic acid (2-bromo-6-methanesulfonyl-pyridin-4-ylmethyl)-amide | | 1 |
| 1-(4-Fluorophenyl)-1H-pyrazolo[3,4-c]pyridine-4-carboxylic acid (2-methanesulfonyl-6-methyl-pyridin-4-ylmethyl)-amide | | 5 |
| 1-(4-Fluorophenyl)-1H-pyrazolo[3,4-c]pyridine-4-carboxylic acid (2-methanesulfonyl-thiazol-5-ylmethyl)-amide | | 17 |
| 2-(1-{[1-(4-Fluorophenyl)-1H-pyrazolo[3,4-c]pyridine-4-carbonyl]-amino}-propyl)-5-methyl-oxazole-4-carboxylic acid methyl ester | | 27 |
| 1-(4-Fluorophenyl)-1H-pyrazolo[3,4-c]pyridine-4-carboxylic acid [1-(5-methyl-4-methylcarbamoyl-oxazol-2-yl)-propyl]-amide | | 9 |
| 1-(4-Fluorophenyl)-1H-pyrazolo[3,4-c]pyridine-4-carboxylic acid [1-(4-carbamoyl-5-methyl-oxazol-2-yl)-propyl]-amide | | 26 |
| {[2-(1-{[1-(4-Fluorophenyl)-1H-pyrazolo[3,4-c]pyridine-4-carbonyl]-amino}-propyl)-5-methyl-oxazole-4-carbonyl]-amino}-acetic acid methyl ester | | 26 |
| 1-(4-Fluorophenyl)-1H-pyrazolo[3,4-c]pyridine-4-carboxylic acid {1-[4-(cyanomethyl-carbamoyl)-5-methyl-oxazol-2-yl]-propyl}-amide | | 18 |
| 1-(4-Fluorophenyl)-1H-pyrazolo[3,4-c]pyridine-4-carboxylic acid {1-[4-(carbamoylmethyl-carbamoyl)-5-methyl-oxazol-2-yl]-propyl}-amide | | 25 |
| 1-(4-Fluorophenyl)-1H-pyrazolo[3,4-c]pyridine-4-carboxylic acid [(S)-1-(2-methanesulfonyl-oxazol-4-yl)-propyl]-amide | | 4 |
| 1-(4-Fluorophenyl)-1H-pyrazolo[3,4-c]pyridine-4-carboxylic acid [(S)-1-(1H-pyrazol-4-yl)-propyl]-amide | | 36 |
| 1-(4-Fluorophenyl)-1H-pyrazolo[3,4-c]pyridine-4-carboxylic acid [(S)-1-(2-methanesulfonyl-6-methoxy-pyridin-4-yl)-ethyl]-amide | | 0.4 |
| 1-(4-Fluorophenyl)-1H-pyrazolo[3,4-c]pyridine-4-carboxylic acid [(S)-1-(5-methanesulfonyl-thiophen-3-yl)-propyl]-amide | | 0.3 |
| [4-((S)-1-{[1-(4-Fluorophenyl)-1H-pyrazolo[3,4-c]pyridine-4-carbonyl]-amino}-propyl)-pyrazol-1-yl]-acetic acid ethyl ester | | 25 |
| 1-(4-Fluorophenyl)-1H-pyrazolo[3,4-c]pyridine-4-carboxylic acid [2-(methanesulfonyl-methyl-amino)-pyrimidin-5-ylmethyl]-amide | | 2 |
| 1-(4-Fluorophenyl)-1H-pyrazolo[3,4-c]pyridine-4-carboxylic acid (2-morpholin-4-yl-pyrimidin-5-ylmethyl)-amide | | 8 |
| 1-(4-Fluorophenyl)-1H-pyrazolo[3,4-c]pyridine-4-carboxylic acid [(S)-1-(2-methanesulfonyl-pyridin-4-yl)-ethyl-2,2,2-D3]-amide | | 1 |
| 1-(4-Fluorophenyl)-1H-pyrazolo[3,4-c]pyridine-4-carboxylic acid [(S)-1-(2-methanesulfonyl-pyridin-4-yl)-ethyl-1,2,2,2-D4]-amide | | 1 |
| 1-(4-Fluorophenyl)-1H-pyrazolo[3,4-c]pyridine-4-carboxylic acid [(S)-1-(2-methanesulfonyl-thiazol-4-yl)-ethyl]-amide | | 4 |
| 1-(4-Fluorophenyl)-1H-pyrazolo[3,4-c]pyridine-4-carboxylic acid [(S)-1-(4-methanesulfonyl-1H-pyrrol-2-yl)-propyl]-amide | | 1 |
| 1-(4-Fluorophenyl)-1H-pyrazolo[3,4-c]pyridine-4-carboxylic acid [(S)-1-(2-methanesulfonyl-pyridin-4-yl)-2-(2-oxo-1,3-dioxolan-4-yl)-ethyl]-amide | | 6 |
| 1-(4-Fluorophenyl)-1H-pyrazolo[3,4-c]pyridine-4-carboxylic acid [(R)-1-(4-methanesulfonyl-1-methyl-1H-pyrrol-2-yl)-propyl]-amide | | 7 |
| 1-(4-Fluorophenyl)-1H-pyrazolo[3,4-c]pyridine-4-carboxylic acid [(S)-1-(2-dimethylamino-6-methanesulfonyl-pyridin-4-yl)-ethyl]-amide | | 0.2 |
| 1-(4-Fluorophenyl)-1H-pyrazolo[3,4-c]pyridine-4-carboxylic acid {(S)-1-[2-(carbamoylmethyl-methyl-amino)-6-methanesulfonyl-pyridin-4-yl]-ethyl}-amide | | 1 |

TABLE II-continued

| Name | Method A IC$_{50}$ (nM) | Method B IC$_{50}$ (nM) |
|---|---|---|
| 1-(4-Fluorophenyl)-1H-pyrazolo[3,4-c]pyridine-4-carboxylic acid {(R)-1-[1-(toluene-4-sulfonyl)-1H-pyrrol-3-yl]-propyl}-amide | | 23 |
| 1-(4-Fluorophenyl)-1H-pyrazolo[3,4-c]pyridine-4-carboxylic acid {(S)-1-[1-(toluene-4-sulfonyl)-1H-pyrrol-3-yl]-propyl}-amide | | 3 |
| 1-(4-Fluorophenyl)-1H-pyrazolo[3,4-c]pyridine-4-carboxylic acid [(S)-1-(2-methanesulfonyl-6-methylamino-pyridin-4-yl)-ethyl]-amide | | 0.4 |
| 1-(4-Fluorophenyl)-1H-pyrazolo[3,4-c]pyridine-4-carboxylic acid [(R)-1-(2-bromo-pyridin-4-yl)-2-hydroxy-ethyl]-amide | | 2 |
| 1-(4-Fluorophenyl)-1H-pyrazolo[3,4-c]pyridine-4-carboxylic acid {(S)-1-[2-(carbamoylmethyl-amino)-6-methanesulfonyl-pyridin-4-yl]-ethyl}-amide | | 0.6 |
| 1-(4-Fluorophenyl)-1H-pyrazolo[3,4-c]pyridine-4-carboxylic acid [(R)-2-hydroxy-1-(2-methanesulfonyl-pyridin-4-yl)-ethyl]-amide | | 6 |
| 1-(4-Fluorophenyl)-1H-pyrazolo[4,3-c]pyridine-4-carboxylic acid [(S)-1-(2-methanesulfonyl-pyridin-4-yl)-propyl]-amide | | 3 |
| 1-(4-Fluorophenyl)-1H-pyrazolo[3,4-c]pyridine-4-carboxylic acid [(S)-1-(2-methanesulfonyl-6-methylamino-pyridin-4-yl)-propyl]-amide | | 0.3 |
| 1-(4-Fluorophenyl)-1H-pyrazolo[3,4-c]pyridine-4-carboxylic acid [(S)-1-(2-dimethylamino-6-methanesulfonyl-pyridin-4-yl)-propyl]-amide | | 0.2 |
| 1-(4-Fluorophenyl)-1H-pyrazolo[3,4-c]pyridine-4-carboxylic acid [(S)-1-(2-isopropylamino-6-methanesulfonyl-pyridin-4-yl)-propyl]-amide | | 0.2 |
| 1-(4-Fluorophenyl)-1H-pyrazolo[3,4-c]pyridine-4-carboxylic acid {(S)-1-[2-(carbamoylmethyl-amino)-6-methanesulfonyl-pyridin-4-yl]-propyl}-amide | | 0.4 |
| 1-(4-Fluorophenyl)-1H-pyrazolo[3,4-c]pyridine-4-carboxylic acid {(S)-1-[2-(carbamoylmethyl-methyl-amino)-6-methanesulfonyl-pyridin-4-yl]-propyl}-amide | | 0.3 |
| 1-(4-Fluorophenyl)-1H-pyrazolo[3,4-c]pyridine-4-carboxylic acid [2-(acetyl-methyl-amino)-pyrimidin-5-ylmethyl]-amide | | 24 |
| 1-(4-Fluorophenyl)-1H-pyrazolo[3,4-c]pyridine-4-carboxylic acid [(S)-1-(5-methanesulfonyl-1H-pyrrol-3-yl)-propyl]-amide | | 0.9 |
| 1-(4-Fluorophenyl)-1H-pyrazolo[3,4-c]pyridine-4-carboxylic acid [(S)-1-((2S,4R)-2-carbamoyl-1-methanesulfonyl-piperidin-4-yl)-propyl]-amide | | 12 |
| 1-(4-Fluorophenyl)-1H-pyrazolo[3,4-c]pyridine-4-carboxylic acid [(S)-1-((2R,4R)-2-carbamoyl-1-methanesulfonyl-piperidin-4-yl)-propyl]-amide | | 10 |
| 1-(4-Fluorophenyl)-1H-pyrazolo[3,4-c]pyridine-4-carboxylic acid [(S)-1-(2-hydroxymethyl-pyridin-4-yl)-propyl]-amide | | 3 |
| 1-(4-Fluorophenyl)-1H-pyrazolo[3,4-c]pyridine-4-carboxylic acid [(S)-1-(2-methanesulfonyl-thiazol-4-yl)-propyl]-amide | | 0.4 |
| 1-(4-Fluorophenyl)-1H-pyrazolo[3,4-c]pyridine-4-carboxylic acid (1-methanesulfonyl-1H-pyrrolo[2,3-b]pyridin-4-ylmethyl)-amide | | 3 |
| 1-(4-Fluorophenyl)-1H-pyrazolo[3,4-c]pyridine-4-carboxylic acid {1-[2-(methanesulfonyl-methyl-amino)-pyrimidin-5-yl]-propyl}-amide | | 7 |
| 1-(4-Fluorophenyl)-1H-pyrazolo[3,4-c]pyridine-4-carboxylic acid [2-(carbamoylmethyl-methyl-amino)-6-methanesulfonyl-pyridin-4-ylmethyl]-amide | | 3 |
| 1-(4-Fluorophenyl)-1H-pyrazolo[3,4-c]pyridine-4-carboxylic acid [2-(carbamoylmethyl-amino)-6-methanesulfonyl-pyridin-4-ylmethyl]-amide | | 11 |
| 1-(4-Fluorophenyl)-1H-pyrazolo[3,4-c]pyridine-4-carboxylic acid [(S)-1-(2-methanesulfonyl-thiazol-5-yl)-ethyl]-amide | | 6 |
| 1-(4-Fluorophenyl)-1H-pyrazolo[3,4-c]pyridine-4-carboxylic acid [(S)-1-(6-methanesulfonyl-2-oxo-1,2-dihydropyridin-4-yl)-ethyl]-amide | | 3 |
| 1-(4-Fluorophenyl)-1H-pyrazolo[3,4-c]pyridine-4-carboxylic acid (2-morpholin-4-yl-thiazol-5-ylmethyl)-amide | | 16 |

TABLE II-continued

| Name | Method A IC$_{50}$ (nM) | Method B IC$_{50}$ (nM) |
|---|---|---|
| 1-(4-Fluorophenyl)-1H-pyrazolo[3,4-c]pyridine-4-carboxylic acid {(R)-1-[4-methanesulfonyl-1-(toluene-4-sulfonyl)-1H-pyrrol-2-yl]-propyl}-amide | | 16 |
| 1-(4-Fluorophenyl)-1H-pyrazolo[3,4-c]pyridine-4-carboxylic acid [(S)-1-(4-bromo-thiazol-2-yl)-propyl]-amide | | 0.8 |
| 1-(4-Fluorophenyl)-1H-pyrazolo[3,4-c]pyridine-4-carboxylic acid [(S)-1-(4-bromo-thiazol-2-yl)-ethyl]-amide | | 24 |
| 1-(4-Fluorophenyl)-1H-pyrazolo[3,4-c]pyridine-4-carboxylic acid [(S)-1-(3-bromo-isoxazol-5-yl)-propyl]-amide | | 28 |
| 1-(4-Fluorophenyl)-1H-pyrazolo[3,4-c]pyridine-4-carboxylic acid [(S)-1-(4-methanesulfonyl-3,4,5,6-tetrahydro-2H-[1,2']bipyridinyl-4'-yl)-propyl]-amide | | 13 |
| 1-(4-Fluorophenyl)-1H-pyrazolo[3,4-c]pyridine-4-carboxylic acid {(S)-1-[2-(4-methyl-piperazin-1-yl)-pyridin-4-yl]-propyl}-amide | | 8 |
| 1-(4-Fluorophenyl)-1H-pyrazolo[3,4-c]pyridine-4-carboxylic acid [(S)-1-(4,4-difluoro-3,4,5,6-tetrahydro-2H-[1,2']bipyridinyl-4'-yl)-propyl]-amide | | 3 |
| 1-(4-Fluorophenyl)-1H-pyrazolo[3,4-c]pyridine-4-carboxylic acid ((S)-1-{2-[(2-methoxy-ethyl)-methyl-amino]-pyridin-4-yl}-propyl)-amide | | 1 |
| 1-(4-Fluorophenyl)-1H-pyrazolo[3,4-c]pyridine-4-carboxylic acid {(S)-1-[2-(4-acetyl-piperazin-1-yl)-pyridin-4-yl]-propyl}-amide | | 5 |
| 1-(4-Fluorophenyl)-1H-pyrazolo[3,4-c]pyridine-4-carboxylic acid {(S)-1-[2-(1,1-dioxo-1λ6-thiomorpholin-4-yl)-pyridin-4-yl]-propyl}-amide | | 12 |
| 1-(4-Fluorophenyl)-1H-pyrazolo[3,4-c]pyridine-4-carboxylic acid [(R)-1-(2-bromopyridin-4-yl)-2-methoxy-ethyl]-amide | | 0.5 |
| 1-(4-Fluorophenyl)-1H-pyrazolo[3,4-c]pyridine-4-carboxylic acid [(R)-1-(2-methanesulfonyl-pyridin-4-yl)-2-methoxy-ethyl]-amide | | 1 |
| 1-(4-Fluorophenyl)-1H-pyrazolo[3,4-c]pyridine-4-carboxylic acid [(S)-1-(4-methanesulfonyl-thiazol-2-yl)-propyl]-amide | | 0.3 |
| 1-(4-Fluorophenyl)-1H-pyrazolo[3,4-c]pyridine-4-carboxylic acid {(S)-1-[2-(1-hydroxy-1-methyl-ethyl)-pyridin-4-yl]-propyl}-amide | | 0.5 |
| 1-(4-Fluorophenyl)-1H-pyrazolo[3,4-c]pyridine-4-carboxylic acid [1-(2-bromo-pyridin-4-yl)-1-methyl-ethyl]-amide | | 14 |
| 1-(4-Fluorophenyl)-1H-pyrazolo[3,4-c]pyridine-4-carboxylic acid [1-(2-methanesulfonyl-pyridin-4-yl)-1-methyl-ethyl]-amide | | 12 |
| 1-(4-Fluorophenyl)-1H-pyrazolo[3,4-c]pyridine-4-carboxylic acid [1-(2-bromo-pyridin-4-yl)-1-methyl-propyl]-amide | | 11 |
| 1-(4-Fluorophenyl)-1H-pyrazolo[3,4-c]pyridine-4-carboxylic acid [1-(2-methanesulfonyl-pyridin-4-yl)-1-methyl-propyl]-amide | | 6 |
| 1-(4-Fluorophenyl)-1H-pyrazolo[3,4-c]pyridine-4-carboxylic acid [1-(2-bromo-pyridin-4-yl)-1-ethyl-propyl]-amide | | 29 |
| 1-(4-Fluorophenyl)-1H-pyrazolo[3,4-c]pyridine-4-carboxylic acid [1-ethyl-1-(2-methanesulfonyl-pyridin-4-yl)-propyl]-amide | | 16 |
| 1-(4-Fluorophenyl)-1H-pyrazolo[3,4-c]pyridine-4-carboxylic acid [2-(2-hydroxy-2-methyl-propylamino)-6-methanesulfonyl-pyridin-4-ylmethyl]-amide | | 0.7 |
| 1-(4-Fluorophenyl)-1H-pyrazolo[3,4-c]pyridine-4-carboxylic acid [1-ethyl-1-(2-methanesulfonyl-thiazol-5-yl)-propyl]-amide | | 28 |

Method of Use

The compounds of the invention are effective antagonists of the interactions between CCR1 and its chemokine ligands and thus inhibit CCR1-mediated activity. Therefore, in one embodiment of the invention, there is provided methods of treating autoimmune disorders using compounds of the invention. In another embodiment, there is provided methods of treating inflammatory disorders using compounds of the invention.

Without wishing to be bound by theory, by antagonizing the interactions between CCR1 and its chemokine ligands, the compounds block chemotaxis of pro-inflammatory cells including monocytes, macrophages dendritic cells, eosinophils, and T cells (TH1) cells and other CCR1 positive cells to inflamed tissues and thereby ameliorate the chronic inflammation associated with autoimmune diseases. Thus, the inhibition of CCR1 activity is an attractive means for preventing and treating a variety of autoimmune disorders, including inflammatory diseases, autoimmune diseases, organ (Horuk et al. (2001) *JBC* 276 p. 4199) and bone marrow transplant rejection and other disorders associated with an influx of pro-inflammatory cells. For example, the compounds of the invention may be used to prevent or treat acute or chronic inflammation, allergies, contact dermatitis, psoriasis, rheumatoid arthritis, multiple sclerosis, type 1 diabetes, inflammatory bowel disease, Guillain-Barre syndrome, Crohn's disease, ulcerative colitis, graft versus host disease (and other forms of organ or bone marrow transplant rejection), Alzheimer's disease (Halks-Miller et al. (2003) *Ann Neurol* 54 p. 638), Asthma (Jouber et al. (2008) *J. Immun* 180 p. 1268), chronic kidney disease (Topham et al. (1999) *J. Clin. Invest.* 104 p. 1549), sepsis (He et al. (2007) *Am J. Physio* 292 p. G1173), autoimmune myocarditis (Futamats et al. (2006) *J Mol Cell Cardiology* 40 p. 853) and systemic lupus erythematosus. In particular, the compounds may be used to prevent or treat rheumatoid arthritis and multiple sclerosis. Other disorders associated with the trafficking of pro-inflammatory cells will be evident to those of ordinary skill in the art and can also be treated with the compounds and compositions of this invention.

For treatment of the above-described diseases and conditions, a therapeutically effective dose will generally be in the range from about 0.01 mg/kg to about 100 mg/kg of body weight per dosage of a compound of the invention; preferably, from about 0.1 mg/kg to about 20 mg/kg of body weight per dosage. For example, for administration to a 70 kg person, the dosage range would be from about 0.7 mg to about 7000 mg per dosage of a compound of the invention, preferably from about 7.0 mg to about 1400 mg per dosage. Some degree of routine dose optimization may be required to determine an optimal dosing level and pattern. The active ingredient may be administered from 1 to 6 times a day.

General Administration and Pharmaceutical Compositions

When used as pharmaceuticals, the compounds of the invention are typically administered in the form of a pharmaceutical composition. Such compositions can be prepared using procedures well known in the pharmaceutical art and comprise at least one compound of the invention. The compounds of the invention may also be administered alone or in combination with adjuvants that enhance stability of the compounds of the invention, facilitate administration of pharmaceutical compositions containing them in certain embodiments, provide increased dissolution or dispersion, increased antagonist activity, provide adjunct therapy, and the like. The compounds according to the invention may be used on their own or in conjunction with other active substances according to the invention, optionally also in conjunction with other pharmacologically active substances. In general, the compounds of this invention are administered in a therapeutically or pharmaceutically effective amount, but may be administered in lower amounts for diagnostic or other purposes.

Administration of the compounds of the invention, in pure form or in an appropriate pharmaceutical composition, can be carried out using any of the accepted modes of administration of pharmaceutical compositions. Thus, administration can be, for example, orally, buccally (e.g., sublingually), nasally, parenterally, topically, transdermally, vaginally, or rectally, in the form of solid, semi-solid, lyophilized powder, or liquid dosage forms, such as, for example, tablets, suppositories, pills, soft elastic and hard gelatin capsules, powders, solutions, suspensions, or aerosols, or the like, preferably in unit dosage forms suitable for simple administration of precise dosages. The pharmaceutical compositions will generally include a conventional pharmaceutical carrier or excipient and a compound of the invention as the/an active agent, and, in addition, may include other medicinal agents, pharmaceutical agents, carriers, adjuvants, diluents, vehicles, or combinations thereof. Such pharmaceutically acceptable excipients, carriers, or additives as well as methods of making pharmaceutical compositions for various modes or administration are well-known to those of skill in the art. The state of the art is evidenced, e.g., by *Remington: The Science and Practice of Pharmacy,* 20th Edition, A. Gennaro (ed.), Lippincott Williams & Wilkins, 2000; *Handbook of Pharmaceutical Additives*, Michael & Irene Ash (eds.), Gower, 1995; *Handbook of Pharmaceutical Excipients*, A. H. Kibbe (ed.), American Pharmaceutical Ass'n, 2000; H. C. Ansel and N. G. Popovish, *Pharmaceutical Dosage Forms and Drug Delivery Systems,* 5th ed., Lea and Febiger, 1990; each of which is incorporated herein by reference in their entireties to better describe the state of the art.

As one of skill in the art would expect, the forms of the compounds of the invention utilized in a particular pharmaceutical formulation will be selected (e.g., salts) that possess suitable physical characteristics (e.g., water solubility) that is required for the formulation to be efficacious.

The invention claimed is:

1. A compound wherein the compound is:

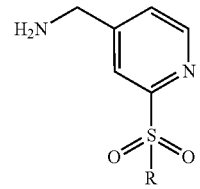

wherein R is chosen from C1-10 alkyl and aryl
and wherein the compound is in the form of a salt.

2. The compound according to claim 1 wherein the compound is

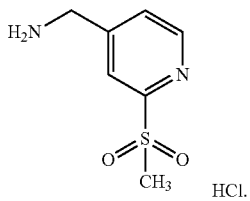

3. A compound wherein the compound is

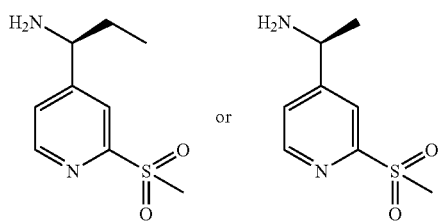

in the form of an HCl salt.

* * * * *